United States Patent
Huigens, III et al.

(10) Patent No.: US 9,856,225 B2
(45) Date of Patent: Jan. 2, 2018

(54) SUBSTITUTED PHENAZINES AS ANTIMICROBIAL AGENTS

(71) Applicant: University of Florida Research Foundation, Incorporated, Gainesville, FL (US)

(72) Inventors: Robert William Huigens, III, Williston, FL (US); Shouguang Jin, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/107,531

(22) PCT Filed: Dec. 23, 2014

(86) PCT No.: PCT/US2014/072165
§ 371 (c)(1),
(2) Date: Jun. 23, 2016

(87) PCT Pub. No.: WO2015/100331
PCT Pub. Date: Jul. 2, 2015

(65) Prior Publication Data
US 2016/0355487 A1  Dec. 8, 2016

Related U.S. Application Data

(60) Provisional application No. 62/010,023, filed on Jun. 10, 2014, provisional application No. 61/920,571, filed on Dec. 24, 2013.

(51) Int. Cl.
| | |
|---|---|
| *A61K 31/498* | (2006.01) |
| *C07D 241/46* | (2006.01) |
| *A61K 45/06* | (2006.01) |
| *C07D 405/12* | (2006.01) |
| *C07D 409/12* | (2006.01) |
| *C07D 241/38* | (2006.01) |

(52) U.S. Cl.
CPC .......... *C07D 241/46* (2013.01); *A61K 31/498* (2013.01); *A61K 45/06* (2013.01); *C07D 241/38* (2013.01); *C07D 405/12* (2013.01); *C07D 409/12* (2013.01)

(58) Field of Classification Search
CPC ............................ A61K 31/498; C07D 241/46
USPC .......................................... 514/250; 544/347
See application file for complete search history.

(56) References Cited

U.S. PATENT DOCUMENTS

| | | |
|---|---|---|
| 2005/0165044 A1 | 7/2005 | Boykin et al. |
| 2008/0121873 A1 | 5/2008 | Katakura et al. |
| 2010/0160346 A1 | 6/2010 | Barnham et al. |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
[No Author Listed], CID 66651970. Compound Summary. Nov. 30, 2012. http://pubchem.ncbi.nlm.nih.gov/compound/66651970. [last accessed Mar. 31, 2015]. 4 pages.
Berge et al., Pharmaceutical salts. J Pharm Sci. Jan. 1977;66(1):1-19.
Borrero et al., Phenazine antibiotic inspired discovery of potent bromophenazine antibacterial agents against *Staphylococcus aureus* and *Staphylococcus epidermidis*. Org Biomol Chem. Feb. 14, 2014;12(6):881-6. doi: 10.1039/c3ob42416b.
Camilli et al., Bacterial small-molecule signaling pathways. Science. Feb. 24, 2006;311(5764):1113-6.

(Continued)

*Primary Examiner* — Douglas M Willis
(74) *Attorney, Agent, or Firm* — Wolf, Greenfield & Sacks, P.C.

(57) ABSTRACT

The present invention provides novel phenazine derivatives, such as compounds of Formula (I) and (II), and pharmaceutically acceptable salts thereof. The compounds of the invention are expected to be antimicrobial agents and may act by a microbial warfare strategy (e.g., a reactive oxygen species (ROS)-based competition strategy). The present invention also provides pharmaceutical compositions, kits, uses, and methods that involve the compounds of the invention and may be useful in preventing or treating a microbial infection (e.g., a bacterial infection) in a subject, inhibiting the growth and/or reproduction of a microorganism (e.g., a bacterium), killing a microorganism (e.g., a bacterium), inhibiting the formation and/or growth of a biofilm, or reducing or clearing a biofilm.

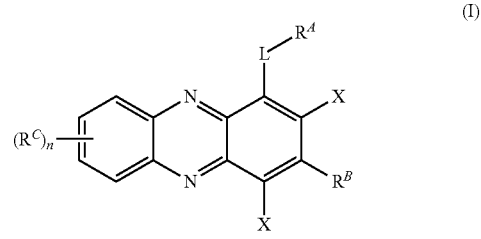

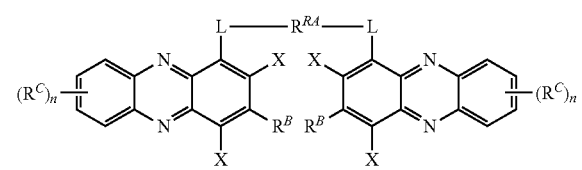

34 Claims, 24 Drawing Sheets

(56) References Cited

OTHER PUBLICATIONS

Ceri et al., The Calgary Biofilm Device: new technology for rapid determination of antibiotic susceptibilities of bacterial biofilms. J Clin Microbiol. Jun. 1999;37(6):1771-6.

Conda-Sheridan et al., Potential chemopreventive agents based on the structure of the lead compound 2-bromo-1-hydroxyphenazine, isolated from *Streptomyces* species, strain CNS284. J Med Chem. Dec. 23, 2010;53(24):8688-99. doi: 10.1021/jm1011066.

Eun et al., DCAP: a broad-spectrum antibiotic that targets the cytoplasmic membrane of bacteria. J Am Chem Soc. Jul. 18, 2012;134(28):11322-5. doi: 10.1021/ja302542j.

Hassan et al., Mechanism of the antibiotic action pyocyanine. J Bacteriol. Jan. 1980;141(1):156-63.

Machan et al., Interaction between Pseudomonas aeruginosa and *Staphylococcus aureus*: description of an anti-staphylococcal substance. J Med Microbiol. Apr. 1991;34(4):213-7.

Ng et al., Bacterial quorum-sensing network architectures. Annu Rev Genet. 2009;43:197-222. doi: 10.1146/annurev-genet-102108-134304.

Priyaja et al., Pyocyanin induced in vitro oxidative damage and its toxicity level in human, fish and insect cell lines for its selective biological applications. Cytotechnology. Jan. 2016;68(1):143-55. doi: 10.1007/s10616-014-9765-5.

Wang et al., Endogenous phenazine antibiotics promote anaerobic survival of Pseudomonas aeruginosa via extracellular electron transfer. J Bacteriol. Jan. 2010;192(1):365-9. doi: 10.1128/JB.01188-09.

Abouelhassan et al., Discovery of quinoline small molecules with potent dispersal activity against methicillin-resistant *Staphylococcus aureus* and *Staphylococcus epidermidis* biofilms using a scaffold hopping strategy. Bioorg Med Chem Lett. Nov. 1, 2014;24(21):5076-80. doi: 10.1016/j.bmcl.2014.09.009.

Breitmaier et al., Carbon-13 nuclear magnetic resonance chemical shifts of substituted phenazines. J. Org. Chem. 1976;41:2104-2108.

Brown et al., New targets and screening approaches in antimicrobial drug discovery. Chem Rev. Feb. 2005;105(2):759-74.

Clatworthy et al., Targeting virulence: a new paradigm for antimicrobial therapy. Nat Chem Biol. Sep. 2007;3(9):541-8.

Fletcher et al., Draining the moat: disrupting bacterial biofilms with natural products. Tetrahedron. Sep. 2014;70(37):6373-6383.

Jennings et al., Biofilm-eradicating properties of quaternary ammonium amphiphiles: simple mimics of antimicrobial peptides. Chembiochem. Oct. 13, 2014;15(15):2211-5. doi: 10.1002/cbic.201402254.

Payne et al., Drugs for bad bugs: confronting the challenges of antibacterial discovery. Nat Rev Drug Discov. Jan. 2007;6(1):29-40.

Price-Whelan et al., Rethinking 'secondary' metabolism:physiological roles for phenazine antibiotics. Nat Chem Biol. Feb. 2006;2(2):71-8. Review. Erratum in: Nat Chem Biol. Apr. 2006;2(4):221.

Rewcastle et al., Potential antitumor agents. 51. Synthesis and antitumor activity of substituted phenazine-1-carboxamides. J Med Chem. May 1987;30(5):843-51.

Vivian, The practical synthesis of 1-phenazinol. Nature. Oct. 6, 1956;178(4536):753.

PCT/US2016/042439, Sep. 20, 2016, Invitation to Pay Additional Fees.

PCT/US2016/042439, Jan. 5, 2017, International Search Report and Written Opinion.

PCT/US2014/072165, Jul. 13, 2015, International Search Report and Written Opinion.

PCT/US2014/072165, Jul. 7, 2016, International Preliminary Report on Patentability.

* cited by examiner

MIC test against *Staphylococcus aureus*

A. No bacteria
B. 100 µM
C. 50 µM
D. 25 µM
E. 12.5 µM
F. 6.25 µM
G. 3.13 µM
H. 1.56 µM
I. 0.78 µM
J. 0.39 µM
K. 0.20 µM
L. 0.10 µM 17a Planktonic Growth Biofilm Formation

SUBSTITUTED PHENAZINES AS ANTIMICROBIAL AGENTS

RELATED APPLICATIONS

The present application is a national stage filing under 35 U.S.C. §371 of international PCT application, PCT/US2014/072165, filed Dec. 23, 2014, which claims priority under 35 U.S.C. §119(e) to U.S. provisional patent applications, U.S. Ser. No. 61/920,571, filed Dec. 24, 2013, and U.S. Ser. No. 62/010,023, filed Jun. 10, 2014, each of which is incorporated herein by reference.

BACKGROUND OF THE INVENTION

The emergence of multidrug resistant microbial infections (e.g., bacterial infections) has led to a serious global crisis. Almost every class of antibiotic that has been introduced into the clinic has been met with the development of drug resistant bacteria (A. E. Clatworthy, E. Pierson, and D. T. Hung, *Nat. Chem. Biol.*, 2007, 3, 541-548; K. Lewis, *Nat. Rev. Drug Discov.*, 2013, 12, 371-387). Despite the growing need for new antimicrobial agents, many pharmaceutical companies have abandoned their antimicrobial discovery programs as the anticipated success with target-based, high-throughput screening (HTS) campaigns has yet to be realized (K. Lewis, *Nat. Rev. Drug Discov.*, 2013, 12, 371-387; S. J. Projan, *Curr. Opin. Microbiol.*, 2003, 6, 427-430; E. D. Brown and G. D. Wright, *Chem. Rev.*, 2005, 105, 759-774; D. J. Payne, M. N. Gwynn, D. J. Holmes, and D. L. Pompliano, *Nat. Rev. Drug Discov.*, 2007, 6, 29-40). The health care emergency that has resulted from drug resistant microbial infections has been gaining momentum over the past four decades as only two new classes of antibiotics have been introduced into the clinic (K. Lewis, *Nat. Rev. Drug Discov.*, 2013, 12, 371-387; E. D. Brown and G. D. Wright, *Chem. Rev.*, 2005, 105, 759-774).

A wide range of microorganisms produce potent antibiotics as agents of microbial warfare and competition. As a result, the large majority of the antibiotic arsenal is based on such natural products discovered in the antibiotic golden era between the 1940s and 1960s (e.g., penicillin, streptomycin, erythromycin, tetracycline, vancomycin) or their synthetic derivatives (Lewis, *Nat. Rev. Drug Discov.*, 2013, 12, 371-387). In fact, very few clinically useful treatment options for microbial infections have been developed from purely synthetic origins (e.g., sulfonamides, quinolones, oxazolidinones).

In addition to infections resulting from planktonic bacteria, biofilms also play a key role in pathogenesis. The NIH has stated that bacterial biofilms are associated with up to 80% of all bacterial infections. Biofilms are notorious for their resistance to conventional antibiotic treatments. Currently, there is a desperate need for clinically useful anti-biofilm agents as there are no FDA-approved drugs that effectively target biofilm machinery. Innovative antimicrobial strategies are needed to meet the biomedical challenges of microbial infections, especially those resulting from multidrug resistant microbial infections and pathogenic bacterial biofilms.

SUMMARY OF THE INVENTION

The present invention provides novel phenazine derivatives, such as compounds of Formula (I) and (II), and salts, hydrates, solvates, polymorphs, co-crystals, tautomers, stereoisomers, and isotopically labeled derivatives thereof:

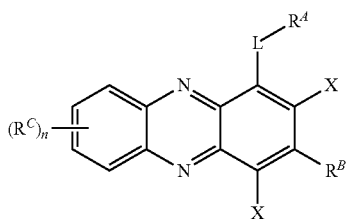

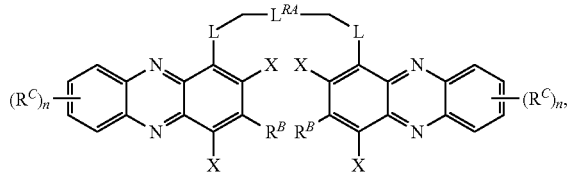

wherein X, $L^{RA}$, L, $R^A$, $R^B$, $R^C$, and n are as described herein. Exemplary compounds of the invention include, but are not limited to:

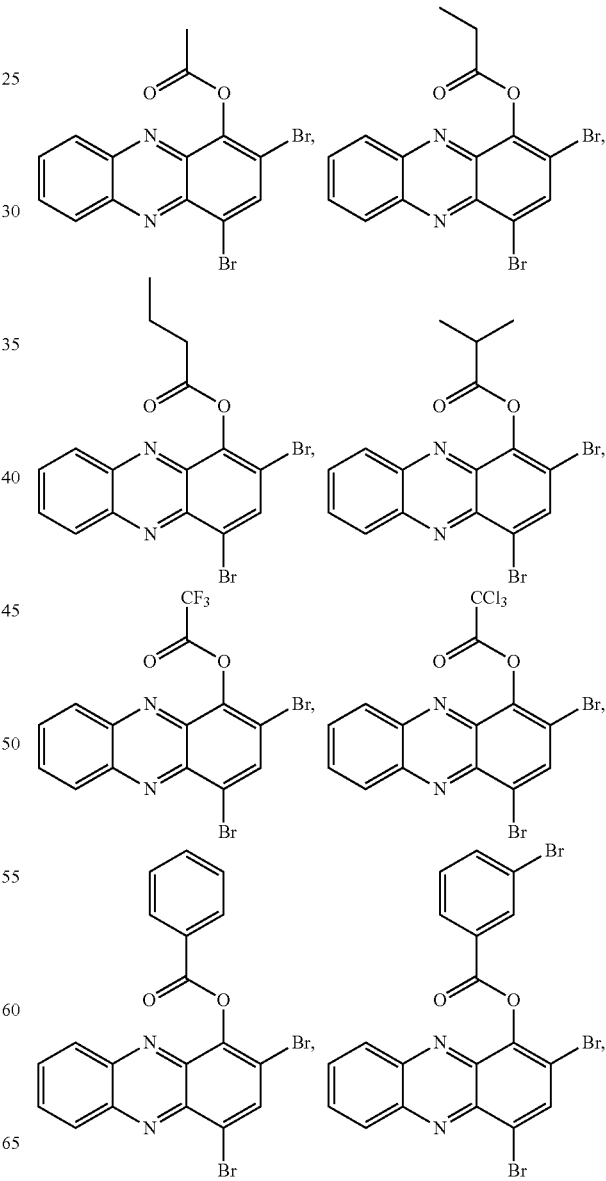

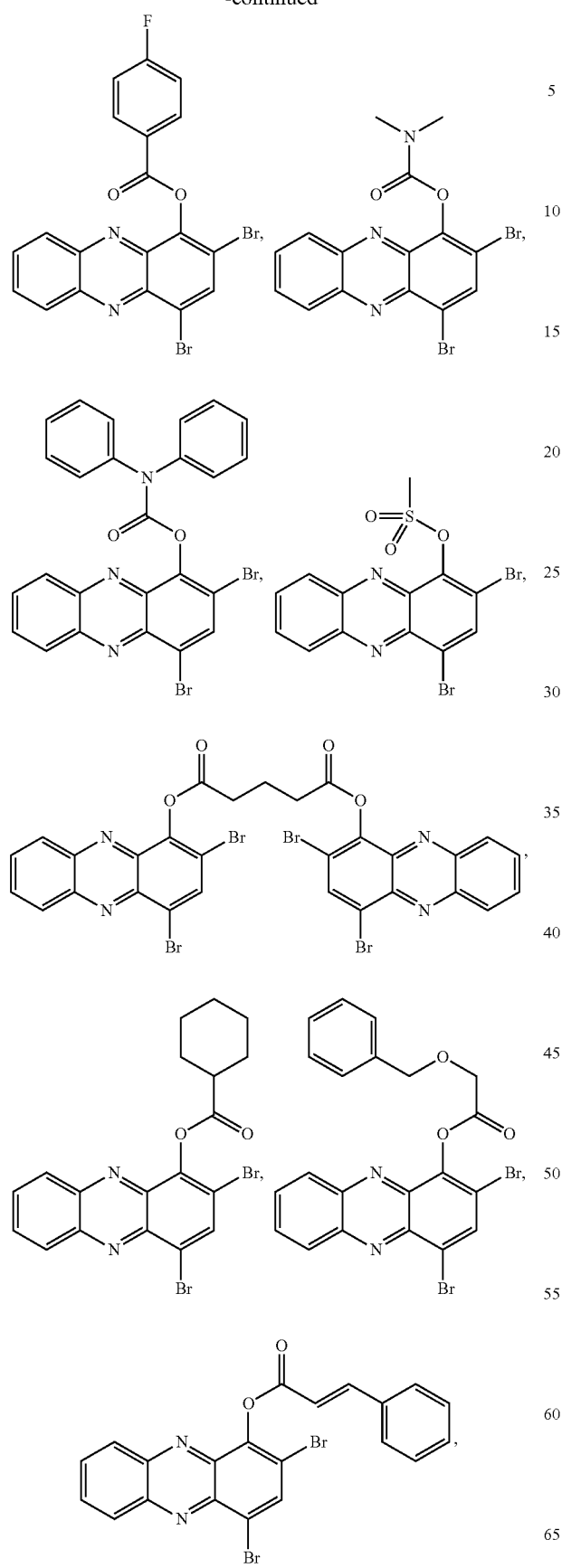
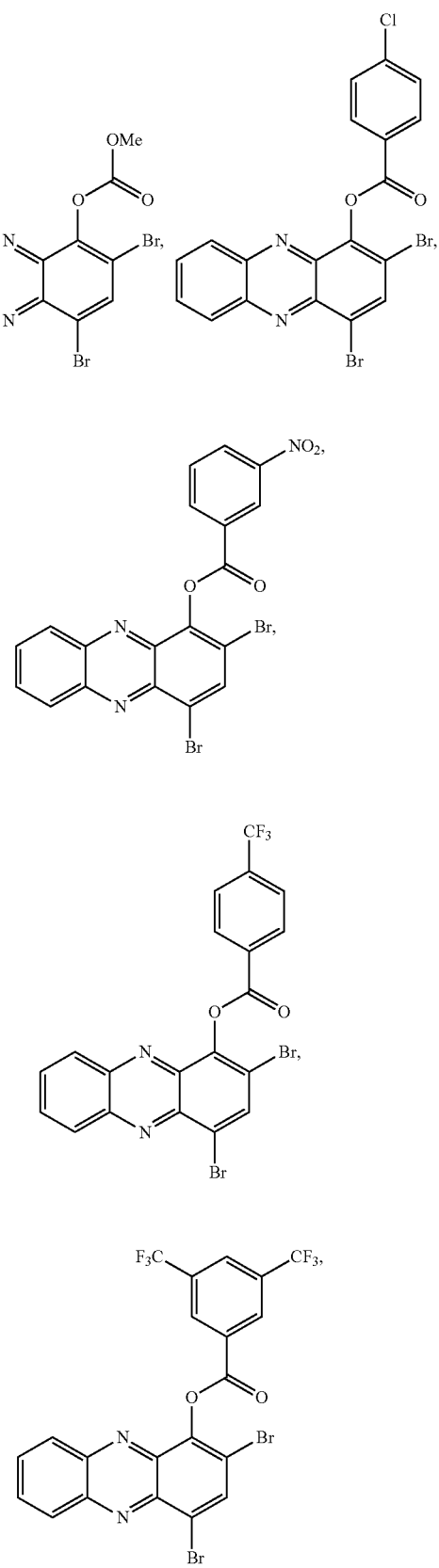

-continued

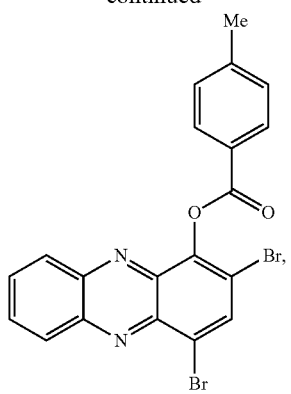

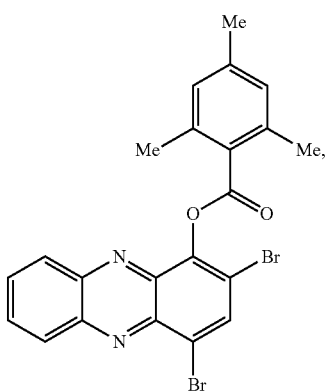

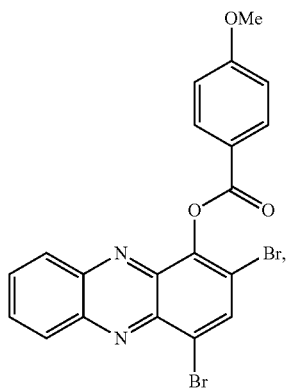

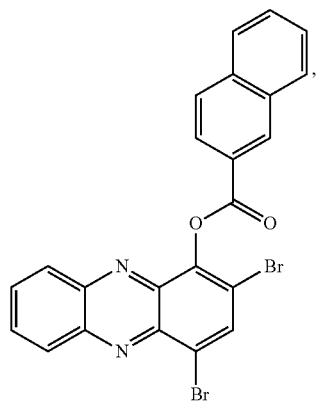

-continued

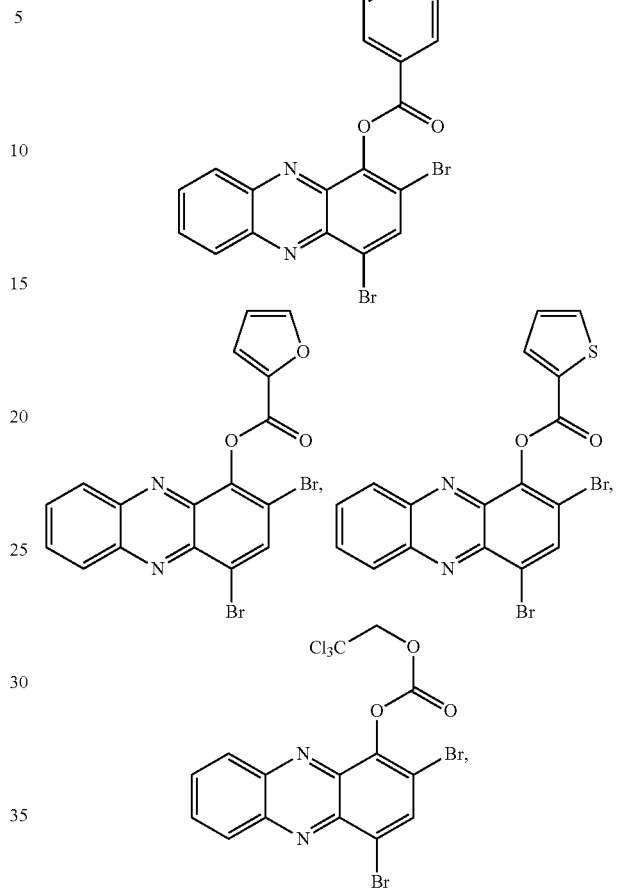

and salts, hydrates, solvates, polymorphs, co-crystals, tautomers, stereoisomers, and isotopically labeled derivatives thereof.

The compounds of the invention exhibit antimicrobial activity (e.g., antibacterial activity). Without wishing to be bound by any particular theory, it is thought that the compounds of the invention may act by a microbial warfare strategy (e.g., a reactive oxygen species (ROS)-based competition strategy) similar to the one employed by *Pseudomonas aeruginosa*. The inventive compounds may generate ROS in, near, or around a microorganism (e.g., a bacterium, archaeon, protist, fungus, or parasite), which may be toxic to the microorganism.

In another aspect, the present invention provides pharmaceutical compositions including a compound of the invention and optionally a pharmaceutically acceptable excipient. In certain embodiments, a pharmaceutical composition of the invention includes a therapeutically effective amount of a compound of the invention for administration to a subject. In certain embodiments, the pharmaceutical composition is useful in a method of the invention (e.g., a method of treating a microbial infection, preventing a microbial infection, inhibiting the growth of a microorganism, inhibiting the reproduction of a microorganism, killing a microorganism, inhibiting the formation and/or growth of a biofilm, or reducing or removing a biofilm). In certain embodiments, the microorganism is a bacterium. In certain embodiments, the bacterium is a Gram-positive bacterium (e.g., a *Staphy-*

*lococcus* species). In certain embodiments, the bacterium is a Gram-negative bacterium (e.g., an *Acinetobacter* species).

Another aspect of the present invention relates to methods of treating and/or preventing a microbial infection in a subject in need thereof, the method including administering to the subject a therapeutically or prophylactically effective amount of a compound or pharmaceutical composition of the invention. In certain embodiments, the microbial infection is treated and/or prevented by the inventive methods. The microbial infections that may be treated and/or prevented by the inventive methods include, but are not limited to, microbial respiratory tract infections, microbial gastrointestinal tract infections, microbial urogenital tract infections, microbial bloodstream infections, microbial ear infections, microbial skin infections, microbial oral infections, microbial dental infections, microbial wound or surgical site infections, microbial infections associated with cystic fibrosis, and microbial infections associated with implanted devices. In certain embodiments, the microbial infection described herein is a bacterial infection. In certain embodiments, the bacterium causing the bacterial infections is a Gram-positive bacterium (e.g., a *Staphylococcus* species). In certain embodiments, the bacterium causing the bacterial infections is a Gram-negative bacterium (e.g., an *Acinetobacter* species). In certain embodiments, the subject is a human. In certain embodiments, the subject is a human with cystic fibrosis. In certain embodiments, the subject is a non-human animal.

In another aspect, the present invention provides methods of inhibiting the growth of a microorganism (e.g., a bacterium, archaeon, protist, fungus, or parasite) in vitro or in vivo.

In yet another aspect, the present invention provides methods of inhibiting the reproduction of a microorganism (e.g., a bacterium, archaeon, protist, fungus, or parasite) in vitro or in vivo.

In yet another aspect, the present invention provides methods of killing a microorganism (e.g., a bacterium, archaeon, protist, fungus, or parasite) in intro or in vivo.

In certain embodiments, an inventive method includes contacting a microorganism (e.g., a bacterium, archaeon, protist, fungus, or parasite) with a compound or pharmaceutical composition of the invention in an amount effective at inhibiting the growth and/or reproduction of or killing the microorganism.

Another aspect of the invention relates to methods of inhibiting the formation and/or growth of, reducing, or removing a biofilm, the method including contacting the biofilm with an effective amount of a compound or pharmaceutical composition of the invention. In certain embodiments, the biofilm includes a microorganism (e.g., a bacterium, archaeon, protist, fungus, or parasite). In certain embodiments, the biofilm includes bacteria. The biofilm may include one or more species of bacteria and/or other microorganisms.

Another aspect of the present invention relates to kits comprising a container with a compound or pharmaceutical composition of the invention. The kits of the invention may include a single dose or multiple doses of the compound or pharmaceutical composition thereof. The provided kits may be useful in a method of the invention (e.g., a method of treating a microbial infection, preventing a microbial infection, inhibiting the growth of a microorganism (e.g., a bacterium, archaeon, protist, fungus, or parasite), inhibiting the reproduction of a microorganism, killing a microorganism, inhibiting the formation and/or growth of a biofilm, or reducing or removing a biofilm). A kit of the invention may further include instructions for using the kit (e.g., instructions for using the compound or pharmaceutical composition included in the kit).

In another aspect, the present invention provides uses of the compounds and pharmaceutical compositions of the invention for manufacturing a medicament for treating and/or preventing a microbial infection.

In another aspect, the present invention provides the compounds and pharmaceutical compositions of the invention for use in methods of preventing and/or treating a microbial infection.

In another aspect, the present invention provides the compounds and pharmaceutical compositions of the invention for treating and/or preventing a microbial infection.

The present application refers to various issued patent, published patent applications, journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is substituted $C_{1-10}$ alkyl (such as substituted $C_{1-6}$ alkyl, e.g., —$CF_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=$CHCH_3$ or

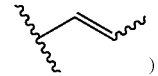
)

may be an (E)- or (Z)-double bond

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

The term "carbocyclyl" or "carbocyclic" refers to a radical of a non aromatic cyclic hydrocarbon group having from 3 to 14 ring carbon atoms ("$C_{3-14}$ carbocyclyl") and zero heteroatoms in the nonaromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Heterocyclyl" or "heterocyclic" refers to a radical of a 3- to 10-membered nonaromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group) if not otherwise provided explicitly. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$,—CHO, —CO$_2$R$^{aa}$, —C(=O)N(R$^{bb}$)$_2$, —C(NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o- nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2 R^{aa}$) include, but are not limited to, p-toluenesulfonamide (Ts), benzenesulfonamide, 2,3,6,-trimethyl-4-methoxybenzenesulfonamide (Mtr), 2,4,6-trimethylbenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$ and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), tert-butoxycarbonyl, methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxido, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Other Definitions

The following definitions are more general terms used throughout the present application:

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) or (II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound and wherein x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Polymorph" refers to a particular polymorphic variant of a given compound. Polymorphism is the ability of a solid substance of a given chemical composition to exist in more than one form or crystalline structure. Polymorphism can exist as a result of differences in crystal packing (packing polymorphism), conformational differences (conformational polymorphism), or changes due to co-crystalization with other chemical entities (pseudopolymorphism). Polymorphism is an important aspect of pharmaceutical development, in which case drugs typically receive regulatory approval for only a single form. Distinct polymorphic forms frequently vary considerably in terms of their physical properties. Altered dissolution rates, thermal stability, and hygroscopicity are frequently observed.

The term "prodrugs" refer to compounds, including derivatives of the compounds of Formula (I) or (II), which have cleavable groups and become by solvolysis or under physiological conditions the compounds of Formula (I) or (II), which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I) or (II) may be preferred.

A "subject" or "patient" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a microbial infection (e.g., a bacterial infection). In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of exposure to microorganisms, in light of a history of symptoms, and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formula (I) or (II) refers to an amount sufficient to elicit the desired biological response, i.e., treating a microbial infection (e.g., a bacterial infection). As will be appreciated by those of ordinary skill in this art, the effective amount of a compound of Formula (I) or (II) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) or (II) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent. In certain embodiments, a therapeutically effective amount is effective for treating a microbial infection (e.g., a bacterial infection) in a subject, for inhibiting the growth and/or reproduction of a microorganism (e.g., a bacterium), for killing a microorganism (e.g., a bacterium), for inhibiting the formation and/or growth of a biofilm, and/or for reducing or clearing a biofilm.

A "prophylactically effective amount" of a compound of Formula (I) or (II) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for preventing a microbial infection (e.g., a bacterial infection) in a subject, for inhibiting the growth and/or reproduction of a microorganism (e.g., a bacterium), for killing a microorganism (e.g., a bacterium), for inhibiting the formation and/or growth of a biofilm, and/or for reducing or clearing a biofilm.

The term "inhibition", "inhibiting", "inhibit," "inhibitory," or "inhibitor" refers to the ability of a compound to reduce, slow, halt, or prevent activity of a particular biological process (e.g., the growth or reproduction) of a microorganism (e.g., a bacterium, archaeon, protist, fungus, or parasite) relative to vehicle.

The term "minimum inhibitory concentration" or "MIC" refers to the lowest concentration of a compound that will inhibit the visible growth of a microorganism (e.g., a bacterium, archaeon, protist, fungus, or parasite) after overnight (e.g., about 16 to about 20 hours) incubation of the microorganism with the compound at about 37° C.

The term "half maximal inhibitory concentration" or "$IC_{50}$" of a compound refers to the concentration of the compound that inhibits the growth of half of an inoculum of a microorganism (e.g., a bacterium, archaeon, protist, fungus, or parasite).

The term "microorganism" refers to a microscopic organism, which may be a single-cell or multicellular organism. In certain embodiments, the microorganism is a bacterium, archaeon, protist, fungus, or parasite. In certain embodiments, the microorganism is a bacterium. In certain embodiments, the length or diameter of a microorganism is at most about 10 cm, at most about 1 cm, at most about 1 mm, at most about 100 µm, at most about 10 µm, at most about 1 µm, at most about 100 nm, or at most about 10 nm. In certain embodiments, the length or diameter of a microorganism is at most about 10 µm.

The term "biofilm" refers to a group of microorganisms (e.g., bacteria) in which cells of the microorganisms stick to each other on a surface. These adherent cells are frequently embedded within a self-produced matrix of extracellular polymeric substance (EPS). The EPS is a polymeric conglomeration generally composed of extracellular DNA, proteins, and polysaccharides. Biofilms may form on living or non-living surfaces and can be prevalent in natural, industrial, and hospital settings. The cells growing in a biofilm are physiologically distinct from planktonic cells of the same microorganism, which are single-cells that may float or swim in a liquid medium. Biofilms have been found to be involved in a wide variety of microbial infections. Biofilms are formed by numerous Gram-negative and Gram-positive bacterial species. Non-limiting examples include *Bacillus* spp, *Staphylococcus* spp, *Pseudomonas* spp, and *Acinetobacter* spp.

The term "microbial warfare" refers to a first microorganism producing a substance (e.g., an antibiotic) that is toxic to a second microorganism but is not toxic or less toxic, compared to the second microorganism, to the first microorganism. When a second microorganism in close proximity to the first microorganism contacts the substance, the growth and/or reproduction of the second microorganism may be inhibited, or the second microorganism may be killed. As a result, the first microorganism may gain a competitive advantage over the second microorganism in close proximity to the first microorganism in terms of survival, growth, and/or reproduction.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise).

Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

The term "planktonic" refers to any of the group of passively floating, drifting, or somewhat motile organisms occurring in a liquid medium (e.g., an aqueous solution). This group includes, but is not limited to, microscopic bacteria, algae, or protozoa.

DETAILED DESCRIPTION OF CERTAIN EMBODIMENTS OF THE INVENTION

The present invention provides novel phenazine derivatives, such as compounds of Formula (I) and (II), and pharmaceutically acceptable salts thereof. The compounds of the invention are expected to be antimicrobial agents and may act by a microbial warfare strategy (e.g., a reactive oxygen species (ROS)-based competition strategy). The present invention also provides pharmaceutical compositions, kits, uses, and methods that involve the compounds of the invention and may be useful in preventing and/or treating a microbial infection in a subject, inhibiting the growth and/or reproduction of a microorganism (e.g., a bacterium, archaeon, protist, fungus, or parasite), killing a microorganism, inhibiting the formation and/or growth of a biofilm, or reducing or removing a biofilm. In certain embodiments, the microorganism is a bacterium. In certain embodiments, the bacterium is a Gram-positive bacterium (e.g., a *Staphylococcus* species). In certain embodiments, the bacterium is a Gram-negative bacterium (e.g., an *Acinetobacter* species).

Many past successes in antibiotic discovery have been grounded on microbial warfare agents/strategies from microorganisms. Therefore, future antimicrobial treatments may also depend on the discovery and implementation of innovative microbial-inspired antimicrobial strategies. One such strategy is the use of redox-active phenazine antibiotics by *Pseudomonas* during competition with other bacteria and fungi through the formation of reactive oxygen species (ROS) (A. Price-Whelan, L. E. P. Dietrich, and D. K. Newman, *Nat. Chem. Biol.*, 2006, 2, 71-78; Z. A. Machan, T. L. Pitt, W. White, D. Watson, G. W. Taylor, P. J. Cole, and R. Wilson, *J. Med. Microbiol.*, 1991, 34, 213-217). One example of this competition is in young cystic fibrosis (CF) patients (Z. A. Machan, T. L. Pitt, W. White, D. Watson, G. W. Taylor, P. J. Cole, and R. Wilson, *J. Med. Microbiol.*, 1991, 34, 213-217). Many times, individuals with CF first develop *Staphylococcus aureus* lung infections when they are young. As the CF patient ages, *Pseudomonas aeruginosa* co-infects the lung and successfully competes against *S. aureus* for this niche using redox-active phenazine antibiotics.

Figure 1:
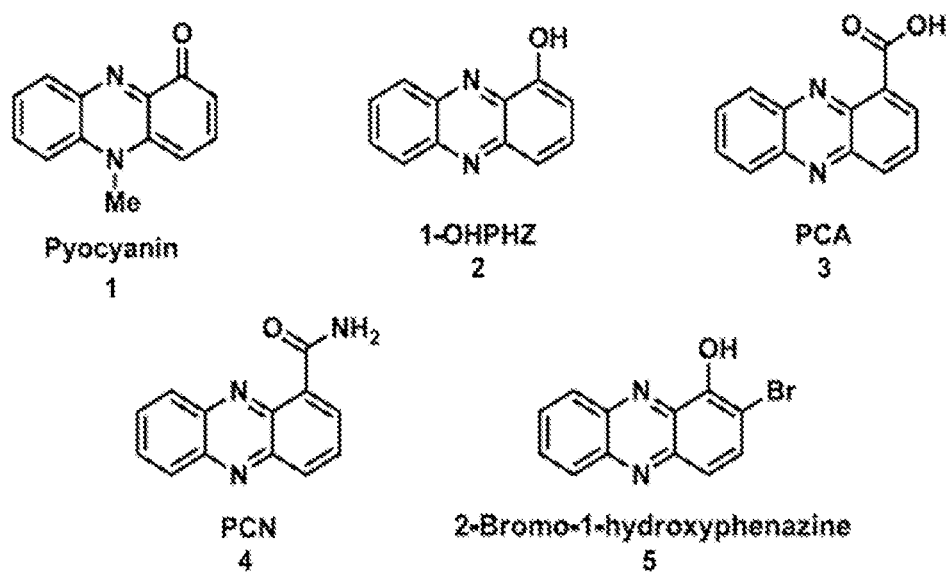
FIG. 1 shows the chemical structures of several naturally occurring phenazine derivatives 1-5.
Figure 2:
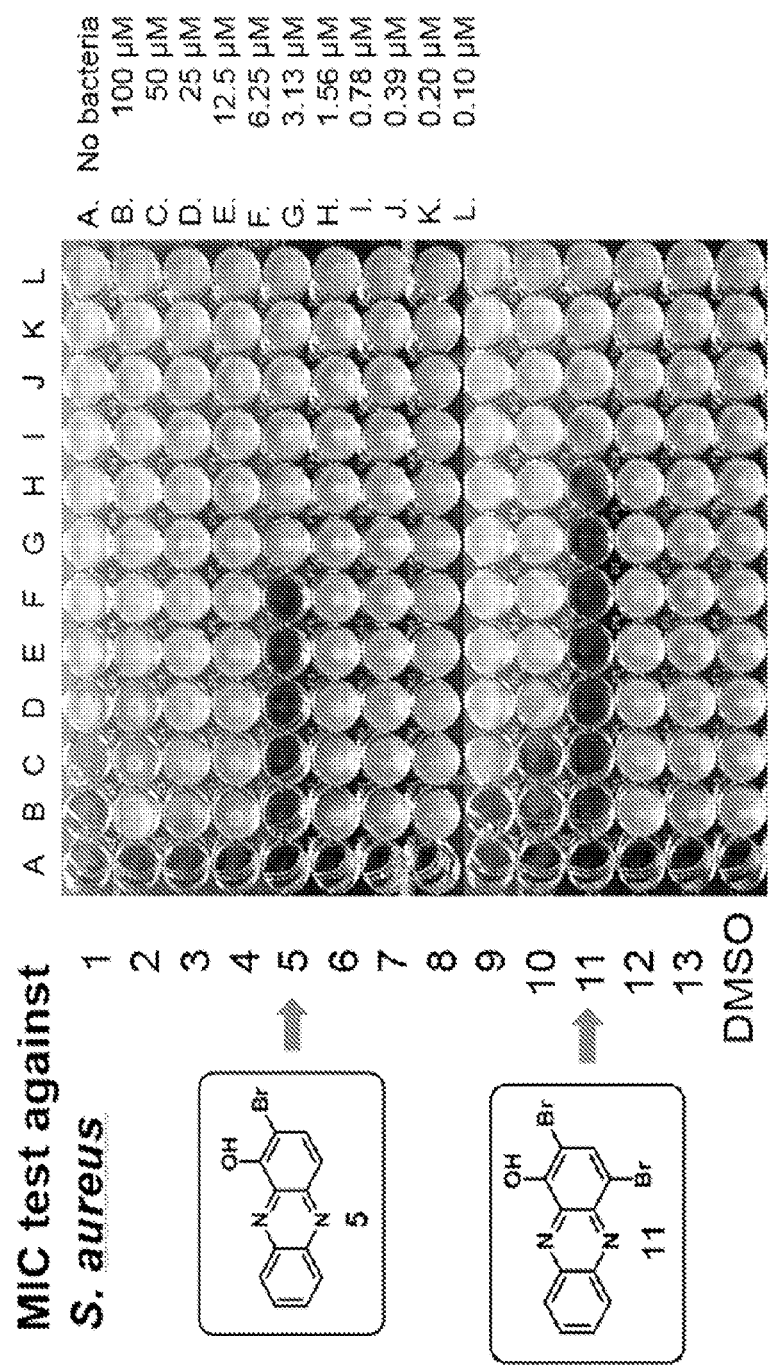
FIG. 2 depicts exemplary results of minimum inhibitory concentration (MIC) experiments of compounds 1-13 against *Staphylococcus aureus*.

Certain phenazine derivatives, such as compounds 1-5 (FIG. 1) are known antimicrobial agents. Pyocyanin (compound 1) is one of the toxins produced by the Gram negative bacterium *Pseudomonas aeruginosa*. It is thought that *Pseudomonas aeruginosa* employs a microbial warfare strategy by producing these toxins in competing with other microorganisms (e.g., other bacteria). Pyocyanin is able to oxidize and reduce other molecules (Hassan et al., *J. Bacteriology* 1980, 141, 156-163) and can kill microbes competing against *Pseudomonas aeruginosa* as well as mammalian cells of the lungs that *Pseudomonas aeruginosa* has infected during cystic fibrosis. Due to its redox-active properties, pyocyanin can generate reactive oxygen species (ROS), which may be toxic to bacteria. It has been reported that the reduction potential and redox-cycling capabilities of phenazine are electronically influenced by functional group substitutions on the phenazinyl ring system (Price-Whelan et al., *Nat. Chem. Biol.*, 2006, 2, 71-78; Wang et al., *J. Bacteriol.*, 2010, 192, 365-369). Therefore, the redox-active properties of a phenazine derivative may be altered by structurally modifying the phenazine derivative. However, there is no teaching or suggestion in the art on how a known phenazine derivative may be structurally modified to improve its properties, such as antimicrobial activity.

The compounds of the invention are improved phenazine derivatives and showed unexpected and superior properties compared to known phenazine derivatives, such as enhanced inhibitory activity against bacteria, e.g., *Staphylococcus aureus* (*S. aureus*) and *Staphylococcus epidermidis* (*S. epidermidis*). *Staphylococcus aureus* is a human pathogen that is notorious for life-threatening drug resistant infections in hospitals and the community (H. F. Chambers and F. R. DeLeo, *Nat. Rev. Microbiol.*, 2009, 7, 629-641). In the United States alone, there are more annual deaths from methicillin-resistant *Staphylococcus aureus* (MRSA) related microbial infections than AIDS (IDSA Policy Paper d CID 2011:52 (Suppl 5) d S397). *Staphylococcus epidermidis* is also a pathogen of great importance as it is particularly prevalent in persistent microbial infections associated with catheters (I. Uckay, D. Pittet, P. Vaudaux, H. Sax, D. Lew, and F. Waldvogel, *Ann. Med.*, 2009, 41, 109-119).

Without wishing to be bound by any particular theory, it is thought that the compounds of the invention may act by a microbial warfare strategy (e.g., an ROS-based competition strategy) similar to the one employed by *Pseudomonas aeruginosa*. The inventive compounds may be capable of undergoing reduction and oxidation (redox) reactions and forming ROS in, near, or around a microorganism (e.g., a bacterium, archaeon, protist, fungus, or parasite). An inventive compound may accept a single electron, yielding a relatively stable anion radical, and may readily undergo a redox cycle. A compound of the invention may be reduced by the nicotinamide adenine dinucleotide (NADH$^+$) in a microorganism and may divert electron flow within the microorganism from the normal cytochrome pathway to an ROS-producing pathway. As a result, the production of ROS, such as $O_2^-$ and $H_2O_2$, which are toxic to the microorganism, may be increased.

Furthermore, compounds disclosed herein are effective agents for the inhibition of biofilm growth and/or clearance of existing biofilms. Bacterial biofilms are surface-attached bacterial communities that are encased within a secreted matrix of biomolecules (i.e., extracellular DNA, proteins, polysaccharides) known as the extracellular polymeric substance (EPS). Bacterial cells within a biofilm take on a completely different physiology than their free-swimming planktonic counterparts and are notorious for being highly resistant to conventional antibiotic treatments and host immune responses (Donlan, R. M. and Costerton, J. W. *Clin. Microbiol. Rev.* 2002, 15, 167-193). The National Institutes of Health has reported that biofilms are present in up to 80% of all bacterial infections. Unfortunately, biofilms are notorious for their resistance to conventional antibiotic treatments, and therefore our current arsenal of antibiotics does not include agents that effectively target biofilm machinery or clear established biofilms in a clinical setting. Such antibiofilm agents would lead to significant breakthroughs in how bacterial infections are treated and would result in the effective treatment of many life-threatening bacterial infections.

Bacterial biofilm formation is governed by a signaling process known as quorum sensing, which is used by bacteria to monitor population density and control bacterial virulence (Camilli, A. and Bassler, B. L. *Science* 2006, 311, 1113-1116; Ng, W.-L. and Bassler, B. L. *Annu. Rev. Genet.* 2009, 43, 197-222). Quorum sensing is used by free-swimming, individual planktonic bacteria to coordinate the simultaneous attachment and colonization of a surface followed by biofilm formation and maturation. The coordinated surface attachment of bacteria overwhelms immune responses mounted by host organisms, enabling the successful colonization of surfaces (i.e., tissue surfaces) by bacteria. Bacterial biofilms are known to be greater than 1000-fold more resistant to conventional antibiotics when compared to their planktonic counterparts. Therapeutic strategies targeting quorum sensing and/or biofilm formation and dispersion phenotypes have become a promising antibacterial strategy as small molecules capable of inhibiting bacterial biofilm formation via non-growth inhibitory mechanisms or clearing pre-formed bacterial biofilms are of clinical importance. Without wishing to be bound by any particular theory, compounds described herein may function by disrupting quorum sensing, leading to inhibitors of biofilm formation and clearing of pre-formed biofilms.

Compounds

One aspect of the invention relates to compounds that are believed to be antimicrobial agents. In certain embodiments, the compounds of the invention are compounds of Formula (I):

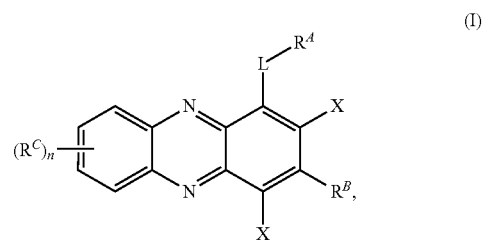

and pharmaceutically acceptable salts, solvates, hydrates, polymorphs, co-crystals, tautomers, stereoisomers, isotopically labeled derivatives, and prodrugs thereof, wherein:

each instance of X is independently a halogen;

L is —OC(=O)O—, —OC(=O)—, —C(=O)O—, —NR$^L$C(=O)—, —C(=O)NR$^L$—, —OC(=O)NR$^L$—, —NR$^L$C(=O)O—, —NR$^L$C(=O)NR$^L$—, —OS(=O)$_2$—, —S(=O)$_2$O—, —NR$^L$S(=O)$_2$—, —S(=O)$_2$NR$^L$—, or —NR$^L$S(=O)$_2$NR$^L$—;

each instance of R$^L$ is independently hydrogen, substituted or unsubstituted alkyl, or a nitrogen protecting group;

R$^A$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom;

R$^B$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1}$, —N(R$^{B1}$)$_2$, —SR$^{B1}$, —CN, —SCN, —C(=NR$^{B1}$)R$^{B1}$, —C(=NR$^{B1}$)OR$^{B1}$, —C(=NR$^{B1}$)N(R$^{B1}$)$_2$, —C(=O)R$^{B1}$, —C(=O)OR$^{B1}$, —C(=O)N(R$^{B1}$)$_2$, —NO$_2$, —NR$^{B1}$C(=O)R$^{B1}$, —NR$^{B1}$C(=O)OR$^{B1}$, —NR$^{B1}$C(=O)N(R$^{B1}$)$_2$, —OC(=O)R$^{B1}$, —OC(=O)OR$^{B1}$, or —OC(=O)N(R$^{B1}$)$_2$;

each instance of R$^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{B1}$ are joined to form a substituted or unsubstituted heterocyclic ring;

each instance of R$^C$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C1}$, —$N(R^{C1})_2$, —$SR^{C1}$, —CN, —SCN, —$C(=NR^{C1})R^{C1}$, —$C(=NR^{C1})OR^{C1}$, —$C(=NR^{C1})N(R^{C1})_2$, —$C(=O)R^{C1}$, —$C(=O)OR^{C1}$, —$C(=O)N(R^{C1})_2$, —$NO_2$, —$NR^{C1}C(=O)R^{C1}$, —$NR^{C1}C(=O)OR^{C1}$, —$NR^{C1}C(=O)N(R^{C1})_2$, —$OC(=O)R^{C1}$, —$OC(=O)OR^{C1}$, or —$OC(=O)N(R^{C1})_2$, or two instances of $R^C$ are joined to form a substituted or unsubstituted carbocyclic, substituted or unsubstituted heterocyclic, substituted or unsubstituted aryl, or substituted or unsubstituted heteroaryl ring;

each instance of $R^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{C1}$ are joined to form a substituted or unsubstituted heterocyclic ring; and n is 0, 1, 2, 3, or 4.

In certain embodiments, the compounds of the invention are compounds of Formula (II):

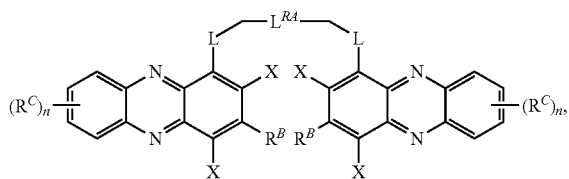

(II)

and pharmaceutically acceptable salts, solvates, hydrates, polymorphs, co-crystals, tautomers, stereoisomers, isotopically labeled derivatives, and prodrugs thereof, wherein:

each instance of X is independently a halogen;

$L^{RA}$ is a linker selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene, substituted and unsubstituted heteroarylene, and combinations thereof;

L is —OC(=O)O—, —OC(=O)—, —C(=O)O—, —$NR^LC(=O)$—, —$C(=O)NR^L$—, —$OC(=O)NR^L$—, —$NR^LC(=O)O$—, —$NR^LC(=O)NR^L$—, —$OS(=O)_2$—, —$S(=O)_2O$—, —$NR^LS(=O)_2$—, —$S(=O)_2NR^L$—, or —$NR^LS(=O)_2NR^L$—;

each instance of $R^L$ is independently hydrogen, substituted or unsubstituted alkyl, or a nitrogen protecting group;

$R^B$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{B1}$, —$N(R^{B1})_2$, —$SR^{B1}$, —CN, —SCN, —$C(=NR^{B1})R^{B1}$, —$C(=NR^{B1})OR^{B1}$, —$C(=NR^{B1})N(R^{B1})_2$, —$C(=O)R^{B1}$, —$C(=O)OR^{B1}$, —$C(=O)N(R^{B1})_2$, —$NO_2$, —$NR^{B1}C(=O)R^{B1}$, —$NR^{B1}C(=O)OR^{B1}$, —$NR^{B1}C(=O)N(R^{B1})_2$, —$OC(=O)R^{B1}$, —$OC(=O)OR^{B1}$, or —$OC(=O)N(R^{B1})_2$;

each instance of $R^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{B1}$ are joined to form a substituted or unsubstituted heterocyclic ring;

each instance of $R^C$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C1}$, —$N(R^{C1})_2$, —$SR^{C1}$, —CN, —SCN, —$C(=NR^{C1})R^{C1}$, —$C(=NR^{C1})OR^{C1}$, —$C(=NR^{C1})N(R^{C1})_2$, —$C(=O)R^{C1}$, —$C(=O)OR^{C1}$, —$C(=O)N(R^{C1})_2$, —$NO_2$, —$NR^{C1}C(=O)R^{C1}$, —$NR^{C1}C(=O)OR^{C1}$, —$NR^{C1}C(=O)N(R^{C1})_2$, —$OC(=O)R^{C1}$, —$OC(=O)OR^{C1}$, or —$OC(=O)N(R^{C1})_2$, or two instances of $R^C$ are joined to form a substituted or unsubstituted carbocyclic, substituted or unsubstituted heterocyclic, substituted or unsubstituted aryl, or substituted or unsubstituted heteroaryl ring;

each instance of $R^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{C1}$ are joined to form a substituted or unsubstituted heterocyclic ring; and n is 0, 1, 2, 3, or 4.

In compounds of Formula (I) and (II), each instance of X is independently a halogen (e.g., —F, —Cl, —Br, or —I). In certain embodiments, at least one instance of X is independently —F. In certain embodiments, at least one instance of X is independently —Cl. In certain embodiments, at least one instance of X is independently —Br. In certain embodiments, at least one instance of X is independently —I. In certain embodiments of Formula (I), both instances of X are —F. In certain embodiments of Formula (I), both instances of X are —Cl. In certain embodiments of Formula (I), both instances of X are —Br. In certain embodiments of Formula (I), both instances of X are —I. In certain embodiments of Formula (II), all four instances of X are —F. In certain embodiments of Formula (II), all four instances of X are —Cl. In certain embodiments of Formula (II), all four instances of X are —Br. In certain embodiments of Formula (II), all four instances of X are —I.

In compounds of Formula (I) and (II), L is a divalent linker connecting $R^A$ or $L^{RA}$ to the tricyclic heteroaryl ring system. In certain embodiments, L is is —OC(=O)O—. In certain embodiments, L is —OC(=O)— or —C(=O)O—. In certain embodiments, L is —OC(=O)—. In certain embodiments, L is —C(=O)O—. In certain embodiments, L is —$NR^LC(=O)$—. In certain embodiments, L is —NHC(=O)—. In certain embodiments, L is —$NR^LC(=O)$—, wherein $R^L$ is unsubstituted $C_{1-6}$ alkyl or $C_{1-6}$ alkyl substituted with at least one halogen. In certain embodiments, L is —$NR^LC(=O)$—, wherein $R^L$ is a nitrogen protecting group. In certain embodiments, L is —$C(=O)NR^L$—. In certain embodiments, L is —$C(=O)NH$—. In certain embodiments, L is —$C(=O)NR^L$—, wherein $R^L$ is unsubstituted $C_{1-6}$ alkyl or $C_{1-6}$ alkyl substituted with at least one halogen. In certain embodiments, L is —$C(=O)NR^L$—, wherein $R^L$ is a nitrogen protecting group. In certain embodiments, L is —$OC(=O)NR^L$—. In certain embodiments, L is —$OC(=O)NH$—. In certain embodiments, L is —$OC(=O)NR^L$—, wherein $R^L$ is unsubstituted $C_{1-6}$ alkyl or $C_{1-6}$ alkyl substituted with at least one halogen. In certain embodiments, L is —$OC(=O)NR^L$—, wherein $R^L$ is a nitrogen protecting group. In certain embodiments, L is —$NR^LC(=O)O$—. In certain embodiments, L is —$NHC(=O)O$—. In certain embodiments, L is —$NR^LC(=O)O$—, wherein $R^L$ is unsubstituted $C_{1-6}$ alkyl or $C_{1-6}$ alkyl substituted with at least one halogen. In certain embodiments, L is —$NR^LC(=O)O$—, wherein $R^L$ is a nitrogen protecting group. In certain embodiments, L is —$NR^LC(=O)NR^L$—. In certain embodiments, L is —$NHC(=O)NH$—. In certain embodiments, L is —$NR^LC(=O)NR^L$—, wherein at least one instance of $R^L$ is unsubstituted $C_{1-6}$ alkyl or $C_{1-6}$ alkyl substituted with at least one halogen. In certain embodiments, L is —$NR^LC(=O)NR^L$—, wherein at least one instance of $R^L$ is a nitrogen protecting group. In certain embodiments, L is —$OS(=O)_2$—. In certain embodiments, L is —$S(=O)_2O$—. In certain embodiments, L is —$NR^LS(=O)_2$—. In certain embodiments, L is —$NHS(=O)_2$—. In certain embodiments, L is —$NMeS(=O)_2$—. In certain embodiments, L is —$S(=O)_2NR^L$—. In certain embodiments, L is —$S(=O)_2NH$—. In certain embodiments, L is —$S(=O)_2NMe$-. In certain embodiments, L is —$NR^LS(=O)_2NR^L$—. In certain embodiments, L is —$NHS(=O)_2NH$—.

In compounds of Formula (I) and (II), L may include one or more substituents $R^L$. In certain embodiments, at least one instance of $R^L$ is H. In certain embodiments, both two instances of $R^L$ are H. In certain embodiments, at least one instance of $R^L$ is unsubstituted alkyl. In certain embodiments, at least one instance of $R^L$ is substituted alkyl. In certain embodiments, at least one instance of $R^L$ is unsubstituted $C_{1-6}$ alkyl. In certain embodiments, at least one instance of $R^L$ is substituted $C_{1-6}$ alkyl. In certain embodiments, at least one instance of $R^L$ is $C_{1-6}$ alkyl substituted with at least one halogen. In certain embodiments, at least one instance of $R^L$ is unsubstituted methyl. In certain embodiments, both two instances of $R^L$ are unsubstituted methyl. In certain embodiments, one instance of $R^L$ is H; and the other instance of $R^L$ is unsubstituted methyl. In certain embodiments, at least one instance of $R^L$ is substituted methyl. In certain embodiments, at least one instance of $R^L$ is —$CH_2F$. In certain embodiments, at least one instance of $R^L$ is —$CHF_2$. In certain embodiments, at least one instance of $R^L$ is —$CF_3$. In certain embodiments, at least one instance of $R^L$ is Bn. In certain embodiments, at least one instance of $R^L$ is ethyl. In certain embodiments, at least one instance of $R^L$ is propyl. In certain embodiments, at least one instance of $R^L$ is butyl. In certain embodiments, at least one instance of $R^L$ is pentyl. In certain embodiments, at least one instance of $R^L$ is hexyl. In certain embodiments, at least one instance of $R^L$ is a nitrogen protecting group. In certain embodiments, at least one instance of $R^L$ is Bn, Boc, Cbz, Fmoc, trifluoroacetyl, triphenylmethyl, acetyl, or Ts. In certain embodiments, two instances of $R^L$ are different. In certain embodiments, two instances of $R^L$ are the same.

Compounds of Formula (I) include a substituent $R^A$ that is attached to linker L. In certain embodiments, $R^A$ is H. In certain embodiments, $R^A$ is substituted alkyl. In certain embodiments, $R^A$ is unsubstituted alkyl. In certain embodiments, $R^A$ is unsubstituted $C_{1-6}$ alkyl. In certain embodiments, $R^A$ is substituted $C_{1-6}$ alkyl. In certain embodiments, $R^A$ is $C_{1-6}$ alkyl substituted with at least one halogen. In certain embodiments, $R^A$ is —$CH_3$. In certain embodiments, $R^A$ is substituted methyl. In certain embodiments, $R^A$ is —$CH_2F$. In certain embodiments, $R^A$ is —$CHF_2$. In certain embodiments, $R^A$ is —$CF_3$. In certain embodiments, $R^A$ is —$CCl_3$. In certain embodiments, $R^A$ is Bn. In certain embodiments, $R^A$ is ethyl. In certain embodiments, $R^A$ is propyl. In certain embodiments, $R^A$ is —$(CH_2)_2CH_3$. In certain embodiments, $R^A$ is —$CH(CH_3)_2$. In certain embodiments, $R^A$ is butyl. In certain embodiments, $R^A$ is pentyl. In certain embodiments, $R^A$ is hexyl. In certain embodiments, $R^A$ is substituted or unsubstituted alkoxyalkyl. In certain embodiments, $R^A$ is unsubstituted alkoxyalkyl. In certain embodiments, $R^A$ is substituted or unsubstituted —$CH_2O(C_{1-6}alkyl)$. In certain embodiments, $R^A$ is substituted or unsubstituted —$CH_2O(aralkyl)$. In certain embodiments, $R^A$ is —$CH_2OCH_2Bn$. In certain embodiments, $R^A$ is substituted alkenyl. In certain embodiments, $R^A$ is alkenyl substituted with a substituted or unsubstituted aryl ring. In certain embodiments, $R^A$ is alkenyl substituted with an unsubstituted aryl ring. In certain embodiments, $R^A$ is styryl. In certain embodiments, $R^A$ is unsubstituted alkenyl. In certain embodiments, $R^A$ is substituted or unsubstituted $C_{1-6}$ alkenyl. In certain embodiments, $R^A$ is vinyl or allyl. In certain embodiments, $R^A$ is substituted alkynyl. In certain embodiments, $R^A$ is unsubstituted alkynyl. In certain embodiments, $R^A$ is ethynyl or propargyl. In certain embodiments, $R^A$ is substituted carbocyclyl. In certain embodiments, $R^A$ is unsubstituted carbocyclyl. In certain embodiments, $R^A$ is saturated carbocyclyl. In certain embodiments, $R^A$ is unsaturated carbocyclyl. In certain embodiments, $R^A$ is carbocyclyl including zero, one, two, or three double bonds in the carbocyclic ring system. In certain embodiments, $R^A$ is monocyclic carbocyclyl. In certain embodiments, $R^A$ is 3- to 7-membered, monocyclic carbocyclyl. In certain embodiments, $R^A$ is cylcopropyl. In certain embodiments, $R^A$ is cyclobutyl. In certain embodiments, $R^A$ is cyclopentyl. In certain embodiments, $R^A$ is cyclohexyl. In certain embodiments, $R^A$ is cycloheptyl. In certain embodiments, $R^A$ is bicyclic carbocyclyl. In certain embodiments, $R^A$ is 5- to 13-membered, bicyclic carbocyclyl. In certain embodiments, $R^A$ is substituted heterocyclyl. In certain embodiments, $R^A$ is unsubstituted heterocyclyl. In certain embodiments, $R^A$ is saturated heterocyclyl. In certain embodiments, $R^A$ is unsaturated heterocyclyl. In certain embodiments, $R^A$ is heterocyclyl including zero, one, two, or three double bonds in the heterocyclic ring system. In certain embodiments, $R^A$ is heterocyclyl, wherein one, two, or three atoms in the heterocyclic ring system are independently selected from the group consisting of nitrogen, oxygen, and sulfur. In certain embodiments, $R^A$ is monocyclic heterocyclyl. In certain embodiments, $R^A$ is 3- to 7-membered, monocyclic heterocyclyl. In certain embodiments, $R^A$ is bicyclic heterocyclyl. In certain embodiments, $R^A$ is 5- to 13-membered, bicyclic heterocyclyl. In certain embodiments, $R^A$ is substituted aryl. In certain embodiments, $R^A$ is unsubstituted aryl. In certain embodiments, $R^A$ is substituted or unsubstituted aryl fused with a substituted or unsubstituted 5- or 6-membered carbocyclic ring. In certain embodiments, $R^A$ is unsubstituted aryl fused with a unsubstituted 5- or 6-membered carbocyclic ring. In certain embodiments, $R^A$ is substituted or unsubstituted aryl fused with a substituted or unsubstituted 5- or 6-membered heterocyclic ring. In certain embodiments, $R^A$ is unsubstituted aryl fused with a unsubstituted 5- or 6-membered heterocyclic ring. In certain embodiments, $R^A$ is of the formula:

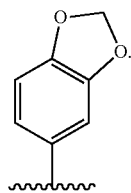 [SMILES: *c1ccc2c(c1)OCO2]

In certain embodiments, $R^A$ is 6- to 14-membered aryl. In certain embodiments, $R^A$ is 6- to 10-membered aryl. In certain embodiments, $R^A$ is substituted phenyl. In certain embodiments, $R^A$ is phenyl substituted with one, two, three, four, or five substituents independently selected from the group consisting of halogen, unsubstituted $C_{1-6}$ alkyl, $C_{1-6}$ alkyl substituted with at least one halogen, —$NO_2$, and —$OR^{A1}$, wherein $R^{A1}$ is unsubstituted $C_{1-6}$ alkyl, $C_{1-6}$ alkyl substituted with at least one halogen, or an oxygen protecting group. In certain embodiments, $R^A$ is phenyl substituted with at least one unsubstituted $C_{1-6}$ alkyl. In certain embodiments, $R^A$ is phenyl substituted with one unsubstituted $C_{1-6}$ alkyl. In certain embodiments, $R^A$ is of the formula:

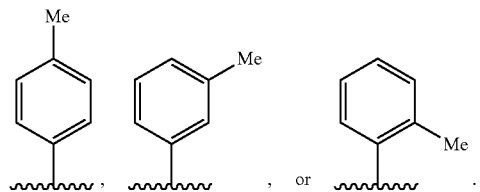

In certain embodiments, $R^A$ is of the formula:

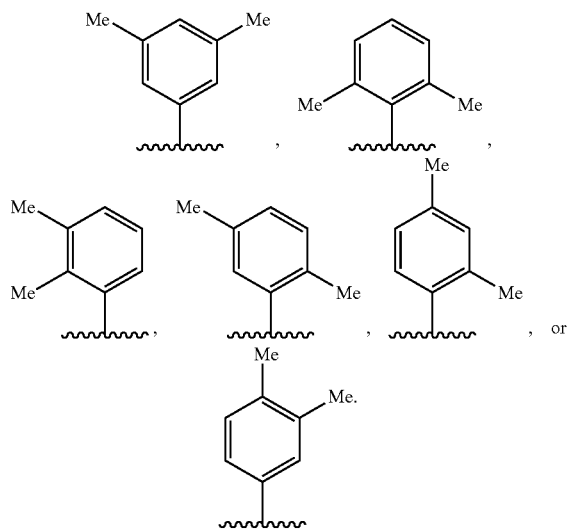

In certain embodiments, $R^A$ is phenyl substituted with at least two unsubstituted $C_{1-6}$ alkyl groups. In certain embodiments, $R^A$ is phenyl substituted with at least three unsubstituted $C_{1-6}$ alkyl groups. In certain embodiments, $R^A$ is of the formula:

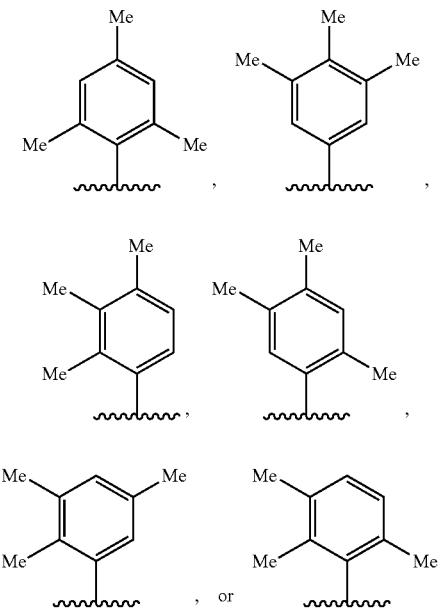

In certain embodiments, $R^A$ is phenyl substituted with one —$CF_3$. In certain embodiments, $R^A$ is of the formula:

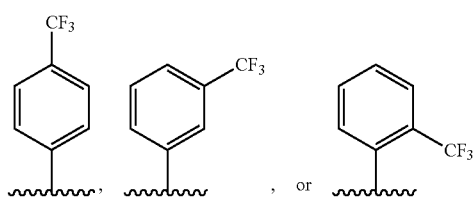

In certain embodiments, $R^A$ is phenyl substituted with two —$CF_3$ groups. In certain embodiments, $R^A$ is of the formula:

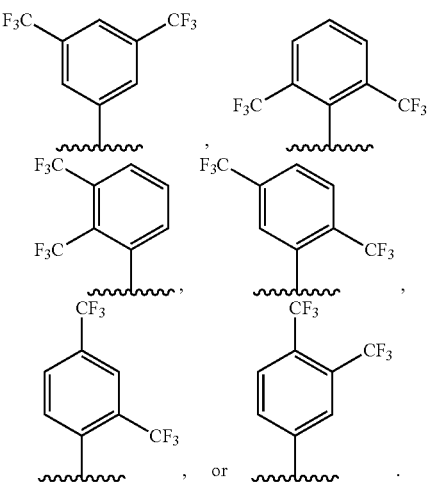

In certain embodiments, $R^A$ is phenyl substituted with at least one halogen. In certain embodiments, $R^A$ is phenyl substituted with one halogen. In certain embodiments, $R^A$ is of the formula:

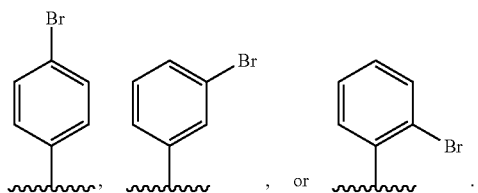

In certain embodiments, $R^A$ is of the formula

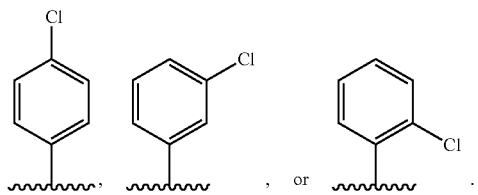

In certain embodiments, $R^A$ is of the formula:

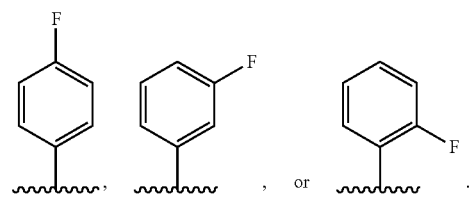

In certain embodiments, $R^A$ is phenyl substituted with at least one $—NO_2$. In certain embodiments, $R^A$ is phenyl substituted with one $—NO_2$. In certain embodiments, $R^A$ is of the formula:

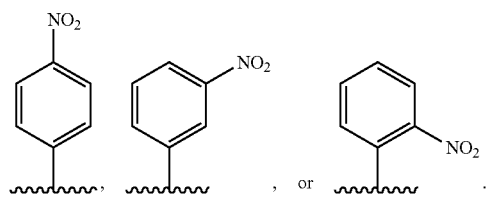

In certain embodiments, $R^A$ is phenyl substituted with at least one $—OR^{A1}$. In certain embodiments, $R^A$ is phenyl substituted with one $—OR^{A1}$. In certain embodiments, $R^A$ is of the formula:

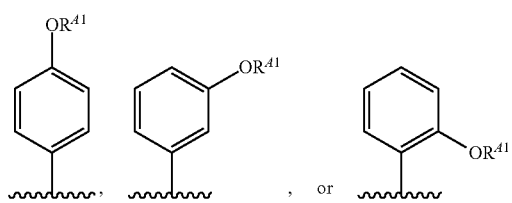

In certain embodiments, $R^A$ is of the formula:

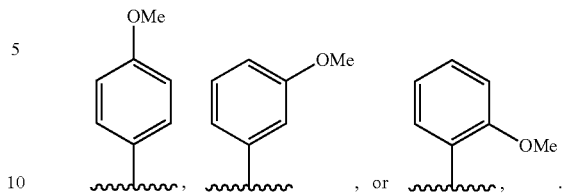

In certain embodiments, $R^A$ is unsubstituted phenyl. In certain embodiments, $R^A$ is substituted naphthyl. In certain embodiments, $R^A$ is unsubstituted naphthyl. In certain embodiments, $R^A$ is substituted heteroaryl. In certain embodiments, $R^A$ is unsubstituted heteroaryl. In certain embodiments, $R^A$ is heteroaryl, wherein one, two, three, or four atoms in the heteroaryl ring system are independently selected from the group consisting of nitrogen, oxygen, and sulfur. In certain embodiments, $R^A$ is monocyclic heteroaryl. In certain embodiments, $R^A$ is 5-membered, monocyclic heteroaryl. In certain embodiments, $R^A$ is substituted furyl. In certain embodiments, $R^A$ is unsubstituted furyl. In certain embodiments, $R^A$ is of the formula:

In certain embodiments, $R^A$ is substituted thiophenyl. In certain embodiments, $R^A$ is unsubstituted thiophenyl. In certain embodiments, $R^A$ is of the formula:

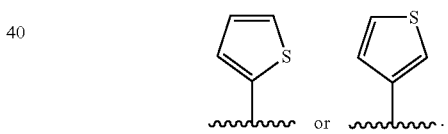

In certain embodiments, $R^A$ is 6-membered, monocyclic heteroaryl. In certain embodiments, $R^A$ is substituted pyridyl. In certain embodiments, $R^A$ is unsubstituted pyridyl. In certain embodiments, $R^A$ is bicyclic heteroaryl, wherein the point of attachment may be on any atom of the bicyclic heteroaryl ring system, as valency permits. In certain embodiments, $R^A$ is 9-membered, bicyclic heteroaryl. In certain embodiments, $R^A$ is 10-membered, bicyclic heteroaryl. In certain embodiments, $R^A$ is a nitrogen protecting group when attached to a nitrogen atom. In certain embodiments, $R^A$ is Bn, Boc, Cbz, Fmoc, trifluoroacetyl, triphenylmethyl, acetyl, or Ts when attached to a nitrogen atom. In certain embodiments, $R^A$ is an oxygen protecting group when attached to an oxygen atom. In certain embodiments, $R^A$ is silyl, TBDPS, TBDMS, TIPS, TES, TMS, MOM, THP, t-Bu, Bn, allyl, acetyl, pivaloyl, or benzoyl when attached to an oxygen atom.

In compounds of Formula (II), $L^{RA}$ is a divalent linker connecting L of one tricyclic heteroaryl ring system to L of a second tricyclic heteroaryl ring system. As generally defined herein, $L^{RA}$ is a linker selected from the group consisting of the following divalent moieties: substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene, substituted and unsubstituted heteroarylene, and combinations thereof.

Reference to $L^{RA}$ being a combination of at least two instances of the divalent moieties described herein refers to a linker consisting of at least one instance of a first divalent moiety and at least one instance of a second divalent moiety, wherein the first and second divalent moieties are the same or different and are within the scope of the divalent moieties described herein, and the instances of the first and second divalent moieties are consecutive covalently attached to each other. For example, when $L^{RA}$ is a combination of alkylene and heteroalkylene, linkers -alkylene-heteroalkylene-, -alkylene-(heteroalkylene)$_2$-, and -heteroalkylene-alkylene-heteroalkylene- are all within the scope of $L^{RA}$, wherein each instance of alkylene in any one of the linkers may be the same or different, and each instance of heteroalkylene in any one of the linkers may be the same or different.

In certain embodiments, $L^{RA}$ comprises at least one instance of substituted or unsubstituted alkylene, e.g., substituted or unsubstituted $C_{1-6}$alkylene, substituted or unsubstituted $C_{1-2}$alkylene, substituted or unsubstituted $C_{2-3}$alkylene, substituted or unsubstituted $C_{3-4}$alkylene, substituted or unsubstituted $C_{4-5}$alkylene, substituted or unsubstituted $C_{5-6}$alkylene, substituted or unsubstituted $C_{3-6}$alkylene, or substituted or unsubstituted $C_{4-6}$alkylene. Exemplary alkylene groups include unsubstituted alkylene groups such as methylene (—CH$_2$—), ethylene (—(CH$_2$)$_2$—), n-propylene (—(CH$_2$)$_3$—), n-butylene (—(CH$_2$)$_4$—), n-pentylene (—(CH$_2$)$_5$—), and n-hexylene (—(CH$_2$)$_6$—).

In certain embodiments, $L^{RA}$ comprises at least one instance of substituted or unsubstituted alkenylene, e.g., substituted or unsubstituted $C_{2-6}$alkenylene, substituted or unsubstituted $C_{2-3}$alkenylene, substituted or unsubstituted $C_{3-4}$alkenylene, substituted or unsubstituted $C_{4-5}$alkenylene, or substituted or unsubstituted $C_{5-6}$alkenylene.

In certain embodiments, $L^{RA}$ comprises at least one instance of substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene.

In certain embodiments, $L^{RA}$ comprises at least one instance of substituted or unsubstituted heteroalkylene, e.g., substituted or unsubstituted hetero$C_{1-6}$alkylene, substituted or unsubstituted hetero$C_{1-2}$alkylene, substituted or unsubstituted hetero$C_{2-3}$alkylene, substituted or unsubstituted hetero$C_{3-4}$alkylene, substituted or unsubstituted hetero$C_{4-5}$alkylene, or substituted or unsubstituted hetero$C_{5-6}$alkylene. Exemplary heteroalkylene groups include unsubstituted heteroalkylene groups such as —(CH$_2$)$_2$—O(CH$_2$)$_2$—, —OCH$_2$—, —CH$_2$O—, —O(CH$_2$)$_2$—, —(CH$_2$)$_2$O—, —O(CH$_2$)$_3$—, —(CH$_2$)$_3$O—, —O(CH$_2$)$_4$—, —(CH$_2$)$_4$O—, —O(CH$_2$)$_5$—, —(CH$_2$)$_5$O—, —O(CH$_2$)$_6$—, and —O(CH$_2$)$_6$O—, and amide groups (e.g., —NH—C(=O)— and —C(=O)NH—).

In certain embodiments, $L^{RA}$ comprises at least one instance of substituted or unsubstituted heteroalkenylene, e.g., substituted or unsubstituted hetero$C_{2-6}$alkenylene, substituted or unsubstituted hetero$C_{2-3}$alkenylene, substituted or unsubstituted hetero$C_{3-4}$alkenylene, substituted or unsubstituted hetero$C_{4-5}$alkenylene, or substituted or unsubstituted hetero$C_{5-6}$alkenylene.

In certain embodiments, $L^{RA}$ comprises at least one instance of substituted or unsubstituted heteroalkynylene, e.g., substituted or unsubstituted hetero$C_{2-6}$alkynylene, substituted or unsubstituted hetero$C_{2-3}$alkynylene, substituted or unsubstituted hetero$C_{3-4}$-alkynylene, substituted or unsubstituted hetero$C_{4-5}$alkynylene, or substituted or unsubstituted hetero$C_{5-6}$alkynylene.

In certain embodiments, $L^{RA}$ comprises at least one instance of substituted or unsubstituted carbocyclylene, e.g., substituted or unsubstituted $C_{3-6}$carbocyclylene, substituted or unsubstituted $C_{3-4}$carbocyclylene, substituted or unsubstituted $C_{4-5}$ carbocyclylene, or substituted or unsubstituted $C_{5-6}$ carbocyclylene.

In certain embodiments, $L^{RA}$ comprises at least one instance of substituted or unsubstituted heterocyclylene, e.g., substituted or unsubstituted 3-6 membered heterocyclylene, substituted or unsubstituted 3-4 membered heterocyclylene, substituted or unsubstituted 4-5 membered heterocyclylene, or substituted or unsubstituted 5-6 membered heterocyclylene.

In certain embodiments, $L^{RA}$ comprises at least one instance of substituted or unsubstituted arylene, e.g., substituted or unsubstituted phenylene.

In certain embodiments, $L^{RA}$ comprises at least one instance of substituted or unsubstituted heteroarylene, e.g., substituted or unsubstituted 5- to 6-membered heteroarylene.

In certain embodiments, $L^{RA}$ is a linker that contains an asymmetric carbon/stereocenter, i.e., an sp$^3$ hybridized carbon atom bearing 4 different groups attached thereto. In certain embodiments, the compound comprising such an $L^{RA}$ group is enantiomerically enriched or substantially enantiomerically enriched. In certain embodiments, the compound comprising such an $L^{RA}$ group is racemic.

In certain embodiments, $L^{RA}$ is a linker group as defined herein comprising one of the following divalent moieties directly (covalently) attached to L:

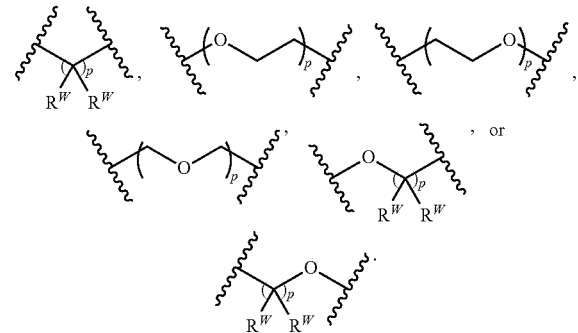

wherein:

each instance of p is independently an integer between 1 to 10, inclusive; and each instance of $R^W$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two $R^W$ groups are joined to form a 3-6 membered ring.

As described herein, p of any of the below formulae is independently an integer between 1 to 10, inclusive, e.g., 1, 2, 3, 4, 5, 6, 7, 8, 9, or 10:

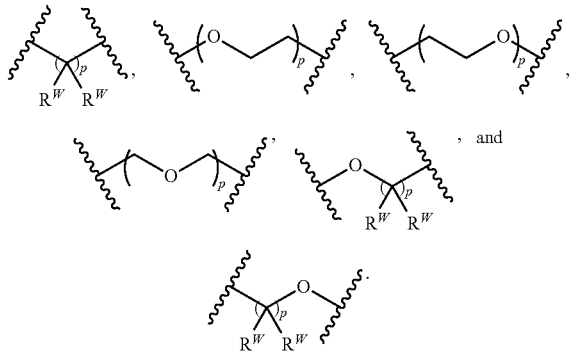

In certain embodiments, p is 1, 2, 3, 4, or 5. In certain embodiments, p is 2. In certain embodiments, p is 3. In certain embodiments, p is 4. In certain embodiments, p is 5. In certain embodiments, each instance of $R^W$ is independently hydrogen; halogen; or substituted or unsubstituted alkyl (e.g., methyl).

In certain embodiments, $L^{RA}$ is a linker group as defined herein comprising one of the following divalent moieties directly (covalently) attached to L:

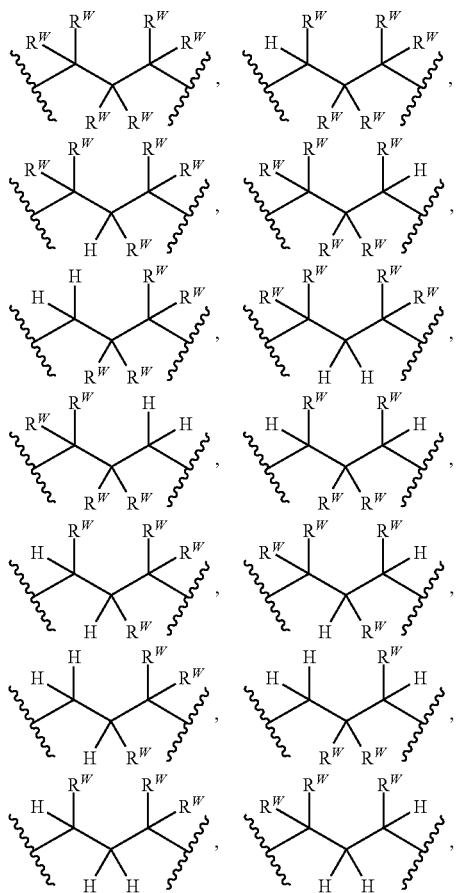

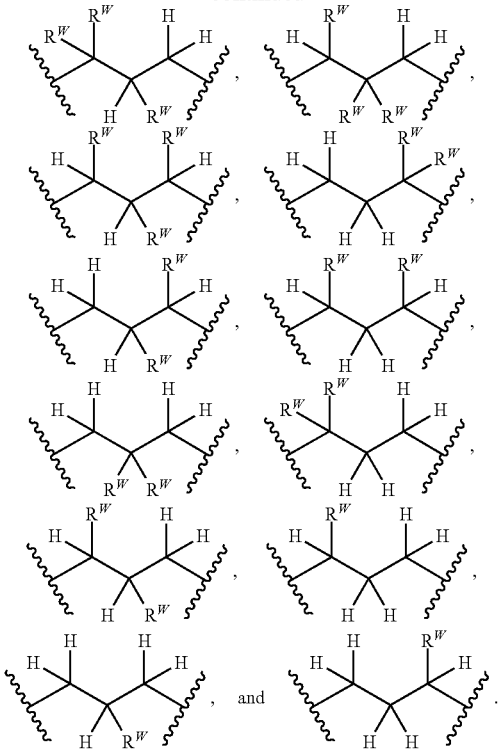

As described herein, each instance of $R^W$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two $R^W$ groups are joined to form a 3-6 membered ring. In any of the above formulae, as described herein, each instance of $R^W$ is independently hydrogen; halogen; substituted or unsubstituted alkyl (e.g., methyl).

In certain embodiments, $L^{RA}$ is a linker comprising a combination of 1 to 20 consecutive covalently bonded divalent moieties described herein, e.g., 2 to 20, 3 to 20, 4 to 20, 5 to 20, 6 to 20, 8 to 20, 9 to 20, 10 to 20, 2 to 10, 2 to 9, 2 to 8, 2 to 7, 2 to 6, or 2 to 5 divalent moieties, inclusive. In certain embodiments, $L^{RA}$ is a linker comprising a combination of 2 to 6 consecutive covalently bonded divalent moieties, inclusive. In certain embodiments, $L^{RA}$ is a linker comprising a combination of 1, 2, 3, 4, 5, 6, 7, 8, 9, 10, 11, 12, 13, 14, 15, 16, 17, 18, 19, or 20 consecutive covalently bonded divalent moieties. In certain embodiments, $L^{RA}$ is a linker comprising a combination of 2 consecutive covalently bonded divalent moieties. In certain embodiments, $L^{RA}$ is a linker comprising a combination of 2 consecutive covalently bonded divalent moieties. In certain embodiments, $L^{RA}$ is a linker comprising a combination of 4 consecutive covalently bonded divalent moieties. In certain embodiments, $L^{RA}$ is a linker comprising a combination of 5 consecutive covalently bonded divalent moieties. In certain embodiments, $L^{RA}$ is a linker comprising a combination of 6 consecutive covalently bonded divalent moieties.

In certain embodiments, $L^{RA}$ is a linker 1 to 20 consecutive covalently bonded atoms in length, inclusive, e.g., 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, 2 to 6, 2 to 5, 2 to 4, 3 to 6, 3 to 5 or 3 to 4 consecutive covalently bonded atoms in length, inclusive. In certain embodiments, $L^{RA}$ is a linker 1, 2, 3, 4, 5, 6, 7, 8, 9, 10, 11, 12, 13, 14, 15, 16, 17, 18, 19, or 20 consecutive covalently bonded atoms in length. In certain embodiments, $L^{RA}$ is a linker 1, 2, 3, 4, 5, or 6 consecutive covalently bonded atoms in length. In certain embodiments, $L^{RA}$ is a linker 2, 3, 4, or 5 consecutive covalently bonded atoms in length. In certain embodiments, $L^{RA}$ is a linker 2, 3, or 4 consecutive covalently bonded atoms in length. In certain embodiments, $L^{RA}$ is a linker 2 consecutive covalently bonded atoms in length. In certain embodiments, $L^{RA}$ is a linker 3 consecutive covalently bonded atoms in length. In certain embodiments, $L^{RA}$ is a linker 4 consecutive covalently bonded atoms in length.

In certain embodiments, $L^{RA}$ is a linker group as defined herein comprising one of the following divalent moieties directly (covalently) attached to L:

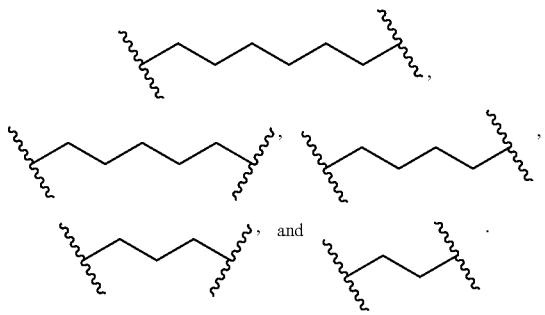

Compounds of Formula (I) and (II) include a substituent $R^B$ that is attached to the phenazinyl ring. In certain embodiments, $R^B$ is H. In certain embodiments, $R^B$ is halogen. In certain embodiments, $R^B$ is F. In certain embodiments, $R^B$ is Cl. In certain embodiments, $R^B$ is Br. In certain embodiments, $R^B$ is I (iodine). In certain embodiments, $R^B$ is substituted acyl. In certain embodiments, $R^B$ is unsubstituted acyl. In certain embodiments, $R^B$ is acetyl. In certain embodiments, $R^B$ is substituted alkyl. In certain embodiments, $R^B$ is unsubstituted alkyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is —$CH_3$. In certain embodiments, $R^B$ is substituted methyl. In certain embodiments, $R^B$ is —$CF_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is substituted alkenyl. In certain embodiments, $R^B$ is unsubstituted alkenyl. In certain embodiments, $R^B$ is substituted or unsubstituted $C_{1-6}$ alkenyl. In certain embodiments, $R^B$ is substituted alkynyl. In certain embodiments, $R^B$ is unsubstituted alkynyl. In certain embodiments, $R^B$ is substituted carbocyclyl. In certain embodiments, $R^B$ is unsubstituted carbocyclyl. In certain embodiments, $R^B$ is saturated carbocyclyl. In certain embodiments, $R^B$ is unsaturated carbocyclyl. In certain embodiments, $R^B$ is carbocyclyl including zero, one, two, or three double bonds in the carbocyclic ring system. In certain embodiments, $R^B$ is monocyclic carbocyclyl. In certain embodiments, $R^B$ is 3- to 7-membered, monocyclic carbocyclyl. In certain embodiments, $R^B$ is cylcopropyl. In certain embodiments, $R^B$ is bicyclic carbocyclyl. In certain embodiments, $R^B$ is 5- to 13-membered, bicyclic carbocyclyl. In certain embodiments, $R^B$ is substituted heterocyclyl. In certain embodiments, $R^B$ is unsubstituted heterocyclyl. In certain embodiments, $R^B$ is saturated heterocyclyl. In certain embodiments, $R^B$ is unsaturated heterocyclyl. In certain embodiments, $R^B$ is heterocyclyl including zero, one, two, or three double bonds in the heterocyclic ring system. In certain embodiments, $R^B$ is heterocyclyl, wherein one, two, or three atoms in the heterocyclic ring system are independently selected from the group consisting of nitrogen, oxygen, and sulfur. In certain embodiments, $R^B$ is monocyclic heterocyclyl. In certain embodiments, $R^B$ is 3- to 7-membered, monocyclic heterocyclyl. In certain embodiments, $R^B$ is bicyclic heterocyclyl. In certain embodiments, $R^B$ is 5- to 13-membered, bicyclic heterocyclyl. In certain embodiments, $R^B$ is substituted aryl. In certain embodiments, $R^B$ is unsubstituted aryl. In certain embodiments, $R^B$ is 6- to 14-membered aryl. In certain embodiments, $R^B$ is 6- to 10-membered aryl. In certain embodiments, $R^B$ is substituted phenyl. In certain embodiments, $R^B$ is phenyl substituted with at least one halogen. In certain embodiments, $R^B$ is unsubstituted phenyl. In certain embodiments, $R^B$ is substituted naphthyl. In certain embodiments, $R^B$ is unsubstituted naphthyl. In certain embodiments, $R^B$ is substituted heteroaryl. In certain embodiments, $R^B$ is unsubstituted heteroaryl. In certain embodiments, $R^B$ is heteroaryl, wherein one, two, three, or four atoms in the heteroaryl ring system are independently selected from the group consisting of nitrogen, oxygen, and sulfur. In certain embodiments, $R^B$ is monocyclic heteroaryl. In certain embodiments, $R^B$ is 5-membered, monocyclic heteroaryl. In certain embodiments, $R^B$ is 6-membered, monocyclic heteroaryl. In certain embodiments, $R^B$ is substituted pyridyl. In certain embodiments, $R^B$ is unsubstituted pyridyl. In certain embodiments, $R^B$ is bicyclic heteroaryl, wherein the point of attachment may be on any atom of the bicyclic heteroaryl ring system, as valency permits. In certain embodiments, $R^B$ is 9-membered, bicyclic heteroaryl. In certain embodiments, $R^B$ is 10-membered, bicyclic heteroaryl. In certain embodiments, $R^B$ is —$OR^{B1}$. In certain embodiments, $R^B$ is —OMe. In certain embodiments, $R^B$ is —OH. In certain embodiments, $R^B$ is —$SR^{B1}$. In certain embodiments, $R^B$ is —SMe. In certain embodiments, $R^B$ is —SH. In certain embodiments, $R^B$ is —$N(R^{B1})_2$. In certain embodiments, $R^B$ is —$NMe_2$. In certain embodiments $R^B$ is —NHMe. In certain embodiments, $R^B$ is —$NH_2$. In certain embodiments, $R^B$ is —CN. In certain embodiments, $R^B$ is —SCN. In certain embodiments, $R^B$ is —$C(=NR^{B1})R^{B1}$, —$C(=NR^{B1})OR^{B1}$, or —$C(=NR^{B1})N(R^{B1})_2$. In certain embodiments, $R^B$ is —$C(=O)R^{B1}$ or —$C(=O)OR^{B1}$. In certain embodiments, $R^B$ is —$C(=O)N(R^{B1})_2$. In certain embodiments, $R^B$ is —$C(=O)NMe_2$, —$C(=O)NHMe$, or —$C(=O)NH_2$. In certain embodiments, $R^B$ is —$NO_2$. In certain embodiments, $R^B$ is —$NR^{B1}C(=O)R^{B1}$, —$NR^{B1}C(=O)OR^{B1}$, or —$NR^{B1}C(=O)N(R^{B1})_2$. In certain embodiments, $R^B$ is —$OC(=O)R^{B1}$, —$OC(=O)OR^{B1}$, or —$OC(=O)N(R^{B1})_2$.

In certain embodiments, at least one instance of $R^{B1}$ is H. In certain embodiments, at least one instance of $R^{B1}$ is substituted acyl. In certain embodiments, at least one instance of $R^{B1}$ is unsubstituted acyl. In certain embodiments, at least one instance of $R^{B1}$ is acetyl. In certain embodiments, at least one instance of $R^{B1}$ is substituted alkyl. In certain embodiments, at least one instance of $R^{B1}$ is unsubstituted alkyl. In certain embodiments, at least one instance of $R^{B1}$ is unsubstituted $C_{1-6}$ alkyl. In certain embodiments, at least one instance of $R^{B1}$ is methyl. In certain embodiments, at least one instance of $R^{B1}$ is ethyl. In certain embodiments, at least one instance of $R^{B1}$ is propyl. In certain embodiments, at least one instance of $R^{B1}$ is butyl. In certain embodiments, at least one instance of $R^{B1}$ is pentyl. In certain embodiments, at least one instance of $R^{B1}$ is hexyl. In certain embodiments, at least one instance of $R^{B1}$ is substituted alkenyl. In certain embodiments, at least one instance of $R^{B1}$ is unsubstituted alkenyl. In certain embodiments, at least one instance of $R^{B1}$ is substituted alkynyl. In certain embodiments, at least one instance of $R^{B1}$ is unsubstituted alkynyl. In certain embodiments, at least one instance of $R^{B1}$ is substituted carbocyclyl. In certain embodiments, at least one instance of $R^{B1}$ is unsubstituted carbocyclyl. In certain embodiments, at least one instance of $R^{B1}$ is saturated carbocyclyl. In certain embodiments, at least one instance of $R^{B1}$ is unsaturated carbocyclyl. In certain embodiments, at least one instance of $R^{B1}$ is carbocyclyl including zero, one, two, or three double bonds in the carbocyclic ring system. In certain embodiments, at least one instance of $R^{B1}$ is 3- to 7-membered, monocyclic carbocyclyl. In certain embodiments, at least one instance of $R^{B1}$ is cylcopropyl. In certain embodiments, at least one instance of $R^{B1}$ is 5- to 13-membered, bicyclic carbocyclyl. In certain embodiments, at least one instance of $R^{B1}$ is substituted heterocyclyl. In certain embodiments, at least one instance of $R^{B1}$ is unsubstituted heterocyclyl. In certain embodiments, at least one instance of $R^{B1}$ is saturated heterocyclyl. In certain embodiments, at least one instance of $R^{B1}$ is unsaturated heterocyclyl. In certain embodiments, at least one instance of $R^{B1}$ is heterocyclyl including zero, one, two, or three double bonds in the heterocyclic ring system. In certain embodiments, at least one instance of $R^{B1}$ is heterocyclyl, wherein one, two, or three atoms in the heterocyclic ring system are independently selected from the group consisting of nitrogen, oxygen, and sulfur. In certain embodiments, at least one instance of $R^{B1}$ is 3- to 7-membered, monocyclic heterocyclyl. In certain embodiments, at least one instance of $R^{B1}$ is 5- to 13-membered, bicyclic heterocyclyl. In certain embodiments, at least one instance of $R^{B1}$ is substituted or unsubstituted aryl. In certain embodiments, at least one instance of $R^{B1}$ is 6- to 14-membered aryl. In certain embodiments, at least one instance of $R^{B1}$ is 6- to 10-membered aryl. In certain embodiments, at least one instance of $R^{B1}$ is monocyclic aryl. In certain embodiments, at least one instance of $R^{B1}$ is substituted phenyl. In certain embodiments, at least one instance of $R^{B1}$ is unsubstituted phenyl. In certain embodiments, at least one instance of $R^{B1}$ is bicyclic aryl. In certain embodiments, at least one instance of $R^{B1}$ is naphthyl. In certain embodiments, at least one instance of $R^{B1}$ is substituted or unsubstituted heteroaryl. In certain embodiments, at least one instance of $R^{B1}$ is heteroaryl, wherein one, two, three, or four atoms in the heteroaryl ring system are independently selected from the group consisting of nitrogen, oxygen, and sulfur. In certain embodiments, at least one instance of $R^{B1}$ is monocyclic heteroaryl. In certain embodiments, at least one instance of $R^{B1}$ is 5-membered, monocyclic heteroaryl. In certain embodiments, at least one instance of $R^{B1}$ is 6-membered, monocyclic heteroaryl. In certain embodiments, at least one instance of $R^{B1}$ is pyridyl. In certain embodiments, at least one instance of $R^{B1}$ is bicyclic heteroaryl, wherein the point of attachment may be on any atom of the bicyclic heteroaryl ring system, as valency permits. In certain embodiments, at least one instance of $R^{B1}$ is 9-membered, bicyclic heteroaryl. In certain embodiments, at least one instance of $R^{B1}$ is 10-membered, bicyclic heteroaryl. In certain embodiments, at least one instance of $R^{B1}$ is a nitrogen protecting group when attached to a nitrogen atom. In certain embodiments, at least one instance of $R^{B1}$ is Bn, Boc, Cbz, Fmoc, trifluoroacetyl, triphenylmethyl, acetyl, or Ts when attached to a nitrogen atom. In certain embodiments, $R^{B1}$ is an oxygen protecting group when attached to an oxygen atom. In certain embodiments, $R^{B1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{B1}$ is a sulfur protecting group when attached to a sulfur atom. In certain embodiments, $R^{B1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{B1}$ are joined to form a substituted or unsubstituted heterocyclic ring. In certain embodiments, two instances of $R^{B1}$ are joined to form a saturated or unsaturated heterocyclic ring. In certain embodiments, two instances of $R^{B1}$ are joined to form a heterocyclic ring including zero, one, two, or three double bonds in the heterocyclic ring system. In certain embodiments, two instances of $R^{B1}$ are joined to form a heterocyclic ring, wherein one, two, or three atoms in the heterocyclic ring system are independently selected from the group consisting of nitrogen, oxygen, and sulfur. In certain embodiments, two instances of $R^{B1}$ are joined to form a 3- to 7-membered, monocyclic heterocyclic ring. In certain embodiments, two instances of $R^{B1}$ are joined to form a 5- to 13-membered, bicyclic heterocyclic ring.

Compounds of Formula (I) and (II) may include one or more substituents $R^C$ that are attached to the phenazinyl ring. In certain embodiments, at least one instance of $R^C$ is H. In certain embodiments, all instances of $R^C$ are H. In certain embodiments, at least one instance of $R^C$ is halogen. In certain embodiments, at least one instance of $R^C$ is F. In certain embodiments, at least one instance of $R^C$ is Cl. In certain embodiments, at least one instance of $R^C$ is Br. In certain embodiments, at least one instance of $R^C$ is I (iodine). In certain embodiments, at least one instance of $R^C$ is substituted acyl. In certain embodiments, at least one instance of $R^C$ is unsubstituted acyl. In certain embodiments, at least one instance of $R^C$ is acetyl. In certain embodiments, at least one instance of $R^C$ is substituted alkyl. In certain embodiments, at least one instance of $R^C$ is unsubstituted alkyl. In certain embodiments, at least one instance of $R^C$ is unsubstituted $C_{1-6}$ alkyl. In certain embodiments, at least one instance of $R^C$ is substituted $C_{1-6}$ alkyl. In certain embodiments, at least one instance of $R^C$ is $C_{1-6}$ alkyl substituted with at least one halogen. In certain embodiments, at least one instance of $R^C$ is —$CH_3$. In certain embodiments, at least one instance of $R^C$ is substituted methyl. In certain embodiments, at least one instance of $R^C$ is —$CH_2F$. In certain embodiments, at least one instance of $R^C$ is —$CHF_2$. In certain embodiments, at least one instance of $R^C$ is —$CF_3$. In certain embodiments, at least one instance of $R^C$ is ethyl. In certain embodiments, at least one instance of $R^C$ is propyl. In certain embodiments, at least one instance of $R^C$ is butyl. In certain embodiments, at least one instance of $R^C$ is pentyl. In certain embodiments, at least one instance of $R^C$ is hexyl. In certain embodiments, at least one instance of $R^C$ is substituted alkenyl. In certain embodiments, at least one instance of $R^C$ is unsubstituted alkenyl. In certain embodiments, at least one instance of $R^C$ is substituted or unsubstituted $C_{1-6}$ alkenyl. In certain embodiments, at least one instance of $R^C$ is substituted alkynyl. In certain embodiments, at least one instance of $R^C$ is unsubstituted alkynyl. In certain embodiments, at least one instance of $R^C$ is substituted carbocyclyl. In certain embodiments, at least one instance of $R^C$ is unsubstituted carbocyclyl. In certain embodiments, at least one instance of $R^C$ is saturated carbocyclyl. In certain embodiments, at least one instance of $R^C$ is unsaturated carbocyclyl. In certain embodiments, at least one instance of $R^C$ is carbocyclyl including zero, one, two, or three double bonds in the carbocyclic ring system. In certain embodiments, at least one instance of $R^C$ is monocyclic carbocyclyl. In certain embodiments, at least one instance of $R^C$ is 3- to 7-membered, monocyclic carbocyclyl. In certain embodiments, at least one instance of $R^C$ is cylcopropyl. In certain embodiments, at least one instance of $R^C$ is cyclobutyl. In certain embodiments, at least one instance of $R^C$ is cyclopentyl. In certain embodiments, at least one instance of $R^C$ is cyclohexyl. In certain embodiments, at least one instance of $R^C$ is cycloheptyl. In certain embodiments, at least one instance of $R^C$ is bicyclic carbocyclyl. In certain embodiments, at least one instance of $R^C$ is 5- to 13-membered, bicyclic carbocyclyl. In certain embodiments, at least one instance of $R^C$ is substituted heterocyclyl. In certain embodiments, at least one instance of $R^C$ is unsubstituted heterocyclyl. In certain embodiments, at least one instance of $R^C$ is saturated heterocyclyl. In certain embodiments, at least one instance of $R^C$ is unsaturated heterocyclyl. In certain embodiments, at least one instance of $R^C$ is heterocyclyl including zero, one, two, or three double bonds in the heterocyclic ring system. In certain embodiments, at least one instance of $R^C$ is heterocyclyl, wherein one, two, or three atoms in the heterocyclic ring system are independently selected from the group consisting of nitrogen, oxygen, and sulfur. In certain embodiments, at least one instance of $R^C$ is monocyclic heterocyclyl. In certain embodiments, at least one instance of $R^C$ is 3- to 7-membered, monocyclic heterocyclyl. In certain embodiments, at least one instance of $R^C$ is bicyclic heterocyclyl. In certain embodiments, at least one instance of $R^C$ is 5- to 13-membered, bicyclic heterocyclyl. In certain embodiments, at least one instance of $R^C$ is substituted aryl. In certain embodiments, at least one instance of $R^C$ is unsubstituted aryl. In certain embodiments, at least one instance of $R^C$ is 6- to 14-membered aryl. In certain embodiments, at least one instance of $R^C$ is 6- to 10-membered aryl. In certain embodiments, at least one instance of $R^C$ is substituted phenyl. In certain embodiments, at least one instance of $R^C$ is phenyl substituted with at least one halogen. In certain embodiments, at least one instance of $R^C$ is unsubstituted phenyl. In certain embodiments, at least one instance of $R^C$ is substituted naphthyl. In certain embodiments, at least one instance of $R^C$ is unsubstituted naphthyl. In certain embodiments, at least one instance of $R^C$ is substituted heteroaryl. In certain embodiments, at least one instance of $R^C$ is unsubstituted heteroaryl. In certain embodiments, at least one instance of $R^C$ is heteroaryl, wherein one, two, three, or four atoms in the heteroaryl ring system are independently selected from the group consisting of nitrogen, oxygen, and sulfur. In certain embodiments, at least one instance of $R^C$ is monocyclic heteroaryl. In certain embodiments, at least one instance of $R^C$ is 5-membered, monocyclic heteroaryl. In certain embodiments, at least one instance of $R^C$ is 6-membered, monocyclic heteroaryl. In certain embodiments, at least one instance of $R^C$ is substituted pyridyl. In certain embodiments, at least one instance of $R^C$ is unsubstituted pyridyl. In certain embodiments, at least one instance of $R^C$ is bicyclic heteroaryl, wherein the point of attachment may be on any atom of the bicyclic heteroaryl ring system, as valency permits. In certain embodiments, at least one instance of $R^C$ is 9-membered, bicyclic heteroaryl. In certain embodiments, at least one instance of $R^C$ is 10-membered, bicyclic heteroaryl. In certain embodiments, at least one instance of $R^C$ is —$OR^{C1}$. In certain embodiments, at least one instance of $R^C$ is —OMe. In certain embodiments, at least one instance of $R^C$ is —OEt. In certain embodiments, at least one instance of $R^C$ is —OPr. In certain embodiments, at least one instance of $R^C$ is —OBu. In certain embodiments, at least one instance of $R^C$ is —O(pentyl). In certain embodiments, at least one instance of $R^C$ is —O(hexyl). In certain embodiments, at least one instance of $R^C$ is —OBn. In certain embodiments, at least one instance of $R^C$ is —OPh. In certain embodiments, at least one instance of $R^C$ is —OH. In certain embodiments, at least one instance of $R^C$ is —$SR^{C1}$. In certain embodiments, at least one instance of $R^C$ is —SMe. In certain embodiments, at least one instance of $R^C$ is —SH. In certain embodiments, at least one instance of $R^C$ is —$N(R^{C1})_2$. In certain embodiments, at least one instance of $R^C$ is —$NMe_2$. In certain embodiments, at least one instance of $R^C$ is —NHMe. In certain embodiments, at least one instance of $R^C$ is —$NH_2$. In certain embodiments, at least one instance of $R^C$ is —CN. In certain embodiments, at least one instance of $R^C$ is —SCN. In certain embodiments, at least one instance of $R^C$ is —$C(=NR^{C1})R^{C1}$, —$C(=NR^{C1})OR^{C1}$, or —$C(=NR^{C1})N(R^{C1})_2$. In certain embodiments, at least one instance of $R^C$ is —$C(=O)R^{C1}$ or —$C(=O)OR^{C1}$. In certain embodiments, at least one instance of $R^C$ is —$C(=O)N(R^{C1})_2$. In certain embodiments, at least one instance of $R^C$ is —$C(=O)NMe_2$, —$C(=O)NHMe$, or —$C(=O)NH_2$. In certain embodiments, at least one instance of $R^C$ is —$NO_2$. In certain embodiments, at least one instance of $R^C$ is —$NR^{C1}C(=O)R^{C1}$, —$NR^{C1}C(=O)OR^{C1}$, or —$NR^{C1}C(=O)N(R^{C1})_2$. In certain embodiments, at least one instance of $R^C$ is —$OC(=O)R^{C1}$, —$OC(=O)OR^{C1}$, or —$OC(=O)N(R^{C1})_2$. In certain embodiments, at least one instance of $R^C$ is halogen, substituted or unsubstituted alkyl, —$OR^{C1}$, or —CN. In certain embodiments, at least one instance of $R^C$ is halogen, unsubstituted $C_{1-6}$ alkyl, —O(unsubstituted $C_{1-6}$ alkyl), or —CN.

In certain embodiments, two instances of $R^C$ are joined to form a substituted or unsubstituted carbocyclic ring. In certain embodiments, two instances of $R^C$ are joined to form a saturated or unsaturated carbocyclic ring. In certain embodiments, two instances of $R^C$ are joined to form a carbocyclic ring including zero, one, two, or three double bonds in the carbocyclic ring system. In certain embodiments, two instances of $R^C$ are joined to form a 3- to 7-membered, monocyclic carbocyclic ring. In certain embodiments, two instances of $R^C$ are joined to form a 3-membered carbocyclic ring. In certain embodiments, two instances of $R^C$ are joined to form a 4-membered carbocyclic ring. In certain embodiments, two instances of $R^C$ are joined to form a 5-membered carbocyclic ring. In certain embodiments, two instances of $R^C$ are joined to form a 6-membered carbocyclic ring. In certain embodiments, two instances of $R^C$ are joined to form a 7-membered carbocyclic ring. In certain embodiments, two instances of $R^C$ are joined to form a 5- to 13-membered, bicyclic carbocyclic ring.

In certain embodiments, two instances of $R^C$ are joined to form a substituted or unsubstituted heterocyclic ring. In certain embodiments, two instances of $R^C$ are joined to form a saturated or unsaturated heterocyclic ring. In certain embodiments, two instances of $R^C$ are joined to form a heterocyclic ring including zero, one, two, or three double bonds in the heterocyclic ring system. In certain embodiments, two instances of $R^C$ are joined to form a heterocyclic ring, wherein one, two, or three atoms in the heterocyclic ring system are independently selected from the group consisting of nitrogen, oxygen, and sulfur. In certain embodiments, two instances of $R^C$ are joined to form a 3- to 7-membered, monocyclic heterocyclic ring. In certain embodiments, two instances of $R^C$ are joined to form a 5- to 13-membered, bicyclic heterocyclic ring.

In certain embodiments, two instances of $R^C$ are joined to form a substituted or unsubstituted aryl ring. In certain embodiments, two instances of $R^C$ are joined to form a 6- to 14-membered aryl ring. In certain embodiments, two instances of $R^C$ are joined to form a 6- to 10-membered aryl ring. In certain embodiments, two instances of $R^C$ are joined to form a monocyclic aryl ring. In certain embodiments, two instances of $R^C$ are joined to form a phenyl ring. In certain embodiments, two instances of $R^C$ are joined to form a bicyclic aryl ring. In certain embodiments, two instances of $R^C$ are joined to form a naphthyl ring.

In certain embodiments, two instances of $R^C$ are joined to form a substituted or unsubstituted heteroaryl ring. In certain embodiments, two instances of $R^C$ are joined to form a monocyclic heteroaryl ring, wherein one, two, or three atoms in the heteroaryl ring system are independently selected from the group consisting of nitrogen, oxygen, and sulfur. In certain embodiments, two instances of $R^C$ are joined to form a 5-membered, monocyclic heteroaryl ring. In certain embodiments, two instances of $R^C$ are joined to form a 6-membered, monocyclic heteroaryl ring. In certain embodiments, two instances of $R^C$ are joined to form a pyridyl ring. In certain embodiments, two instances of $R^C$ are joined to form a bicyclic heteroaryl ring, wherein one, two, three, or four atoms in the heteroaryl ring system are independently selected from the group consisting of nitrogen, oxygen, and sulfur. In certain embodiments, two instances of $R^C$ are joined to form a 9-membered, bicyclic heteroaryl ring. In certain embodiments, two instances of $R^C$ are joined to form a 10-membered, bicyclic heteroaryl ring.

In certain embodiments, at least one instance of $R^{C1}$ is H. In certain embodiments, at least one instance of $R^{C1}$ is substituted acyl. In certain embodiments, at least one instance of $R^{C1}$ is unsubstituted acyl. In certain embodiments, at least one instance of $R^{C1}$ is acetyl. In certain embodiments, at least one instance of $R^{C1}$ is substituted alkyl. In certain embodiments, at least one instance of $R^{C1}$ is unsubstituted alkyl. In certain embodiments, at least one instance of $R^{C1}$ is unsubstituted $C_{1-6}$ alkyl. In certain embodiments, at least one instance of $R^{C1}$ is methyl. In certain embodiments, at least one instance of $R^{C1}$ is ethyl. In certain embodiments, at least one instance of $R^{C1}$ is propyl. In certain embodiments, at least one instance of $R^{C1}$ is butyl. In certain embodiments, at least one instance of $R^{C1}$ is pentyl. In certain embodiments, at least one instance of $R^{C1}$ is hexyl. In certain embodiments, at least one instance of $R^C$ is substituted alkenyl. In certain embodiments, at least one instance of $R^{C1}$ is unsubstituted alkenyl. In certain embodiments, at least one instance of $R^{C1}$ is substituted alkynyl. In certain embodiments, at least one instance of $R^{C1}$ is unsubstituted alkynyl. In certain embodiments, at least one instance of $R^{C1}$ is substituted carbocyclyl. In certain embodiments, at least one instance of $R^{C1}$ is unsubstituted carbocyclyl. In certain embodiments, at least one instance of $R^{C1}$ is saturated carbocyclyl. In certain embodiments, at least one instance of $R^{C1}$ is unsaturated carbocyclyl. In certain embodiments, at least one instance of $R^{C1}$ is carbocyclyl including zero, one, two, or three double bonds in the carbocyclic ring system. In certain embodiments, at least one instance of $R^{C1}$ is 3- to 7-membered, monocyclic carbocyclyl. In certain embodiments, at least one instance of $R^{C1}$ is cylcopropyl. In certain embodiments, at least one instance of $R^{C1}$ is cyclobutyl. In certain embodiments, at least one instance of $R^{C1}$ is cyclopentyl. In certain embodiments, at least one instance of $R^{C1}$ is cyclohexyl. In certain embodiments, at least one instance of $R^{C1}$ is cycloheptyl. In certain embodiments, at least one instance of $R^{C1}$ is 5- to 13-membered, bicyclic carbocyclyl. In certain embodiments, at least one instance of $R^{C1}$ is substituted heterocyclyl. In certain embodiments, at least one instance of $R^{C1}$ is unsubstituted heterocyclyl. In certain embodiments, at least one instance of $R^{C1}$ is saturated heterocyclyl. In certain embodiments, at least one instance of $R^{C1}$ is unsaturated heterocyclyl. In certain embodiments, at least one instance of $R^{C1}$ is heterocyclyl including zero, one, two, or three double bonds in the heterocyclic ring system. In certain embodiments, at least one instance of $R^{C1}$ is heterocyclyl, wherein one, two, or three atoms in the heterocyclic ring system are independently selected from the group consisting of nitrogen, oxygen, and sulfur. In certain embodiments, at least one instance of $R^{C1}$ is 3- to 7-membered, monocyclic heterocyclyl. In certain embodiments, at least one instance of $R^{C1}$ is 5- to 13-membered, bicyclic heterocyclyl. In certain embodiments, at least one instance of $R^{C1}$ is substituted or unsubstituted aryl. In certain embodiments, at least one instance of $R^{C1}$ is 6- to 14-membered aryl. In certain embodiments, at least one instance of $R^{C1}$ is 6- to 10-membered aryl. In certain embodiments, at least one instance of $R^{C1}$ is monocyclic aryl. In certain embodiments, at least one instance of $R^{C1}$ is substituted phenyl. In certain embodiments, at least one instance of $R^{C1}$ is unsubstituted phenyl. In certain embodiments, at least one instance of $R^{C1}$ is bicyclic aryl. In certain embodiments, at least one instance of $R^{C1}$ is naphthyl. In certain embodiments, at least one instance of $R^{C1}$ is substituted or unsubstituted heteroaryl. In certain embodiments, at least one instance of $R^{C1}$ is heteroaryl, wherein one, two, three, or four atoms in the heteroaryl ring system are independently selected from the group consisting of nitrogen, oxygen, and sulfur. In certain embodiments, at least one instance of $R^{C1}$ is monocyclic heteroaryl. In certain embodiments, at least one instance of $R^{C1}$ is 5-membered, monocyclic heteroaryl. In certain embodiments, at least one instance of $R^{C1}$ is 6-membered, monocyclic heteroaryl. In certain embodiments, at least one instance of $R^{C1}$ is pyridyl. In certain embodiments, at least one instance of $R^{C1}$ is bicyclic heteroaryl, wherein the point of attachment may be on any atom of the bicyclic heteroaryl ring system, as valency permits. In certain embodiments, at least one instance of $R^{C1}$ is 9-membered, bicyclic heteroaryl. In certain embodiments, at least one instance of $R^{C1}$ is 10-membered, bicyclic heteroaryl. In certain embodiments, at least one instance of $R^{C1}$ is a nitrogen protecting group when attached to a nitrogen atom. In certain embodiments, at least one instance of $R^{C1}$ is Bn, Boc, Cbz, Fmoc, trifluoroacetyl, triphenylmethyl, acetyl, or Ts when attached to a nitrogen atom. In certain embodiments, $R^{C1}$ is an oxygen protecting group when attached to an oxygen atom. In certain embodiments, $R^{C1}$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^{C1}$ is a sulfur protecting group when attached to a sulfur atom. In certain embodiments, $R^{C1}$ is acetamidomethyl, t-Bu, 3-nitro-2-pyridine sulfenyl, 2-pyridine-sulfenyl, or triphenylmethyl when attached to a sulfur atom. In certain embodiments, two instances of $R^{C1}$ are joined to form a substituted or unsubstituted heterocyclic ring. In certain embodiments, two instances of $R^{C1}$ are joined to form a saturated or unsaturated heterocyclic ring. In certain embodiments, two instances of $R^{C1}$ are joined to form a heterocyclic ring including zero, one, two, or three double bonds in the heterocyclic ring system. In certain embodiments, two instances of $R^{C1}$ are joined to form a heterocyclic ring, wherein one, two, or three atoms in the heterocyclic ring system are independently selected from the group consisting of nitrogen, oxygen, and sulfur. In certain embodiments, two instances of $R^{C1}$ are joined to form a 3- to 7-membered, monocyclic heterocyclic ring. In certain embodiments, two instances of $R^{C1}$ are joined to form a 5- to 13-membered, bicyclic heterocyclic ring.

In certain embodiments, n is 0. In certain embodiments, n is 1. In certain embodiments, n is 2. In certain embodiments, n is 3. In certain embodiments, n is 4.

In certain embodiments, the compound of Formula (I) is of the formula:

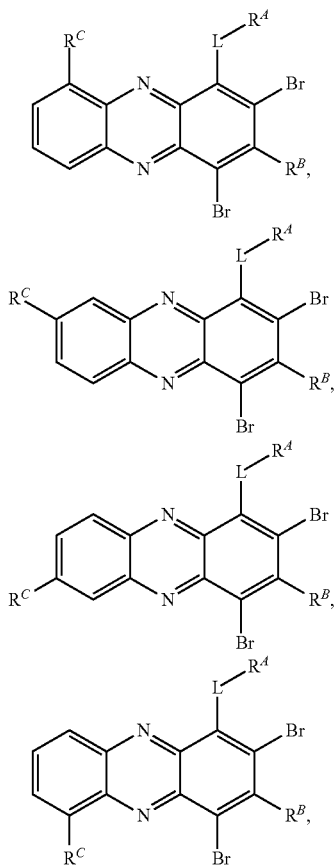

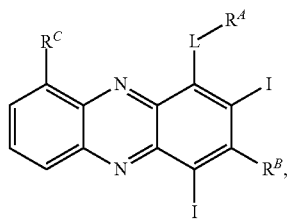

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

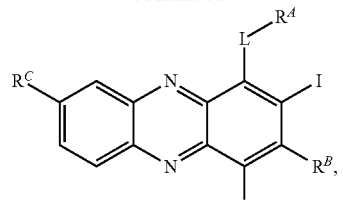

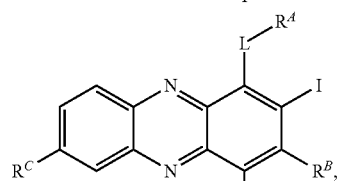

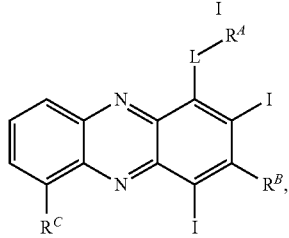

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

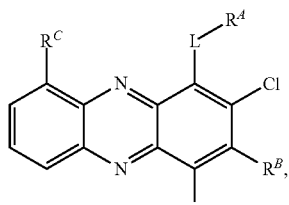

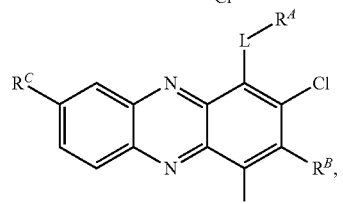

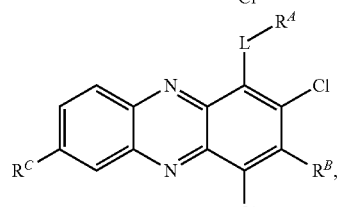

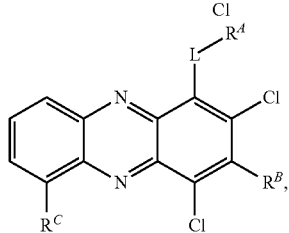

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

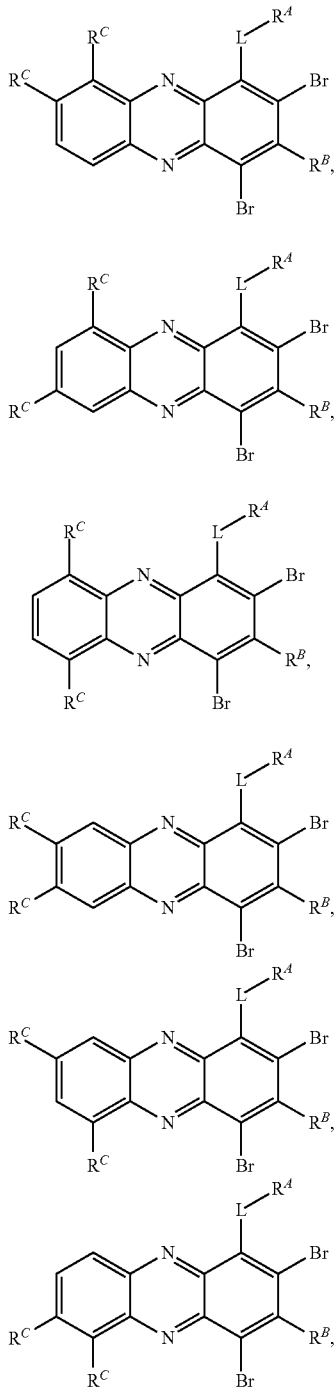

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

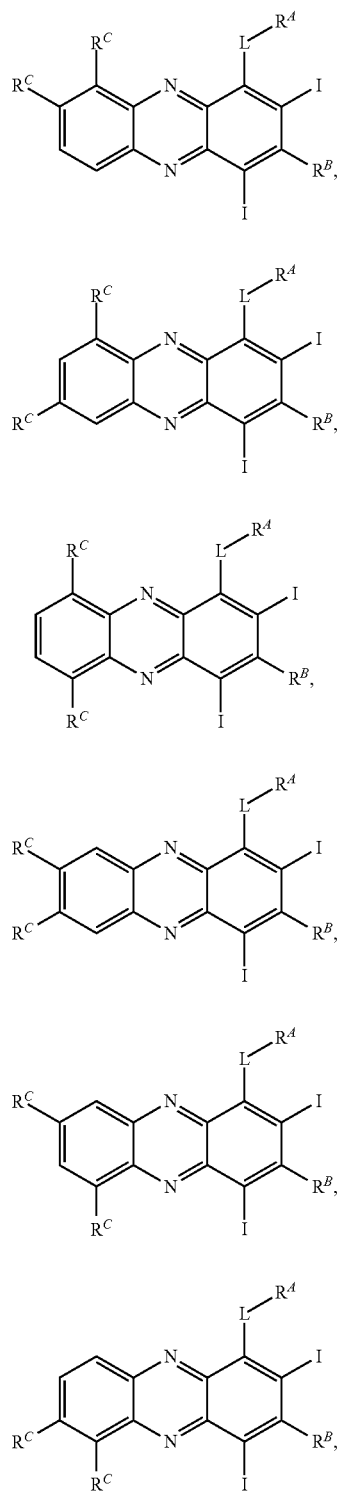

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

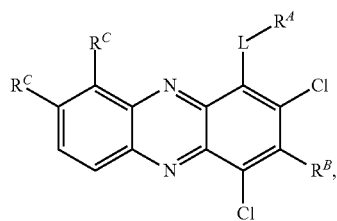

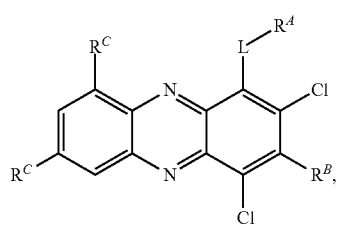

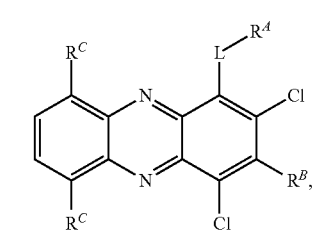

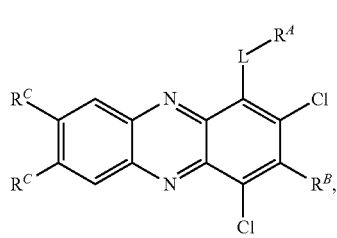

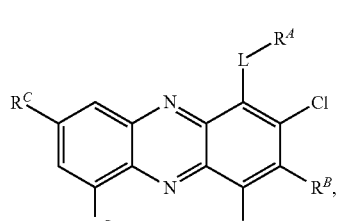

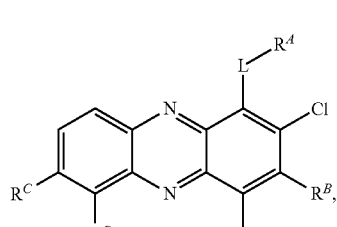

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

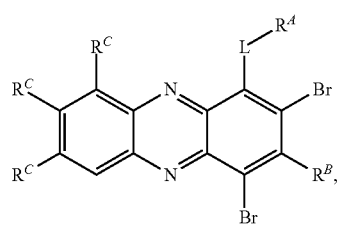

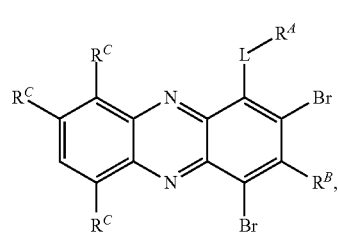

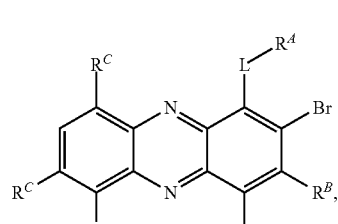

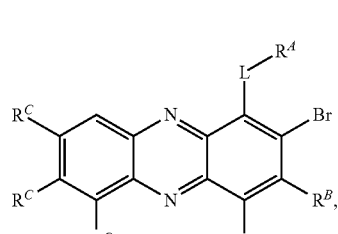

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

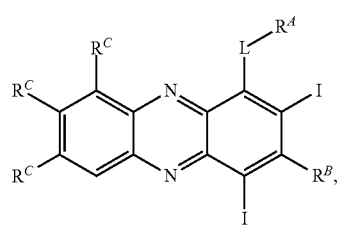

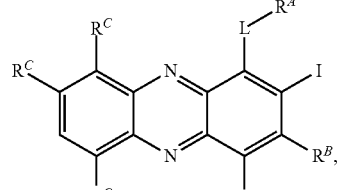

-continued

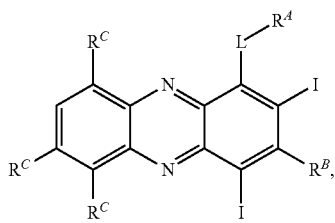

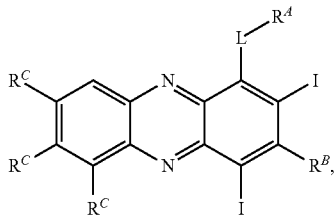

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

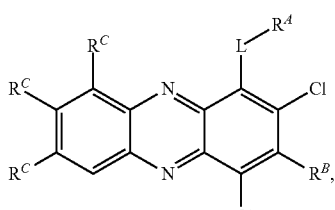

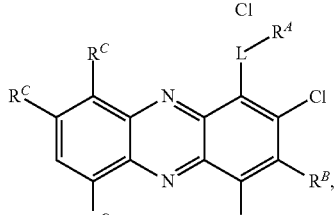

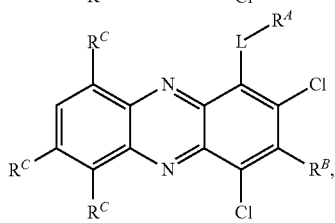

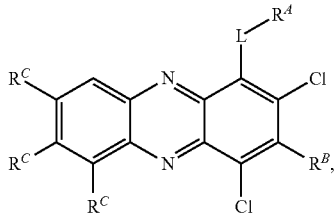

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

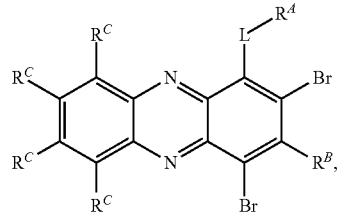

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

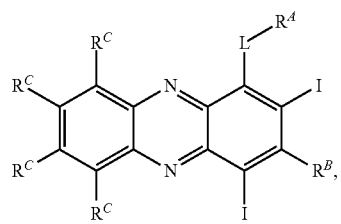

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

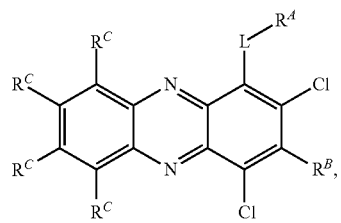

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

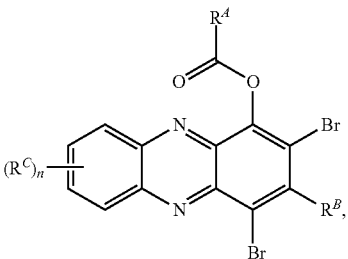

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

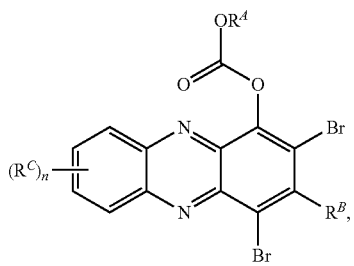

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

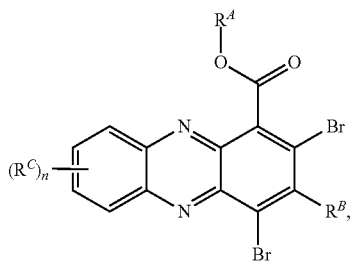

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

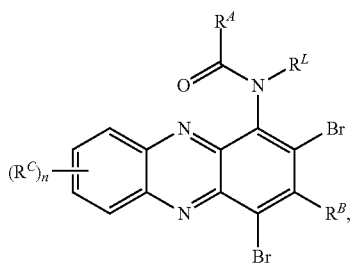

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

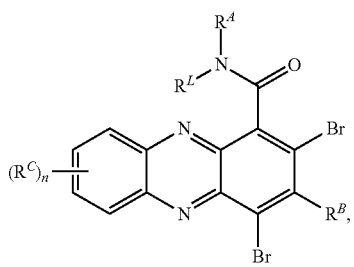

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

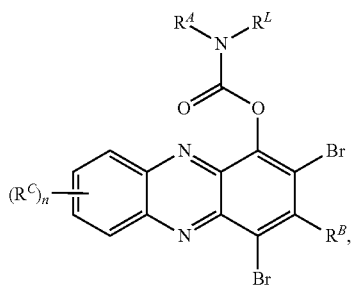

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

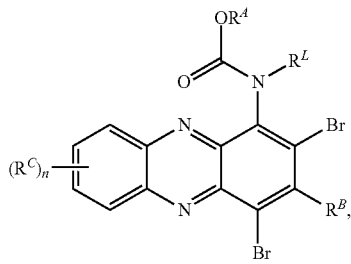

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

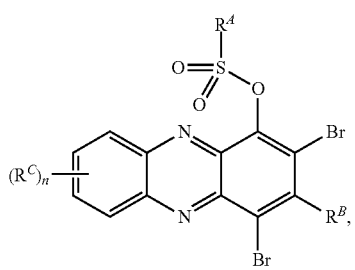

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

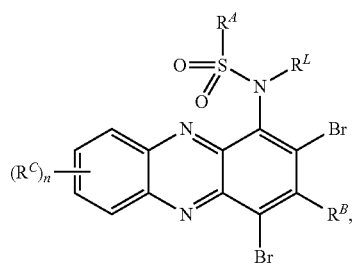

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

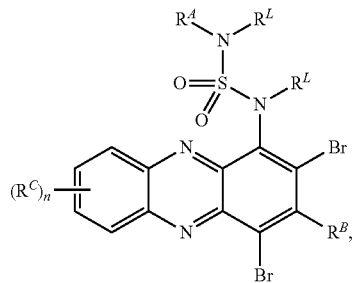

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

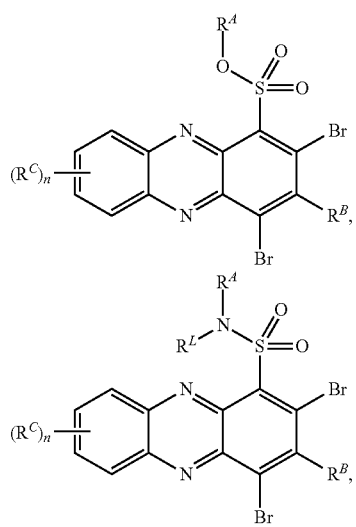

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

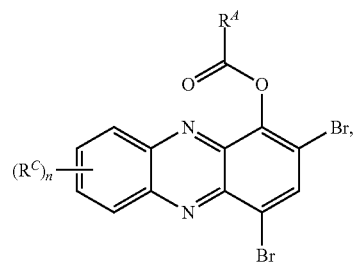

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

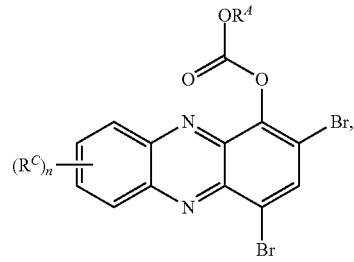

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

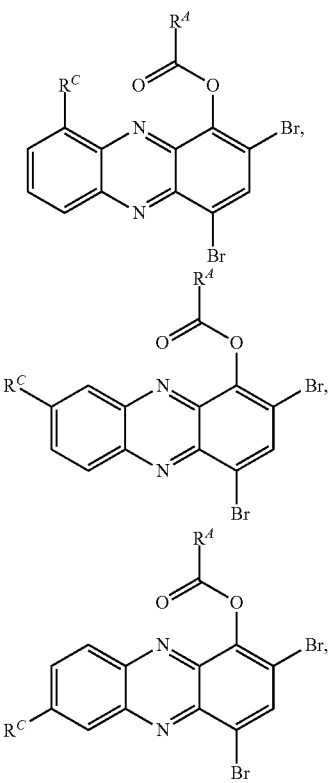

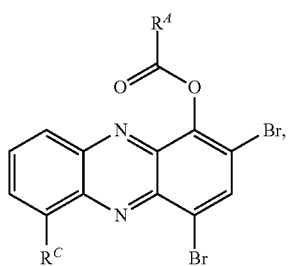

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

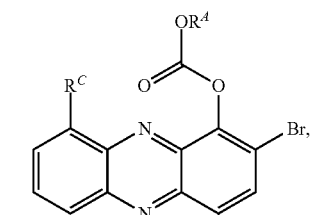

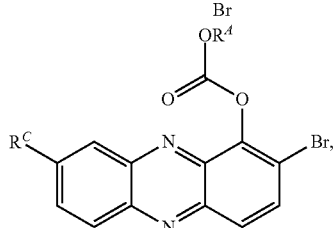

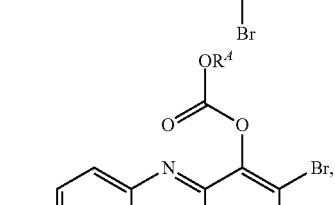

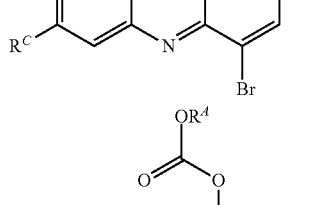

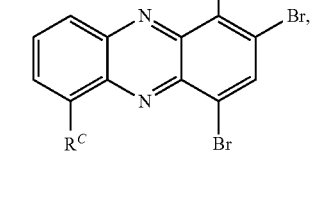

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

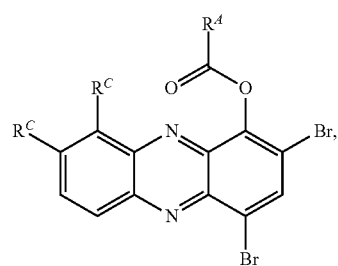

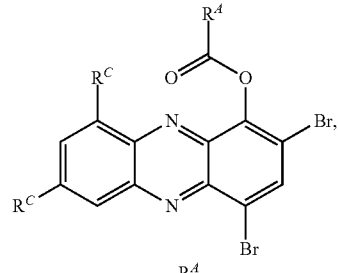

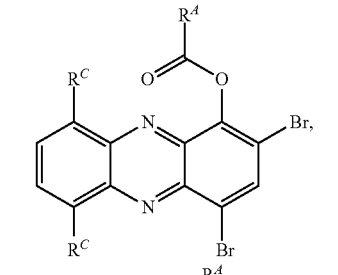

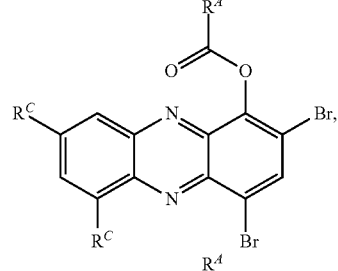

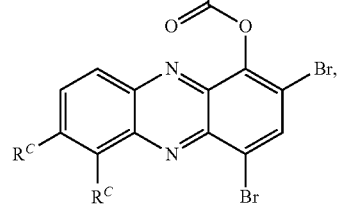

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

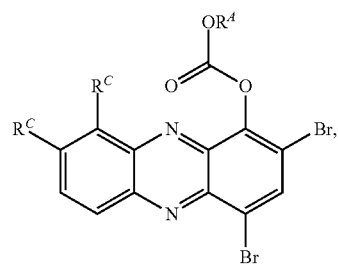

-continued

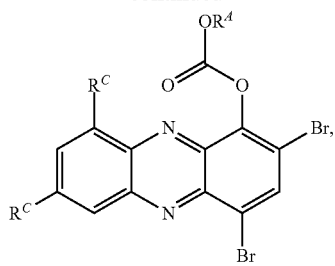

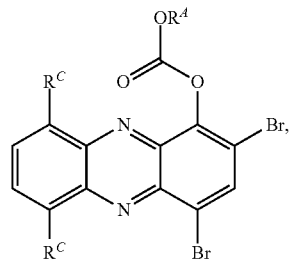

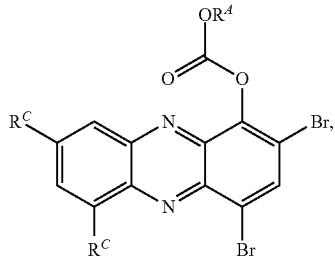

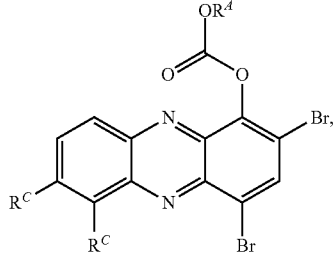

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

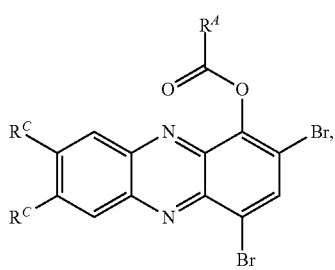

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

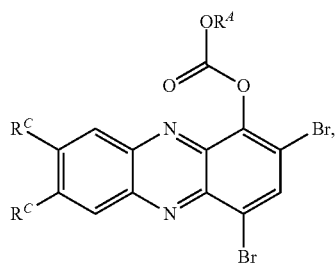

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

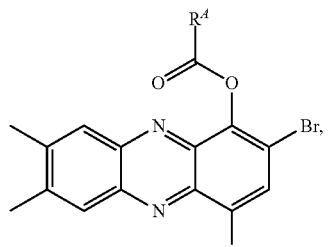

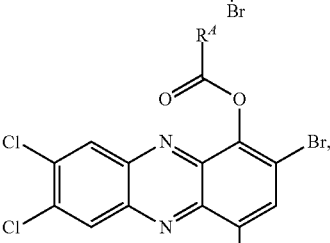

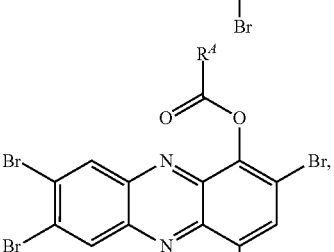

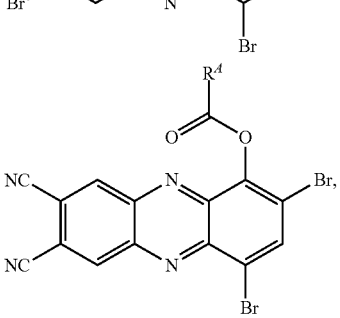

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

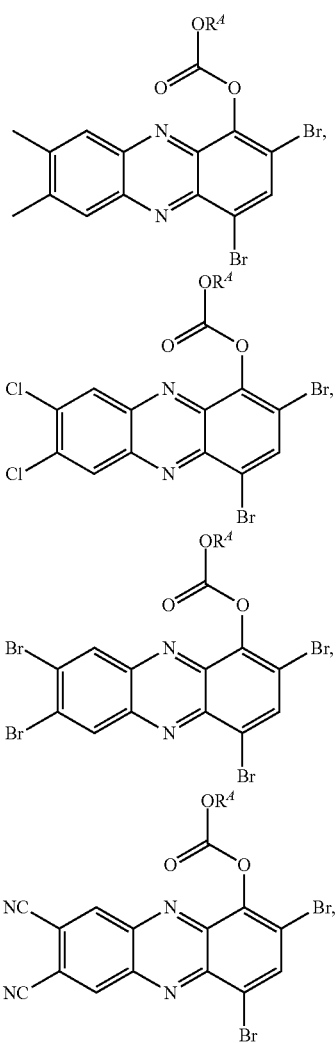

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

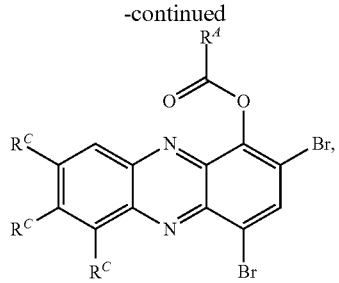

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

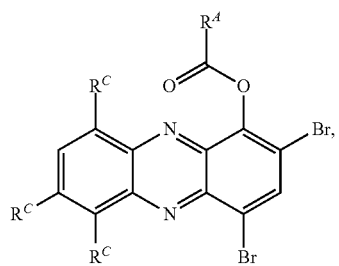

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

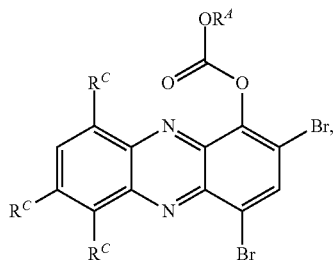

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

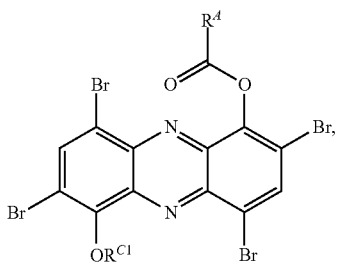

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

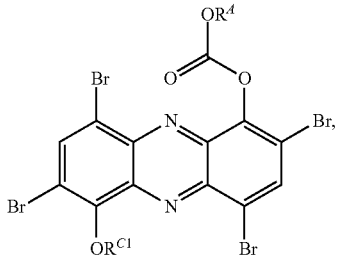

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

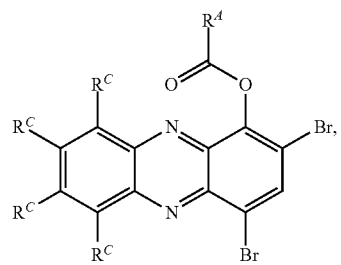

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

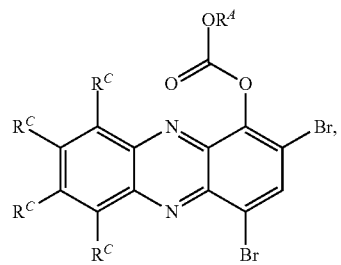

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

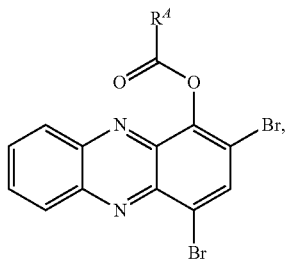

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

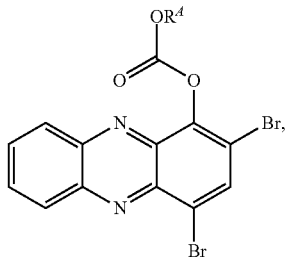

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

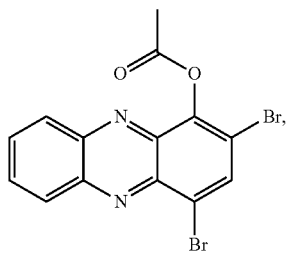 [SMILES: CC(=O)Oc1c(Br)cc(Br)c2nc3ccccc3nc12]

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

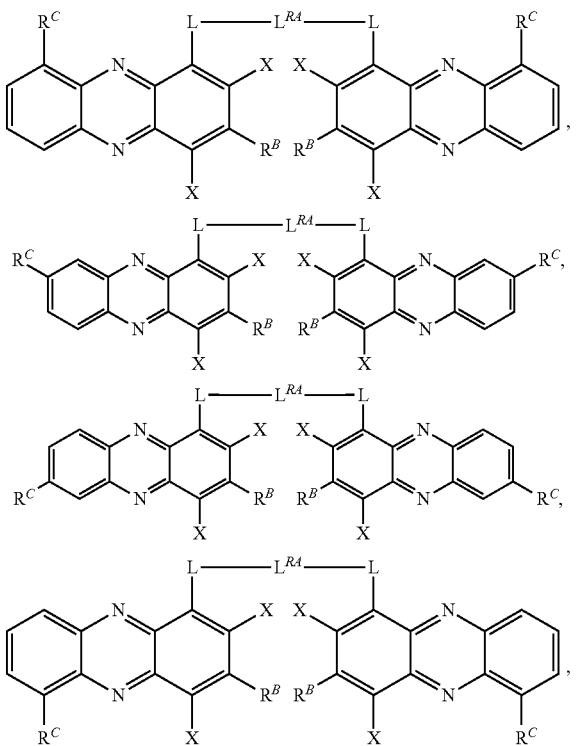

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

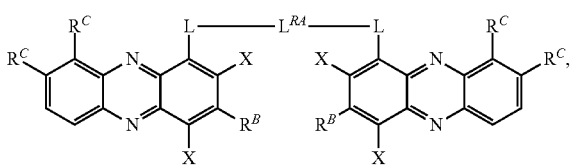

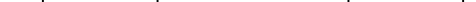

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

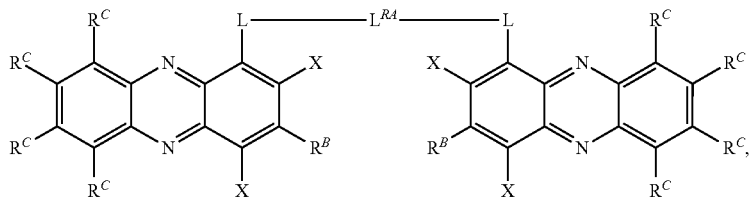

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

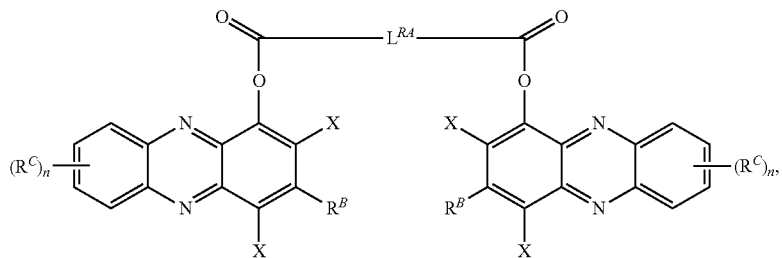

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

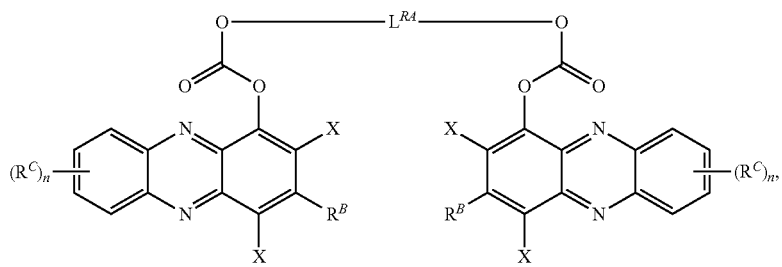

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

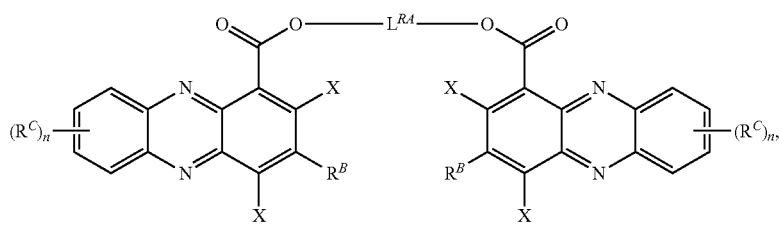

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

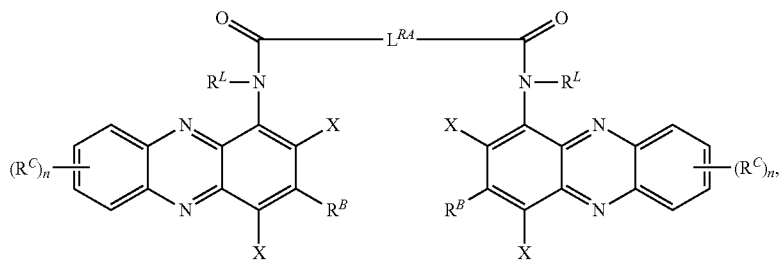

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

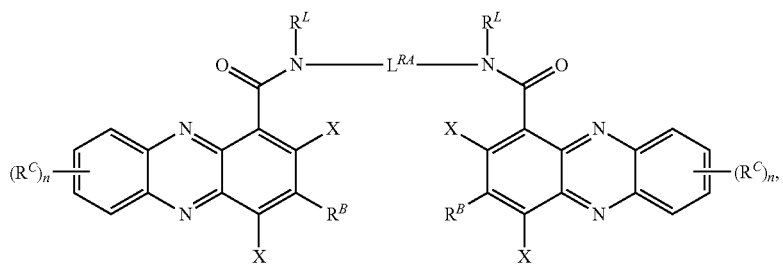

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

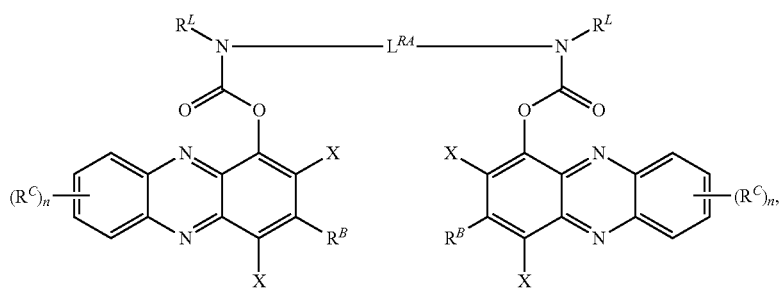

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

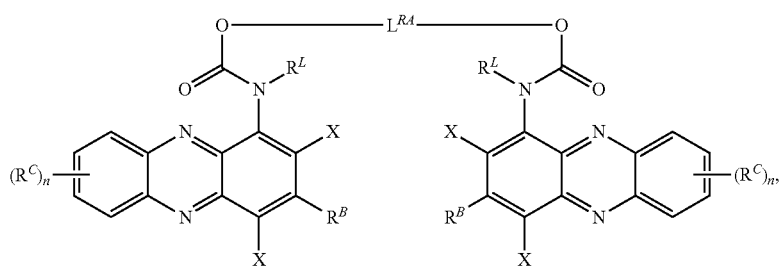

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

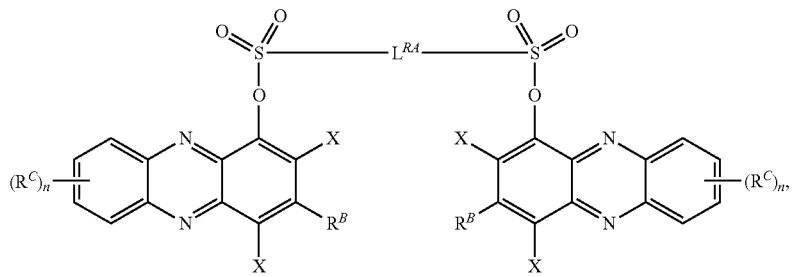

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

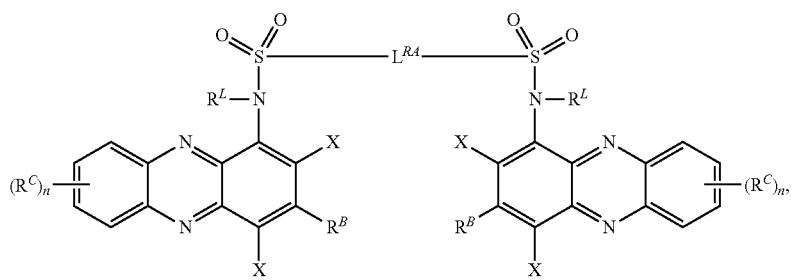

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

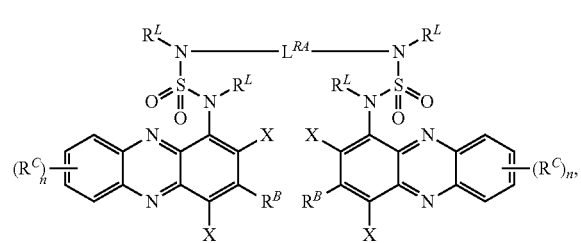

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

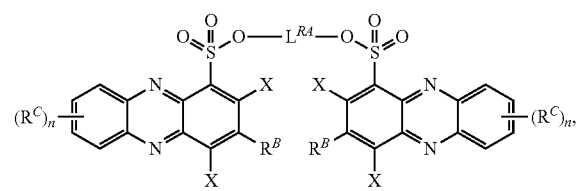

In certain embodiments, the compound of Formula (II) is of the formula:

-continued

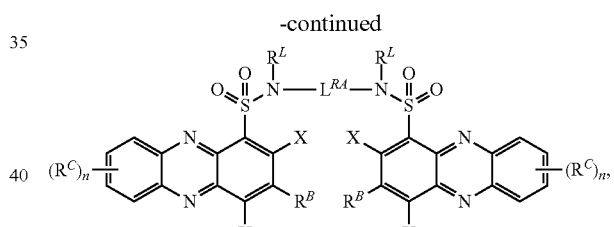

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

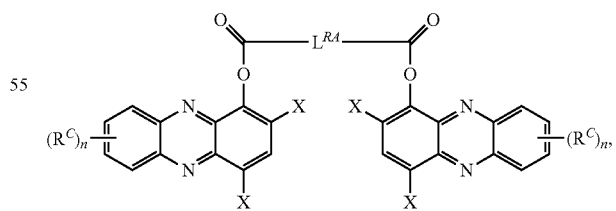

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

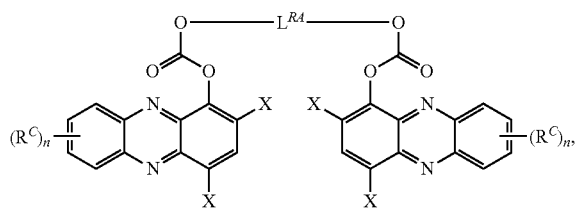

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

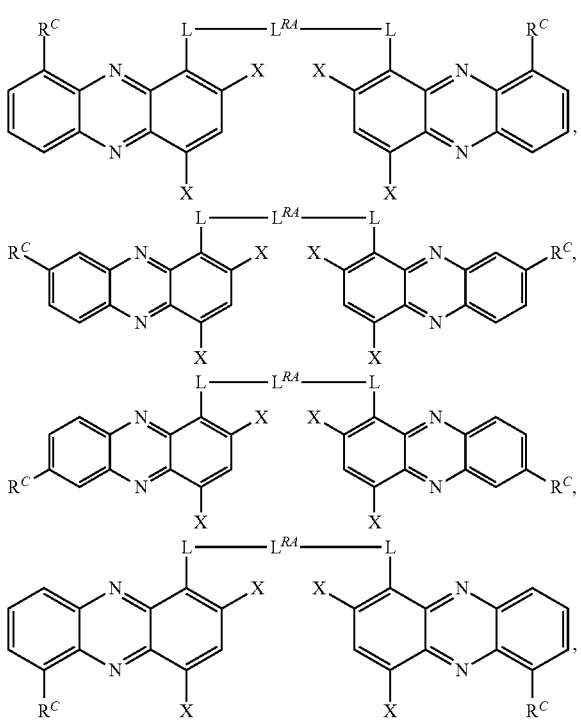

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

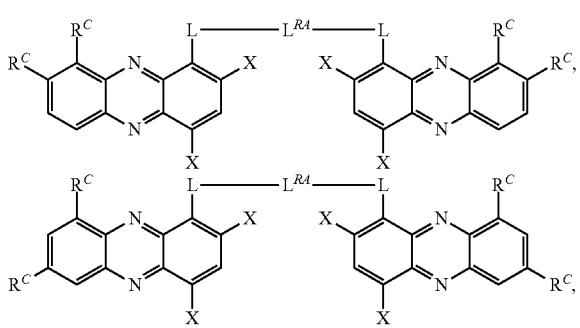

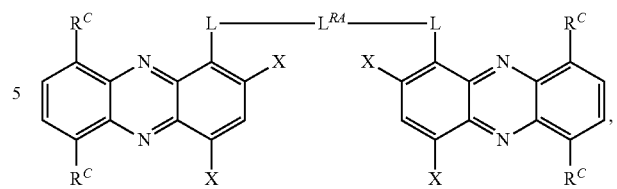

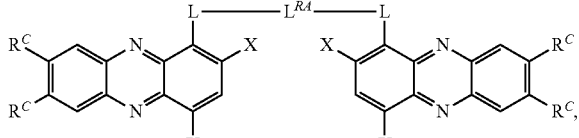

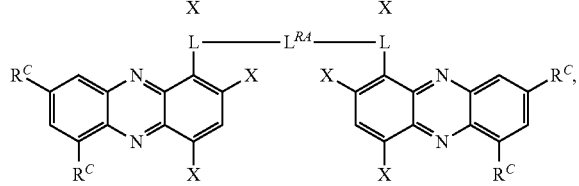

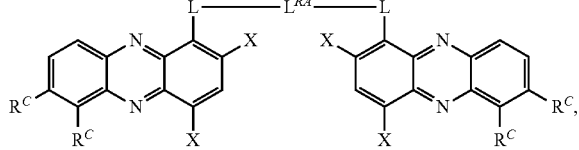

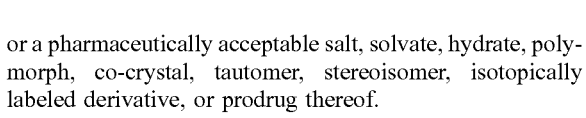

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

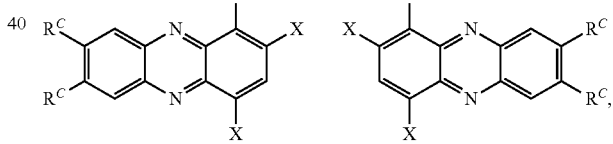

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

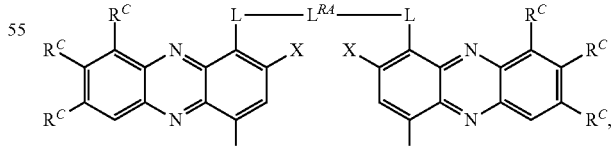

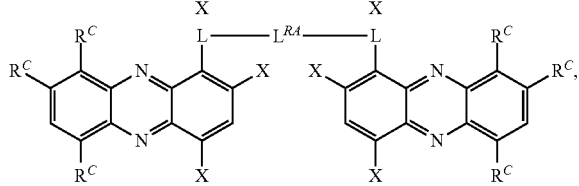

-continued

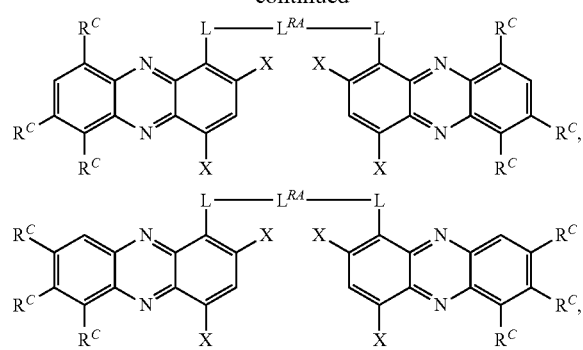

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

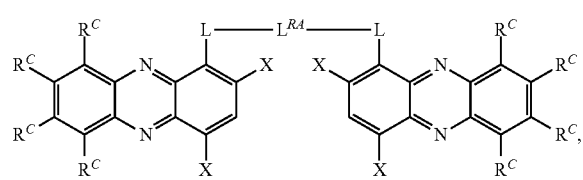

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

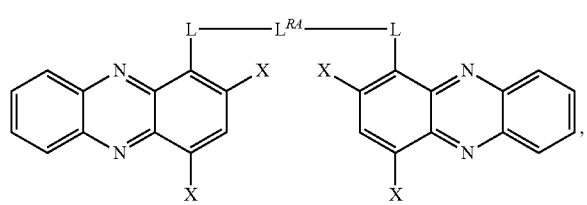

or a pharmaceutically acceptable salt, solvate, hydrate, polymorph, co-crystal, tautomer, stereoisomer, isotopically labeled derivative, or prodrug thereof.

In certain embodiments, the compound of Formula (I) or (II) is of the formula:

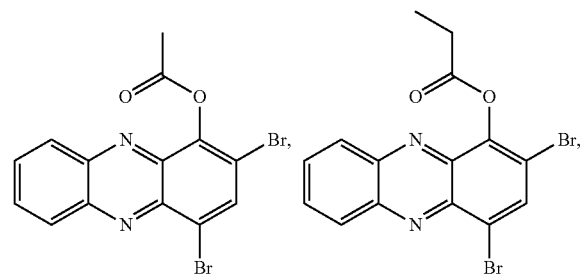

-continued

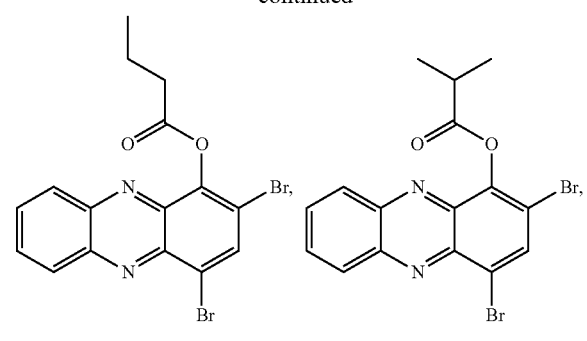

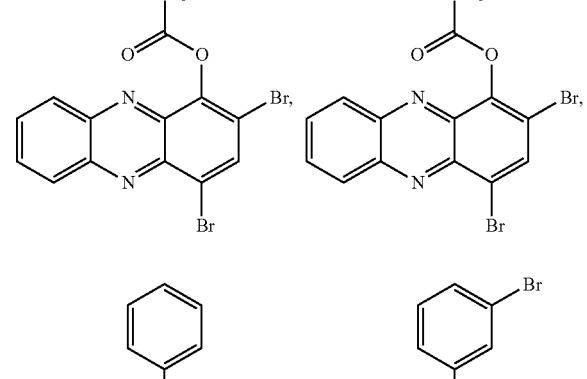

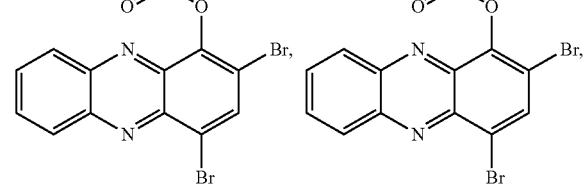

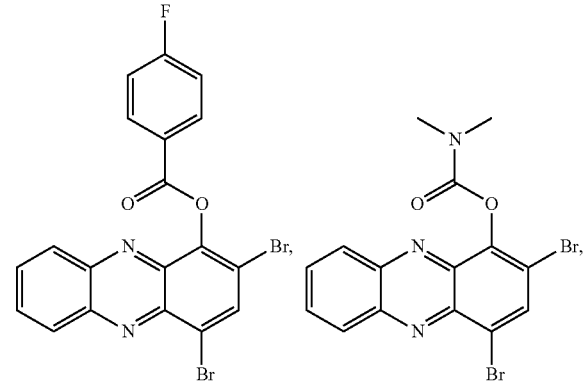

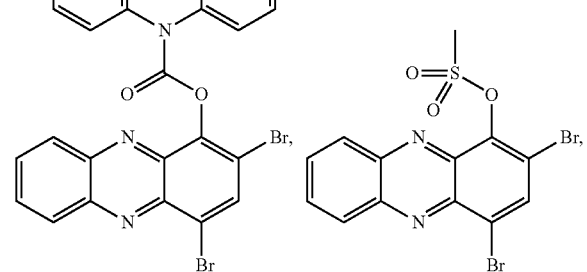

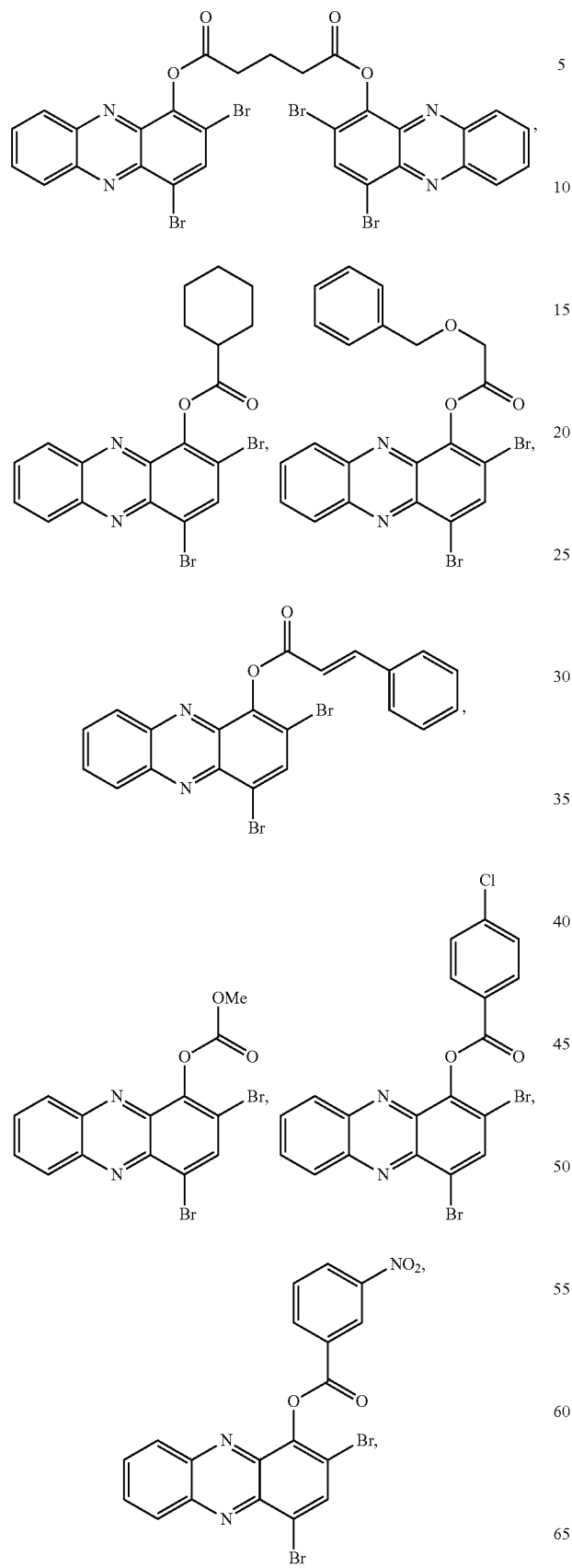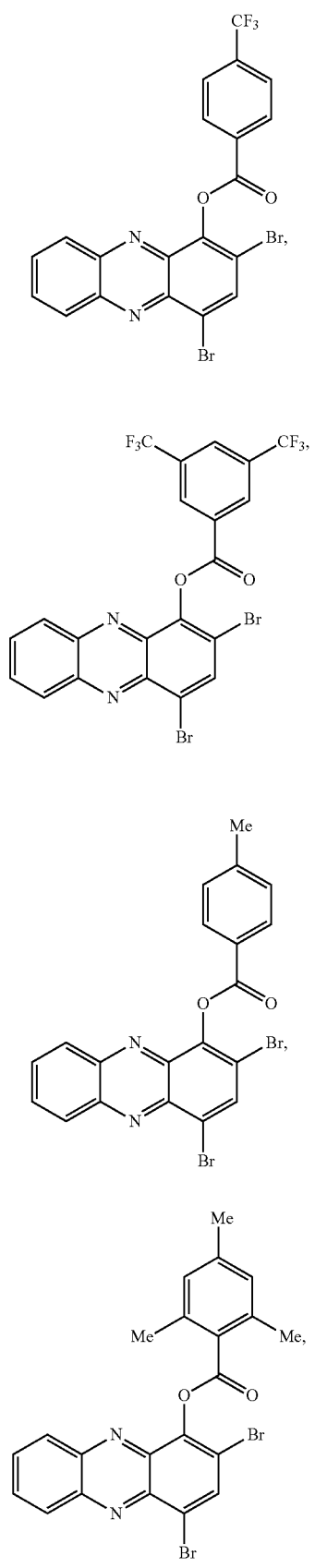

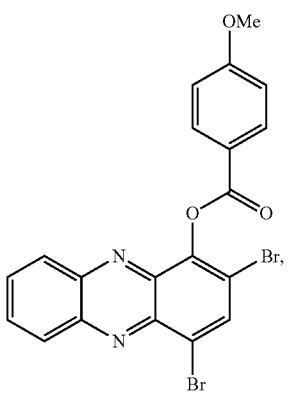

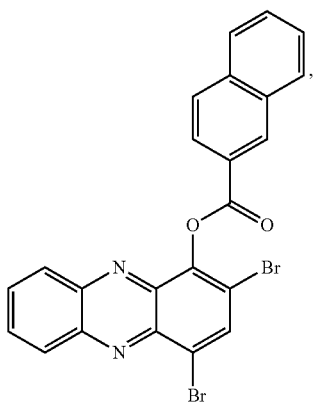

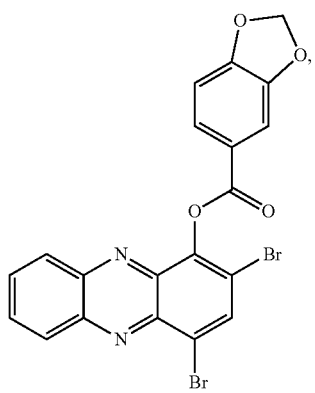

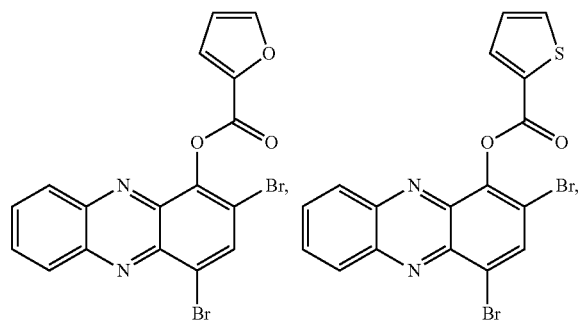

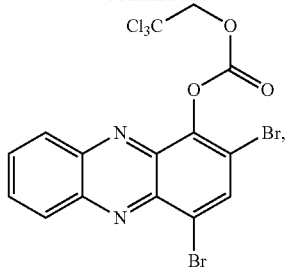

or a pharmaceutically acceptable salt, solvate, hydrate, polymorph, co-crystal, tautomer, stereoisomer, isotopically labeled derivative, or prodrug thereof.

In certain embodiments, the compounds of the invention are the compounds described herein, and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds described herein, and pharmaceutically acceptable salts thereof. In certain embodiments, the compounds of the invention are the compounds of Formula (I) or (II), and pharmaceutically acceptable salts, solvates, hydrates, polymorphs, co-crystals, tautomers, stereoisomers, isotopically labeled derivatives, and prodrugs thereof. In certain embodiments, the compounds of the invention are the compounds of Formula (I) or (II), and pharmaceutically acceptable salts thereof.

In certain embodiments, the compounds of the invention are substantially pure. In certain embodiments, a compound of the invention is at least about 90%, at least about 95%, at least about 97%, at least about 98%, at least about 99%, or at least about 99.5% free of impurities.

The compounds of the invention have been found to be antimicrobial agents (e.g., antibacterial agents). Without wishing to be bound by a particular theory, the compounds of the invention may be redox-active and may generate reactive oxygen species (ROS). The inventive compounds may thus act as microbial warfare agents and inhibit the growth and/or reproduction of or kill a microorganism (e.g., a bacterium, archaeon, protist, fungus, or parasite) by oxidizing and/or reducing molecules (e.g., a catalase, cytokine, nicotinamide adenine dinucleotide phosphate (NADPH), and nicotinamide adenine dinucleotide phosphate (NADP$^+$)) in, near, or around the microorganism. The activity of a compound of the invention against a microorganism may be measured by the minimum inhibitory concentration (MIC) of the compound in inhibiting the viability, growth, or replication of the microorganism. In certain embodiments, the MIC of a compound of the invention is an MIC in inhibiting the viability the microorganism. In certain embodiments, the MIC value of an inventive compound in inhibiting a microorganism is at most about 30 nM, at most about 100 nM, at most about 300 nM, at most about 1 µM, at most about 3 µM, at most about 10 µM, at most about 30 µM, or at most about 100 µM. In certain embodiments, MIC values are measured according to the guidelines of the Clinical and Laboratory Standards Institute (CLSI) (which is incorporated herein by reference) (e.g., a broth microdilution method). In certain embodiments, MIC values are measured by a method described herein.

The activity of a compound of the invention against a microorganism may also be measured by the half maximal inhibitory concentration (IC$_{50}$) of the compound in inhibiting the viability, growth, or replication of the microorganism. In certain embodiments, the $IC_{50}$ of a compound of the invention is an MIC in inhibiting the viability the microorganism. In certain embodiments, the $IC_{50}$ value of an inventive compound in inhibiting a microorganism is at most about 30 nM, at most about 100 nM, at most about 300 nM, at most about 1 µM, at most about 3 µM, at most about 10 µM, at most about 30 µM, or at most about 100 µM. In certain embodiments, $IC_{50}$ values are measured according to the guidelines of the CLSI (e.g., a microdilution method). In certain embodiments, $IC_{50}$ values are measured by a method described herein.

The compounds of the invention may selectively inhibit the growth and/or reproduction of or kill a microorganism. In certain embodiments, a compound of the invention is more active in inhibiting the growth and/or reproduction of or killing a first microorganism (e.g., a microorganism described herein) than in inhibiting the growth and/or reproduction of or killing a host cell. In certain embodiments, a compound of the invention is more active in inhibiting the growth and/or reproduction of or killing a first microorganism than in inhibiting the growth and/or reproduction of or killing a second microorganism. The selectivity of an inventive compound in inhibiting the growth and/or reproduction of or killing a first microorganism over a host cell or a second microorganism may be determined by the quotient of the MIC value of the inventive compound in inhibiting the growth and/or reproduction of or killing the host cell or second microorganism over the MIC value of the inventive compound in inhibiting the growth and/or reproduction of or killing the first microorganism. The selectivity of an inventive compound in inhibiting the growth and/or reproduction of or killing a first microorganism over a host cell or a second microorganism may also be determined by the quotient of the $IC_{50}$ value of the inventive compound in inhibiting the growth and/or reproduction of or killing the host cell or second microorganism over the $IC_{50}$ value of the inventive compound in inhibiting the growth and/or reproduction of or killing the first microorganism. In certain embodiments, the selectivity of an inventive compound in inhibiting the growth and/or reproduction of or killing a first microorganism over a host cell or a second microorganism is at least about 3-fold, at least about 10-fold, at least about 30-fold, at least about 100-fold, at least about 1,000-fold, at least about 10,000-fold, or at least about 100,000-fold.

Pharmaceutical Compositions, Kits, and Administration

The present invention also provides pharmaceutical compositions comprising a compound of the invention (e.g., a compound of Formula (I) or (II), or pharmaceutically acceptable salts thereof), and optionally a pharmaceutically acceptable excipient. In certain embodiments, the compound of the invention is provided in an effective amount in the pharmaceutical composition. In certain embodiments, the effective amount of the compound is a therapeutically effective amount. In certain embodiments, the effective amount of the compound is a prophylactically effective amount. The pharmaceutical compositions of the invention may be useful in the inventive methods. In certain embodiments, the pharmaceutical compositions are useful in treating and/or preventing a microbial infection (e.g., a bacterial infection). In certain embodiments, the pharmaceutical compositions are useful in treating microbial infection. In certain embodiments, the pharmaceutical compositions are useful in preventing a microbial infection. In certain embodiments, the pharmaceutical compositions are useful in inhibiting the growth of a microorganism (e.g., a microorganism described herein). In certain embodiments, the pharmaceutical compositions are useful in inhibiting the reproduction of a microorganism. In certain embodiments, the pharmaceutical compositions are useful in killing a microorganism. In certain embodiments, the pharmaceutical compositions are useful in inhibiting the formation and/or growth of a biofilm. In certain embodiments, the pharmaceutical compositions are useful in reducing or removing a biofilm.

Pharmaceutical compositions described herein can be prepared by any method known in the art of pharmacology. In general, such preparatory methods include the steps of bringing the compound of the invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a microbial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat.

Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents to improve their potency, efficacy, and/or bioavailability, reduce and/or modify their metabolism, inhibit their excretion, and/or modify their distribution within the body. It will also be appreciated that the therapy employed may achieve a desired effect for the same disorder, and/or it may achieve different effects. In certain embodiments, the combination of a compound of the invention and an additional pharmaceutical agent shows a synergistic effect.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents in combination be utilized at levels that do not exceed the levels at which they are utilized individually. In some embodiments, the levels utilized in combination will be lower than those utilized individually.

Exemplary additional pharmaceutical agents include, but are not limited to, antibiotics (e.g., antibacterial agents, antiviral agents, anti-fungal agents), anti-inflammatory agents, anti-pyretic agents, and pain-relieving agents. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is an antibiotic. In certain embodiments, the additional pharmaceutical agent is an antibiotic effective against a microorganism described herein. In certain embodiments, the additional pharmaceutical agent is an antibiotic effective against a bacterium. In certain embodiments, the additional pharmaceutical agent is an antibiotic effective against a Gram-positive bacterium (e.g., a *Staphylococcus* species). In certain embodiments, the additional pharmaceutical agent is an antibiotic effective against a Gram-negative bacterium (e.g., an *Acinetobacter* species). In certain embodiments, the additional pharmaceutical agent is an antibiotic effective against a multidrug-resistant bacterium. In certain embodiments, the additional pharmaceutical agent is a β-lactam antibiotic. In certain embodiments, the additional pharmaceutical agent is a penicillin (i.e., a penam, such as an aminopenicillin (e.g., amoxicillin, an ampicillin (e.g., pivampicillin, hetacillin, bacampicillin, metampicillin, talampicillin), epicillin), a carboxypenicillin (e.g., a carbenicillin (e.g., carindacillin), ticarcillin, temocillin), a ureidopenicillin (e.g., azlocillin, piperacillin, mezlocillin), a mecillinam (e.g., pivmecillinam), sulbenicillin, benzylpenicillin, clometocillin, benzathine benzylpenicillin, procaine benzylpenicillin, azidocillin, penamecillin, phenoxymethylpenicillin, propicillin, benzathine phenoxymethylpenicillin, pheneticillin, a cloxacillin (e.g., dicloxacillin, flucloxacillin), oxacillin, methicillin, nafcillin), a penem (e.g., faropenem), a carbapenem (e.g., biapenem, ertapenem, an antipseudomonal (e.g., doripenem, imipenem, meropenem), panipenem), a cephalosporin (i.e., a cephem, such as cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, a cephamycin (e.g, cefoxitin, cefotetan, cefmetazole), a carbacephem (e.g., loracarbef), cefixime, ceftriaxone, an antipseudomonal (e.g., ceftazidime, cefoperazone), cefcapene, cefdaloxime, cefdinir, cefditoren, cefetamet, cefmenoxime, cefodizime, cefotaxime, cefpimizole, cefpiramide, cefpodoxime, cefsulodin, cefteram, ceftibuten, ceftiolene, ceftizoxime, an oxacephem (e.g., flomoxef, latamoxef), cefepime, cefozopran, cefpirome, cefquinome, ceftobiprole, ceftaroline fosamil, ceftiofur, cefquinome, cefovecin), a monobactam (e.g., aztreonam, tigemonam, carumonam, nocardicin A), an aminoglycoside (e.g., amikacin, gentamicin, kanamycin, neomycin, netilmicin, tobramycin, paromomycin, spectinomycin), an ansamycin (e.g., geldanamycin, herbimycin, rifaximin), a glycopeptide (e.g., teicoplanin, vancomycin, telavancin), a lincosamide (e.g., clindamycin, lincomycin), a lipopeptide (e.g., daptomycin), a macrolide (e.g., azithromycin, clarithromycin, dirithromycin, erythromycin, roxithromycin, troleandomycin, telithromycin, spiramycin), a nitrofuran (e.g., furazolidone, nitrofurantoin), an oxazolidonone (e.g., linezolid, posizolid, radezolid, torezolid), a polypeptide (e.g., bacitracin, colistin, polymyxin B), a quinolone (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin), a sulfonamide (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim, sulfonamidochrysoidine), a tetracycline (e.g., demeclocycline, doxycycline, minocycline, oxytetracycline, tetracycline), clofazimine, dapsone, capreomycin, cycloserine, ethambutol, ethionamide, isoniazid, pyrazinamide, rifampin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, or trimethoprim. In certain embodiments, the additional pharmaceutical agent is an antiviral agent. In certain embodiments, the additional pharmaceutical agent is (−)-Oseltamivir, β-D-ribofuranose, 1-acetate 2,3,5-tribenzoate, 1-Docosanol, 2-Amino-6-chloropurine, 5-Iodo-2'-deoxyuridine, 6-Chloropurine, Abacavir sulfate, Abacavir-epivir mixt., Acyclovir, Acyclovir sodium, Adefovir dipivoxil, Amantadine (e.g., Amantadine hydrochloride), Amantadine hydrochloride, anti-HIV agent (e.g., Abacavir, Amprenavir, Atazanavir, Azidothymidine, Bryostatin (e.g., Bryostatin 1, Bryostatin 10, Bryostatin 11, Bryostatin 12, Bryostatin 13, Bryostatin 14, Bryostatin 15, Bryostatin 16, Bryostatin 17, Bryostatin 18, Bryostatin 19, Bryostatin 2, Bryostatin 20, Bryostatin 3, Bryostatin 4, Bryostatin 5, Bryostatin 6, Bryostatin 7, Bryostatin 8, Bryostatin 9), Dideoxycytidine, Dideoxyinosine, Efavirenz, Indinavir, Lamivudine, Lopinavir, Nevirapine, Ritonavir, Saquinavir, Stavudine, Tenofovir), Azauridine, ombivir, Deoxynojirimycin, Docosanol, Fomivirsen sodium, Foscarnet, Ganciclovir, Integrase inhibitors (e.g., SCITEP, Chloropeptin I, Complestatin, Dolutegravir, Elvitegravir, L 708906, L 731988, MK 2048, Raltegravir, Raltegravir potassium), MK 5172, MK 8742, Palivizumab, Pegylated interferon alfa-2b, Phosphonoacetic acid, Ribavirin, Simeprevir, Sofosbuvir, Tubercidin, Vidarabine, or virus entry inhibitor (e.g., Enfuvirtide, Maraviroc). In certain embodiments, the additional pharmaceutical agent is a fungicide. In certain embodiments, the additional pharmaceutical agent is (−)-Fumagillin, (−)-Metalaxyl, 1,2,5-Fluorocytosine, Acrisorcin, Anilazine, Antifouling agent, Azoxystrobin, Benomyl, Bordeaux mixture, Captan, Carbendazim, Caspofungin acetate, Chlorothalonil, Clotrimazole, Dichlofluanid, Dinocap, Dodine, Fenhexamid, Fenpropimorph, Ferbam, Fluconazole, Fosetyl Al, Griseofulvin, Guanidine (e.g., Agmatine, Amiloride hydrochloride, Biguanide (e.g., Imidodicarbonimidic diamide, N,N-dimethyl-,hydrochloride (1:1) (e.g., Metformin hydrochloride), Metformin), Cimetidine, Guanethidine, Guanfacine, Guanidine, Guanidinium, Methylguanidine, Sulfaguanidine), Iprobenfos, Iprodione, Isoprothiolane, Itraconazole, Ketoconazole, Mancozeb, Metalaxyl, Metiram, Miconazole, Natamycin, Nystatin, Oxycarboxine, Pentachloronitrobenzene, Prochloraz, Procymidone, Propiconazole, Pyrazophos, Reduced viscotoxin A3, Salicylanilide, Tebuconazole, Terbinafine, Thiabendazole, Thiophanate, Thiophanate methyl, Triadimefon, Vinclozolin, or Voriconazole. In certain embodiments, the additional pharmaceutical agent is a protozoacide. In certain embodiments, the additional pharmaceutical agent is Amebicide, Antimalarial (e.g., Artemisinin, Chloroquine (e.g., Chloroquine phosphate), Mefloquine, Sulfadoxine), Coccidiostat, Leishmanicide, Trichomonacide, or Trypanosomicide (e.g., Eflornithine). In certain embodiments, the additional pharmaceutical agent is a parasiticide. In certain embodiments, the additional pharmaceutical agent is antihelmintic (e.g., Abamectin, Dimethylformocarbothialdine, Niclosamide, Schistosomicide), protozoacide (e.g., Amebicide, antimalarial (e.g., Artemisinin, chloroquine (e.g., chloroquine phosphate), Mefloquine, Sulfadoxine), coccidiostat, leishmanicide, trichomonacide, or trypanosomicide (e.g., Eflomithine)).

Also encompassed by the invention are kits (e.g., pharmaceutical packs). The kits provided may comprise a compound or pharmaceutical composition of the invention and a container (e.g., a vial, ampule, bottle, syringe, dispenser package, tube, inhaler, and/or other suitable container). In some embodiments, a kit of the invention further includes a second container comprising an excipient (e.g., pharmaceutically acceptable excipient) for dilution or suspension of an inventive compound or pharmaceutical composition. In some embodiments, the compound or pharmaceutical composition of the invention provided in a first container and a second container are combined to form one unit dosage form.

In one aspect, the present invention provides kits including a first container comprising a compound or pharmaceutical composition of the invention. In certain embodiments, a kit of the invention includes a first container comprising a compound of Formula (I) or (II), or a pharmaceutically acceptable salt thereof, or a pharmaceutical composition thereof.

In certain embodiments, the kits are useful in treating and/or preventing a microbial infection in a subject in need thereof. In certain embodiments, the kits are useful in treating a microbial infection in a subject in need thereof. In certain embodiments, the kits are useful in preventing a microbial infection in a subject in need thereof. In certain embodiments, the microbial infection is a bacterial infection. In certain embodiments, the bacterial infection is an infection caused by a Gram-positive bacterium. In certain embodiments, the bacterial infection is an infection caused by a Gram-negative bacterium. In certain embodiments, the kits are useful in inhibiting the growth of a microorganism. In certain embodiments, the kits are useful in inhibiting the reproduction of a microorganism. In certain embodiments, the kits are useful in killing a microorganism. In certain embodiments, the kits are useful in inhibiting the formation and/or growth of a biofilm. In certain embodiments, the kits are useful in reducing or removing a biofilm. In certain embodiments, the kits are useful for screening a library of compounds to identify a compound that is useful in the methods of the invention. In certain embodiments, the kits further include instructions for using the kit (e.g., for administering to a subject in need of treatment of a microbial infection a compound or pharmaceutical composition of the invention, for contacting a microorganism with a compound or pharmaceutical composition of the invention, or for contacting a biofilm with a compound or pharmaceutical composition of the invention). The kits may also include information as required by a regulatory agency such as the U.S. Food and Drug Administration (FDA). In certain embodiments, the information included in the kits is prescribing information. In certain embodiments, the kits and instructions provide for treating and/or preventing a microbial infection in a subject in need thereof. In certain embodiments, the kits and instructions provide for treating a microbial infection in a subject in need thereof. In certain embodiments, the kits and instructions provide for preventing a microbial infection in a subject in need thereof. In certain embodiments, the kits and instructions provide for inhibiting the growth of a microorganism. In certain embodiments, the kits and instructions provide for inhibiting the reproduction of a microorganism. In certain embodiments, the kits and instructions provide for killing a microorganism. In certain embodiments, the kits and instructions provide for screening a library of compounds to identify a compound that is useful in the methods of the invention. The kit of the invention may include one or more additional agents described herein (e.g., additional pharmaceutical agents) as a separate composition.

Methods of Treatment and Uses

The present invention also provides methods for treating and/or preventing a microbial infection (e.g., a bacterial infection) in a subject in need thereof. In certain embodiments, the present invention provides methods for treating a microbial infection in a subject in need thereof. In certain embodiments, the microbial infection is treated by the inventive methods. In certain embodiments, the present invention provides methods for preventing a microbial infection in a subject in need thereof. In certain embodiments, the microbial infection is prevented by the inventive methods.

In certain embodiments, the subject described herein is an animal. In certain embodiments, the subject is a non-human animal. In certain embodiments, the subject is a mammal. In certain embodiments, the subject is a human. In certain embodiments, the subject is a human with cystic fibrosis. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent, dog, or non-human primate. In certain embodiments, the subject is a non-human transgenic animal, such as a transgenic mouse or transgenic pig.

In certain embodiments, the methods of the invention include administering to a subject in need thereof an effective amount of a compound or pharmaceutical composition of the invention. In certain embodiments, the methods of the invention include administering to a subject in need thereof an effective amount of a compound of Formula (I) or (II), or a pharmaceutically acceptable salt thereof, or a pharmaceutical composition thereof. In certain embodiments, the methods of the invention include administering to a subject in need thereof a therapeutically effective amount of a compound of the invention, or a pharmaceutical composition thereof. In certain embodiments, the methods of the invention include administering to a subject in need thereof a prophylactically effective amount of a compound of the invention, or a pharmaceutical composition thereof.

In certain embodiments, the microbial infection that is treated and/or prevented by the inventive methods or using the inventive compounds or pharmaceutical compositions thereof is caused by a multidrug-resistant microorganism. In certain embodiments, the microbial infection is a microbial respiratory tract infection. In certain embodiments, the microbial infection is microbial pneumonia. In certain embodiments, the microbial infection is microbial sinusitis. In certain embodiments, the microbial infection is a microbial gastrointestinal tract infection. In certain embodiments, the microbial infection is microbial diarrhea. In certain embodiments, the microbial infection is a microbial urogenital tract infection. In certain embodiments, the microbial infection is a microbial bloodstream infection. In certain embodiments, the microbial infection is microbial hemolytic uremic syndrome. In certain embodiments, the microbial infection is microbial endocarditis. In certain embodiments, the microbial infection is a microbial ear infection. In certain embodiments, the microbial infection is a microbial skin infection. In certain embodiments, the microbial infection is a microbial oral infection. In certain embodiments, the microbial infection is a microbial dental infection. In certain embodiments, the microbial infection is gingivitis. In certain embodiments, the microbial infection is dental plaque caused by a microorganism. In certain embodiments, the microbial infection is meningitis. In certain embodiments, the microbial infection is a microbial wound or surgical site infection. In certain embodiments, the microbial infection is a microbial burn wound infection. In certain embodiments, the microbial infection is a microbial infection associated with cystic fibrosis. In certain embodiments, the microbial infection is a microbial infection associated with an implanted device. In certain embodiments, the microbial infection is a microbial infection associated with a dental implant. In certain embodiments, the microbial infection is a microbial infection associated with a catheter. In certain embodiments, the microbial infection is a microbial infection associated with a heart valve. In certain embodiments, the microbial infection is a microbial infection associated with an intrauterine device. In certain embodiments, the microbial infection is a microbial infection associated with a joint prosthesis. In certain embodiments, the microbial infection is a bacterial infection. In certain embodiments, the bacterial infection is caused by a Gram-positive bacterium (e.g., a Gram-positive bacterium described herein). In certain embodiments, the bacterial infection is caused by a Gram-negative bacterium (e.g., a Gram-negative bacterium described herein). In certain embodiments, the bacterial infection is caused by a multidrug-resistant bacterium. In certain embodiments, the bacterial infection is a methicillin-resistant *Staphylococcus aureus* (MRSA)-related infection. In certain embodiments, the bacterial infection is caused by *Acinetobacter baumannii*. In certain embodiments, the microbial infection is caused by an archaeon. In certain embodiments, the microbial infection is caused by a protist. In certain embodiments, the microbial infection is caused by a protozoon. In certain embodiments, the microbial infection is caused by an alga. In certain embodiments, the microbial infection is caused by a fungus. In certain embodiments, the microbial infection is caused by yeast. In certain embodiments, the microbial infection is caused by a mold. In certain embodiments, the microbial infection is caused by a parasite. In certain embodiments, the microbial infection is a microbial infection associated with a biofilm.

Another aspect of the present invention relates to methods of inhibiting the growth of a microorganism using a compound of the invention, or a pharmaceutical composition thereof. In certain embodiments, an inventive method selectively inhibits the growth of a first microorganism (e.g., a microorganism described herein), compared to the inhibition of the growth of a host cell or a second microorganism. In certain embodiments, the growth of a microorganism is inhibited by the inventive methods. In certain embodiments, the growth of a first microorganism is selectively inhibited by the inventive methods, compared to the inhibition of the growth of a host cell or a second microorganism.

Another aspect of the present invention relates to methods of inhibiting the reproduction of a microorganism using a compound of the invention, or a pharmaceutical composition thereof. In certain embodiments, an inventive method selectively inhibits the reproduction of a first microorganism (e.g., a microorganism described herein), compared to the inhibition of the reproduction of a host cell or a second microorganism. In certain embodiments, the reproduction of a microorganism is inhibited by the inventive methods. In certain embodiments, the reproduction of a first microorganism is selectively inhibited by the inventive methods, compared to the inhibition of the reproduction of a host cell or a second microorganism.

Another aspect of the present invention relates to methods of inhibiting the viability of a microorganism using a compound of the invention, or a pharmaceutical composition thereof. In certain embodiments, an inventive method selectively inhibits the viability of a first microorganism (e.g., a microorganism described herein), compared to the inhibition of the viability of a host cell or a second microorganism. In certain embodiments, the viability of a microorganism is inhibited by the inventive methods. In certain embodiments, the viability of a first microorganism is selectively inhibited by the inventive methods, compared to the inhibition of the viability of a host cell or a second microorganism.

Another aspect of the present invention relates to methods of killing a microorganism using a compound of the invention, or a pharmaceutical composition thereof. In certain embodiments, an inventive method selectively kills a first microorganism (e.g., a microorganism described herein), compared to the killing of a host cell or a second microorganism. In certain embodiments, a microorganism is killed by the inventive methods. In certain embodiments, a first microorganism is selectively killed by the inventive methods, compared to the killing of a host cell or a second microorganism.

In certain embodiments, the methods of the invention include contacting a microorganism with an effective amount of a compound or pharmaceutical composition of the invention. In certain embodiments, the methods of the invention include contacting a microorganism with an effective amount of a compound of Formula (I) or (II), or a pharmaceutically acceptable salt thereof, or a pharmaceutical composition thereof. In certain embodiments, the methods of the invention include contacting a microorganism with a therapeutically effective amount of a compound of the invention, or a pharmaceutical composition thereof. In certain embodiments, the methods of the invention include contacting a microorganism with a prophylactically effective amount of a compound of the invention, or a pharmaceutical composition thereof.

In a growth process of a microorganism (e.g., a bacterium), the microorganism may secrete viscous substances to form a biofilm. A biofilm is typically formed on a living or non-living, solid or liquid surface. In certain embodiments, a biofilm is formed on the surface of a biological sample (e.g., a tooth, oral soft tissue, middle ear, gastrointestinal tract, urogenital tract, respiratory tract, or eye). In certain embodiments, a biofilm is formed on the surface of an implanted device (e.g., a dental implant, catheter, heart valve, intrauterine device, or joint prosthesis). In certain embodiments, the biofilm is present in vitro. In certain embodiments, the biofilm is present in vivo. In certain embodiments, the biofilm described herein comprises a microorganism. In certain embodiments, the biofilm comprises a bacterium. Free-floating microorganisms may accumulate on a surface, and the resulting biofilm may grow. In a biofilm, the concentration of microorganisms may be high and/or the resistance of the microorganisms in the biofilm to antimicrobial agents may be high. Antimicrobials may be inactivated or fail to penetrate into the biofilm. Therefore, microbial infections associated with a biofilm (e.g., microbial infections caused by a biofilm) are typically more difficult to treat than microbial infections not associated with a biofilm.

Another aspect of the present invention relates to methods of inhibiting the formation of a biofilm using a compound of the invention, or a pharmaceutical composition thereof. In certain embodiments, the formation of a biofilm is inhibited by the inventive methods.

Another aspect of the present invention relates to methods of inhibiting the growth of a biofilm using a compound of the invention, or a pharmaceutical composition thereof. In certain embodiments, the growth of a biofilm is inhibited by the inventive methods.

Another aspect of the present invention relates to methods of reducing a biofilm using a compound of the invention, or a pharmaceutical composition thereof. In certain embodiments, a biofilm is reduced by the inventive methods, e.g., reduced by at least 10%, at least 20%, at least 30%, at least 50%, at least 70%, at least 90%, at least 99%, at least 99.9%, or at least 99.99%, in terms of the volume of the biofilm. In certain embodiments, a biofilm is reduced by the inventive methods by not more than 10%, not more than 20%, not more than 30%, not more than 50%, not more than 70%, not more than 90%, not more than 99%, not more than 99.9%, or not more than 99.99%, in terms of the volume of the biofilm. In certain embodiments, a biofilm is reduced by the inventive methods by at least 10%, at least 20%, at least 30%, at least 50%, at least 70%, at least 90%, at least 99%, at least 99.9%, or at least 99.99%, in terms of the number of microorganisms (e.g., bacteria) in the biofilm. In certain embodiments, a biofilm is reduced by the inventive methods by not more than 10%, not more than 20%, not more than 30%, not more than 50%, not more than 70%, not more than 90%, not more than 99%, not more than 99.9%, or not more than 99.99%, in terms of the number of microorganisms (e.g., bacteria) in the biofilm.

Another aspect of the present invention relates to methods of removing a biofilm (e.g., eradicating a biofilm (e.g., reducing the volume of the biofilm by at least 99% and/or killing essentially all (e.g., at least 99%) of the microorganisms (e.g., bacteria) in the biofilm)) using a compound of the invention, or a pharmaceutical composition thereof. In certain embodiments, a biofilm is removed by the inventive methods. In certain embodiments, a biofilm reduced or removed by a method of the invention does not regrow one day, two days, four days, one week, two weeks, three weeks, or one month subsequent to the biofilm being subject to the method.

In certain embodiments, the methods of the invention include contacting a biofilm with an effective amount of a compound or pharmaceutical composition of the invention. In certain embodiments, the methods of the invention include contacting a biofilm with an effective amount of a compound of Formula (I) or (II), or a pharmaceutically acceptable salt thereof, or a pharmaceutical composition thereof. In certain embodiments, the methods of the invention include contacting a biofilm with a therapeutically effective amount of a compound of the invention, or a pharmaceutical composition thereof. In certain embodiments, the methods of the invention include contacting a biofilm with a prophylactically effective amount of a compound of the invention, or a pharmaceutical composition thereof.

In certain embodiments, the microorganism described herein is a bacterium. In certain embodiments, the bacterium is a Gram-positive bacterium. In certain embodiments, the bacterium is a multidrug-resistant bacterium. In certain embodiments, the bacterium is a *Staphylococcus* species. In certain embodiments, the bacterium is a *Staphylococcus aureus* (*S. aureus*) strain. In certain embodiments, the bacterium is ATCC 25923. In certain embodiments, the bacterium is methicillin-resistant *Staphylococcus aureus* (MRSA). In certain embodiments, the bacterium is the methicillin-resistant *Staphylococcus aureus* clinical isolate (MRSA-2, a clinical isolate from a patient treated at Shands Hospital; obtained from the Emerging Pathogens Institute at the University of Florida), such as the methicillin-resistant *Staphylococcus aureus* clinical isolate reported in Abouelhassan et al., *Bioorg. Med. Chem. Lett.*, 2014, 24, 5076. In certain embodiments, the bacterium is a *Staphylococcus epidermidis* (*S. epidermidis*) strain. In certain embodiments, the bacterium is ATCC 12228. In certain embodiments, the bacterium is a *Staphylococcus auricularis, Staphylococcus carnosus, Staphylococcus condimenti, Staphylococcus massiliensis, Staphylococcus piscifermentans, Staphylococcus simulans, Staphylococcus capitis, Staphylococcus caprae, Staphylococcus saccharolyticus, Staphylococcus devriesei, Staphylococcus haemolyticus, Staphylococcus hominis, Staphylococcus chromogenes, Staphylococcus felis, Staphylococcus delphini, Staphylococcus hyicus, Staphylococcus intermedius, Staphylococcus lutrae, Staphylococcus microti, Staphylococcus muscae, Staphylococcus pseudintermedius, Staphylococcus rostri, Staphylococcus schleiferi, Staphylococcus lugdunensis, Staphylococcus arlettae, Staphylococcus cohnii, Staphylococcus equorum, Staphylococcus gallinarum, Staphylococcus kloosii, Staphylococcus leei, Staphylococcus nepalensis, Staphylococcus saprophyticus, Staphylococcus succinus, Staphylococcus xylosus, Staphylococcus fleurettii, Staphylococcus lentus, Staphylococcus sciuri, Staphylococcus stepanovicii, Staphylococcus vitulinus, Staphylococcus simulans, Staphylococcus pasteuri*, or *Staphylococcus warneri* strain. In certain embodiments, the bacterium is a *Streptococcus* species. In certain embodiments, the bacterium is a *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus viridans*, or *Streptococcus zooepidemicus* strain. In certain embodiments, the bacterium is an *Entero-* coccus species. In certain embodiments, the bacterium is an *Enterococcus avium, Enterococcus durans, Enterococcus faecalis, Enterococcus faecium, Enterococcus gallinarum, Enterococcus hirae,* or *Enterococcus solitarius* strain. In certain embodiments, the bacterium is a *Listeria* species. In certain embodiments, the bacterium is a *Listeria fleischmannii, Listeria grayi, Listeria innocua, Listeria ivanovii, Listeria marthii, Listeria monocytogenes, Listeria rocourtiae, Listeria seeligeri, Listeria weihenstephanensis,* or *Listeria welshimeri* strain. In certain embodiments, the bacterium is a *Clostridium* species. In certain embodiments, the bacterium is a *Clostridium acetobutylicum, Clostridium argentinense, Clostridium aerotolerans, Clostridium baratii, Clostridium beijerinckii, Clostridium bifermentans, Clostridium botulinum, Clostridium butyricum, Clostridium cadaveris, Clostridium cellulolyticum, Clostridium chauvoei, Clostridium clostridioforme, Clostridium colicanis, Clostridium difficile, Clostridium estertheticum, Clostridium fallax, Clostridium feseri, Clostridium formicaceticum, Clostridium histolyticum, Clostridium innocuum, Clostridium kluyveri, Clostridium ljungdahlii, Clostridium lavalense, Clostridium leptum, Clostridium novyi, Clostridium oedematiens, Clostridium paraputrificum, Clostridium perfringens* (Alias: *Clostridium welchii*), *Clostridium phytofermentans, Clostridium piliforme, Clostridium ragsdalei, Clostridium ramosum, Clostridium scatologenes, Clostridium septicum, Clostridium sordellii, Clostridium sporogenes, Clostridium sticklandii, Clostridium tertium, Clostridium tetani, Clostridium thermocellum, Clostridium thermosaccharolyticum,* or *Clostridium tyrobutyricum* strain. In certain embodiments, the bacterium is a Gram-negative bacterium. In certain embodiments, the Gram-negative bacterium is an *Escherichia* species. In certain embodiments, the Gram-negative bacterium is an *Escherichia coli* (*E. coli*) strain (e.g., ATCC 33475, K-12, CFT073, ATCC 43895). In certain embodiments, the Gram-negative bacterium is an *Escherichia albertii* strain, *Escherichia blattae* strain, *Escherichia fergusonii* strain, *Escherichia hermannii* strain, or *Escherichia vulneris* strain. In certain embodiments, the Gram-negative bacterium is a *Pseudomonas* species. In certain embodiments, the Gram-negative bacterium is a *Pseudomonas aeruginosa* strain. In certain embodiments, the Gram-negative bacterium is a *Pseudomonas alcaligenes* strain, *Pseudomonas anguilliseptica* strain, *Pseudomonas argentinensis* strain, *Pseudomonas borbori* strain, *Pseudomonas citronellolis* strain, *Pseudomonas flavescens* strain, *Pseudomonas mendocina* strain, *Pseudomonas nitroreducens* strain, *Pseudomonas oleovorans* strain, *Pseudomonas pseudoalcaligenes* strain, *Pseudomonas resinovorans* strain, *Pseudomonas straminea* strain, *Pseudomonas chlororaphis* strain, *Pseudomonas fluorescens* strain, *Pseudomonas pertucinogena* strain, *Pseudomonas putida* strain, *Pseudomonas stutzeri* strain, or *Pseudomonas syringae* strain. In certain embodiments, the Gram-negative bacterium is a *Klebsiella* species. In certain embodiments, the Gram-negative bacterium is a *Klebsiella granulomatis* strain, *Klebsiella oxytoca* strain, *Klebsiella pneumoniae* strain, *Klebsiella terrigena* strain, or *Klebsiella planticola* strain. In certain embodiments, the Gram-negative bacterium is a *Salmonella* species. In certain embodiments, the Gram-negative bacterium is a *Salmonella bongori* strain or *Salmonella enterica* strain, e.g., *Salmonella typhi*. In certain embodiments, the Gram-negative bacterium is an *Acinetobacter* species. In certain embodiments, the Gram-negative bacterium is an *Acinetobacter baumannii* strain. In certain embodiments, the Gram-negative bacterium is an *Acinetobacter baylyi* strain, *Acinetobacter bouvetii* strain, *Acinetobacter calcoaceticus* strain, *Acinetobacter gerneri* strain, *Acinetobacter grimontii* strain, *Acinetobacter haemolyticus* strain, *Acinetobacter johnsonii* strain, *Acinetobacter junii* strain, *Acinetobacter lwoffii* strain, *Acinetobacter parvus* strain, *Acinetobacter pittii* strain, *Acinetobacter radioresistens* strain, *Acinetobacter schindleri* strain, *Acinetobacter tandoii* strain, *Acinetobacter tjernbergiae* strain, *Acinetobacter towneri* strain, *Acinetobacter ursingii* strain, or *Acinetobacter gyllenbergii* strain.

In certain embodiments, the microorganism described herein is an archaeon. In certain embodiments, the microorganism is a protist. In certain embodiments, the microorganism is a protozoon. In certain embodiments, the microorganism is an alga. In certain embodiments, the microorganism is a fungus. In certain embodiments, the microorganism is yeast. In certain embodiments, the microorganism is a mold. In certain embodiments, the microorganism is a parasite.

In certain embodiments, the microorganism described herein is present in vitro. In certain embodiments, the microorganism is present in vivo.

In certain embodiments, a method of the invention is an in vitro method. In certain embodiments, a method of the invention is an in vivo method.

In another aspect, the present invention provides uses of the compounds and pharmaceutical compositions of the invention for manufacturing a medicament for treating and/or preventing a microbial infection (e.g., a bacterial infection).

In another aspect, the present invention provides the compounds and pharmaceutical compositions of the invention for use in methods of treating and/or preventing a microbial infection (e.g., a bacterial infection).

In another aspect, the present invention provides the compounds and pharmaceutical compositions of the invention for treating and/or preventing a microbial infection (e.g., a bacterial infection).

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1

Synthesis of the Compounds

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

All reactions were carried out under an atmosphere of argon unless otherwise specified. Anhydrous solvents were transferred via syringe to flame-dried glassware, which was cooled under a stream of dry argon. Anhydrous tetrahydrofuran, acetonitrile, diethyl ether, dichloromethane, toluene, and all chemical reagents for synthesis were used without further purification. Analytical thin layer chromatography (TLC) was performed using 250 μm silica gel 60 F254 pre-coated plates (EMD Chemicals Inc.). Flash column chromatography was performed using 230-400 Mesh 60 Å silica gel (Sorbent Technologies).

NMR experiments were recorded using broadband probes on a Varian Mercury-Plus-400 spectrometer via VNMR-J software (400 MHz for $^1$H and 100 MHz for $^{13}$C) and a Bruker Avance-III-500 spectrometer via TOPSPIN software (500 MHz for $^1$H and 126 MHz for $^{13}$C). All spectra have been formatted and presented using MESTRENOVA (Mnova) software. Spectra were obtained in the following solvents (reference peaks also included for $^1$H and $^{13}$C NMRs): CDCl$_3$ ($^1$H NMR: 7.26 ppm; $^{13}$C NMR: 77.23 ppm), d$_6$-DMSO ($^1$H NMR: 2.50 ppm; $^{13}$C NMR: 39.52 ppm), CD$_3$OD ($^1$H NMR: 3.31 ppm; $^{13}$C NMR: 49.00 ppm), d$_6$-benzene ($^1$H NMR: 7.16 ppm; $^{13}$C NMR: 128.06 ppm). NMR samples where the respective solvent peaks were buried in the sample signals were referenced with TMS at 0.00 ppm for $^1$H NMR experiments. NMR experiments were performed at room temperature unless otherwise indicated. Chemical shift values (δ) are reported in parts per million (ppm) for all $^1$H NMR and $^{13}$C NMR spectra. $^1$H NMR multiplicities are reported as: s=singlet, d=doublet, t=triplet, q=quartet, hept=heptet, m=multiplet, and br=broad.

In one set of experiments, compounds 1, 2, 5, and 11 were synthesized from phenazine methosulfate using previously reported synthetic protocols (E. Breitmaier, *J. Org. Chem.*, 1976, 41, 2104-2108; D. L. Vivan, Nature, 1956, 178, 753; M. Conda-Sheridan, L. Marler, E. J. Park, T. P. Kondratyuk, K. Jermihov, A. D. Mesecar, J. M. Pezzulo, R. N. Asolkar, W. Fenical, and M. Cushman, *J. Med. Chem.*, 2010, 53, 8688-8699). In addition, compounds 3, 8-10, 12, and 13 were synthesized using a previously described route (G. W. Rewcastle, W. A. Denny, and B. C. Baguley, *J. Med. Chem.*, 1987, 30, 843-851). Compound 3 was diversified via amidation reaction to the naturally occurring compound 4 using thionyl chloride followed directly by treatment with aqueous ammonia. Curtius rearrangement of compound 3 readily afforded compound 6 while oxidation of compound 3 with hydrogen peroxide yielded compound 7.

In another set of experiments, compound 9 was converted into compound 14 through Curtius rearrangement. The carboxylic acid of 9 was also transformed to the corresponding primary amide in 15 using thionyl chloride followed directly by treatment with aqueous ammonia. Compounds 6 and 14 were dibrominated using N-bromosuccinimide to yield bromophenazines 16 and 17. 2,5-Dibromoaniline was converted to 6,9-dibromophenazine-1-carboxylic acid 18 using the 2-step protocol (Jourdan-Ullmann coupling, followed by reductive ring closure with sodium borohydride). Finally, 1-methoxyphenazine was brominated in the 4-position to make compound 19, which was demethylated to make compound 20 using a known route (M. Conda-Sheridan, L. Marler, E. J. Park, T. P. Kondratyuk, K. Jermihov, A. D. Mesecar, J. M. Pezzulo, R. N. Asolkar, W. Fenical, and M. Cushman, *J. Med. Chem.*, 2010, 53, 8688-8699).

In another set of experiments, the phenolic hydroxyl group of compound 11 was functionalized. Compounds 21-26 were prepared by condensing compound 11 with various acid chlorides. Additionally, compound 27 was synthesized by refluxing compound 11 with methyl iodide in acetone (M. Conda-Sheridan, L. Marler, E. J. Park, T. P. Kondratyuk, K. Jermihov, A. D. Mesecar, J. M. Pezzulo, R. N. Asolkar, W. Fenical and M. Cushman, *J. Med. Chem.*, 2010, 53, 8688-8699).

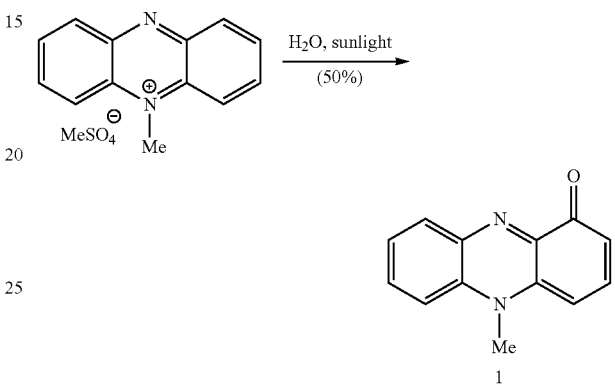

Pyocyanin (1). Phenazine methosulfate (204 mg, 0.667 mmol) was added to 200 mL deionized water, and the resulting mixture was subjected to direct sunlight for 30 minutes initially, followed by 5-10 minute periods of sunlight exposure during 8 hours. A dark green pigmentation was rapidly produced. The reaction was left stirring overnight and quenched with 50 mL of 10% aqueous sodium carbonate. The resulting deep blue solution was extracted exhaustively with 75 mL portions of chloroform. The organic layers were collected and dried with sodium sulfate, filtered, and concentrated under reduced pressure. The crude reaction was then purified by column chromatography (sequential elution using 100% ethyl acetate, 19:1 ethyl acetate:methanol, 9:1 ethyl acetate:methanol) to furnish 59 mg (50% yield) of pyocyanin 1 as a blue solid.

$^1$H NMR (400 MHz, d$_6$-DMSO): δ 8.12 (d, J=7.8 Hz, 1H), 7.95 (m, 1H), 7.89 (m, 1H) 7.66 (t, J=8.7 Hz, 1H), 7.55 (t, 7.2 Hz, 1H), 6.26 (d, 9.3 Hz, 1H), 6.12 (d, 8.0 Hz, 1H), 3.91 (s, 3H); (500 MHz, CD$_3$OD): δ 8.18 (br s, 1H), 7.99-7.89 (m, 2H), 7.78 (br s, 1H), 7.61 (t, J=7.7 Hz, 1H), 6.48 (d, J=8.8 Hz, 1H), 6.38 (d, J=7.6 Hz, 1H), 4.12 (br s, 3H).

$^{13}$C NMR (126 MHz, CD$_3$OD): δ 178.1, 146.8, 146.6, 137.9, 137.4, 136.2, 134.3, 133.8, 127.2, 116.5, 115.6, 94.4, 36.1.

HRMS (ESI): m/z calc. for $C_{13}H_{11}N_2O$ [M+H]$^+$: 211.0866, found: 211.0857.

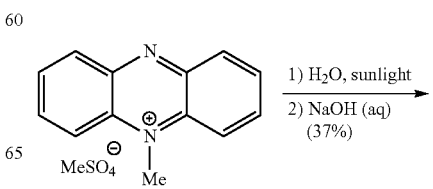

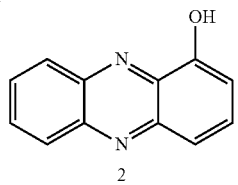

2

1-Hydroxyphenazine (2). Phenazine methosulfate (604 mg, 1.97 mmol) was added to 600 mL deionized water, and the resulting mixture was placed in direct sunlight for 30 minutes until a dark green color was observed. The reaction mixture was then positioned by a window receiving direct sunlight over the course of 58 hours. After this time, 11.5 grams sodium hydroxide in 35 mL water was slowly added to the reaction vessel, and stirring was continued for an additional 36 hours. The resulting purple solution was then transferred to a separatory funnel and washed with ether (to remove phenazine as a side product in this reaction). The aqueous layer was then acidified with 30 mL glacial acetic acid and extracted with ether (2×). The organic layers were collected, dried with sodium sulfate, filtered, and concentrated. The desired product was purified using flash chromatography (2:1 hexanes:ethyl acetate) to deliver 145 mg (37% yield) 1-hydroxyphenazine 2 as a bright yellow solid.

$^1$H NMR (400 MHz, CDCl$_3$): δ 8.30-8.17 (m, 3H), 7.89-7.80 (m, 2H), 7.80-7.73 (m, 2H), 7.24 (dd, J=6.7, 1.8 Hz, 1H).

$^{13}$C NMR (100 MHz, CDCl$_3$): δ 151.9, 144.4, 144.0, 141.4, 134.9, 132.0, 131.0, 130.7, 129.9, 129.4, 120.1, 109.1.

HRMS (DART): m/z calc. for C$_{12}$H$_8$N$_2$O [M+H]$^+$: 197.0709, found: 197.0717.

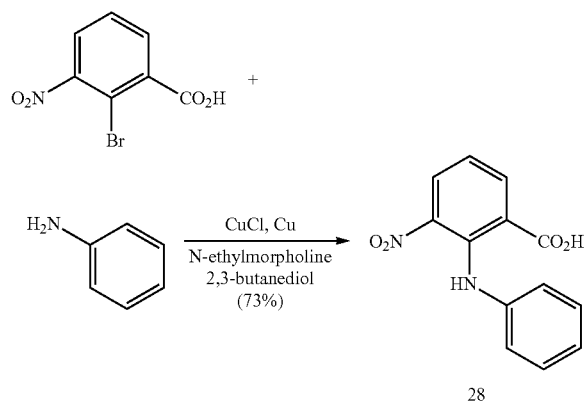

28

3-Nitro-2-(phenylamino)benzoic acid (28). In a round bottom flask were sequentially added 2-bromo-3-nitrobenzoic acid (845 mg 3.43 mmol), copper(I) chloride (34 mg, 0.34 mmol), copper powder (11 mg, 0.17 mmol), aniline (0.470 mL, 5.15 mmol), N-ethylmorpholine (0.87 mL, 6.86 mmol), and 2,3-butanediol (2.14 mL). The reaction mixture was then heated to 70° C., stirred for 16 hours, diluted with 18 mL 0.1 N ammonium hydroxide solution, and filtered over CELITE. The filtrate was poured slowly into 5 mL 2 N aqueous hydrochloric acid, and the yellow precipitate was filtered to yield the crude product which was recrystallized from toluene to afforded 886 mg (73% yield) of 3-nitro-2-(phenylamino)benzoic acid 28 as an amorphous yellow solid.

$^1$H NMR (400 MHz, d$_6$-DMSO): δ 13.80 (br s, 1H), 9.88 (s, 1H), 8.21 (dd, J=7.8, 1.7 Hz, 1H), 8.07 (dd, J=8.2, 1.8 Hz, 1H), 7.24 (t, J=7.9 Hz, 2H), 7.10 (t, J=8.0 Hz, 1H), 6.99 (t, J=7.4 Hz, 1H), 6.91 (d, J=7.8 Hz, 2 H).

$^{13}$C NMR (100 MHz, d$_6$-DMSO): δ 168.6, 141.4, 139.9, 138.8, 136.7, 130.8, 129.2, 123.1, 120.5, 119.0, 118.1.

HMRS (DART): m/z calc. for C$_{13}$H$_{11}$N$_2$O$_4$ [M+H]$^+$: 259.0713, found: 259.0719.

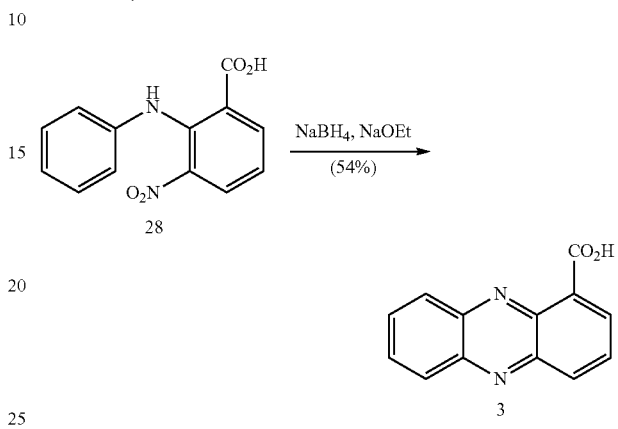

Phenazine-1-carboxylic acid (3). 3-Nitro-2-(phenylamino)benzoic acid (200 mg, 0.77 mmol) was dissolved in 20 mL 2 N sodium ethoxide in ethanol and treated with sodium borohydride (176 mg, 4.65 mmol). The reaction was heated to 65° C. and allowed to stir for 24 hours. After this time, the reaction was poured into ice, quenched with 25 mL 2 N aqueous hydrochloric acid, and extracted with dichloromethane 3×50 mL. The organic layers were collected and washed with 15 mL brine, dried with sodium sulfate, filtered, and concentrated under reduced pressure. The crude mixture was subjected to column chromatography using dichloromethane to elute to provide 100 mg (54% yield) of phenazine-1-carboxylic acid 3 as a yellow solid. A highly pure sample of compound 3 was obtained from column chromatography sequentially eluting with 100% hexanes, 3:1 hexanes:ethyl acetate, 49:49:2 hexanes:ethyl acetate:dichloromethane, and 99:1 ethyl acetate:dichloromethane.

$^1$H NMR (400 MHz, CDCl$_3$): δ 15.59 (s, 1H), 9.00 (dd, J=7.1, 1.5 Hz, 1H), 8.55 (dd, J=8.8, 1.5 Hz, 1H), 8.36 (d, J=8.2 Hz, 1H), 8.30 (d, J=8.3 Hz, 1H), 8.09-7.96 (m, 3H).

$^{13}$C NMR (100 MHz, CDCl$_3$): δ 166.1, 144.2, 143.5, 140.1, 139.9, 137.6, 135.3, 133.4, 131.9, 130.5, 130.2, 128.1, 125.0.

HRMS (DART): m/z calc. for C$_{13}$H$_9$N$_2$O$_2$[M+H]$^+$: 225.0659, found: 225.0668; calc. C$_{13}$H$_8$N$_2$O$_2$Na [M+Na]$^+$: 247.0478, found: 247.0482.

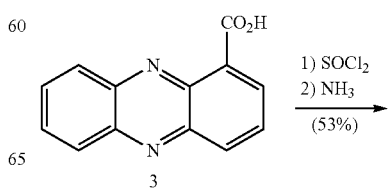

3

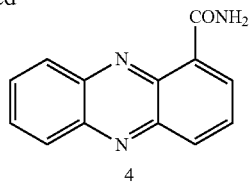

Phenazine-1-carboxamide (4). To penazine-1-carboxylic acid (189 mg, 0.79 mmol) in 4 mL toluene was added thionyl chloride (0.295 mL, 3.94 mmol) dropwise. The resulting solution was then heated to 65° C. for 4 hours. After this time, the volatiles were removed under reduced pressure, and the resulting crude acid chloride was taken up in dichloromethane (5 mL). To this solution was added 0.5 mL 30% aqueous ammonia at ambient temperature resulting in an immediate precipitation of a yellow solid. Stirring was continued overnight, and the reaction was filtered and washed with a small amount of cold dichloromethane. The crude material was passed over a short silica plug, eluting with ethyl acetate to yield 100 mg (53% yield) of phenazine-1-carboxamide 4 as a green-yellow solid.

$^1$H NMR (400 MHz, CDCl$_3$): δ 10.74 (br s, 1H), 9.02 (dd, J=7.2, 1.5 Hz, 1H), 8.44 (dd, J=8.7, 1.6, 1H), 8.30 (m, 1H), 8.24 (m, 1H), 8.01-7.89 (m, 3H), 6.27 (br s, 1H).

$^{13}$C NMR (100 MHz, CDCl$_3$): δ 166.8, 143.7, 143.3, 141.7, 141.0, 136.2, 134.5, 132.0, 131.3, 130.1, 130.0, 129.3, 129.1.

HRMS (DART): m/z calc. for C$_{13}$H$_{10}$N$_3$O [M+H]$^+$: 224.0818, found: 224.0817.

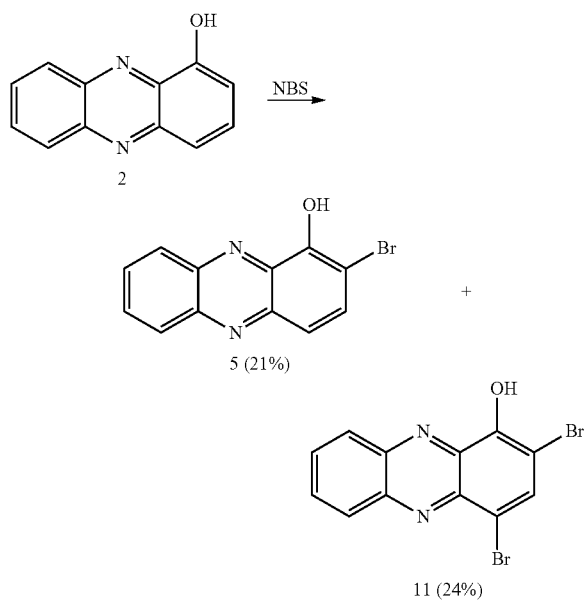

2-Bromophenazin-1-ol (5) and 2,4-dibromophenazin-1-ol (11). 1-Hydroxyphenazine (120 mg, 0.612 mmol) and N-bromosuccinimide (NBS, 120 mg, 0.730 mmol) were dissolved in 12 mL toluene and heated at 50° C. for 5 hours. The reaction contents were then concentrated, taken up in dichloromethane, and adsorbed onto silica for purification. Column chromatography eluting with dichloromethane furnished 35 mg (21% yield) of 2-bromophenazin-1-ol 5 as a yellow solid and 51 mg (24% yield) of 2,4-dibromophenazin-1-ol 11 as a yellow solid. These two products were optimally separated on TLC and column chromatography using 85:15 hexanes:ethyl acetate.

2-Bromophenazin-1-ol (5): $^1$H NMR (400 MHz, CDCl$_3$): δ 8.52 (br s, 1H), 8.30-8.18 (m, 2H), 7.94-7.82 (m, 3H), 7.71 (d, J=9.5 Hz, 1H). $^{13}$C NMR (100 MHz, CDCl$_3$): δ 149.3, 144.3, 143.0, 141.5, 135.5, 134.5, 131.5, 131.3, 130.0, 129.3, 121.0, 103.7. HRMS (DART): m/z calc. for C$_{12}$H$_7$N$_2$OBr [M+H]$^+$: 274.9815, found: 274.9824.

2,4-Dibromophenazin-1-ol (11): $^1$H NMR (400 MHz, CDCl$_3$): δ 8.54 (br s, 1H), 8.43-8.38 (m, 1H), 8.30-8.24 (m, 2H), 7.98-7.90 (m, 2H); (400 MHz, d$_6$-DMSO) δ 11.58 (s, 1H), 8.44 (s, 1H), 8.40-8.31 (m, 2H), 8.11-8.03 (m, 2H). $^{13}$C NMR (100 MHz, CDCl$_3$): δ 149.3, 144.3, 141.6, 140.1, 137.4, 134.4, 132.3, 131.9, 130.4, 129.0, 113.1, 103.2. HRMS (DART): m/z calc. for C$_{12}$H$_6$N$_2$OBr$_2$ [M+H]$^+$: 354.8900, found: 354.8909.

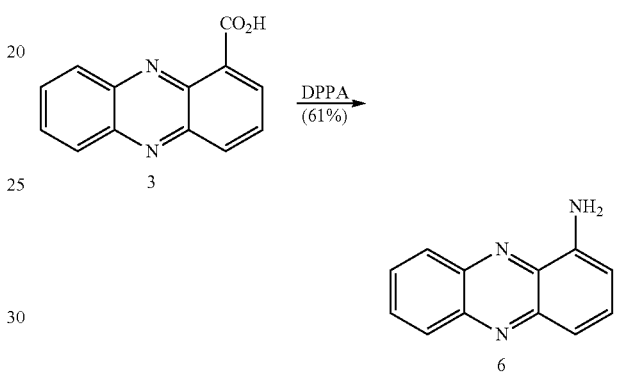

Phenazin-1-amine (6). To phenazine-1-carboxylic acid (100 mg, 0.446 mmol) in a 10:1 solution of tetrahydrofuran:triethylamine (2.2 mL) was slowly added diphenylphosphoryl azide (DPPA, 105 µL, 0.491 mmol). The reaction contents were allowed to stir for 3 hours at ambient temperature. After this time, deionized water (0.5 mL) was added, and the reaction was refluxed for 2 hours resulting in a deep red solution. After cooling, the reaction mixture was quenched with a saturated solution of aqueous potassium carbonate and extracted with ethyl acetate. The organic layers were collected and subsequently washed with brine, dried with sodium sulfate, filtered, and concentrated under reduced pressure. Purification of the crude residue by flash chromatography using 9:1 hexane:ethyl acetate to elute afforded 53 mg (61%) phenazin-1-amine 6 as a red solid.

$^1$H NMR (400 MHz, CDCl$_3$): δ 8.26-8.17 (m, 2H), 7.86-7.72 (m, 2H), 7.64 (dd J=8.8, 7.2 Hz, 1H), 7.57 (dd, J=8.8, 1.4 Hz, 1H), 6.92 (dd, J=7.2, 1.3 Hz, 1H), 5.10 (s, 2H).

$^{13}$C NMR (100 MHz, CDCl$_3$): δ 144.2, 144.2, 143.8, 141.4, 135.4, 132.3, 130.6, 129.9, 129.7, 129.5, 117.4, 107.9.

HRMS (DART): m/z calc. for C$_{12}$H$_{10}$N$_3$ [M+H]$^+$: 196.0869, found: 196.0873.

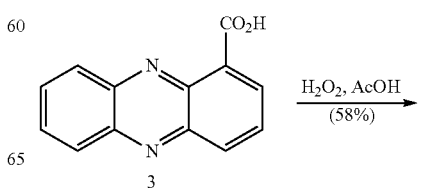

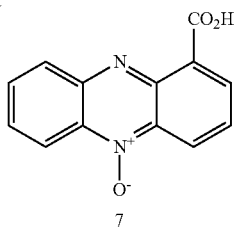

1-Carboxyphenazine 5-oxide (7). Phenazine-1-carboxylic acid (34.5 mg, 0.154 mmol) was dissolved in 6 mL glacial acetic acid and treated with 30% hydrogen peroxide (0.70 mL, 6.12 mmol). The reaction was heated to 55° C. and allowed to stir for 17 hours. The reaction was then diluted with 200 mL of deionized water resulting in a yellow solid to precipitate. The yellow solid was filtered on a vacuum funnel. A second crop of crystals was obtained by storing the filtrate overnight at 2° C. The combined solids were dried in vacuo to deliver 21.5 mg (58% yield) of 1-carboxyphenazine 5-oxide 7 as a yellow solid in high purity.

$^1$H NMR (400 MHz, CDCl$_3$): δ 15.70 (s, 1H), 8.96 (d, J=8.0 Hz, 1H), 8.91 (d, J=8.0 Hz, 1H), 8.71 (d, J=9.0 Hz, 1H), 8.26 (d, J=8.9 Hz, 1H), 7.99 (t, J=8.0 Hz, 1H), 7.95-7.82 (m, 2H).

$^{13}$C NMR (100 MHz, CDCl$_3$): δ 165.7, 143.0, 142.7, 138.0, 135.9, 135.8, 133.8, 131.2, 129.6, 129.0, 125.7, 124.4, 119.5.

HRMS (ESI): m/z calc. for $C_{13}H_9N_2O_3$[M+H]$^+$: 241.0608, found: 241.0613; and calc. $C_{13}H_8N_2O_3Na$ [M+Na]$^+$: 263.0427, found: 263.0427.

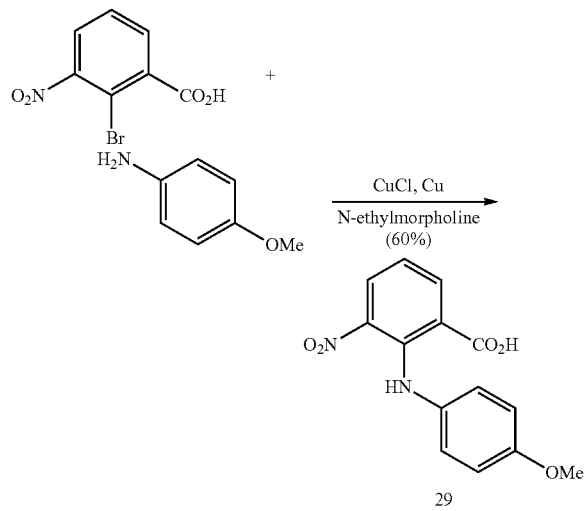

2-((4-Methoxyphenyl)amino)-3-nitrobenzoic acid (29). In a round bottom flask were sequentially added 2-bromo-3-nitrobenzoic acid (1.00 g, 4.06 mmol), copper(I) chloride (40 mg, 0.40 mmol), copper powder (13 mg, 0.20 mmol), p-anisidine (0.687 mL, 6.09 mmol), N-ethylmorpholine (1.03 mL, 8.12 mmol), and 2,3-butanediol (2.5 mL). The reaction mixture was heated to 70° C. with stirring for 16 hours, diluted with 25 mL 0.1 N aqueous ammonium hydroxide, and filtered over CELITE. The filtrate was poured slowly into 5 mL 2 N aqueous hydrochloric acid, and the resulting yellow precipitate was filtered to yield 703 mg (60% yield) of 2-((4-methoxyphenyl)amino)-3-nitrobenzoic acid 29 as an amorphous orange solid. This product appeared to be ≤80% pure by NMR. A small sample of this product was purified for analytical purposes via column chromatography eluting with 3:1 ethyl acetate:hexanes.

$^1$H NMR (400 MHz, CD$_3$OD): 8.23 (dd, J=7.8, 1.8 Hz, 1H), 7.95 (dd, J=7.8, 1.8 Hz, 1H), 6.93-6.85 (m, 3H), 6.83-6.77 (m, 2H), 3.75 (s, 3H).

$^{13}$C NMR (100 MHz, d$_6$-DMSO): δ 168.9, 155.8, 140.5, 138.8, 136.7, 134.1, 131.1, 121.0, 118.9, 117.5, 114.4, 55.2.

HRMS (DART): m/z calc. for $C_{14}H_{13}N_2O_5$ [M+H]$^+$: 289.0819, found: 289.0812.

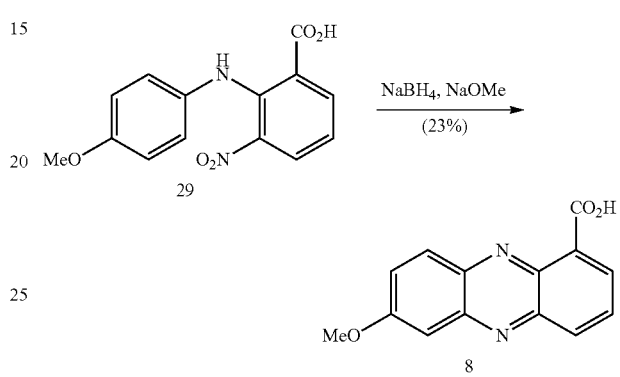

7-Methoxyphenazine-1-carboxylic acid (8).

2-((4-Methoxyphenyl)amino)-3-nitrobenzoic acid (200 mg, 0.69 mmol) was dissolved in 17 mL 2 N sodium methoxide in methanol and treated with sodium borohydride (261 mg, 6.90 mmol) and heated to 60° C. for 40 hours. After that time, the reaction contents were poured into ice, quenched with 2 N aqueous hydrochloric acid, and extracted with dichloromethane (3×50 mL). The combined organic layers were then washed with brine, dried with sodium sulfate, filtered, and concentrated under reduced pressure. The residue was adsorbed onto silica and chromatographed eluting with dichloromethane to deliver 37 mg (23% yield) of 7-methoxyphenazine-1-carboxylic acid 8 as a yellow solid.

$^1$H NMR (400 MHz, CDCl$_3$): δ 15.50 (br s, 1H), 8.88 (dd, J=7.2, 1.4 Hz, 1H), 8.43 (dd, J=8.7, 1.5 Hz, 1H), 8.13 (d, J=9.5 Hz, 1H), 8.00 (dd, J=8.7, 7.1 Hz, 1H), 7.67 (dd, J=9.5, 2.7 Hz, 1H), 7.48 (d, J=2.7 Hz, 1H), 4.08 (s, 3H).

$^{13}$C NMR (100 MHz, CDCl$_3$): δ 166.3, 162.4, 146.0, 143.5, 138.6, 137.4, 135.9, 134.5, 130.5, 129.6, 129.1, 125.2, 104.9, 56.5.

HRMS (ESI): m/z calc. for $C_{14}H_{11}N_2O_3$ [M+H]$^+$: 255.0764, found: 255.0771; and calc. $C_{14}H_{10}N_2O_3Na$ [M+Na]$^+$: 277.0584, found: 277.0586.

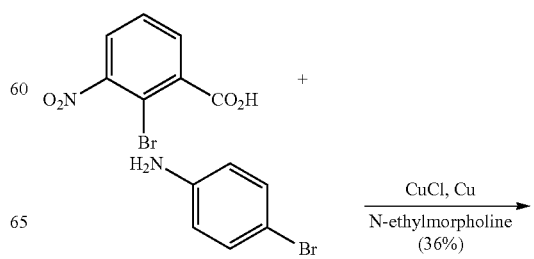

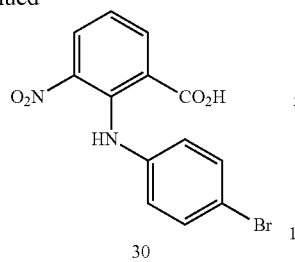

30

2-((4-Bromophenyl)amino)-3-nitrobenzoic acid (30). In a round bottom flask were sequentially added 2-bromo-3-nitrobenzoic acid (1.00 g, 4.06 mmol), copper(I) chloride (40 mg, 0.40 mmol), copper powder (13 mg, 0.20 mmol), 4-bromoaniline (1.05 g, 6.09 mmol), N-ethylmorpholine (1.03 mL, 8.12 mmol), and 2,3-butanediol (2.5 mL). The reaction mixture was then heated to 70° C. with stirring for 16 hours before being diluted with 25 mL 0.1 N aqueous ammonium hydroxide and filtered over CELITE. The filtrate was poured slowly into 5 mL 2 N aqueous hydrochloric acid, and the yellow precipitate was filtered to give 491 mg (36% yield) of 2-((4-bromophenyl)amino)-3-nitrobenzoic acid 30 as an amorphous orange solid.

$^1$H NMR (400 MHz, $d_6$-DMSO): δ 8.17 (d, J=8.0 Hz, 1H), 8.07 (d, J=8.0 Hz, 1H), 7.37 (d, J=7.1 Hz, 2H), 7.18 (t, J=7.9 Hz, 1H), 6.85 (d, J=7.1 Hz, 2H).

$^{13}$C NMR (100 MHz, $d_6$-DMSO): δ 168.1, 141.4, 140.6, 137.8, 136.4, 131.8, 130.3, 122.1, 120.0, 119.8, 114.0.

HRMS (DART): m/z calc. for $C_{13}H_{10}N_2O_4Br$ [M+H]$^+$: 336.9818, found: 336.9821.

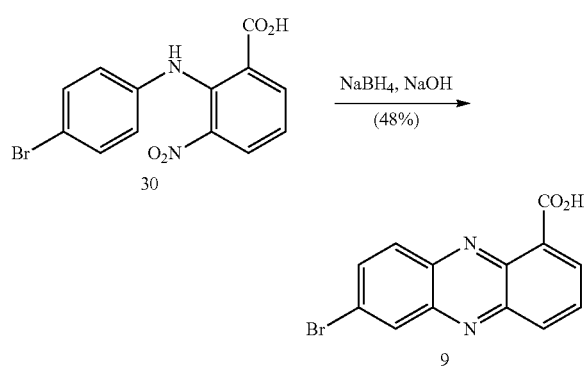

7-Bromophenazine-1-carboxylic acid (9). 2-((4-Bromophenyl)amino)-3-nitrobenzoic acid (450 mg, 1.33 mmol) was dissolved in 22 mL 2 N aqueous sodium hydroxide and treated with sodium borohydride (151 mg, 4.00 mmol). The reaction mixture was then refluxed for 2 hours. After this time, the reaction was cooled on the ice bath, and filtered. The filter cake was washed with a small amount of cold 2 N aqueous sodium hydroxide, taken up in 30 mL deionized water, acidified with glacial acetic acid and filtered to give 194 mg (48% yield) of 7-bromophenazine-1-carboxylic acid 9 as a yellow solid.

$^1$H NMR (500 MHz, $d_6$-DMSO): δ 14.19 (br s, 1H), 8.61 (d, J=2.2 Hz, 1H), 8.54-8.44 (m, 2H), 8.34 (d, J=9.2 Hz, 1H), 8.17 (dd, J=9.2, 2.2 Hz, 1H), 8.11 (dd, J=8.8, 6.9 Hz, 1H).

$^{13}$C NMR (126 MHz, $d_6$-DMSO): δ 166.5, 143.3, 142.8, 140.0, 139.8, 135.6, 133.7, 133.1, 131.2, 131.1, 130.8, 129.7, 125.5.

HRMS (DART): m/z calc. for $C_{13}H_8N_2O_2Br$ [M+H]$^+$: 302.9764, found: 302.9778.

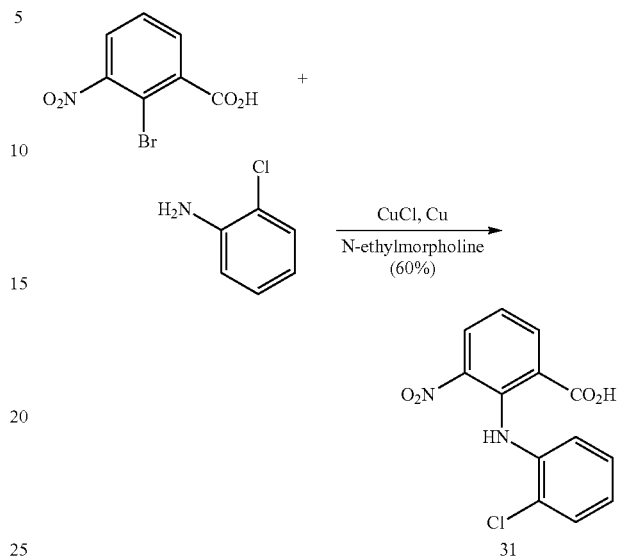

2-((2-Chlorophenyl)amino)-3-nitrobenzoic acid (31). In a round bottom flask were sequentially added 2-bromo-3-nitrobenzoic acid (1.00 g, 4.06 mmol), copper(I) chloride (40 mg, 0.40 mmol), copper powder (13 mg, 0.20 mmol), 2-chloroaniline (0.640 mL, 6.09 mmol), N-ethylmorpholine (1.03 mL, 8.12 mmol), and 2,3-butanediol (2.5 mL). The mixture was heated to 70° C. with stirring for 16 hours, diluted with 25 mL 0.1 N aqueous ammonium hydroxide, and filtered over CELITE. The filtrate was poured slowly into 5 mL 2 N aqueous hydrochloric acid, and the resulting yellow precipitate was filtered to yield the crude product which was recrystallized from toluene to afforded 712 mg (60% yield) of 2-((2-chlorophenyl)amino)-3-nitrobenzoic acid 31 as an amorphous yellow solid. This product appeared to be ≤80% pure by NMR. A small sample of this product was purified for analytical purposes via column chromatography eluting with 3:1 ethyl acetate:hexanes.

$^1$H NMR (400 MHz, $d_6$-DMSO): δ 10.06 (br s, 1H), 8.26 (d, J=7.7 Hz, 1H), 8.10 (d, J=8.0 Hz, 1H), 7.47 (d, J=7.8 Hz, 1H), 7.19-7.07 (m, 2H), 7.01 (t, J=7.3 Hz, 1H), 6.82 (d, J=8.0 Hz, 1H).

$^{13}$C NMR (100 MHz, $d_6$-DMSO): δ 168.7, 139.6, 138.3, 138.1, 136.9, 131.0, 130.0, 127.6, 124.3 (2), 120.6, 119.7, 117.1.

HRMS (DART): m/z calc. for $C_{13}H_{10}N_2O_4Cl$ [M+H]$^+$: 293.0324, found: 293.0332.

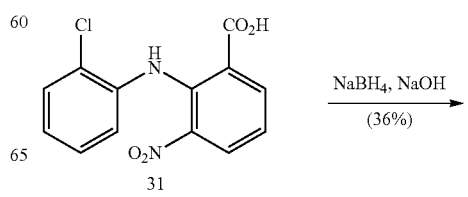

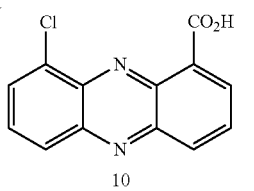

9-Chlorophenazine-1-carboxylic acid (10). 2-((2-Chlorophenyl)amino)-3-nitrobenzoic acid (200 mg, 0.68 mmol) was dissolved in 17 mL 2 N aqueous sodium hydroxide, treated with sodium borohydride (155 mg, 4.10 mmol), and heated to 70° C. for 5 hours. After this time, the reaction was poured into ice, quenched with 3 mL 2 N aqueous hydrochloric acid, and extracted with dichloromethane (3×50 mL). The combined organic layers were washed with brine, dried with sodium sulfate, filtered, and concentrated under reduced pressure. The residue was adsorbed onto silica and chromatographed using dichloromethane to deliver 63 mg (36% yield) of 9-chlorophenazine-1-carboxylic acid 10 as a yellow solid.

$^1$H NMR (400 MHz, CDCl$_3$): δ 15.40 (s, 1H), 9.04 (dd, J=7.0, 1.3 Hz, 1H), 8.56 (dd, J=8.9, 1.2 Hz, 1H), 8.30 (dd, J=8.9, 0.8 Hz, 1H), 8.15-8.07 (m, 2H), 7.92 (dd, J=8.9, 7.3 Hz, 1H).

$^{13}$C NMR (100 MHz, CDCl$_3$): δ 165.7, 144.6, 143.9, 140.0, 138.3, 137.1, 135.0, 132.2, 132.1, 131.4 (2), 129.2, 125.5.

HRMS (DART): m/z calc. for C$_{13}$H$_8$N$_2$O$_2$Cl [M+H]$^+$: 259.0269, found: 259.0271.

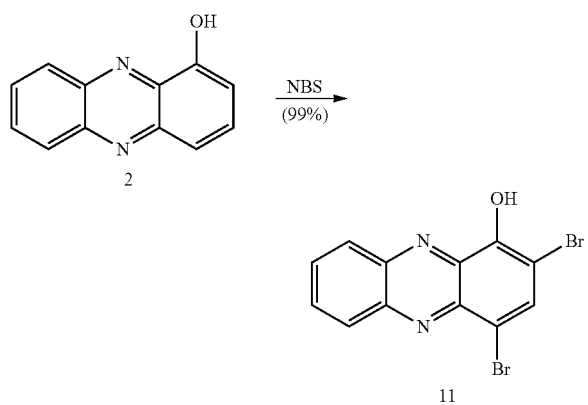

2,4-Dibromophenazin-1-ol (11). 1-Hydroxyphenazine (81 mg, 0.412 mmol) was dissolved in 8 mL toluene and treated with N-bromosuccinimide (162 mg, 0.906 mmol). The reaction was heated to 50° C. for 5.5 hours. The reaction was then allowed to cool to room temperature before being concentrated under reduced pressure. The residue was then adsorbed onto silica using dichloromethane and concentrated under reduced pressure before being applied to a column. Column chromatography using dichloromethane to elute delivered 145 mg (99% yield) 2,4-dibromophenazin-1-ol 11 as a yellow solid. In one experiment, 1.106 grams of 2,4-dibromophenazin-1-ol was synthesized starting from 795 milligrams of 1-hydroxyphenazine (77% yield).

$^1$H NMR (400 MHz, CDCl$_3$): δ 8.54 (br s, 1H), 8.43-8.38 (m, 1H), 8.30-8.24 (m, 2H), 7.98-7.90 (m, 2H).

$^{13}$C NMR (100 MHz, CDCl$_3$): δ 149.3, 144.3, 141.6, 140.1, 137.4, 134.4, 132.3, 131.9, 130.4, 129.0, 113.1, 103.2.

HRMS (DART): m/z calc. for C$_{12}$H$_6$N$_2$OBr$_2$ [M+H]$^+$: 354.8900, found: 354.8909.

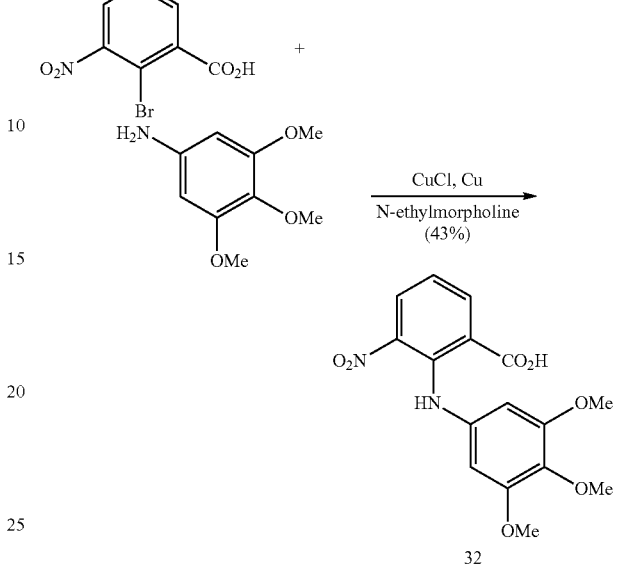

3-Nitro-2-((3,4,5-trimethoxyphenyl)amino)benzoic acid (32). In a round bottom flask were sequentially added 2-bromo-3-nitrobenzoic acid (1.00 g, 4.06 mmol), copper(I) chloride (40 mg, 0.40 mmol), copper powder (13 mg, 0.20 mmol), 3,4,5-trimethoxyaniline (1.12 g, 6.09 mmol), N-ethylmorpholine (1.03 mL, 8.12 mmol), and 2,3-butanediol (2.5 mL). The reaction mixture was heated to 70° C., stirred for 16 hours, diluted with 25 mL 0.1 N aqueous ammonium hydroxide, and filtered over CELITE. The filtrate was poured slowly into 5 mL 2 N aqueous hydrochloric acid, and the resulting yellow precipitate was filtered to yield 605 mg (43% yield) 3-nitro-2-((3,4,5-trimethoxyphenyl)amino)benzoic acid 32 as an amorphous red solid. This product appeared to be ≤80% pure by NMR. A small sample of this product was purified for analytical purposes via column chromatography sequentially eluting with 100% dichloromethane, 1:9 acetone:dichloromethane, 1:3 acetone:dichloromethane, and 100% acetone.

$^1$H NMR (400 MHz, d$_6$-DMSO): δ 12.54 (br s, 1H), 8.25 (dd, J=15.2, 1.6 Hz, 1H), 7.80 (dd, J=8.0, 1.6 Hz, 1H), 6.87 (t, J=8.0 Hz, 1H), 6.07 (s, 2H), 3.66 (s, 6H), 3.58 (s, 3H).

$^{13}$C NMR (100 MHz, d$_6$-DMSO): δ 169.1, 153.1, 139.2, 138.6, 138.5, 136.5, 132.5, 127.7, 127.5 117.0, 94.9, 60.1, 55.5.

HRMS (DART): m/z calc. for C$_{16}$H$_{17}$N$_2$O$_7$ [M+H]$^+$: 349.1039, found: 349.1029.

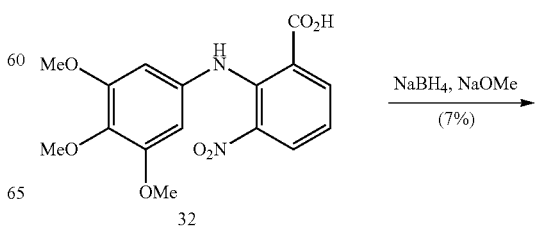

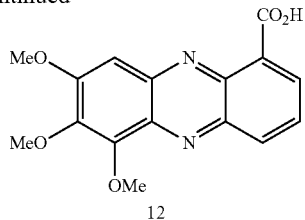

6,7,8-Trimethoxyphenazine-1-carboxylic acid (12). 3-Nitro-2-((3,4,5-trimethoxyphenyl)amino) benzoic acid (450 mg, 1.29 mmol) was dissolved in 32 mL of 2 N sodium methoxide in methanol solution, treated with sodium borohydride (488 mg, 12.90 mmol), and heated to 60° C. for 16 hours. After this time, the reaction was poured into ice, quenched with 2 N aqueous hydrochloric acid, and extracted with dichloromethane (3×75 mL). The combined organic layers were washed with brine, dried with sodium sulfate, filtered, and concentrated under reduced pressure. The crude mixture was adsorbed onto silica and chromatographed using 95:5 dichloromethane:ethyl acetate to give 13 mg (7% yield) of 6,7,8-trimethoxyphenazine-1-carboxylic acid 12 as a yellow solid.

$^1$H NMR (400 MHz, CDCl$_3$): δ 15.73 (br s, 1H), 8.85 (dd, J=7.2, 1.5 Hz, 1H), 8.52 (dd, J=8.6, 1.5 Hz, 1H), 7.90 (dd, J=8.6, 7.1 Hz, 1H), 7.20 (s, 1H), 4.27 (s, 3H), 4.18 (s, 3H), 4.14 (s, 3H).

$^{13}$C NMR (100 MHz, CDCl$_3$): δ 166.7, 159.9, 146.1, 145.5, 140.9, 139.4, 139.1, 138.4, 136.5, 135.3, 128.9, 124.2, 99.8, 62.9, 62.1, 57.2.

HRMS (DART): m/z calc. for C$_{16}$H$_{15}$N$_2$O$_5$ [M+H]$^+$: 315.0975, found: 315.0975.

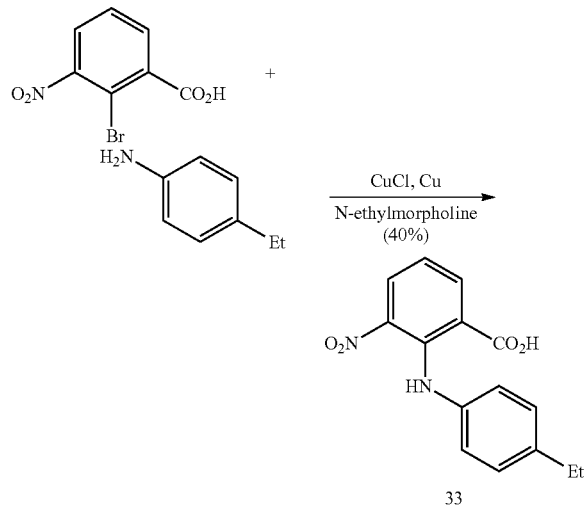

2-((4-Ethylphenyl)amino)-3-nitrobenzoic acid (33). In a round bottom flask were sequentially added 2-bromo-3-nitrobenzoic acid (1.00 g, 4.06 mmol), copper(I) chloride (40 mg, 0.40 mmol), copper powder (13 mg, 0.20 mmol), 4-ethyl aniline (0.757 mL, 6.09 mmol), N-ethylmorpholine (1.03 mL, 8.12 mmol), and 2,3-butanediol (2.5 mL). The mixture was heated to 70° C. with stirring for 16 hours, diluted with 25 mL 0.1 N aqueous ammonium hydroxide, and filtered over CELITE. The filtrate was then poured slowly into 5 mL 2 N aqueous hydrochloric acid and the resulting yellow precipitate was filtered to yield 467 mg (40% yield) of 2-((4-ethylphenyl)amino)-3-nitrobenzoic acid 33 as an amorphous yellow solid.

$^1$H NMR (400 MHz, d$_6$-DMSO): δ 13.79 (br s, 1H), 9.91 (s, 1H), 8.20 (d, J=7.7 Hz, 1H), 8.06 (d, J=8.0 Hz, 1H), 7.14-6.99 (m, 3H), 6.84 (d, J=7.9 Hz, 2H), 2.54 (q, J=7.6 Hz, 2H, partially buried in d$_6$-DMSO), 1.15 (t, J=7.6 Hz, 3H).

$^{13}$C NMR (100 MHz, d$_6$-DMSO): δ 168.8, 139.4 (2), 138.9, 138.8, 136.8, 131.0, 128.4, 119.8, 118.4, 118.3, 27.9, 16.0.

HRMS (ESI): m/z calc. for C$_{15}$H$_{15}$N$_2$O$_4$ [M+H]$^+$: 287.1026, found: 287.1032 and calc. C$_{15}$H$_{14}$N$_2$O$_4$Na [M+Na]+: 309.0846, found: 309.0841.

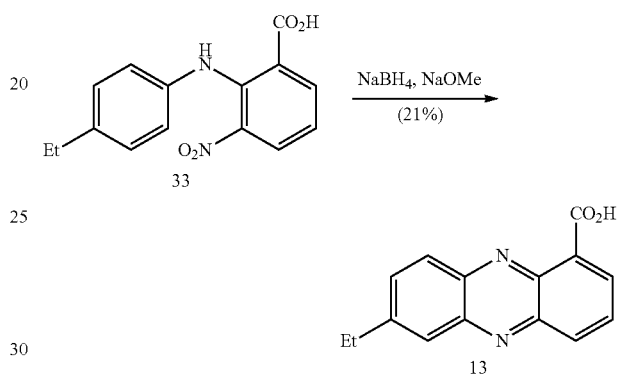

7-Ethylphenazine-1-carboxylic acid (13). 2-((4-Ethylphenyl)amino)-3-nitrobenzoic acid (390 mg, 1.36 mmol) was dissolved in 34 mL of 2 N sodium methoxide in methanol solution, treated with sodium borohydride (514 mg, 13.60 mmol), and heated to 60° C. for 40 hours. After this time, the reaction was poured into ice, quenched with 2 N aqueous hydrochloric acid, and extracted with dichloromethane (3×75 mL). The combined organic layers were washed with brine, dried with sodium sulfate, filtered, and concentrated under reduced pressure. The residue was adsorbed onto silica and chromatographed using dichloromethane to elute 70 mg (21% yield) 7-ethylphenazine-1-carboxylic acid 13 as a yellow solid.

$^1$H NMR (400 MHz, CDCl$_3$): δ 15.52 (br s, 1H), 8.86 (dd, J=7.0, 1.5 Hz, 1H), 8.41 (dd, J=8.8, 1.5 Hz, 1H), 8.09 (d, J=8.9 Hz, 1H), 8.02-7.89 (m, 2H), 7.82 (dd, J=9.0, 1.9 Hz, 1H), 2.97 (q, J=7.6 Hz, 2H), 1.42 (t, J=7.5 Hz, 3H).

$^{13}$C NMR (100 MHz, CDCl$_3$): δ 166.2, 148.9, 144.4, 143.3, 139.5, 138.9, 136.8, 135.6, 135.0, 130.2, 127.5, 126.5, 124.9, 29.4, 14.5.

HRMS (ESI): m/z calc. for C$_{15}$H$_{13}$N$_2$O$_2$ [M+H]$^+$: 253.0972, found: 253.0981 and calc. C$_{15}$H$_{12}$N$_2$O$_2$Na [M+Na]$^+$: 275.0791, found: 275.0788.

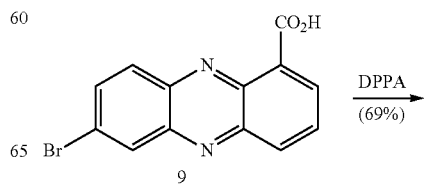

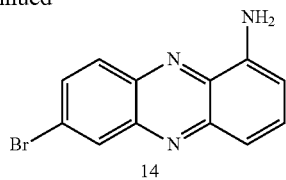

7-Bromophenazin-1-amine (14). 7-Bromophenazine-1-carboxylic acid (200 mg, 0.66 mmol) was taken up in a 10:1 tetrahydrofuran:triethylamine solution (3.5 mL). Diphenylphosphoryl azide (0.17 mL, 0.79 mmol) was then slowly added to the reaction mixture which was allowed to stir for 3 hours at ambient temperature. Deionized water (1.5 mL) was then added to the reaction which was heated to reflux for an additional 2 h. After cooling, the reaction was quenched with saturated aqueous potassium carbonate and extracted with dichloromethane. The organic layer was dried with sodium sulfate, filtered, and concentrated under reduced pressure. Purification of the crude residue by flash chromatography using 9:1 hexanes:ethyl acetate afforded 125 mg (69% yield) of 7-bromophenazin-1-amine 14 as a purple solid.

$^1$H NMR (400 MHz, CDCl$_3$): δ 8.39 (d, J=2.1 Hz, 1H), 8.06 (d, J=9.2 Hz, 1H), 7.81 (dd, J=9.3, 2.1 Hz, 1H), 7.65 (t, J=8.1 Hz, 1H), 7.53 (d, J=8.8 Hz, 1H), 6.93 (d, J=7.8 Hz, 1H), 5.24 (br s, 2H).

$^{13}$C NMR (100 MHz, CDCl$_3$): δ 144.6, 144.3, 144.1, 139.9, 135.4, 133.4, 133.1, 131.6, 131.1, 125.0, 117.3, 108.2.

HRMS (DART): m/z calc. for C$_{12}$H$_9$N$_3$Br [M+H]$^+$: 273.9974, found: 273.9983.

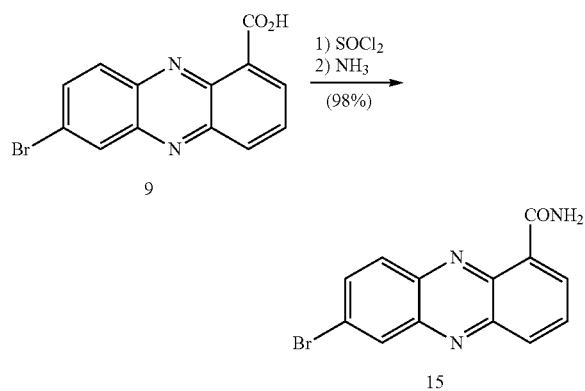

7-Bromophenazine-1-carboxamide (15). 7-Bromophenazine-1-carboxylic acid (50 mg, 0.17 mmol) was dissolved in 1 mL toluene. Thionyl chloride (60 μL, 0.79 mmol) was added to the solution which was then heated at 70° C. for 3 hours. After this time, the volatiles were removed under reduced pressure, and the intermediate acid chloride was taken up in 1 mL of dichloromethane. Addition of 0.1 mL 30% aqueous ammonia at ambient temperature resulted in immediate precipitation of a yellow solid. Stirring was continued overnight, and the reaction was filtered and washed with a small amount of cold dichloromethane. The crude material was passed over a short silica plug, eluting with ethyl acetate, and concentrated to yield 49 mg (98% yield) of 7-bromophenazine-1-carboxamide 15 as a yellow solid.

$^1$H NMR (400 MHz, d$_6$-DMSO): δ 9.48 (br s, 1H), 8.67 (d, J=8.0 Hz, 1H), 8.50 (d, J=2.2 Hz, 1H), 8.38 (dd, J=8.7, 1.6 Hz, 1H), 8.31 (d, J=9.3 Hz, 1H), 8.13-8.02 (m, 2H), 7.80 (br s, 1H).

$^{13}$C NMR (100 MHz, d$_6$-DMSO): δ 165.7, 143.0, 142.7, 140.2, 140.1, 135.0, 134.3, 132.8, 131.2, 131.1, 131.0, 130.8, 125.1.

HRMS (DART): m/z calc. for C$_{13}$H$_9$N$_3$OBr [M+H]$^+$: 301.9923, found: 301.9923.

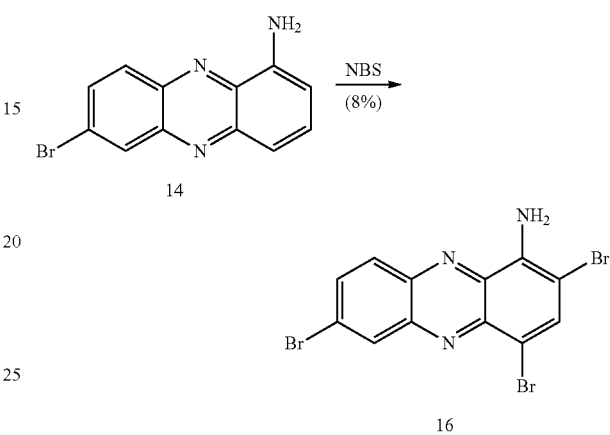

2,4,7-Tribromophenazin-1-amine (16). 7-Bromophenazin-1-amine (70 mg, 0.359 mmol) was dissolved in 7.2 mL toluene and treated with N-bromosuccinimide (134 mg, 0.753 mmol) at ambient temperature for 4 hours. The reaction mixture was then concentrated under reduced pressure, taken up in dichloromethane, and adsorbed onto silica. Column chromatography was used eluting with 19:1 hexanes:ethyl acetate to yield 13 mg (8% yield) of 2,4,7-tribromophenazin-1-amine 16 as a purple solid.

$^1$H NMR (400 MHz, CDCl$_3$): δ 8.56 (d, J=2.1 Hz, 1H), 8.14 (s, 1H), 8.08 (d, J=9.2 Hz, 1H), 7.89 (dd, J=9.2, 2.1 Hz, 1H), 5.66 (br s, 2H).

$^{13}$C NMR (100 MHz CDCl$_3$): δ 143.9, 142.2, 140.6, 140.0, 138.0, 134.9, 134.6, 132.1, 130.6, 126.1, 108.8, 101.5.

HRMS (DART): m/z calc. for C$_{12}$H$_7$N$_3$Br$_3$ [M+H]$^+$: 431.8164, found: 431.8184.

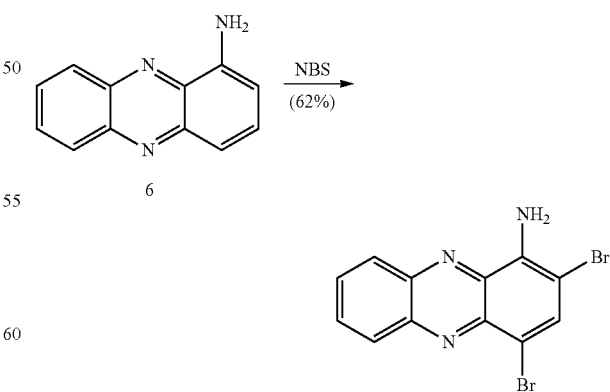

2,4-Dibromophenazin-1-amine (17). Phenazin-1-amine (17 mg, 0.087 mmol) and N-bromosuccinimide (33 mg, 0.182 mmol) were dissolved in 1.7 mL toluene and heated at 50° C. for 8 hours. The contents of the flask were then concentrated under reduced pressure, taken up in dichloromethane, and adsorbed onto silica. Column chromatography was used to purify the desired compound eluting with 85:15 hexanes:ethyl acetate to yield 19 mg (62% yield) of 2,4-dibromophenazin-1-amine 17 as a red solid.

$^1$H NMR (400 MHz, CDCl$_3$): δ 8.32 (dd, J=8.5, 2.1 Hz, 1H), 8.19 (dd, J=8.5, 2.4 Hz, 1H), 8.10 (s, 1H), 7.91-7.76 (m, 2H), 5.64 (br s, 2H).

$^{13}$C NMR (100 MHz CDCl$_3$): δ 143.8, 142.1, 141.4, 140.2, 137.2, 134.6, 131.4, 131.1, 130.1, 129.4, 108.9, 101.1.

HRMS (DART): m/z calc. for C$_{12}$H$_8$N$_3$Br$_2$ [M+H]$^+$: 353.9059, found: 353.9066.

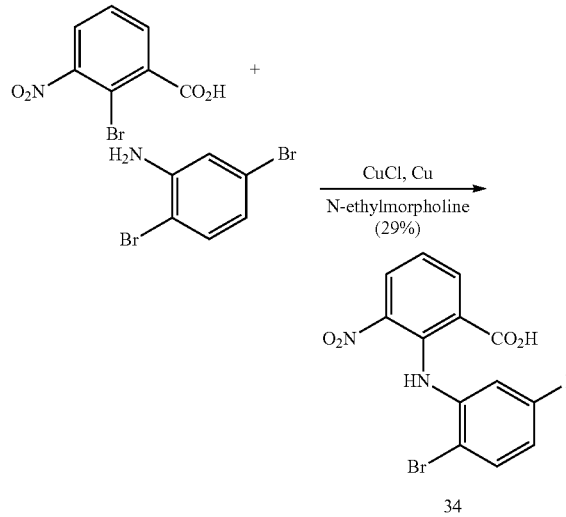

2-((2,5-Dibromophenyl)amino)-3-nitrobenzoic acid (34). In a round bottom flask were sequentially added 2-bromo-3-nitrobenzoic acid (246 mg, 1.00 mmol), copper(I) chloride (10 mg, 0.05 mmol), copper powder (3 mg, 0.10 mmol), 2,5-dibromoaniline (376 mg, 1.50 mmol), N-ethylmorpholine (0.25 mL, 2.00 mmol), and 2,3-butanediol (0.75 mL). The mixture was then heated to 70° C. with stirring for 16 hours, diluted with 25 mL 0.1 N aqueous ammonium hydroxide, and filtered over CELITE. The resulting filtrate was poured slowly into 5 mL 2 N aqueous hydrochloric acid, and the resulting yellow precipitate was filtered to yield 200 mg (47% yield) of 2-((2,5-dibromophenyl)amino)-3-nitrobenzoic acid 34 as a yellow solid.

$^1$H NMR (400 MHz, d$_6$-DMSO): δ 14.02 (br s, 1H), 9.89 (s, 1H), 8.25 (dd, J=7.8, 1.8 Hz, 1H), 8.15 (dd, J=8.1, 1.8 Hz, 1H), 7.60 (d, J=8.6 Hz, 1H), 7.24 (t, J=8.0 Hz, 1H), 7.12 (dd, J=8.6, 2.3 Hz, 1H), 6.94 (d, J=2.3 Hz, 1H).

$^{13}$C NMR (100 MHz, d$_6$-DMSO): δ 168.5, 141.1, 140.3, 137.2, 136.8, 134.7, 130.8, 127.0, 121.6, 121.0 (2), 119.5, 113.6.

HRMS (DART): m/z calc. for C$_{13}$H$_9$N$_2$O$_4$Br$_2$ [M+H]$^+$: 416.8904, found: 416.8922.

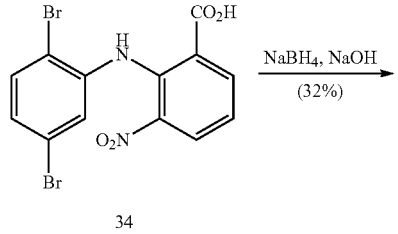

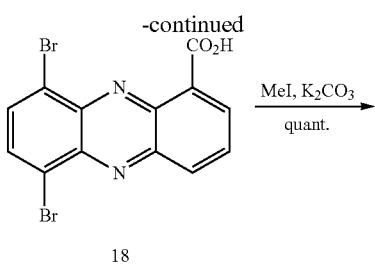

Compound Screened in MIC Experiments

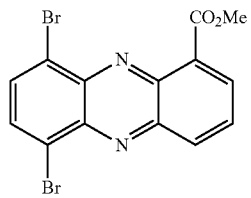

Compound Synthesized for Characterization 6,9-Dibromophenazine-1-carboxylic acid (18) and methyl-6,9-dibromophenazine-1-carboxylate (35). 2-((2,5-Dibromophenyl)amino)-3-nitrobenzoic acid (497 mg, 1.16 mmol) was dissolved in 19 mL 2 N aqueous sodium hydroxide and treated with sodium borohydride (131 mg, 3.47 mmol). The resulting reaction mixture was then refluxed for 1.5 hours. After this time, the reaction was made acidic with 2 N aqueous hydrochloric acid, and the resulting precipitate was filtered. The filter cake was then washed with hot chloroform to afford 143 mg (32% yield) of 6,9-dibromophenazine-1-carboxylic acid 18 as a yellow-green solid. 6,9-Dibromophenazine-1-carboxylic acid displayed extremely low solubility and as a result, and it was difficult to obtain a $^{13}$C NMR spectrum. A small portion of this material was converted to methyl ester 35 for characterization purposes using the following procedure. To a stirred suspension of 6,9-dibromophenazine-1-carboxylic acid (3.7 mg, 0.0097 mmol) in 0.4 mL dimethylformamide was sequentially added potassium carbonate (22 mg, 0.16 mmol) and one drop of iodomethane. The reaction was allowed to stir overnight at room temperature. The reaction was then transferred to a separatory funnel and partitioned between ethyl acetate and water. The organic layer was then washed with brine and collected. The organic layer was then dried with sodium sulfate, filtered, and concentrated under reduced pressure. The crude material was taken up in chloroform and passed over a silica plug to furnish 3.8 mg (quantitative yield) of methyl-6,9-dibromophenazine-1-carboxylate 35 as a yellow solid.

6,9-Dibromophenazine-1-carboxylic acid (18): $^1$H NMR (400 MHz, DMSO-d$_6$): δ 8.72 (d, J=6.9 Hz, 1H), 8.62 (d, J=8.6 Hz, 1H), 8.40-8.31 (m, 2H), 8.23 (t, J=7.9 Hz, 1H). HRMS (DART): m/z calc. for C$_{13}$H$_7$N$_2$O$_2$Br$_2$ [M+H]$^+$: 382.8849, found: 382.8854.

Methyl-6,9-dibromophenazine-1-carboxylate (35): $^1$H NMR (400 MHz, CDCl$_3$): δ 8.55 (dd, J=8.8, 1.4 Hz, 1H), 8.39 (dd, J=7.0, 1.4 Hz, 1H), 8.11-8.06 (m, 2H), 7.97 (dd, J=8.8, 7.0 Hz, 1H), 4.16 (s, 3H). $^{13}$C NMR (100 MHz, CDCl$_3$): δ 167.0, 143.3, 141.4, 141.3, 141.1, 134.2, 134.0 (2), 133.7, 131.6, 130.9, 125.2, 124.1, 53.1. HRMS (DART): m/z calc. for C$_{14}$H$_9$N$_2$O$_2$Br$_2$ [M+H]$^+$: 396.9005, found: 396.9015.

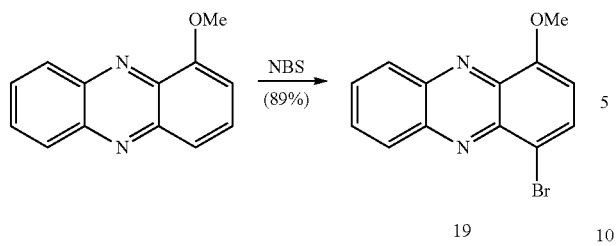
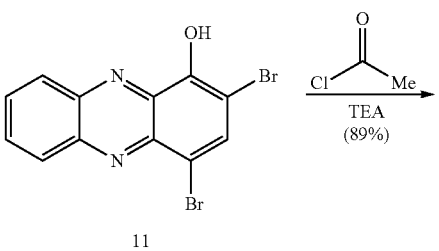

1-Bromo-4-methoxyphenazine (19). 1-Methoxyphenazine (60 mg, 0.29 mmol) was dissolved in a 1:1 toluene:acetonitrile solution (10 mL) and treated with N-bromosuccinimide (53 mg, 0.30 mmol). The resulting reaction mixture was heated to 50° C. and allowed to stir for 14 hours. The reaction was then cooled, adsorbed onto silica gel, and purified via column chromatography eluting with 3:1 hexanes:ethyl acetate to give 73 mg (89% yield) of 1-bromo-4-methoxyphenazine 19 as a yellow solid.

$^1$H NMR (400 MHz, CDCl$_3$): δ 8.36-8.25 (m, 2H), 7.96 (d, J=8.2 Hz, 1H), 7.86-7.75 (m, 2H), 6.84 (d, J=8.2 Hz, 1H), 4.07 (s, 3H).

$^{13}$C NMR (100 MHz, CDCl$_3$): δ 155.1, 143.6, 142.3, 141.0, 137.1, 133.2, 131.4, 131.1, 129.9, 129.8, 114.2, 106.9, 56.7.

HRMS (DART): m/z calc. for C$_{13}$H$_{10}$N$_2$OBr [M+H]$^+$: 288.9971, found: 288.9979.

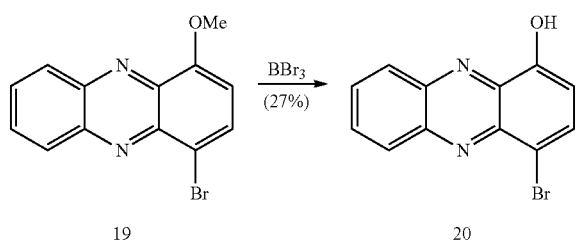

4-Bromophenazin-1-ol (20) 1-Bromo-4-methoxyphenazine (25 mg, 0.086 mmol) was dissolved in 2 mL dichloromethane, and cooled to −78° C. Boron tribromide (0.26 mL, 1.0 M in dichloromethane) was then added to the reaction, and the resulting mixture was allowed to warm to room temperature overnight. The reaction was then refluxed for 1 hour, allowed to cool, and quenched with 3 mL of a saturated aqueous solution of sodium bicarbonate. The resulting mixture was extracted with dichloromethane (3×20 mL). The combined organic layers were dried with sodium sulfate, filtered, and concentrated under reduced pressure. The crude material was subjected to column chromatography eluting with 3:1 hexanes:ethyl acetate to deliver 6.3 mg (27% yield) of 4-bromophenazin-1-ol 20 as a yellow solid.

$^1$H NMR (400 MHz, CDCl$_3$): δ 8.42 (m, 1H), 8.26 (m, 1H), 8.22 (s, 1H), 8.09 (d, J=8.1 Hz, 1H), 7.96-7.86 (m, 2H), 7.15 (d, J=8.1 Hz, 1H).

$^{13}$C NMR (100 MHz CDCl$_3$): δ 151.8, 144.6, 141.5, 141.0, 135.2, 134.7, 131.6 (2), 130.4, 129.0, 112.3, 109.6.

HRMS (DART): m/z calc. for C$_{12}$H$_8$N$_2$OBr [M+H]$^+$: 274.9815, found: 274.9819.

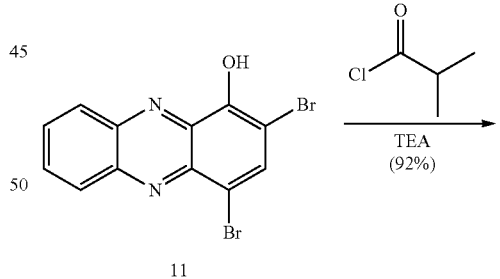

2,4-Dibromophenazin-1-yl acetate (21). 2,4-Dibromophenazin-1-ol (25 mg, 0.071 mmol) was dissolved in 2 mL dichloromethane. Triethylamine (50 μL, 0.35 mmol) was then added followed by the addition of acetyl chloride (15 μL, 0.21 mmol) at room temperature. The reaction mixture was allowed to stir for 30 minutes before being quenched with a saturated aqueous solution of sodium bicarbonate. The resulting mixture was then transferred to a separatory funnel, and dichloromethane was used for extraction. The combined organic layers were dried with sodium sulfate, filtered, and concentrated under reduced pressure. Purification via column chromatography using 9:1 hexanes:ethyl acetate afforded 25 mg (89% yield) of 2,4-dibromophenazin-1-yl acetate 21 as a yellow solid.

$^1$H NMR (400 MHz, CDCl$_3$): δ 8.56-8.29 (m, 1H), 8.34 (s, 1H, partially buried in multiplet), 8.27-8.20 (m, 1H), 7.95-7.85 (m, 2H), 2.61 (s, 3H).

$^{13}$C NMR (100 MHz, CDCl$_3$): δ 168.3, 145.2, 143.7, 143.6, 140.3, 137.8, 135.8, 132.3, 132.0, 130.2, 130.0, 122.3, 117.2, 20.9.

HRMS (DART): m/z calc. for C$_{14}$H$_9$N$_2$O$_2$Br$_2$ [M+H]$^+$: 396.9005, found: 396.9014.

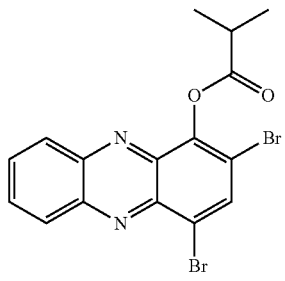

2,4-Dibromophenazin-1-yl isobutyrate (22). 2,4-Dibromophenazin-1-ol (25 mg, 0.071 mmol) was dissolved in 2 mL dichloromethane. Triethylamine (50 μL, 0.35 mmol) was then added followed by the addition of isobutyryl chloride (22 μL, 0.21 mmol) at room temperature. The reaction mixture was allowed to stir for 1 hour before being quenched with a saturated aqueous solution of sodium bicarbonate. The contents were then transferred to a separatory funnel, and dichloromethane was used for extraction. The combined organic layers were dried with sodium sulfate, filtered, and concentrated under reduced pressure. Purification via column chromatography using 19:1 hexanes:ethyl acetate afforded 28 mg (92% yield) of 2,4-dibromophenazin-1-yl isobutyrate 22 as a yellow solid.

$^1$H NMR (400 MHz, CDCl$_3$): δ 8.38-8.30 (m, 2H), 8.19 (m, 1H), 7.94-7.83 (m, 2H), 3.16 (hept, J=7.0 Hz, 1H), 1.55 (d, J=7.0 Hz, 6H).

$^{13}$C NMR (100 MHz, CDCl$_3$): δ 174.5, 145.3, 143.6, 143.5, 140.3, 137.7, 135.9, 132.2, 131.9, 130.2, 129.9, 122.0, 117.0, 34.5, 19.4.

HRMS (DART): m/z calc. for C$_{16}$H$_{13}$N$_2$O$_2$Br$_2$ [M+H]$^+$: 424.9319, found: 424.9327.

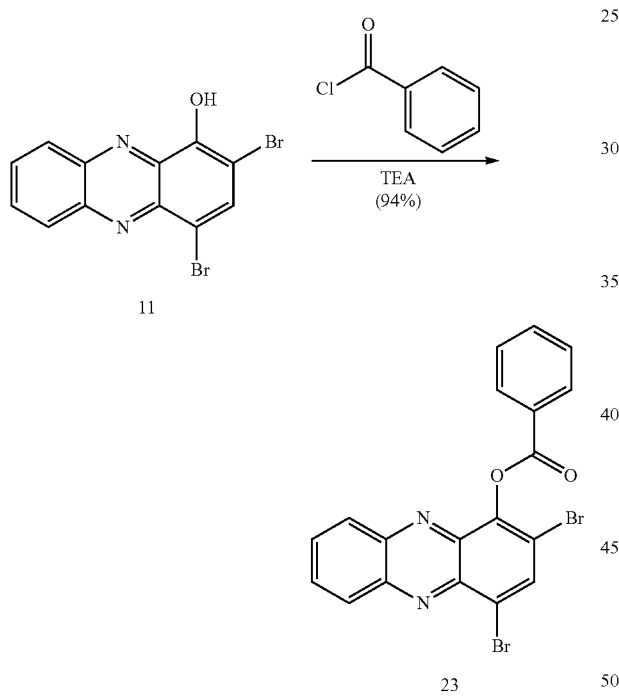

11

23

2,4-Dibromophenazin-1-yl benzoate (23). 2,4-Dibromophenazin-1-ol (25 mg, 0.071 mmol) was dissolved in 2 mL dichloromethane. Triethylamine (50 μL, 0.35 mmol) was then added followed by the addition of benzoyl chloride (25 μL, 0.21 mmol) at room temperature. The reaction mixture was allowed to stir for 1 hour before being quenched with a saturated aqueous solution of sodium bicarbonate. The resulting mixture was then transferred to a separatory funnel, and dichloromethane was used for extraction. The combined organic layers were dried with sodium sulfate, filtered, and concentrated under reduced pressure. Purification via column chromatography using 19:1 hexanes:ethyl acetate afforded 30 mg (94% yield) of 2,4-dibromophenazin-1-yl benzoate 23 as a yellow solid. $^1$H and $^{13}$C NMR spectra are obtained using CDCl$_3$ and d$_6$-benzene as the solvents. Two carbon signals overlap in the $^{13}$C NMR spectra obtained in CDCl$_3$ resulting in 16 signals. All expected 17 carbon signals are observed in the $^{13}$C NMR spectra in d$_6$-benzene.

$^1$H NMR (400 MHz, CDCl$_3$): δ 8.45-8.34 (m, 4H), 8.15 (m, 1H), 7.91 (ddd, J=8.6, 6.7, 1.5 Hz, 1H), 7.84 (ddd, J=8.3, 6.6, 1.5 Hz, 1H), 7.74 (m, 1H), 7.65-7.57 (m, 2H); (400 MHz, d$_6$-benzene) δ 8.46 (d, J=7.3 Hz, 2H), 8.06 (d, J=8.6 Hz, 1H), 7.92 (s, 1H), 7.77 (d, J=8.9 Hz, 1H), 7.21-7.03 (m, 4H), 6.99 (ddd, J=8.4, 6.7, 1.5 Hz, 1H).

$^{13}$C NMR (100 MHz, CDCl$_3$): δ 164.2, 145.5, 143.7, 143.7, 140.4, 138.0, 135.9, 134.3, 132.2, 132.0, 131.0, 130.2, 129.0, 128.9, 122.4, 117.3; (100 MHz, d$_6$-benzene) δ 164.0, 145.9, 143.7, 143.5, 140.6, 138.2, 135.6, 133.9, 131.7, 131.4, 131.1, 130.1, 129.9, 129.5, 128.9, 123.0, 117.6.

HRMS (DART): m/z calc. for C$_{19}$H$_{11}$N$_2$O$_2$Br$_2$ [M+H]$^+$: 458.9162, found: 458.9173.

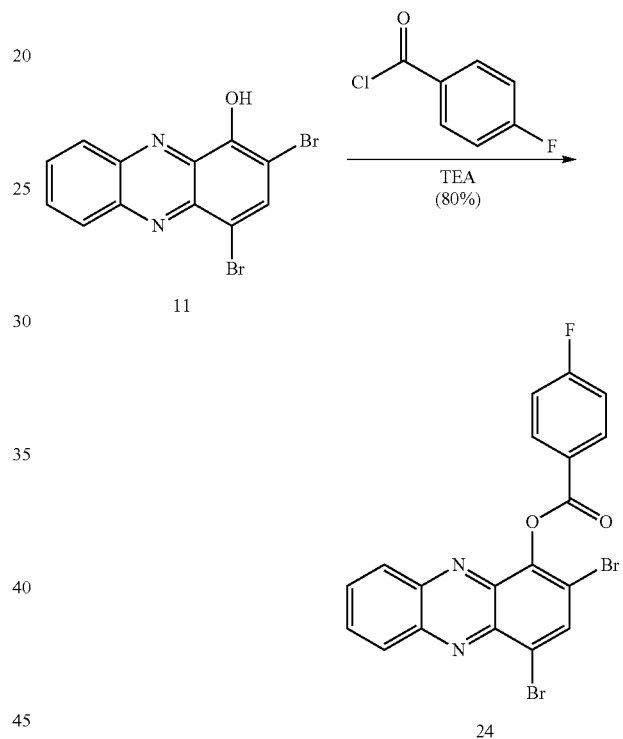

11

24

2,4-Dibromophenazin-1-yl 4-fluorobenzoate (24). 2,4-Dibromophenazin-1-ol (25 mg, 0.071 mmol) was dissolved in 2 mL dichloromethane. Triethylamine (50 μL, 0.35 mmol) was then added followed by the addition of 4-fluorobenzoyl chloride (25 μL, 0.21 mmol) at room temperature. The reaction mixture was allowed to stir for 1 hour before being quenched with a saturated aqueous solution of sodium bicarbonate. The contents were then transferred to a separatory funnel, and dichloromethane was used for extraction. The combined organic layers were dried with sodium sulfate, filtered, and concentrated under reduced pressure. Purification via column chromatography using 19:1 hexanes: ethyl acetate afforded 27 mg (80% yield) of 2,4-dibromophenazin-1-yl 4-fluorobenzoate 24 as a yellow solid.

$^1$H NMR (400 MHz, CDCl$_3$): δ 8.46-8.37 (m, 3H), 8.34 (d, J=8.8 Hz, 1H), 8.13 (d, J=8.4 Hz, 1H), 7.89 (ddd, J=8.6, 6.7, 1.6 Hz, 1H), 7.83 (ddd, J=8.4, 6.7, 1.5 Hz, 1H), 7.32-7.22 (m, 2H).

$^{13}$C NMR (100 MHz, CDCl$_3$): δ 166.7 (d, J=254.2 Hz, 1J C—F coupling), 163.2, 145.3, 143.7, 143.6, 140.3, 137.9, 135.8, 133.7, 133.6, 132.2, 132.0, 130.1 (d, J=9.1 Hz, 3J C—F coupling) 125.1 (d, J=2.9 Hz, 4J C—F coupling), 122.5, 117.3, 116.2 (d, J=21.9 Hz, 2J C—F coupling).

HRMS (DART): m/z calc. for $C_{19}H_{10}N_2O_2Br_2F$ [M+H]$^+$: 476.9068, found: 476.9077.

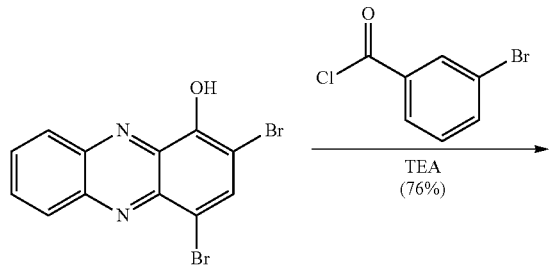

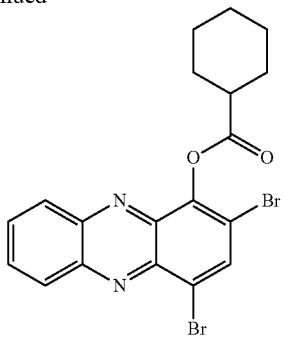

2,4-Dibromophenazin-1-yl cyclohexanecarboxylate (26). 2,4-Dibromophenazin-1-ol (25 mg, 0.071 mmol) was dissolved in 2 mL dichloromethane. Triethylamine (50 µL, 0.35 mmol) was then added followed by the addition of cyclohexanecarbonyl chloride (28 µL, 0.21 mmol) at room temperature. The reaction mixture was allowed to stir for 1 hour before being quenched with a saturated aqueous solution of sodium bicarbonate. The contents were then transferred to a separatory funnel, and dichloromethane was used for extraction. The combined organic layers were dried with sodium sulfate, filtered, and concentrated under reduced pressure. Purification via column chromatography using 19:1 hexanes:ethyl acetate afforded 27 mg (82% yield) of 2,4-dibromophenazin-1-yl cyclohexanecarboxylate 26 as a yellow solid.

2,4-Dibromophenazin-1-yl 3-bromobenzoate (25). 2,4-Dibromophenazin-1-ol (25 mg, 0.071 mmol) was dissolved in 2 mL dichloromethane. Triethylamine (50 µL, 0.35 mmol) was then added followed by the addition of 3-bromobenzoyl chloride (28 µL, 0.21 mmol) at room temperature. The reaction mixture was allowed to stir for 1 hour before being quenched with a saturated aqueous solution of sodium bicarbonate. The contents were then transferred to a separatory funnel, and dichloromethane was used for extraction. The combined organic layers were dried with sodium sulfate, filtered, and concentrated under reduced pressure. Purification via column chromatography using 19:1 hexanes:ethyl acetate afforded 29 mg (76% yield) of 2,4-dibromophenazin-1-yl 3-bromobenzoate 25 as a yellow solid.

$^1$H NMR (400 MHz, CDCl$_3$): δ 8.53 (t, J=1.7 Hz, 1H), 8.39 (s, 1H), 8.36 (dd, J=8.8, 1.6 Hz, 1H), 8.31 (dt, J=8.0, 1.3 Hz, 1H), 8.15 (m, 1H), 7.91 (ddd, J=8.6, 6.6, 1.6 Hz, 1H), 7.88-7.81 (m, 2H), 7.49 (t, J=7.9 Hz, 1H).

$^{13}$C NMR (100 MHz, CDCl$_3$): δ 163.0, 145.1, 143.8, 143.7, 140.4, 137.8, 137.3, 135.8, 133.8, 132.3, 132.1, 130.8, 130.6, 130.2, 130.1, 129.5, 123.1, 122.7, 117.3.

HRMS (DART): m/z calc. for $C_{19}H_{10}N_2O_2Br_3$ [M+H]$^+$: 536.8267, found: 536.8267.

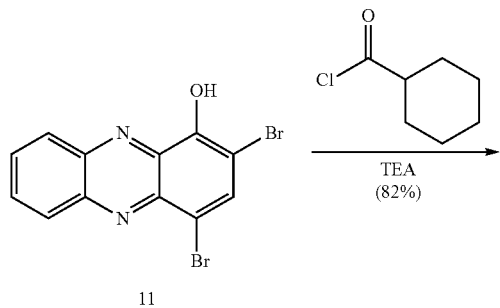

$^1$H NMR (400 MHz, CDCl$_3$): 8.37-8.29 (m, 2H), 8.19 (m, 1H), 7.95-7.82 (m, 2H), 2.93 (tt, J=11.0, 3.7 Hz, 1H), 2.38-2.23 (m, 2H), 2.00-1.70 (m, 5H), 1.55-1.34 (m, 3H).

$^{13}$C NMR (100 MHz, CDCl$_3$): δ 173.4, 145.3, 143.6, 143.5, 140.3, 137.8, 135.9, 132.2, 131.9, 130.1, 130.0, 121.9, 117.1, 43.3, 29.4, 26.0, 25.6.

HRMS (DART): m/z calc. for $C_{19}H_7N_2O_2Br_2$ [M+H]$^+$: 464.9632, found: 464.9647.

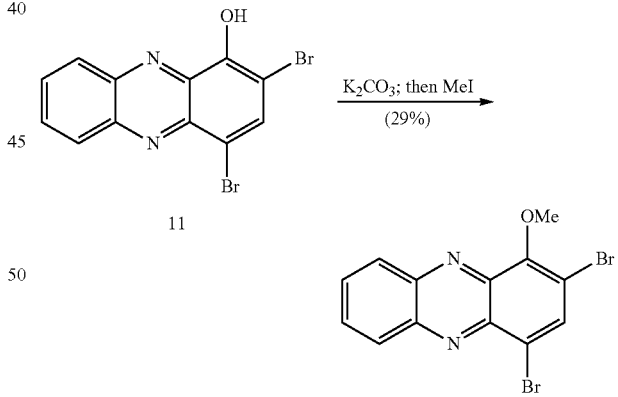

2,4-Dibromo-1-methoxyphenazine (27). Potassium carbonate (39 mg, 0.28 mmol) was added to a stirring solution of 2,4-dibromo-1-hydroxyphenazine (20 mg, 0.056 mmol) in 1 mL anhydrous acetone. The resulting mixture was allowed to stir at room temperature for 30 minutes before iodomethane (35 µL, 0.57 mmol) was added to the reaction. The resulting reaction mixture was then allowed to stir for an additional 6 hours. The reaction contents were then partitioned between deionized water and chloroform. The organic contents were then extracted with chloroform, dried with sodium sulfate, filtered, and concentrated under reduced pressure. The residue was purified by column chromatography using 8:1 hexanes:ethyl acetate to afford 5.9 mg (29% yield) of 2,4-dibromo-1-methoxyphenazine 27 as a yellow solid.

$^1$H NMR (400 MHz, CDCl$_3$): δ 8.39-8.33 (m, 2H), 8.32 (s, 1H), 7.96-7.87 (m, 2H), 4.31 (s, 3H).

$^{13}$C NMR (100 MHz, CDCl$_3$): δ 153.3, 143.4, 143.0, 140.9, 139.2, 136.7, 132.0, 131.8, 130.1, 130.0, 119.3, 116.1, 62.9.

HRMS (ESI): m/z calc. for C$_{13}$H$_9$N$_2$OBr$_2$ [M+H]$^+$: 368.9056, found: 368.9068.

Yield: 76% yield; 49.3 mg of 4a was isolated as a yellow solid.

$^1$H NMR (400 MHz, CDCl$_3$): δ 8.36-8.30 (m, 1H), 8.33 (s, 1H), 8.23-8.18 (m, 1H), 7.93-7.82 (m, 2H), 2.93 (q, J=7.6 Hz, 2H), 1.46 (t, J=7.6 Hz, 3H).

$^{13}$C NMR (100 MHz, CDCl$_3$): δ 171.9, 145.2, 143.6, 143.5, 140.3, 137.7, 135.8, 132.2, 132.0, 130.1, 129.9, 122.1, 117.1, 27.7, 9.6.

HRMS (DART): calc. for C$_{15}$H$_{11}$Br$_2$N$_2$O$_2$ [M+H]$^+$: 410.9162, found: 410.9165.

MP: 126-127° C.

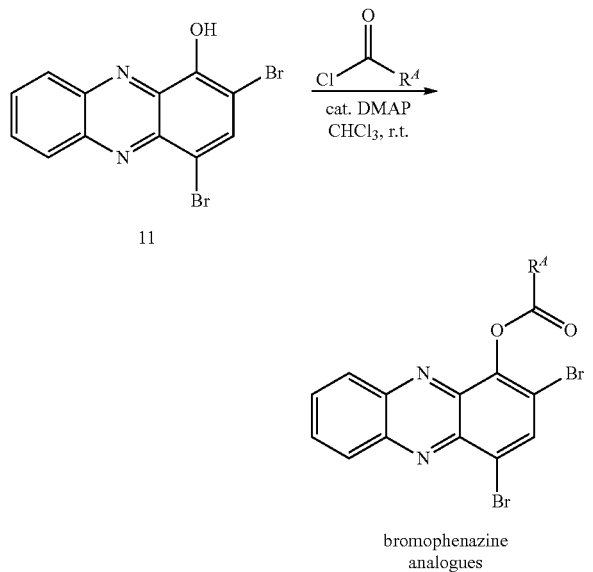

bromophenazine analogues

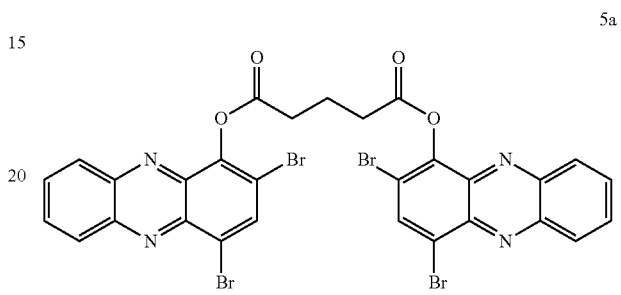

5a

Yield: 72% yield; 38.5 mg of 5a was isolated as a yellow solid.

$^1$H NMR (400 MHz, CDCl$_3$): δ 8.36 (s, 2H), 8.33 (ddd, J=8.8, 1.4, 0.7 Hz, 2H), 8.25 (ddd, J=8.7, 1.4, 0.7 Hz, 2H), 7.87 (ddd, J=8.8, 6.6, 1.4 Hz, 2H), 7.78 (ddd, J=8.7, 6.6, 1.4 Hz, 2H), 3.32 (t, J=7.1 Hz, 4H), 2.63 (p, J=7.2 Hz, 2H).

$^{13}$C NMR (100 MHz, CDCl$_3$): δ 170.5, 145.1, 143.7, 143.5, 140.3, 137.6, 135.8, 132.4, 132.0, 130.1, 129.9, 122.4, 117.1, 33.4, 21.0.

HRMS (DART): calc. for C$_{29}$H$_{17}$Br$_4$N$_4$O$_4$ [M+H]$^+$: 804.7940, found: 804.7927.

MP: 208-209° C.

General Procedure for Analogue Synthesis from 1-hydroxy-2,4-dibromophenazine 11: To a stirring solution of 1-hydroxy-2,4-dibromophenazine 11 (35 mg, 0.100 mmol), triethylamine (4.0 equivalents), and catalytic 4-dimethylaminopyridine in chloroform (3 mL) was added the respective acid chloride or reagent (1.2 equivalents) at room temperature. The reaction was allowed to stir for an additional hour before being quenched with an aqueous solution of sodium bicarbonate. The resulting mixture was then transferred to a separatory funnel and ethyl acetate was added to extract the crude product. The organic layer was sequentially washed with sodium bicarbonate and brine before the organic layer was collected. The organic layer was then dried with anhydrous sodium sulfate, filtered, and concentrated via rotavap. The respective bromophenazine analogue was purified via flash column chromatography using hexanes:ethyl acetate:dichloromethane (91:1:8 to 82:10:8) to elute giving pure bromophenazine analogues as a yellow solid.

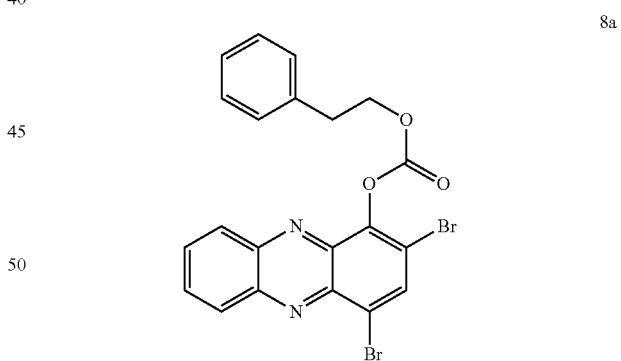

8a

Yield: 88% yield; 68.9 mg of 8a was isolated as a yellow solid.

$^1$H NMR (400 MHz, CDCl$_3$): δ 8.37-8.33 (m, 1H), 8.35 (s, 1H), 8.18 (m, 1H), 7.94-7.86 (m, 2H), 7.52-7.48 (m, 2H), 7.44-7.33 (m, 3H), 4.90 (s, 2H), 4.74 (s, 2H).

$^{13}$C NMR (100 MHz, CDCl$_3$): δ 168.1, 144.6, 143.8, 143.5, 140.3, 137.4, 137.1, 135.7, 132.5, 132.1, 130.2, 129.8, 128.8, 128.6, 128.4, 122.6, 117.1, 73.7, 67.0.

HRMS (DART): calc. for C$_{21}$H$_{15}$Br$_2$N$_2$O$_3$ [M+H]$^+$: 502.9425, found: 502.9413.

MP: 99-101° C.

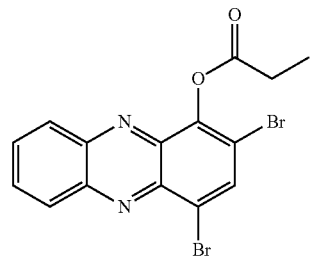

4a

9a

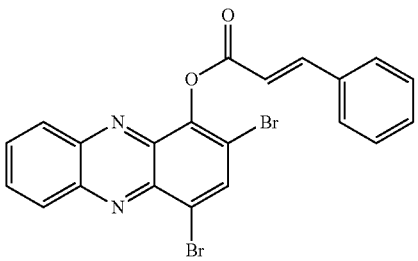

Yield: 63% yield; 40.0 mg of 9a was isolated as a yellow solid.

$^1$H NMR (400 MHz, CDCl$_3$): δ 8.39 (s, 1H), 8.37 (ddd, J=8.3, 1.7, 0.7 Hz, 1H), 8.24 (ddd, J=8.3, 1.7, 0.7 Hz, 1H), 8.07 (d, J=16.0 Hz, 1H), 7.95-7.85 (m, 2H), 7.72-7.66 (m, 2H), 7.50-7.45 (m, 3H), 6.94 (d, J=16.0 Hz, 1H).

$^{13}$C NMR (100 MHz, CDCl$_3$): δ 164.3, 148.4, 145.3, 143.7, 143.6, 140.4, 138.0, 135.9, 134.3, 132.3, 132.0, 131.3, 130.2, 130.1, 129.3, 128.8, 122.3, 117.4, 116.2.

HRMS (DART): calc. for C$_{21}$H$_{13}$Br$_2$N$_2$O$_2$ [M+H]$^+$: 484.9319, found: 484.9309.

MP: 231-232° C.

12a

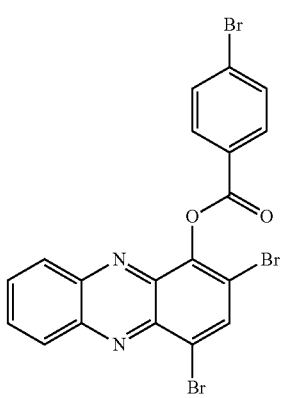

Yield: >99% yield; 20.5 mg of 12a was isolated as a yellow solid.

$^1$H NMR (400 MHz, CDCl$_3$): δ 8.39 (s, 1H), 8.36 (d, J=8.7 Hz, 1H), 8.25 (d, J=7.7 Hz, 2H), 8.13 (d, J=8.8 Hz, 1H), 7.91 (m, 1H), 7.85 (m, 1H), 7.76 (d, J=8.0 Hz, 2H).

$^{13}$C NMR (100 MHz, CDCl$_3$): δ 163.6, 145.2, 143.8, 143.6, 140.3, 137.8, 135.8, 132.4, 132.4, 132.3, 132.1, 130.2, 130.1, 129.7, 127.7, 122.6, 117.3.

HRMS (DART): calc. for C$_{19}$H$_{10}$Br$_3$N$_2$O$_2$ [M+H]$^+$: 538.8248, found: 538.8252.

MP: 232-235° C.

14a

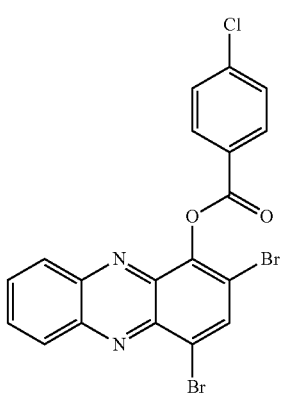

Yield: >99% yield; 16.4 mg of 14a was isolated as a yellow solid.

$^1$H NMR (400 MHz, CDCl$_3$): δ 8.39 (s, 1H), 8.36 (m, 1H), 8.33 (d, J=8.4 Hz, 2H), 8.13 (d, J=8.7 Hz, 1H), 7.91 (ddd, J=8.5, 6.6, 1.6 Hz, 1H), 7.85 (ddd, J=8.3, 6.6, 1.5 Hz, 1H), 7.59 (d, J=8.8 Hz, 2H).

$^{13}$C NMR (100 MHz, CDCl$_3$): δ 163.4, 145.2, 143.7, 143.6, 140.9, 140.3, 137.8, 135.8, 132.3, 132.3, 132.1, 130.2, 130.1, 129.4, 127.3, 122.6, 117.3.

HRMS (DART): calc. for C$_{19}$H$_{10}$Br$_2$ClN$_2$O$_2$[M+H]: 492.8771, found: 492.8767.

MP: 228-229° C.

15a

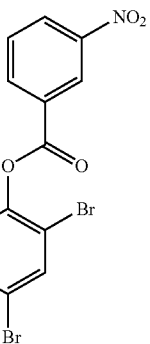

Yield: 78% yield; 19.4 mg of 15a was isolated as a yellow solid.

$^1$H NMR (400 MHz, CDCl$_3$): δ 9.23 (t, J=1.9 Hz, 1H), 8.70 (m, 1H), 8.60 (m, 1H), 8.41 (s, 1H), 8.37 (m, 1H), 8.12 (m, 1H), 7.97-7.79 (m, 3H).

$^{13}$C NMR (100 MHz, CDCl$_3$): δ 162.2, 148.7, 144.8, 143.8, 143.6, 140.3, 137.5, 136.5, 135.7, 132.5, 132.2, 130.7, 130.3, 130.2, 129.9, 128.7, 125.9, 123.0, 117.3.

HRMS (DART): calc. for C$_{19}$H$_{10}$Br$_2$N$_3$O$_4$ [M+H]$^+$: 503.9013, found: 503.8997.

MP: 216-217° C.

16a

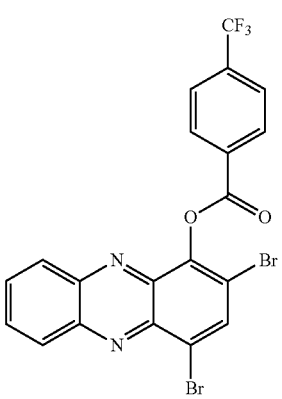

Yield: 90% yield; 39.1 mg of 16a was isolated as a yellow solid.

$^1$H NMR (400 MHz, CDCl$_3$): δ 8.52 (d, J=7.9 Hz, 2H), 8.40 (s, 1H), 8.37 (m, 1H), 8.13 (m, 1H), 7.97-7.80 (m, 2H), 7.88 (d, J=9.3 Hz, 2H).

$^{13}$C NMR (100 MHz, CDCl$_3$): δ 163.1, 145.1, 143.8, 143.6, 140.4, 137.7, 135.8, 135.7 (q, J$_{CF}$=33 Hz), 132.4, 132.2, 132.1, 131.4, 130.2, 130.0, 126.1 (q, J$_{CF}$=3.7 Hz), 123.8 (q, J$_{CF}$=273 Hz), 122.8, 117.3.

HRMS (DART): calc. for $C_{20}H_{10}Br_2F_3N_2O_2[M+H]^+$: 526.9036, found: 526.9027.

MP: 222-223° C.

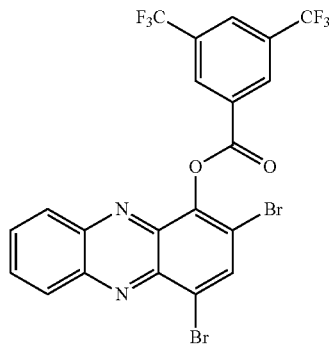

17a

Yield: >99% yield; 27.8 mg of 17a was isolated as a yellow solid.

$^1$H NMR (400 MHz, CDCl$_3$): δ 8.80-8.80 (m, 2H), 8.41 (s, 1H), 8.38 (ddd, J=8.7, 1.5, 0.7 Hz, 1H), 8.25 (m, 1H), 8.12 (ddd, J=8.6, 1.5, 0.7 Hz, 1H), 7.93 (ddd, J=8.7, 6.6, 1.6 Hz, 1H), 7.87 (ddd, J=8.6, 6.6, 1.5 Hz, 1H).

$^{13}$C NMR (100 MHz, CDCl$_3$): δ 161.7, 144.6, 143.9, 143.6, 140.3, 137.4, 135.7, 132.9 (q, J$_{CF}$=34 Hz), 132.6, 132.3, 131.1, 130.9 (q, J$_{CF}$=3.5 Hz), 130.2, 129.9, 127.7 (sept, J$_{CF}$=3.6 Hz), 123.2, 123.0 (q, J$_{CF}$=273 Hz), 117.3.

HRMS (DART): calc. for $C_{21}H_9Br_2F_6N_2O_2[M+H]$: 594.8910, found: 594.8902.

MP: 191-192° C.

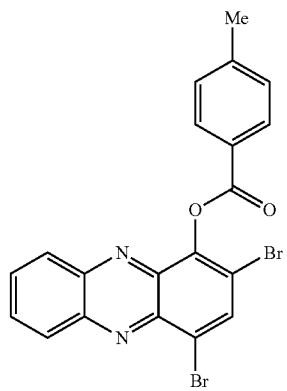

18a

Yield: 96% yield; 19.3 mg of 18a was isolated as a yellow solid.

$^1$H NMR (400 MHz, CDCl$_3$): δ 8.39 (s, 1H), 8.35 (ddd, J=8.7, 1.5, 0.7 Hz, 1H), 8.31-8.26 (m, 2H), 8.15 (ddd, J=8.6, 1.5, 0.7 Hz, 1H), 7.90 (ddd, J=8.7, 6.6, 1.5 Hz, 1H), 7.83 (ddd, J=8.6, 6.6, 1.5 Hz, 1H), 7.44-7.38 (m, 2H), 2.52 (s, 3H).

$^{13}$C NMR (100 MHz, CDCl$_3$): δ 164.2, 145.5, 145.2, 143.6, 143.6, 140.3, 138.0, 135.8, 132.1, 131.9, 131.0, 130.1, 130.1, 129.6, 126.0, 122.2, 117.3, 22.1.

HRMS (DART): calc. for $C_{20}H_{13}Br_2N_2O_2$ $[M+H]^+$: 472.9319, found: 472.9314.

MP: 213-214° C.

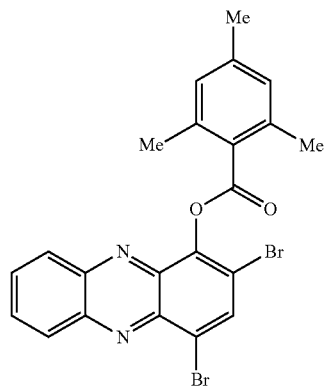

19a

Yield: 97% yield; 32.7 mg of 19a was isolated as a yellow solid.

$^1$H NMR (400 MHz, CDCl$_3$): δ 8.40 (s, 1H), 8.38 (m, 1H), 8.22 (m, 1H), 7.97-7.86 (m, 2H), 7.02 (s, 2H), 2.80 (s, 6H), 2.38 (s, 3H).

$^{13}$C NMR (100 MHz, CDCl$_3$): δ 167.2, 145.5, 143.7, 143.5, 140.9, 140.4, 137.9, 137.7, 136.1, 132.4, 132.0, 130.3, 129.6, 129.3, 128.7, 122.4, 117.4, 21.5, 21.4.

HRMS (DART): calc. for $C_{22}H_{17}Br_2N_2O_2$ $[M+H]^+$: 500.9620, found: 500.9632.

MP: 179-180° C.

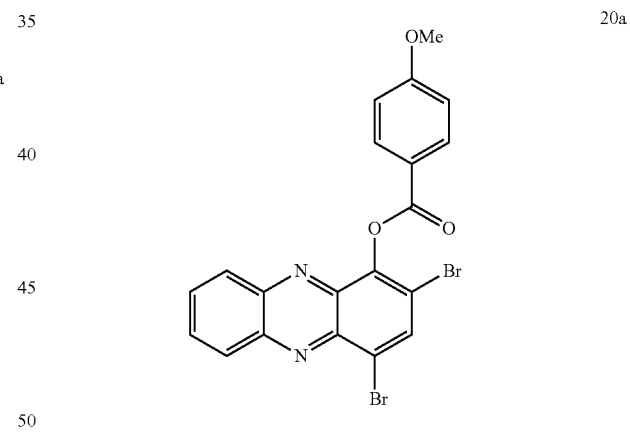

20a

Yield: 83% yield; 37.7 mg of 20a was isolated as a yellow solid.

$^1$H NMR (400 MHz, CDCl$_3$): δ 8.39 (s, 1H), 8.38-8.31 (m, 3H), 8.15 (ddd, J=8.7, 1.6, 0.8 Hz, 1H), 7.90 (ddd, J=8.8, 6.6, 1.6 Hz, 1H), 7.84 (ddd, J=8.1, 6.7, 1.5 Hz, 1H), 7.11-7.05 (m, 2H), 3.95 (s, 3H).

$^{13}$C NMR (100 MHz, CDCl$_3$): δ 164.6, 163.9, 145.6, 143.7, 143.7, 140.4, 138.2, 135.9, 133.2, 132.1, 132.0, 130.2, 130.1, 122.2, 121.1, 117.4, 114.3, 55.8.

HRMS (DART): calc. for $C_{20}H_{13}Br_2N_2O_3$ $[M+H]^+$: 488.9268, found: 488.9253.

MP: 215-216° C.

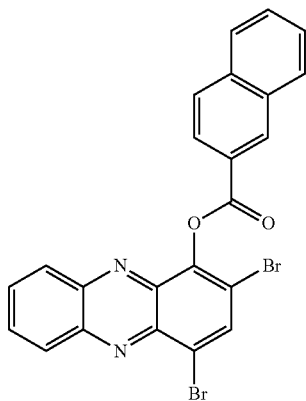

21a

Yield: 97% yield; 80.6 mg of 21a was isolated as a yellow solid.

$^1$H NMR (400 MHz, CDCl$_3$): δ 9.02 (d, J=1.6 Hz, 1H), 8.42 (s, 1H), 8.36 (ddd, J=8.7, 1.4, 0.7 Hz, 1H), 8.35 (dd, J=8.7, 1.8 Hz, 1H), 8.13 (ddd, J=8.7, 1.5, 0.7 Hz, 1H), 8.07 (ddd, J=8.6, 1.2, 0.6 Hz, 1H), 8.04 (d, J=8.6 Hz, 1H), 7.98 (dd, J=8.0, 0.4 Hz, 1H), 7.90 (ddd, J=8.7, 6.6, 1.5 Hz, 1H), 7.82 (ddd, J=8.6, 6.6, 1.5 Hz, 1H), 7.69 (ddd, J=8.2, 6.9, 1.4 Hz, 1H), 7.62 (ddd, J=8.1, 6.9, 1.3 Hz, 1H).

$^{13}$C NMR (100 MHz, CDCl$_3$): δ 164.4, 145.5, 143.7, 143.6, 140.4, 138.0, 136.3, 135.9, 132.9, 132.7, 132.2, 132.0, 130.1, 130.1, 129.8, 129.1, 128.8, 128.1, 127.2, 126.0, 126.0, 122.4, 117.4.

HRMS (DART): calc. for C$_{23}$H$_{13}$Br$_2$N$_2$O$_2$ [M+H]$^+$: 508.9319, found: 508.9307.

MP: 220-221° C.

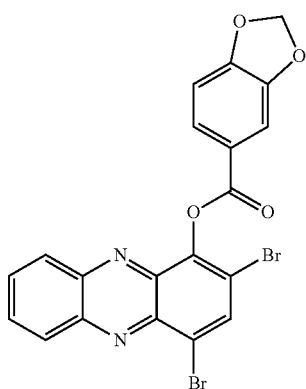

22a

Yield: 88% yield; 80.1 mg of 22a was isolated as a yellow solid.

$^1$H NMR (400 MHz, CDCl$_3$): δ 8.39 (s, 1H), 8.36 (m, 1H), 8.16 (m, 1H), 8.02 (dd, J=8.2, 1.7 Hz, 1H), 7.90 (ddd, J=8.6, 6.7, 1.5 Hz, 1H), 7.85 (ddd, J=8.3, 6.6, 1.5 Hz, 1H), 7.79 (d, J=1.7 Hz, 1H), 7.00 (d, J=8.2 Hz, 1H), 6.14 (s, 2H).

$^{13}$C NMR (100 MHz, CDCl$_3$): δ 163.6, 152.9, 148.3, 145.5, 143.7, 143.6, 140.3, 138.1, 135.9, 132.2, 132.0, 130.2, 130.1, 127.3, 122.6, 122.3, 117.4, 110.7, 108.6, 102.3.

HRMS (DART): calc. for C$_{20}$H$_{11}$Br$_2$N$_2$O$_4$ [M+H]$^+$: 502.9061, found: 502.9049.

MP: 245-246° C.

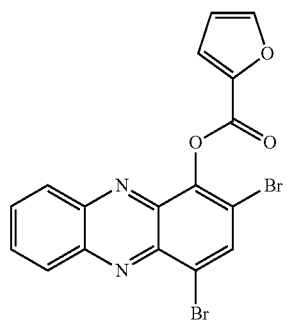

23a

Yield: 75% yield; 58.4 mg of 23a was isolated as a yellow solid.

$^1$H NMR (400 MHz, CDCl$_3$): δ 8.38 (s, 1H), 8.34 (ddd, J=8.5, 1.6, 0.7 Hz, 1H), 8.18 (ddd, J=8.5, 1.6, 0.7 Hz, 1H), 7.90 (ddd, J=8.6, 6.6, 1.6 Hz, 1H), 7.85 (ddd, J=8.2, 6.6, 1.6 Hz, 1H), 7.80 (dd, J=1.8, 0.9 Hz, 1H), 7.64 (dd, J=3.6, 0.9 Hz, 1H), 6.71 (dd, J=3.5, 1.8 Hz, 1H).

$^{13}$C NMR (100 MHz, CDCl$_3$): δ 155.6, 148.0, 144.5, 143.7, 143.6, 143.4, 140.3, 137.8, 135.8, 132.3, 132.1, 130.1, 130.1, 122.7, 121.0, 117.5, 112.7.

HRMS (DART): calc. for C$_{17}$H$_9$Br$_2$N$_2$O$_3$ [M+H]$^+$: 448.8955, found: 448.8957.

MP: 168-169° C.

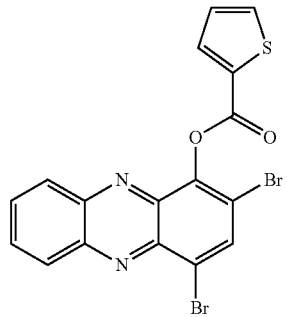

24a

Yield: 89% yield; 37.0 mg of 24a was isolated as a yellow solid.

$^1$H NMR (400 MHz, CDCl$_3$): δ 8.39 (s, 1H), 8.35 (ddd, J=8.8, 1.5, 0.7 Hz, 1H), 8.21-8.15 (m, 2H), 7.90 (ddd, J=8.8, 6.6, 1.6 Hz, 1H), 7.85 (ddd, J=8.8, 6.6, 1.6 Hz, 1H), 7.79 (dd, J=5.0, 1.2 Hz, 1H), 7.28 (dd, J=5.0, 3.8 Hz, 1H).

$^{13}$C NMR (100 MHz, CDCl$_3$): δ 159.4, 144.9, 143.7, 143.6, 140.3, 138.0, 135.9, 135.8, 134.5, 132.2, 132.1, 131.8, 130.2, 130.1, 128.5, 122.6, 117.5.

HRMS (DART): calc. for C$_{17}$H$_9$Br$_2$N$_2$O$_2$S [M+H]$^+$: 464.8726, found: 464.8725.

MP: 186-187° C.

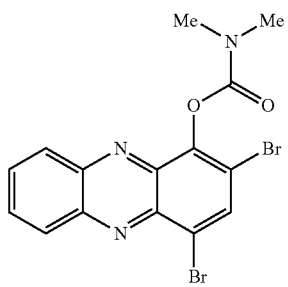

25a

Yield: 39% yield; 24.8 mg of 25a was isolated as a yellow solid.

¹H NMR (400 MHz, CDCl₃): δ 8.38-8.30 (m, 1H), 8.34 (s, 1H), 8.25 (m, 1H), 7.93-7.84 (m, 2H), 3.39 (s, 3H), 3.13 (s, 3H).

¹³C NMR (100 MHz, CDCl₃): δ 153.6, 145.7, 143.6, 143.6, 140.3, 138.6, 135.9, 132.0, 131.9, 130.2, 130.1, 121.6, 117.4, 37.4, 37.3.

HRMS (DART): calc. for $C_{15}H_{12}Br_2N_3O_2$ [M+H]⁺: 425.9271, found: 425.9275.

MP: 158° C. (decomp.).

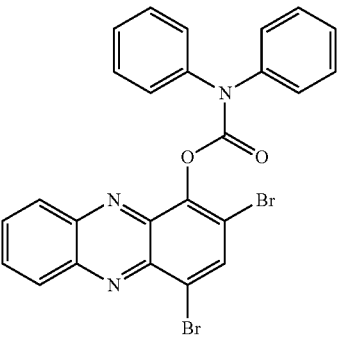

26a

Yield: 97% yield; 84.5 mg of 26a was isolated as a yellow sold.

¹H NMR (400 MHz, CDCl₃): δ 8.40-8.33 (m, 2H), 8.32 (s, 1H), 7.98-7.89 (m, 2H), 7.77-7.51 (m, 4H), 7.42 (t, J=7.7 Hz, 4H), 7.28 (t, J=7.7 Hz, 2H).

¹³C NMR (100 MHz, CDCl₃): δ 151.9, 145.4, 143.6, 143.5, 142.5, 140.3, 138.1, 135.9, 132.2, 131.9, 130.2, 130.0, 129.3, 126.9 (broad signal), 121.8, 117.3.

HRMS (DART): calc. for $C_{25}H_{16}Br_2N_3O_2$ [M+H]⁺: 549.9585, found: 549.9573.

MP: 251-252° C.

Note: ¹H NMR and ¹³C NMR gave broad signal regions despite adequate shimming prior to acquisition; the ¹³C NMR is missing one carbon signal despite excellent signal to noise (2 carbon signals are most likely under the broad signal at 127 ppm).

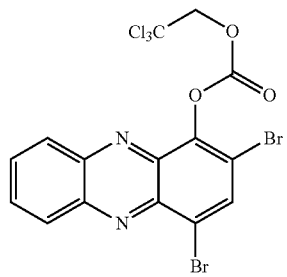

27a

Yield: 82% yield; 32.8 mg of 27a was isolated as a yellow solid.

¹H NMR (400 MHz, CDCl₃): δ 8.39-8.34 (m, 1H), 8.36 (s, 1H), 8.22 (m, 1H), 7.97-7.89 (m, 2H), 5.01 (s, 2H).

¹³C NMR (100 MHz, CDCl₃): δ 151.5, 144.1, 143.9, 143.6, 140.2, 137.3, 135.7, 132.7, 132.3, 130.2, 129.9, 123.3, 116.9, 94.3, 78.0.

HRMS (DART): calc. for $C_{15}H_8Br_2Cl_3N_2O_3$ [M+H]⁺: 530.7915, found: 530.7900.

MP: 135-136° C.

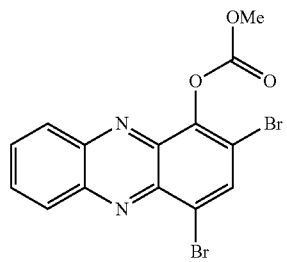

28a

Yield: 65% yield; 41.4 mg of 28a was isolated as a yellow solid.

¹H NMR (400 MHz, CDCl₃): δ 8.36 (m, 1H), 8.35 (s, 1H), 8.29 (m, 1H), 7.96-7.88 (m, 2H), 4.05 (s, 3H).

¹³C NMR (100 MHz, CDCl₃): δ 153.0, 144.6, 143.8, 143.6, 140.3, 137.7, 135.8, 132.5, 132.2, 130.2, 130.0, 122.7, 116.9, 56.6.

HRMS (DART): calc. for $C_{14}H_9Br_2N_2O_3$ [M+H]⁺: 412.8955, found: 412.8953.

MP: 167-168° C.

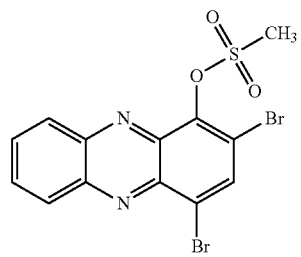

29a

Yield: 88% yield; 43.7 mg of 29a was isolated as a yellow solid.

¹H NMR (400 MHz, CDCl₃): δ 8.42-8.36 (m, 1H), 8.39 (s, 1H), 8.25 (m, 1H), 8.00-7.92 (m, 2H), 3.85 (s, 3H).

¹³C NMR (100 MHz, CDCl₃): δ 143.8, 143.8, 143.5, 140.4, 138.4, 136.2, 133.0, 132.4, 130.4, 129.4, 123.6, 119.8, 41.5.

HRMS (DART): calc. for $C_{13}H_9Br_2N_2O_3S$ [M+H]⁺: 432.8675, found: 432.8686.

MP: 188-189° C.

Example 2

Biological Assays of the Compounds

Compound storage. Solid stocks of the compounds described herein were stored at −80° C. in vials sealed with PARAFILM. Between 2.0 and 4.5 milligrams of each compound was weighed out, and a 10 mM DMSO stock solution of each compound were prepared. DMSO stock solutions were stored at room temperature in the dark (e.g., wrapped in aluminum foil). At this concentration, a few compounds required gentle heating to completely solubilize. DMSO stock solutions were not subjected to any freeze-thaw cycles to prevent compound breakdown. The compounds were stable in DMSO for several weeks under these mild storage conditions, with the exception of pyocyanin. Pyocyanin is unstable in DMSO at room temperature after one day. In NMR experiments, significant decomposition of pyocyanin in d₆-DMSO was observed after 8 hours at room temperature. DMSO stock solutions of about 2 milligrams of pyocyanin were made fresh each day. The hydrolysis stability of select compounds was also tested, e.g., by subjecting these compounds to conditions mimicking the biofilm assays described herein. In one set of exemplary experiments, 3.2 to 4.5 mgs of each of compounds 18a, 12a, 23a, and 21 were treated with 1 mL of sterile water to form a mixture. Each of the mixtures was allowed to be incubated for 24 hours at 37° C. under static conditions analogous to the *S. aureus* biofilm inhibition assays described herein. After 24 hours, each of the mixtures was extracted with dichloromethane and evaluated, using TLC and NMR, for hydrolysis of each of compounds 18a, 12a, 23a, and 21 to compound 11. Compounds 18a, 12a, 23a, and 21 were all found to be stable to hydrolysis.

Antibiotic Susceptibility Tests (MIC Assay Protocol). The minimum inhibitory concentration (MIC) for each compound described herein was determined by the broth microdilution method as recommended by the Clinical and Laboratory Standards Institute (CLSI) (Clinical and Laboratory Standards Institute. 2009. Methods for dilution antimicrobial susceptibility tests for bacteria that grow aerobically; approved standard, eighth edition (M7-A8)). In a 96-well plate, eleven two-fold serial dilutions of each compound were made in a final volume of 100 µL Luria Broth (one column served as a blank; see the MIC assay described herein). Each well was inoculated with $10^5$ bacterial cells at the initial time of incubation, prepared from a fresh log phase culture ($OD_{600}$ of 0.5). The MIC was defined as the lowest concentration of a compound that prevented bacterial growth after incubating of 16 to 20 hours at 37° C. The concentration range tested for each compound during this study was 0.10 to 100 µM. DMSO served as the vehicle and negative control in each microdilution MIC assay. DMSO was serially diluted at the same concentration as the compounds with a top concentration of 1% v/v. Bacterial strains used: *Staphylococcus aureus* (ATCC 25923), *Staphylococcus epidermidis* (ATCC 12228) and *Pseudomonas aeruginosa* (PAO1). Kanamycin was used as a positive control against *Staphylococcus aureus* and *Staphylococcus epidermidis*.

Biofilm Inhibition Protocol for *S. aureus* (ATCC 25923). A serial two-fold dilution of 2× bromophenazine small molecule concentration was made in 100 µL tryptic soy broth (TSB) medium with 0.5% glucose were delivered into 0.1% gelatin (Millipore) coated 96-well tissue culture plates. The same volume of DMSO (vehicle control), was used as a negative control and did not go over 1% v/v in biofilm inhibition assays. To each well, 100 µL of TSB with 0.5% glucose containing $2 \times 10^6$ CFU/mL *Staphylococcus aureus* cells, prepared from fresh culture ($OD_{600}$ of 0.8), was added. The plates were incubated at 37° C. for 24 hours. The wells were gently rinsed by submerging the entire plates in a tub of cold, running tap water. The wells were then fixed with 200 µL methanol for 15 minutes. After the plates were air dried, the biofilms were stained with 100 µL of 1% crystal violet for 10 minutes. The plates were again rinsed with running water. After drying in air, quantitative assessment of biofilm formation was obtained by extracting the crystal violet associated with the remaining biofilm with 100 µL per well of the following bleaching solution (methanol:glacial acetic acid:water (v/v/v)=4:1:5). This bleaching solution dissolved the bound crystal violet and produced a violet-colored solution in each well. The intensity of coloration was determined by measuring the absorbance at 540 nm.

Biofilm Dispersion Protocol for *Staphylococcus aureus* (ATCC 25923): A single colony grown on tryptic soy agar (TSA) solid medium is amplified in 2 milliliters of tryptic soy broth (TSB) medium with 0.5% glucose to an $OD_{600}$=0.8-1.0. The bacterial suspension was then diluted to $1 \times 10^6$ CFU/mL in TSB with 0.5% glucose. Sterile 96-well flat-bottomed polystyrene plates (0.1% gelatin coated overnight) were then filled with 200 µL of this bacterial suspension. The plates were then covered and incubated for 24 hours at 37° C. Following this, the contents of the wells were discarded and washed with 200 µL PBS (one time). Then serial, two-fold dilutions of bromophenazine small molecules in 200 µL PBS were delivered into each well. The plates were then covered and incubated for another 24 hours at room temperature. After this incubation time, the plates were gently washed with water three times (wells were rinsed by submerging the entire plates in a tub of cold, running tap water). Remaining biofilms were then fixed with 200 µL of methanol for 15 minutes. The plates were emptied and left to air dry. Upon drying, 100 µL of 1% crystal violet was added to each well for 10 minutes, then washed three times with water and again air dried. For quantitative assessment of biofilm formation 100 µL per well of bleaching solution (methanol:glacial acetic acid:water (v/v/v)=4:1:5 with rotary shaking for 1 hour) was used. Remaining biofilm was measured using a spectrophotometer (absorbance readings at 540 nm).

Biofilm Inhibition Protocol for *A. baumannii* (ATCC 19606): In a 96-well plate, ten two-fold serial dilutions of each compound tested were made from the highest concentration tested (100 µM) in a final volume of 100 µL in Mueller-Hinton broth (one column served as a blank). Each well was inoculated with ~$7 \times 10^6$ colony forming units per milliliter (corresponding to an $OD_{600}$ of 0.01 prepared directly from an overnight culture). A lid was placed on the 96-well plate which was wrapped in suran wrap, placed in a humidifying chamber and incubated under static conditions at 37° C. for 24 hours. Following incubation, the media and planktonic bacteria were then removed from 96-well plates and the wells were then washed with water. The bacterial biofilms within the microtiter wells were stained with 200 µL of an aqueous 0.1% crystal violet solution that was allowed to stand for 10-20 minutes. The crystal violet stain was then removed, the wells were rinsed with water and dried. The crystal violet stain that remained on the inside of the wells (i.e., stained bacterial biofilm) on the inside of the wells was solubilized by the addition of 200 µL ethanol and absorbance was read at $OD_{540}$ using a spectrophotometer. NOTE: The concentration range tested for each compound was 0.2-100 µM. Single data points for all compounds and DMSO controls were tested in two replicate rows in 96-well plates and corresponding absorbance readings were averaged for the quantification of planktonic growth and biofilm formation. Reported percent biofilm inhibition was determined by the comparison of compound treated wells (the average of the two replicate wells) versus vehicle control wells without compound following background subtraction (i.e., an empty, untreated well) and reported from 2 to 4 independent overnight cultures. DMSO was serially diluted at the same concentration as test compounds with a top concentration of 1% v/v.

Biofilm Dispersion Protocol for *A. baumannii* (ATCC 19606): To a 96-well plate was added a volume of 100 µL Mueller-Hinton broth that was inoculated with ~$7 \times 10^6$ colony forming units per milliliter (corresponding to an $OD_{600}$ of 0.01 prepared directly from an overnight culture). Two columns of wells were left blank to serve as our background wells. A lid was placed on the 96-well plate which was wrapped in suran wrap, placed in a humidifying chamber and incubated under static conditions at room temperature for 24 hours to establish bacterial biofilms. Following this initial incubation at room temperature, the media and planktonic bacteria were then removed from 96-well plates and the wells were then washed with water. Fresh medium was then added and series of ten two-fold serial dilutions of text compound were made in the 96-well plate using a multichannel pipette. A lid was then placed on 96-well plate which was then wrapped in suran wrap, placed in a humidifying chamber and incubated under static conditions at 37° C. for 24 hours. Following this second incubation to test compounds against pre-formed biofilms, the media and planktonic bacteria were again removed from 96-well plates and the wells were then washed with water. The bacterial biofilms within the microtiter wells were stained with 200 μL of an aqueous 0.1% crystal violet solution that was allowed to stand for 10-20 minutes. The crystal violet stain was then removed, the wells were rinsed with water and dried. The crystal violet stain that remained on the inside of the wells (i.e., stained bacterial biofilm) on the inside of the wells was solubilized by the addition of 200 μL ethanol and absorbance was read at $OD_{540}$ using a spectrophotometer. Note: The concentration range tested for each compound was 0.2-100 μM. Single data points for all compounds and DMSO controls were tested in two replicate rows in 96-well plates and corresponding absorbance readings were averaged for the quantification of remaining bacterial biofilms. Reported percent dispersion of biofilms was determined by the comparison of compound treated wells (the average of the two replicate wells) versus vehicle control wells without compound following background subtraction (i.e., an empty, untreated well) and reported from two independent experiments. DMSO was serially diluted at the same concentration as test compounds with a top concentration of 1% v/v.

Figure 3:
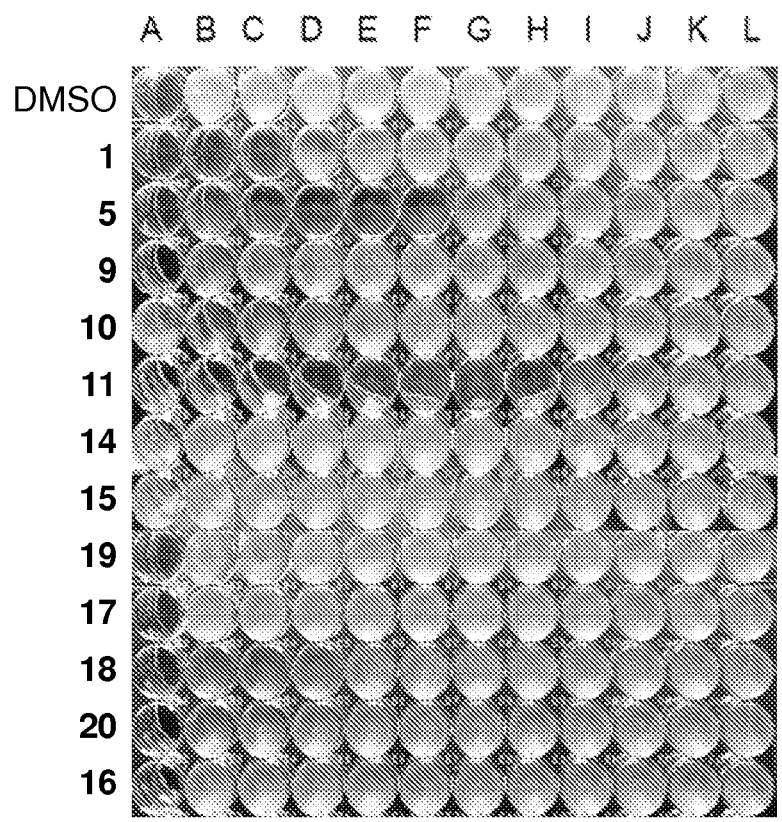
FIG. 3 depicts exemplary results of minimum inhibitory concentration (MIC) experiments of compounds 1, 5, 9-11, and 14-20 against *Staphylococcus aureus*.
Figure 4:
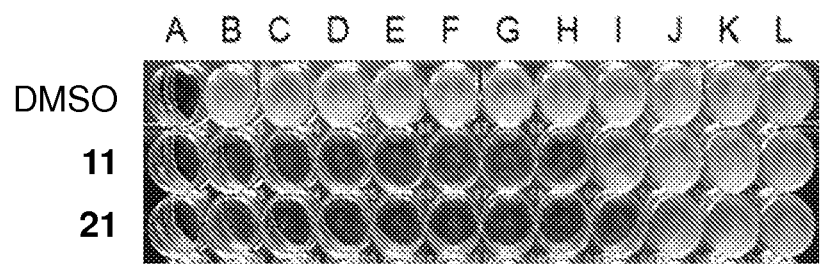
FIG. 4 depicts exemplary results of minimum inhibitory concentration (MIC) experiments of compounds 11 and 21 against *Staphylococcus aureus*.
Figure 5:
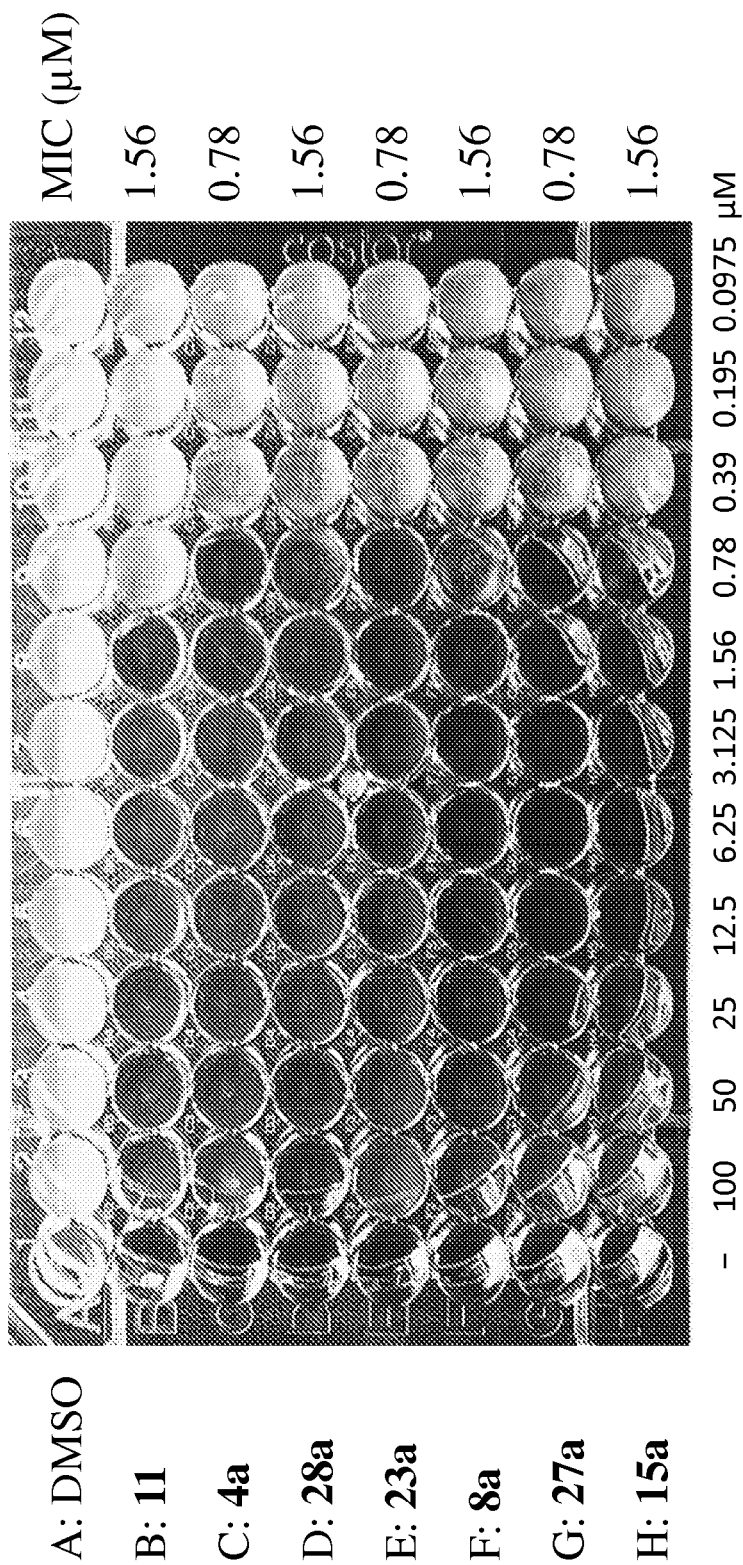
FIG. 5 depicts exemplary results of minimum inhibitory concentration (MIC) experiments of compounds 11, 4a, 28a, 23a, 8a, 27a, and 15a against *Staphylococcus aureus* in a Luria Broth (LB) medium to determine bacterial growth inhibition.
Figure 6:
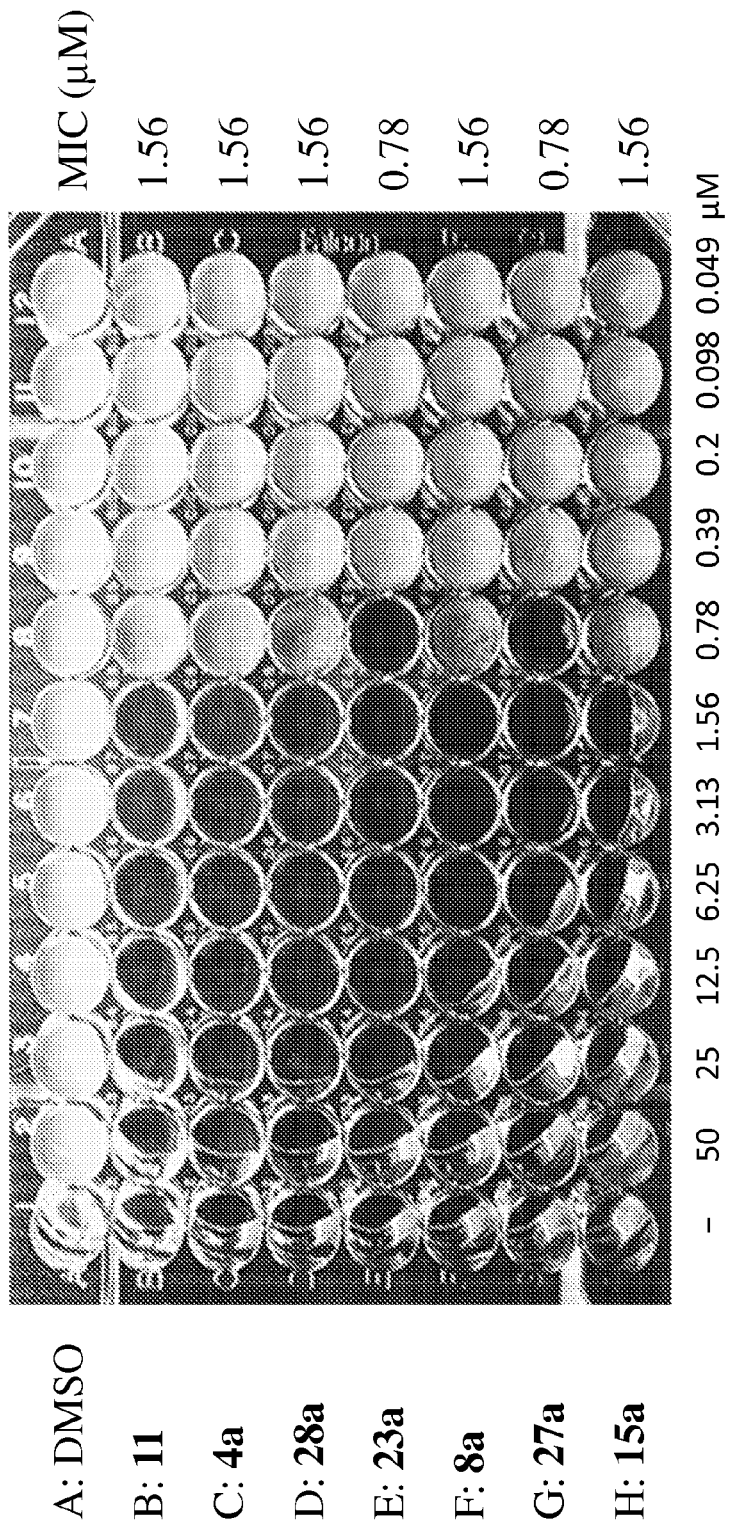
FIG. 6 depicts exemplary results of minimum inhibitory concentration (MIC) experiments of compounds 11, 4a, 28a, 23a, 8a, 27a, and 15a against *Staphylococcus aureus* in a tryptic soy broth (TSB) medium to determine biofilm inhibition.
Figure 7:
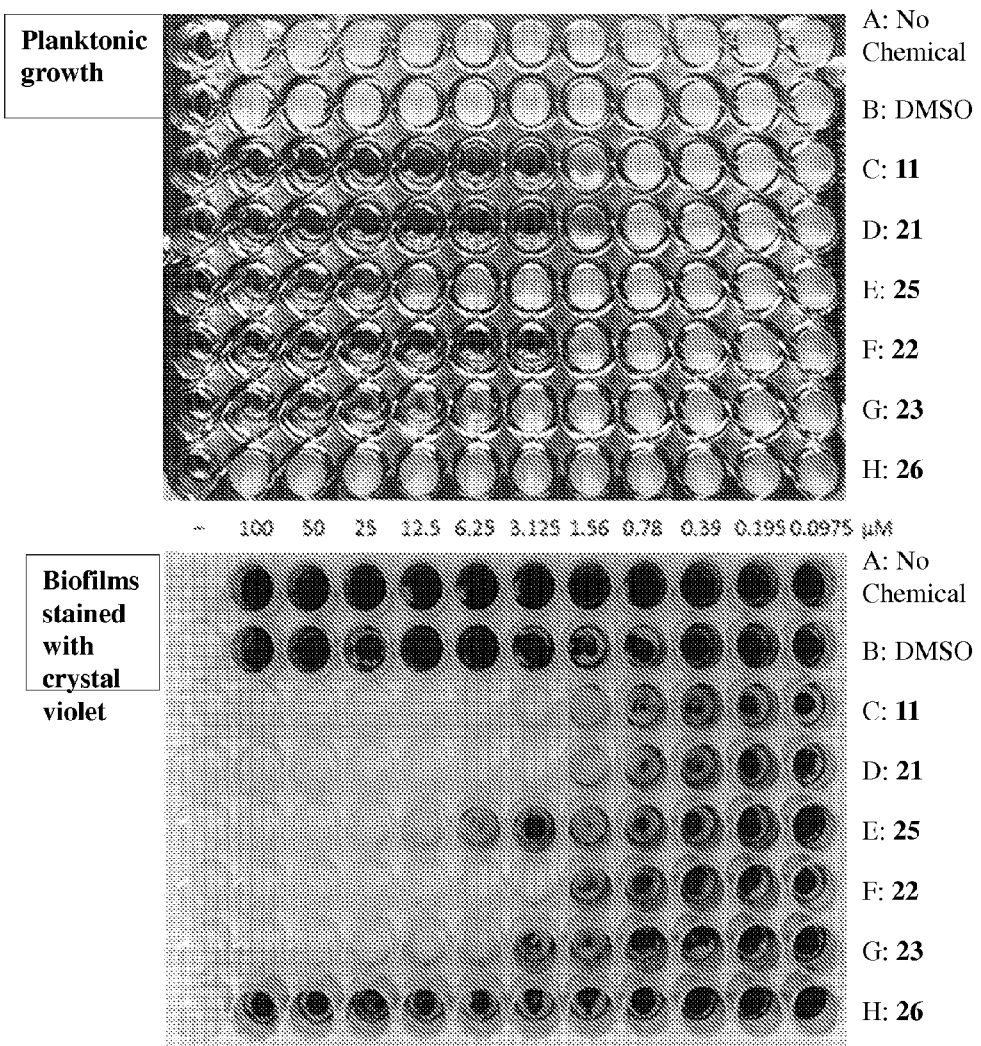
FIG. 7 depicts exemplary results of minimum inhibitory concentration (MIC) experiments of compounds 11, 21, 25, 22, 23, and 26 against *Staphylococcus aureus* to determine both inhibition of planktonic growth and biofilm formation. From this experiment, five bromophenazine small molecules were determined to possess an "antibacterial" phenotype as the biofilm inhibition activity of these compounds correlated closely with growth inhibition. The bromophenazine in the bottom row was determined to be "inactive" as there is no observable growth inhibition or biofilm inhibition at 100 µM.
Figure 8:
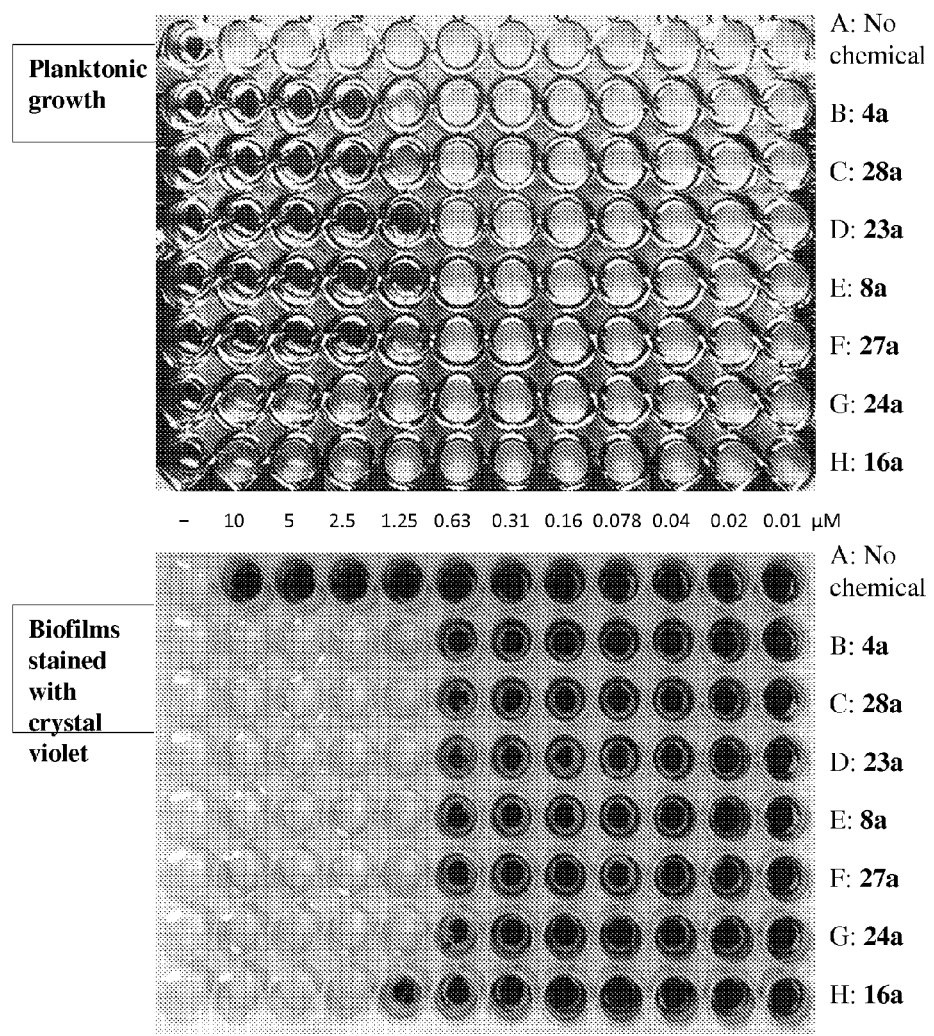
FIG. 8 depicts exemplary results of minimum inhibitory concentration (MIC) experiments of compounds 4a, 28a, 23a, 8a, 27a, 24a, and 16a against *Staphylococcus aureus* to determine both inhibition of planktonic growth and biofilm formation. From this experiment, all seven bromophenazine small molecules were determined to possess an "antibacterial" phenotype as the biofilm inhibition activity of these compounds correlated closely with growth inhibition.
Figure 9:
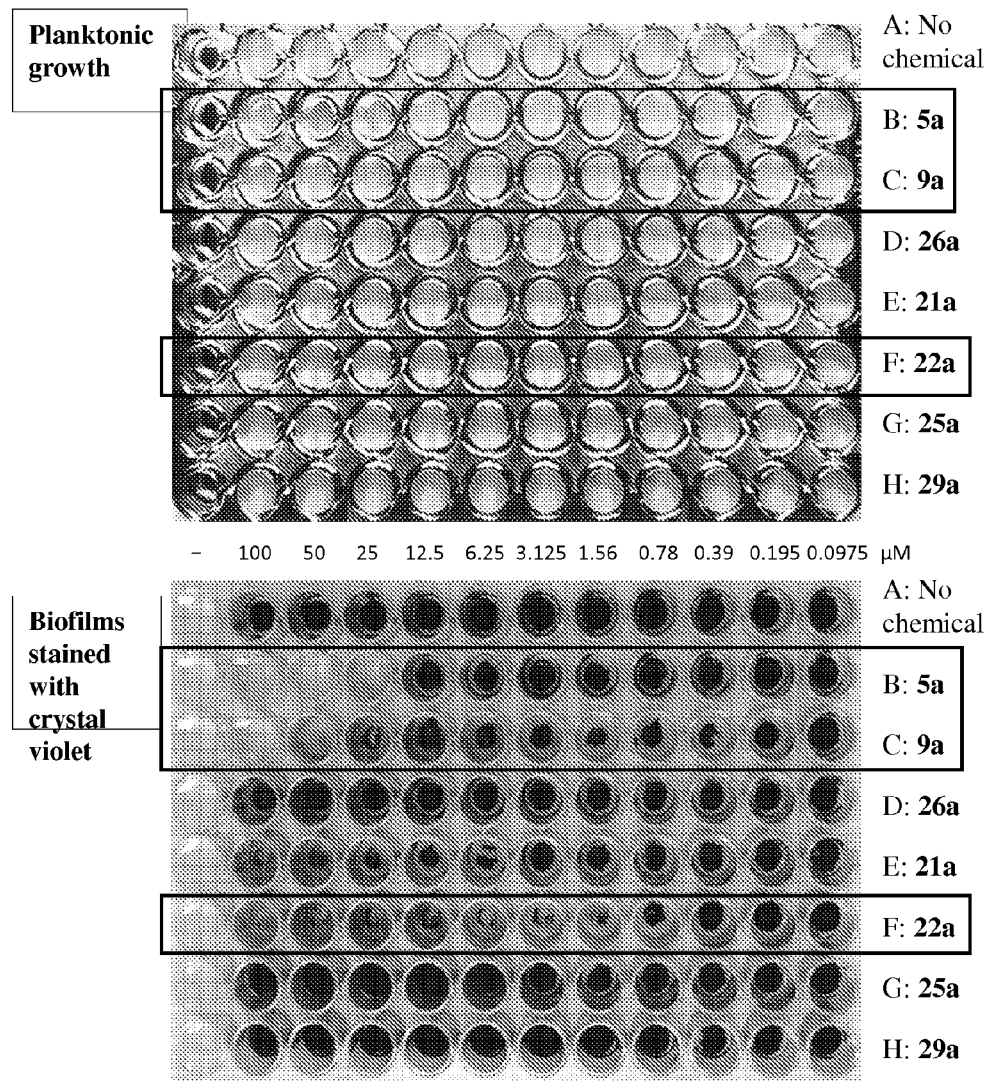
FIG. 9 depicts exemplary results of minimum inhibitory concentration (MIC) experiments of compounds 5a, 9a, 26a, 21a, 22a, 25a, and 29a against *Staphylococcus aureus* to determine both inhibition of planktonic growth and biofilm formation. From this experiment, three bromophenazine small molecules were determined to possess a "biofilm inhibitor" phenotype (outlined in boxes) as these compounds inhibit *S. aureus* biofilm formation while not inhibiting planktonic growth.
Figure 10:
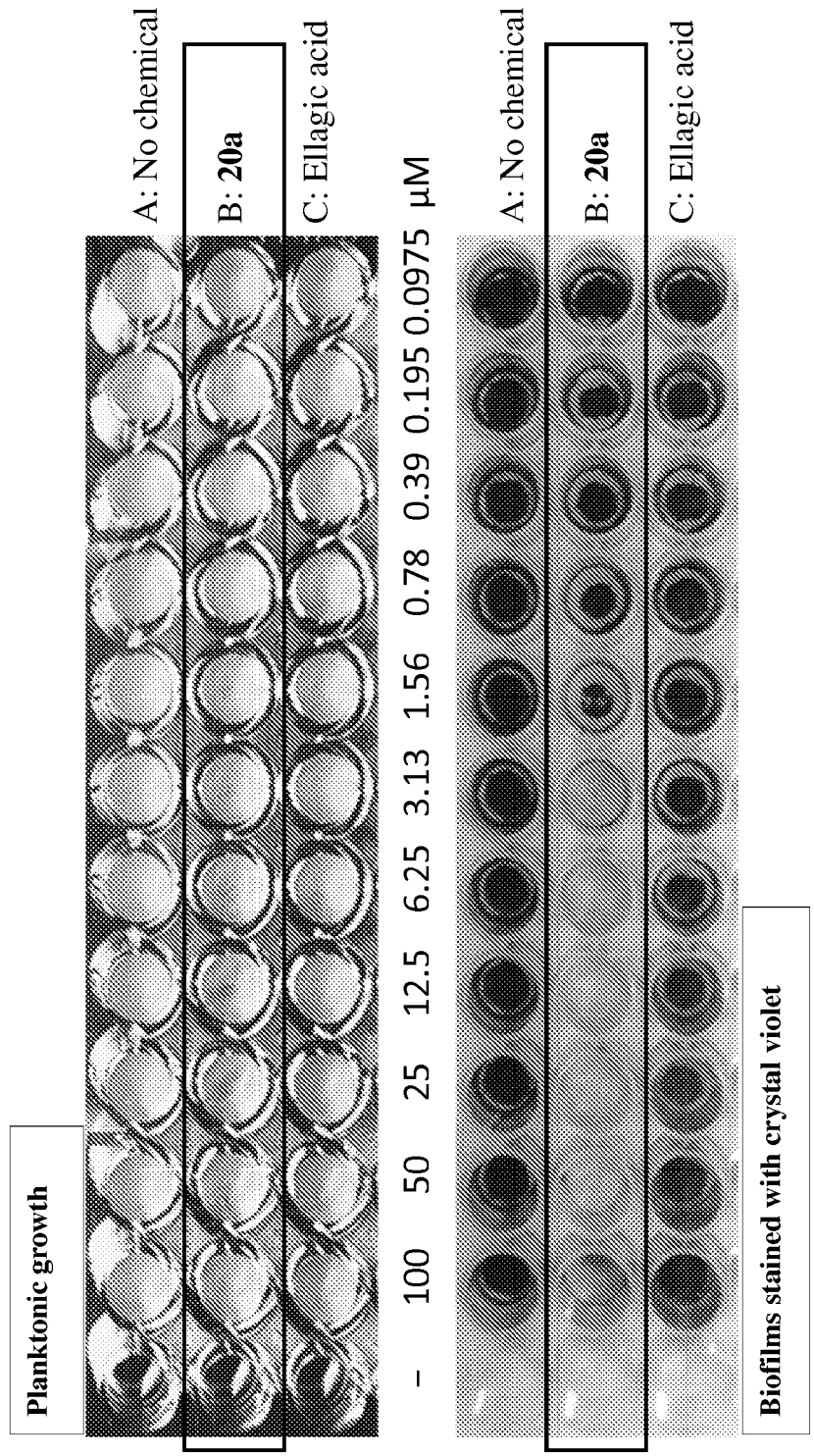
FIG. 10 depicts exemplary results of minimum inhibitory concentration (MIC) experiments of compound 20a and Ellagic acid against *Staphylococcus aureus* to determine both inhibition of planktonic growth and biofilm formation.
Figure 11:
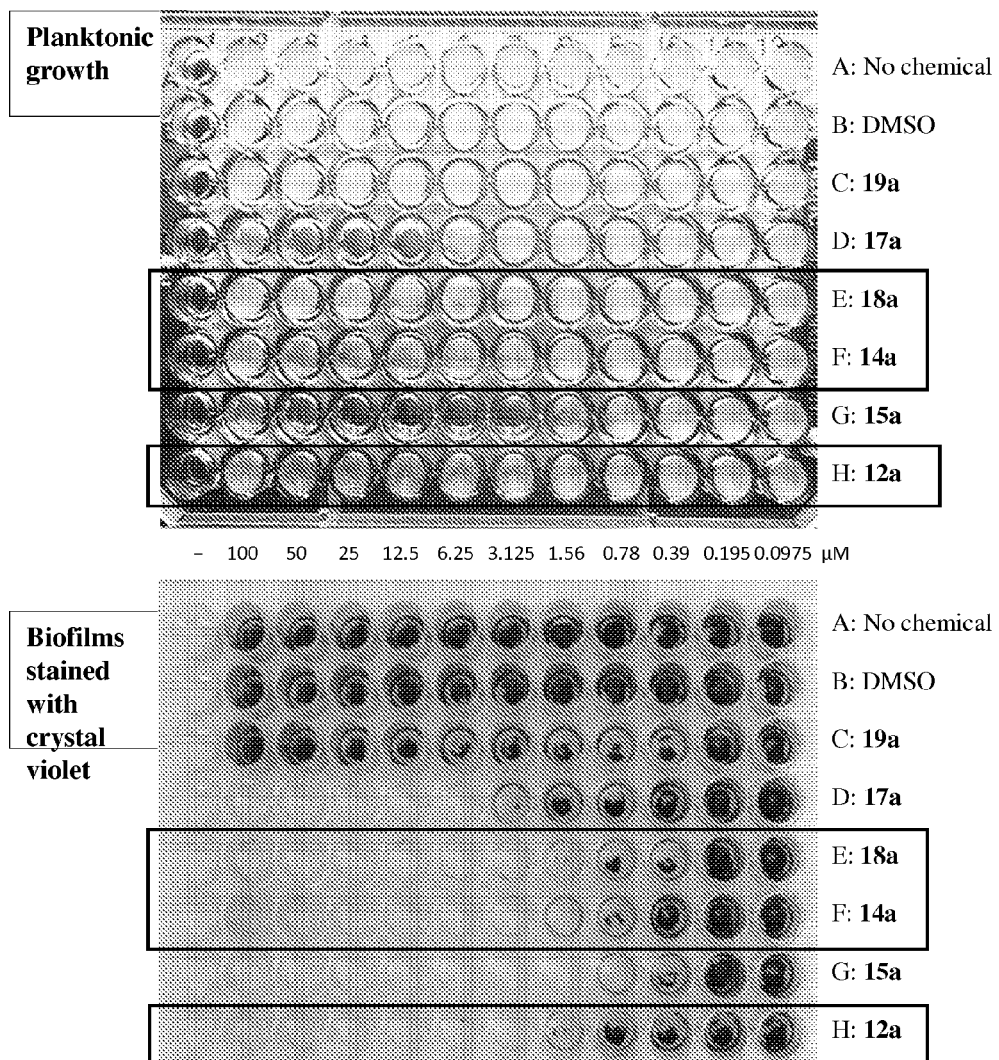
FIG. 11 depicts exemplary results of minimum inhibitory concentration (MIC) experiments of compounds 19a, 17a, 18a, 14a, 15a, and 12a against *Staphylococcus aureus* to determine both inhibition of planktonic growth and biofilm formation.
Figure 12:
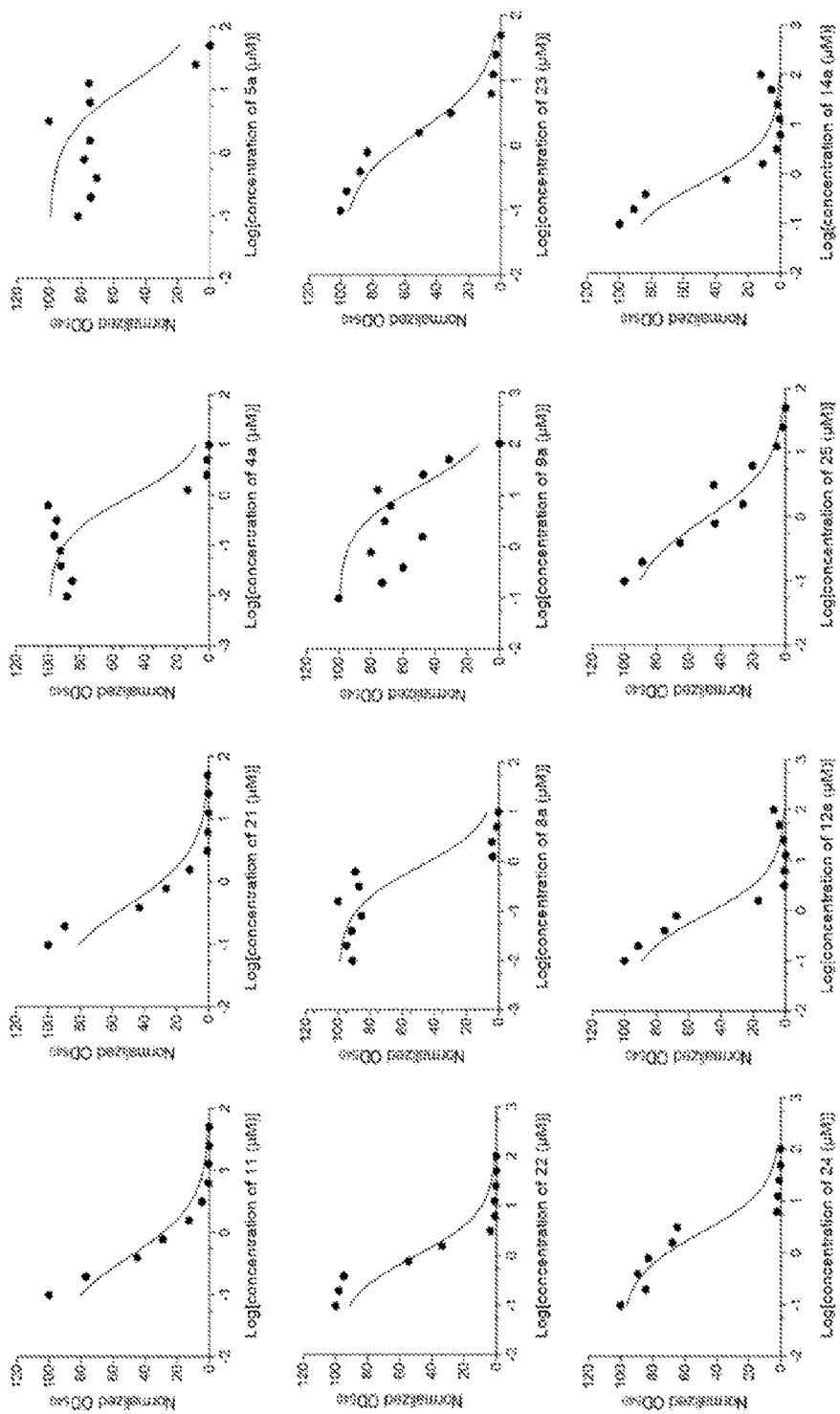
FIG. 12 depicts dose-response curves for biofilm inhibition by compounds 11, 21, 4a, 5a, 22, 8a, 9a, 23, 24, 12a, 25, and 14a against *Staphylococcus aureus*.
Figure 13:
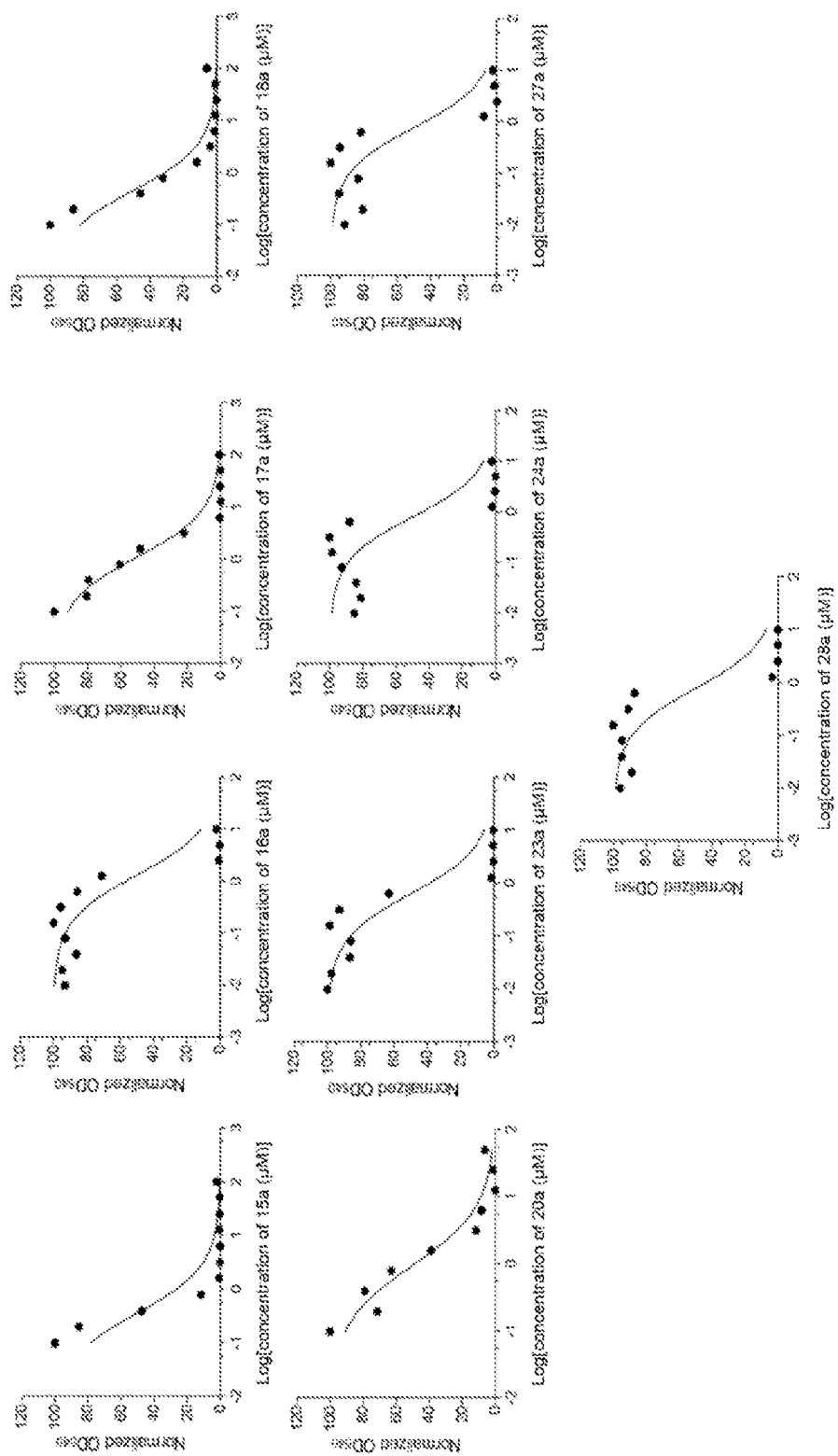
FIG. 13 depicts dose-response curves for biofilm inhibition by compounds 15a, 16a, 17a, 18a, 20a, 23a, 24a, 27a, and 28a against *Staphylococcus aureus*.
Figure 14:
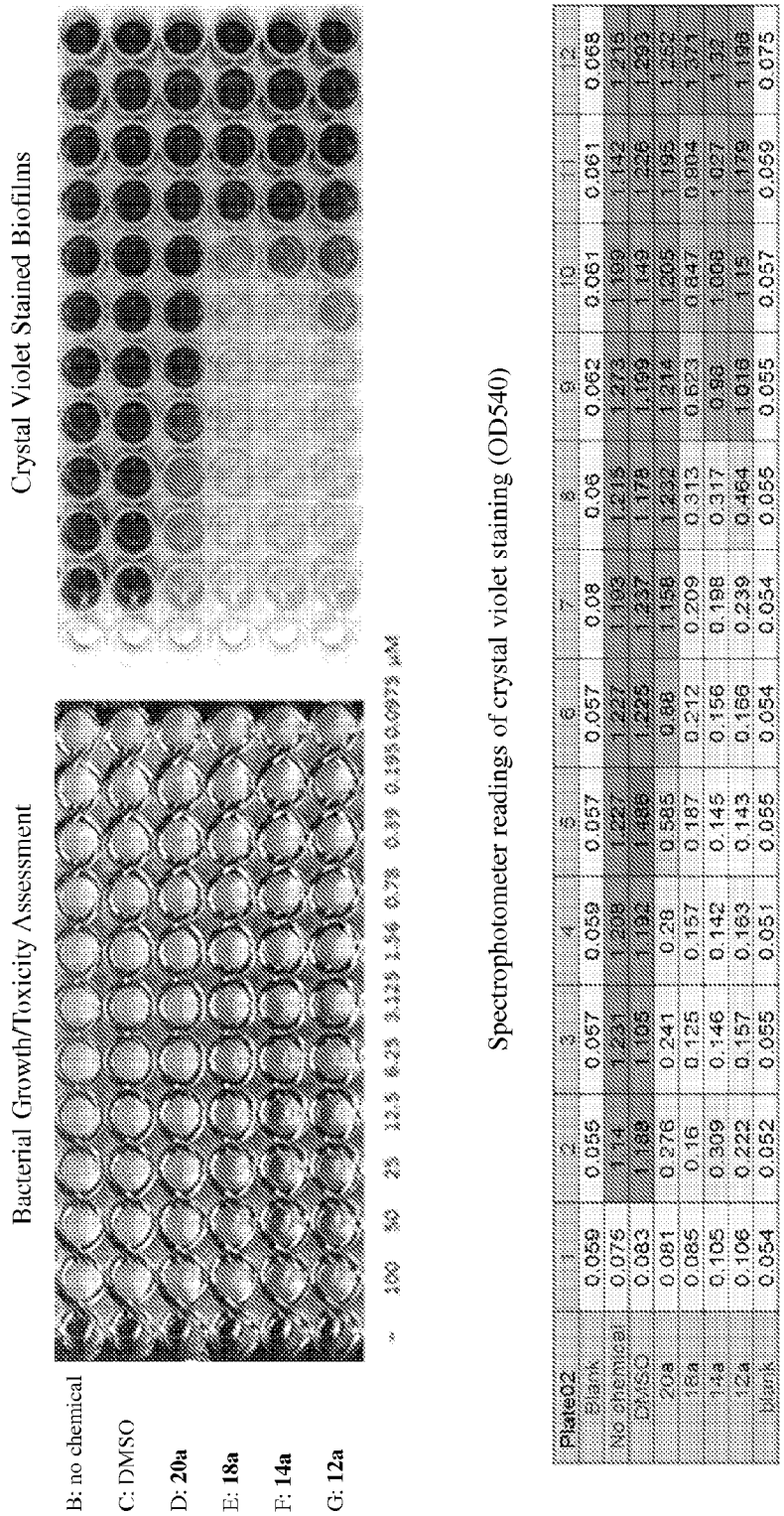
FIG. 14 depicts planktonic growth and biofilm inhibition assay plates (1 of 3) and spectrophotometeric readings for compounds 20a, 18a, 14a, and 12a against *Staphylococcus aureus*.
Figure 15:
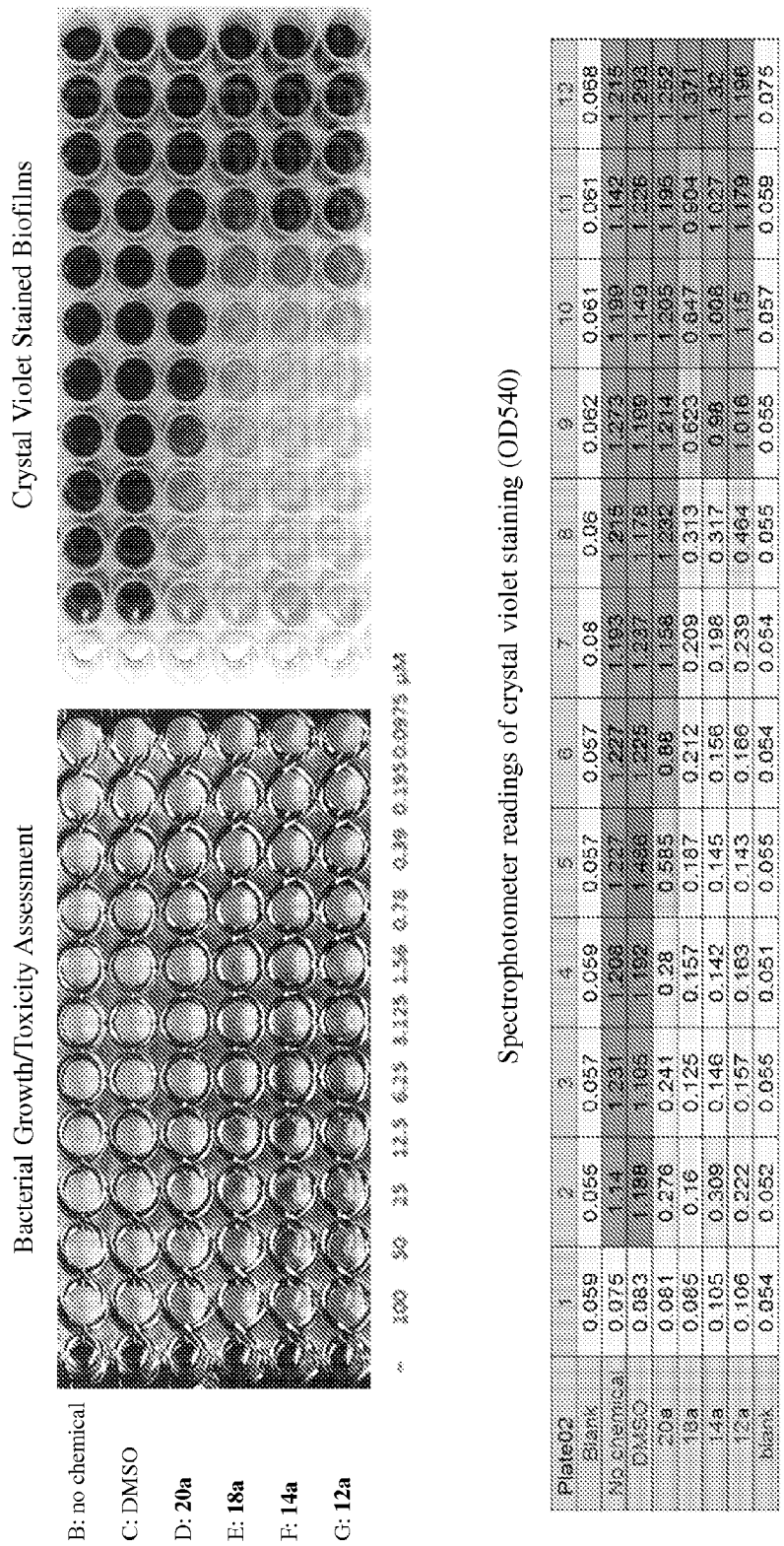
FIG. 15 depicts planktonic growth and biofilm inhibition assay plates (2 of 3) and spectrophotometeric readings for compounds 20a, 18a, 14a, and 12a against *Staphylococcus aureus*.
Figure 16:
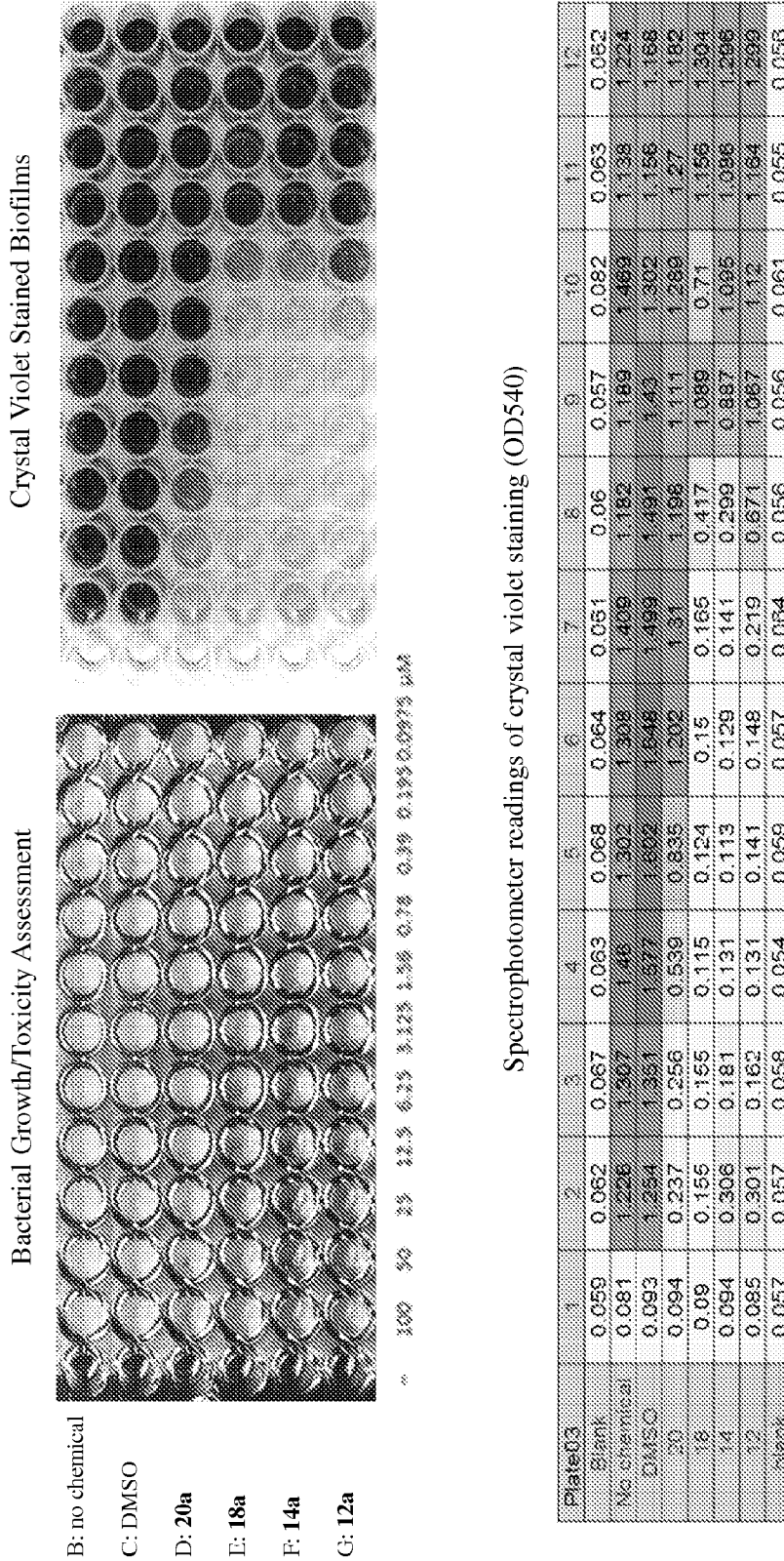
FIG. 16 depicts planktonic growth and biofilm inhibition assay plates (3 of 3) and spectrophotometeric readings for compounds 20a, 18a, 14a, and 12a against *Staphylococcus aureus*.
Figure 17:
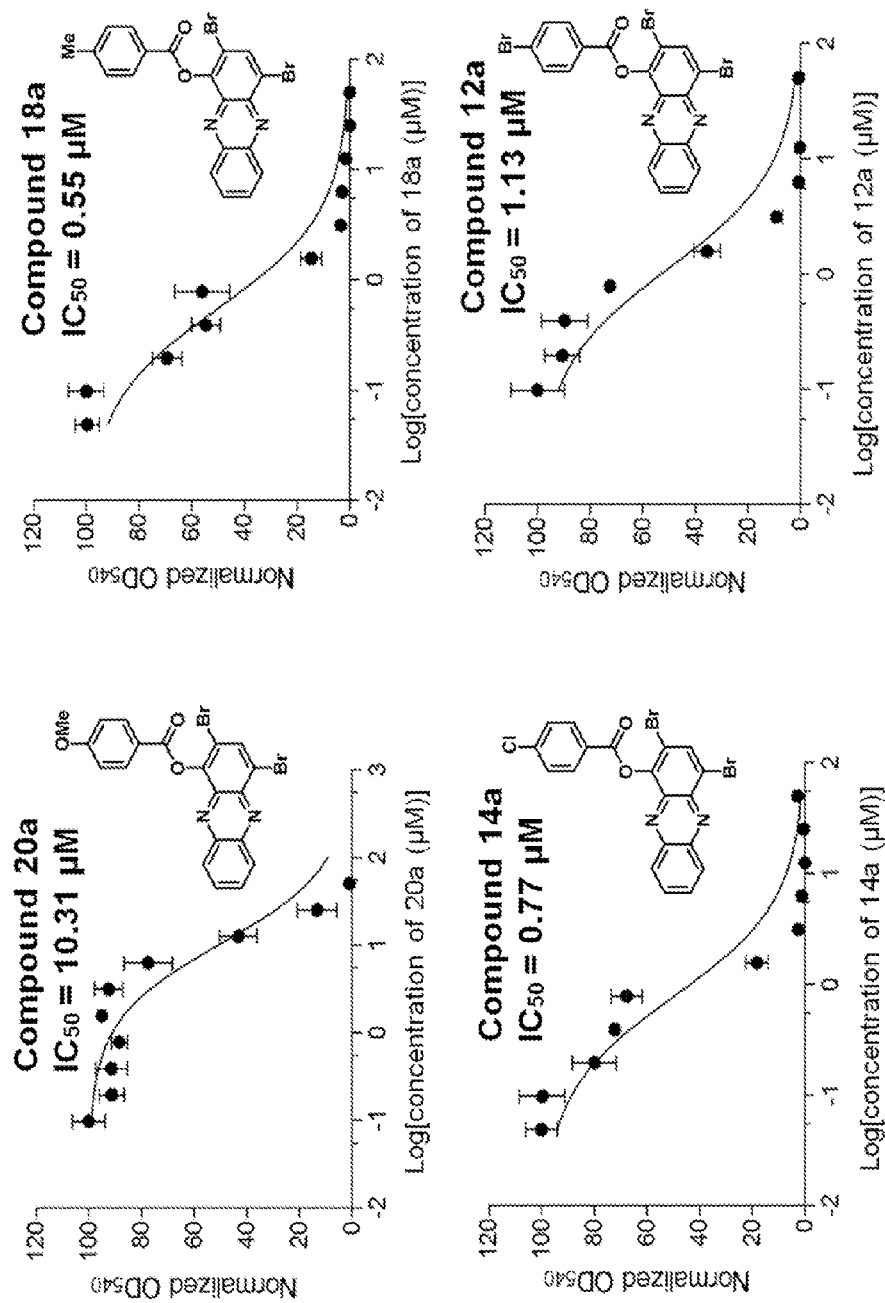
FIG. 17 depicts dose-response curves for biofilm inhibition by compounds 20a, 18a, 14a, and 12a (triplicate data) against *Staphylococcus aureus*.
Figure 18:
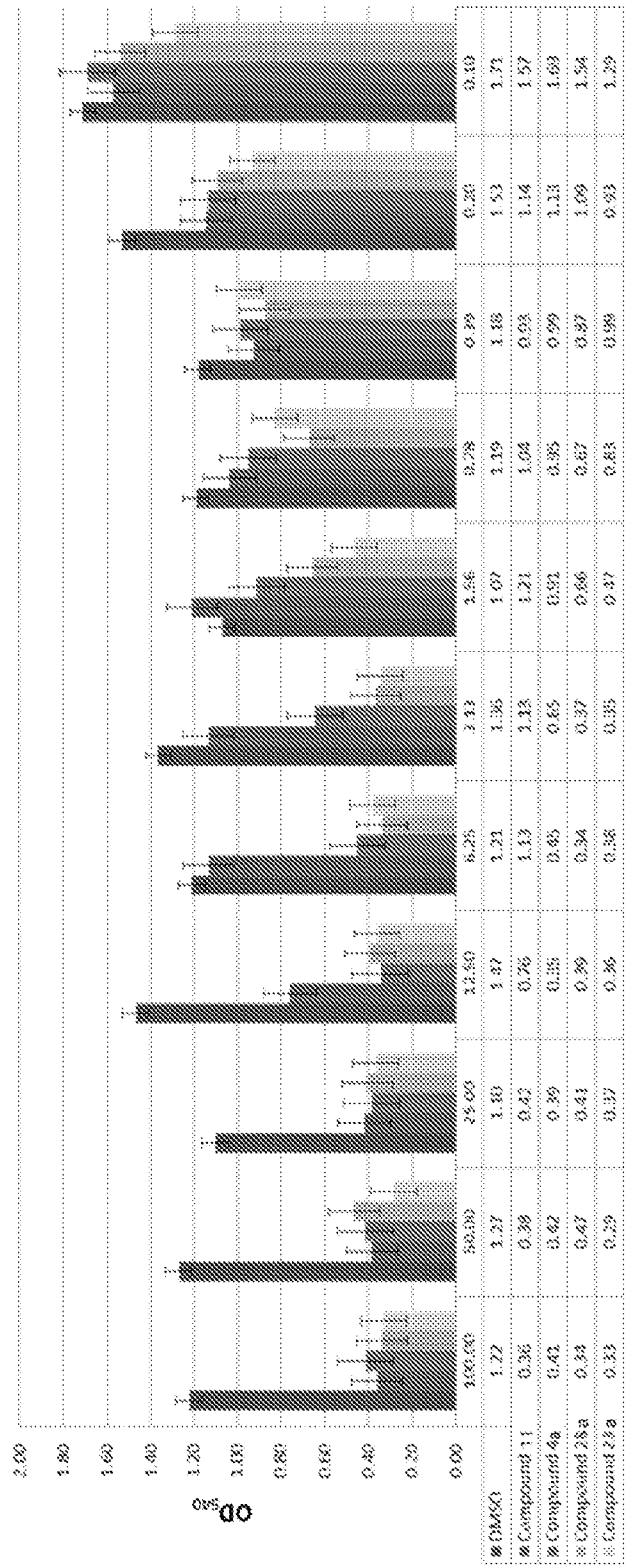
FIG. 18 depicts biofilm dispersion by compounds 11, 4a, 28a, and 23a against *Staphylococcus aureus* in tryptic soy agar (TSA) solid medium and tryptic soy broth (TSB) medium.
Figure 19:
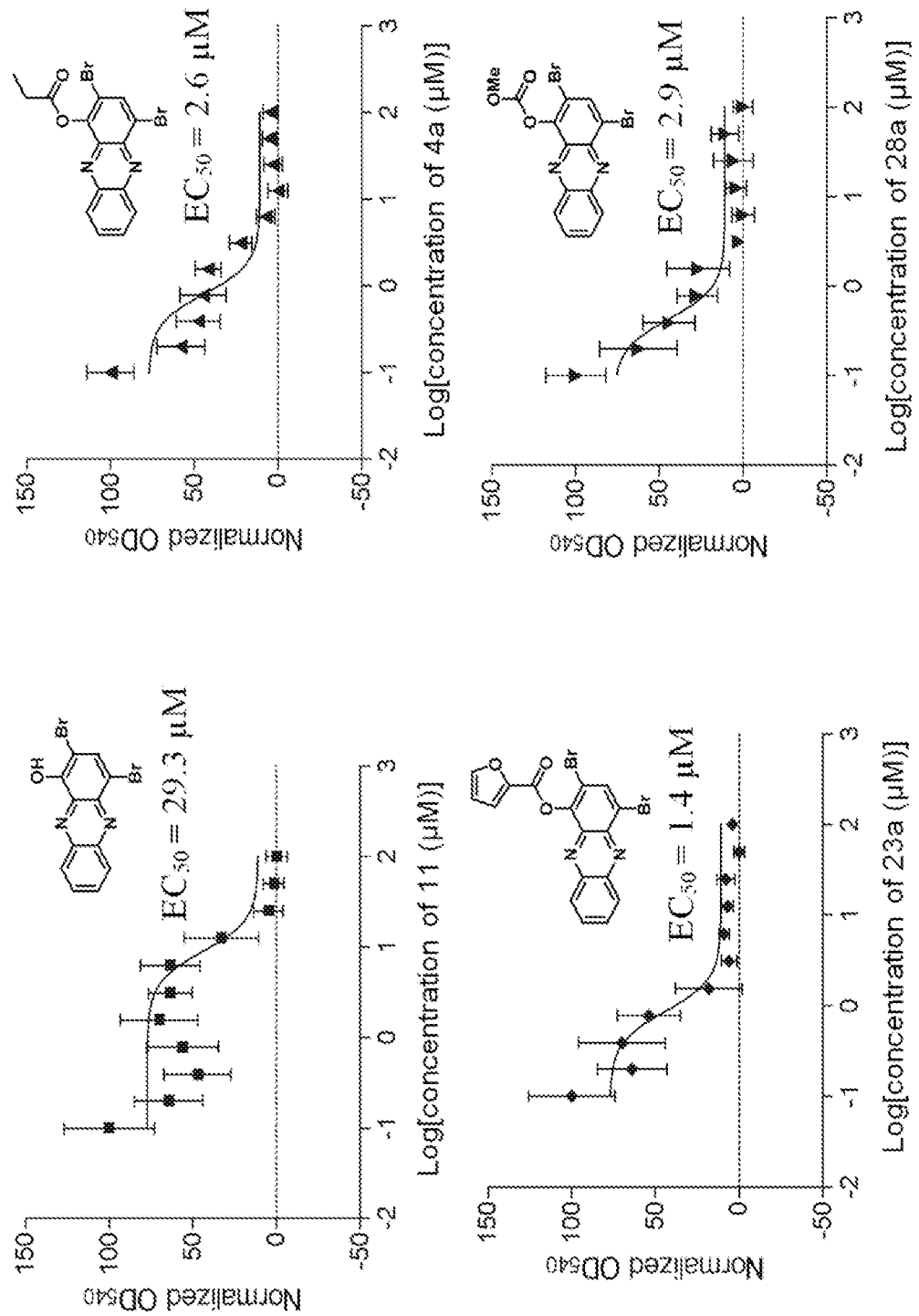
FIG. 19 depicts dose-response curves for biofilm dispersion by compounds 11, 4a, 28a, and 23a against *Staphylococcus aureus*.
Figure 20:
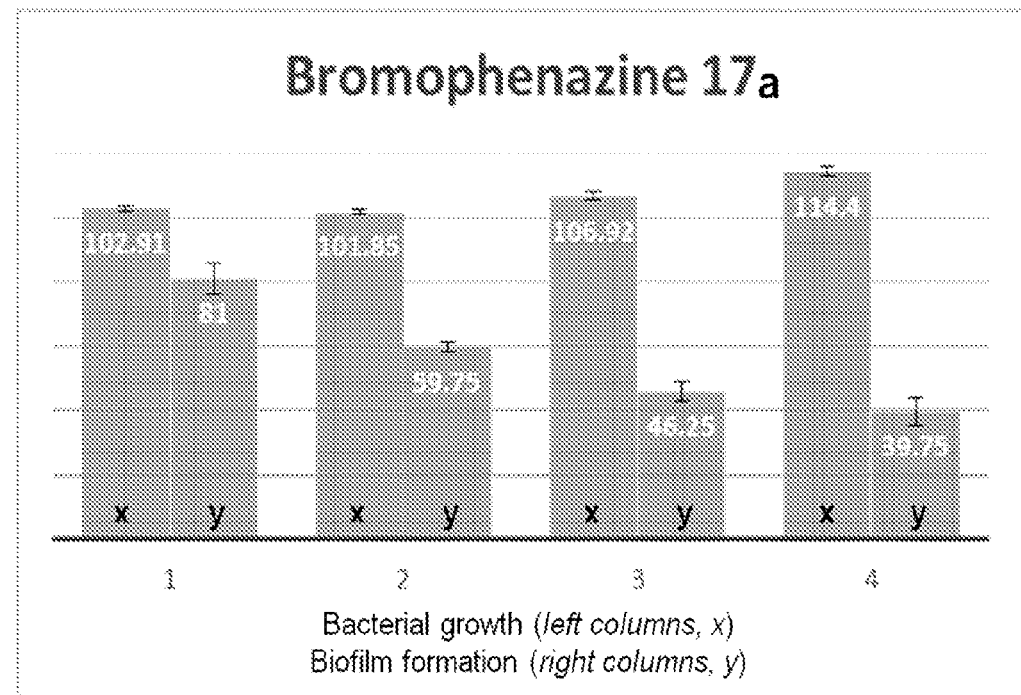
FIG. 20 depicts planktonic growth and biofilm inhibition by compound 17a against *Acinetobacter baumannii* in Mueller-Hinton broth demonstrating dose-dependent increases in planktonic growth while bacterial biofilm formation is inhibited.
Figure 20:
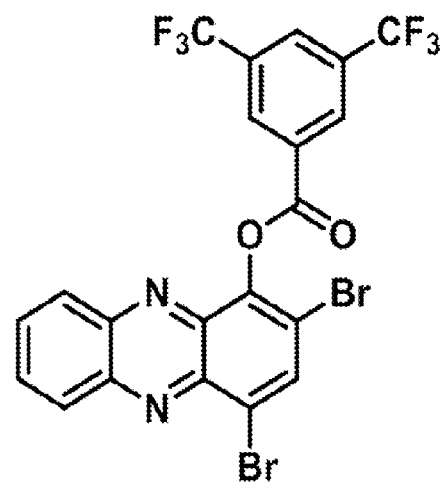
Figure 21:
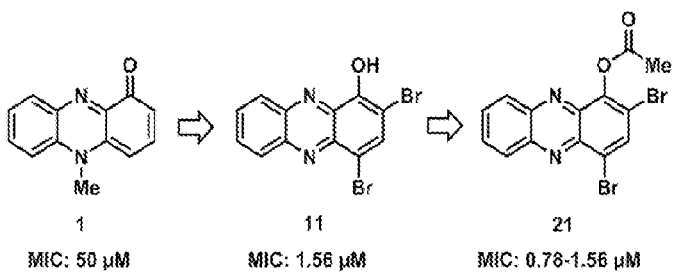
FIG. 21 depicts overall library strategy for the synthesis and identification of novel bromophenazine antibacterial agents. Synthetic yields are shown in parentheses under each analog.
Figure 21:
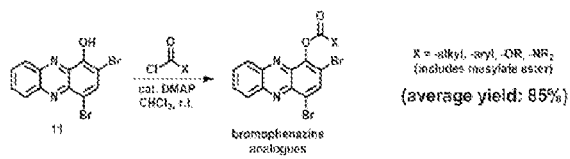
Figure 21:
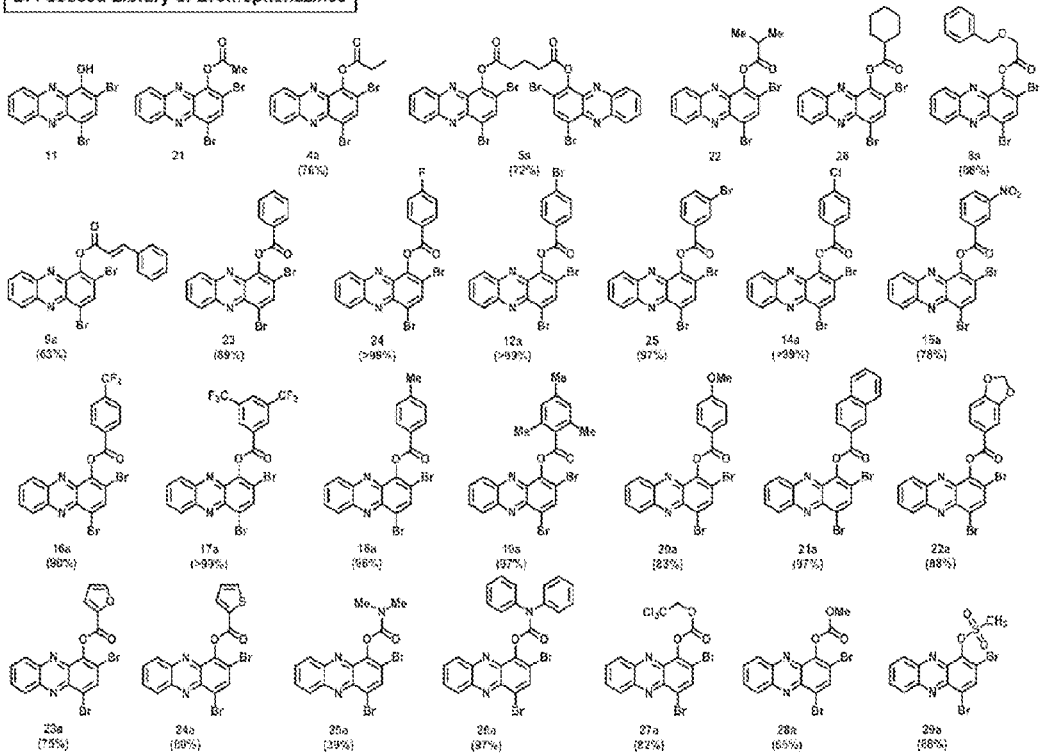
Figure 22:
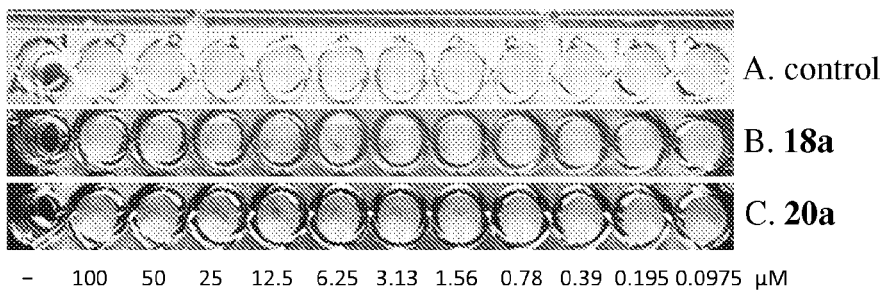
FIG. 22 depicts exemplary results of minimum inhibitory concentration (MIC) experiments of compounds 18a and 20a against *Staphylococcus aureus* to determine inhibition of planktonic growth (top panel) and biofilm formation (middle panel) along with biofilm dispersion for compounds 11, 4a, 28a, and 23a (bottom panel).
Figure 22:
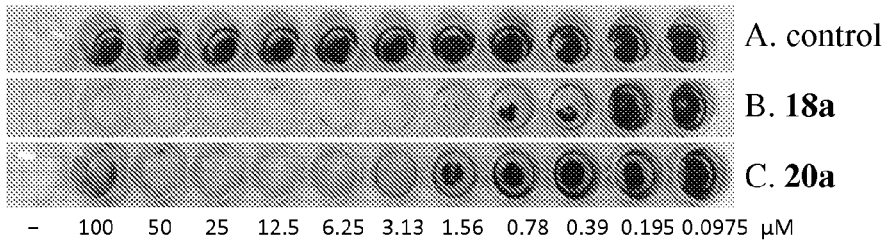
Figure 22:
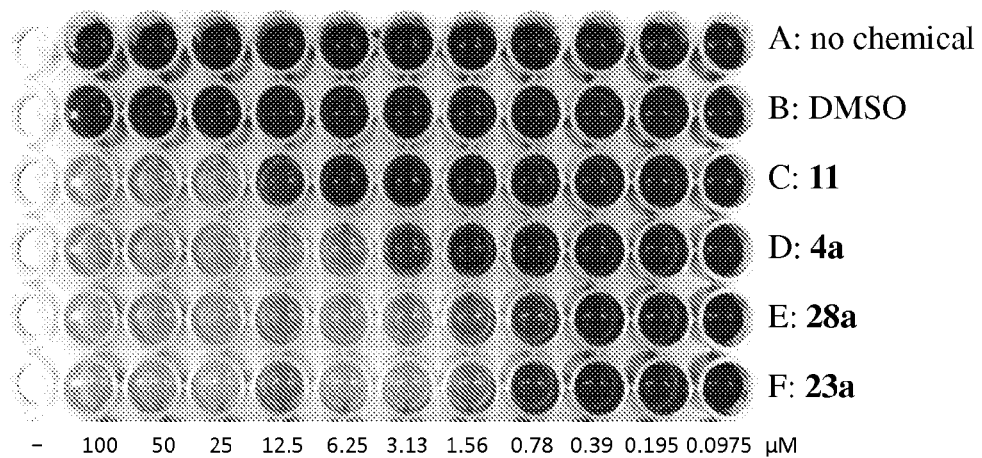
Figure 23:
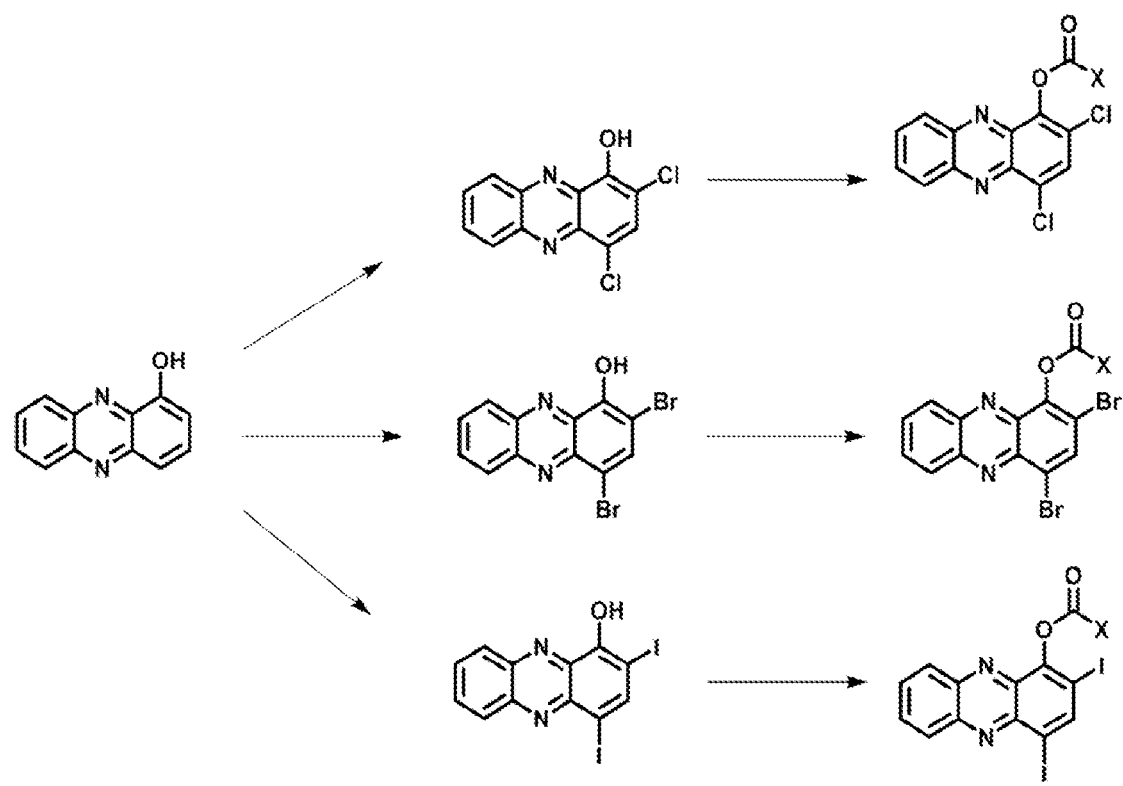
FIG. 23 depicts synthetic routes to provide alternatively halogenated phenazine scaffolds (i.e., chloro and iodo variants).

Exemplary results are shown in Table 1-3 and FIGS. 2-20. As shown in Table 1, compound 11 was 32-fold more potent than compound 1 against Staphylococcus aureus and Staphylococcus epidermidis. Table 1 and FIG. 3 show that compounds 14-20 were inactive as growth inhibitors at the highest concentrations tested (100 μM) against Staphylococcus aureus. In the MIC experiments (Table 1), none of compounds 1-20 demonstrated growth inhibition against PAO1 at the highest concentration tested (100 μM). It is well established that Pseudomonas is resistant to pyocyanin-induced death at very high concentrations (S. S. Barron and J. J. Rowe, Antimicrob. Agents Chemother., 1981, 20, 814-820). The lack of growth inhibition against PAO1 provides evidence that the compounds of the invention, such as compounds 5 and 11, inhibited Staphylococcus aureus and Staphylococcus epidermidis through an ROS-generating mechanism. Table 1 also shows that compound 21 was 32- to 64-fold more potent against Staphylococcus aureus and Staphylococcus epidermidis, respectively, than compound 1. Compounds 22-25 also demonstrated significant growth inhibition activities against Staphylococcus aureus and Staphylococcus epidermidis (Table 1; compound 24 not tested against Staphylococcus epidermidis).

Further microdilution MIC assays were carried out for 11, 21-26, and 4a-29a against Staphylococcus aureus (ATCC 25923) in in Luria Broth media (at ~$10^5$ $CFUmL^{-1}$) to establish the level of growth inhibition for each compound (see FIGS. 5-13). Bromophenazine analogues 4a, 8a, 15a, 23a, 27a, and 28a possessed potent antibacterial activity (MICs 0.78-1.56 μM) while analogues 16a and 17a possessed moderate antibacterial activity (MIC 3.13-12.5 μM). Table 2 shows that four different phenotypes are observed when Staphylococcus aureus is treated with bromophenazines 11, 21-26, and 4a-29a; these include 7 biofilm inhibitors, 15 antibacterial agents, 4 inactive bromophenazines and 2 biofilm promoters. Differentiation of a "biofilm inhibitor" from an antibacterial agent was carried out according to the ratio of MIC/IC50 of biofilm inhibition (based on crystal violet staining dose-response). The most potent biofilm inhibitors (bromophenazines 12a, 14a, 18a and 20a) had an MIC/IC50 biofilm inhibition ratio of >105 to >222. Bromophenazine 24a demonstrated a MIC/IC50 biofilm inhibition ratio of >127 with an MIC >100; however, 24a was classified as "antibacterial" due to the significant amount of planktonic growth inhibition (bacteriostatic activity) that was observed at concentrations between 2.5 μM and 100 μM in biofilm inhibition assays. Following the biofilm inhibition screen, bromophenazines 12a, 14a, 18a and 20a were evaluated in three independent biofilm inhibition experiments against Staphylococcus aureus to obtain replicate data. The triplicate $IC_{50}$ values for biofilm inhibition experiments against Staphylococcus aureus for the most potent bromophenazines are as follows: bromophenazine 12a ($IC_{50}$=1.13 μM), bromophenazine 14a ($IC_{50}$=0.77 μM), bromophenazine 18a ($IC_{50}$=0.55 μM) and bromophenzine 20a ($IC_{50}$=10.31 μM) (see FIGS. 14-17). Interestingly, these four bromophenazine analogues possessing the most promising biofilm inhibition activity all have 4-subsituted phenyl ester groups on the bromophenazine scaffold. In addition to inhibiting biofilm formation, small molecules that are able to disperse or clear preexisting bacterial biofilms would be highly valuable. Six of the bromophenazine analogues (11, 4a, 8a, 23a, 27a, 28a; see Table 2 and FIGS. 18-19) were evaluated in biofilm dispersion assays by allowing Staphylococcus aureus biofilms to establish in 96-well plates for 24 hours at 37° C. After this incubation time, the media and planktonic cells were removed followed by a wash of the 96-well plates with water. Phosphate buffered saline (PBS) was then added to the 96-well plate followed by the addition of bromophenazine compounds (with 2-fold serial dilutions of each compound tested). The resulting plates were then allowed to incubate at room temperature for 24 hours and stained with crystal violet to quantify biofilm dispersion. Four of the six bromophenazines evaluated in biofilm dispersion assays demonstrated moderate to high potency with 23a demonstrating potent dispersion activity ($EC_{50}$=1.4 μM). The remaining three active S. aureus biofilm dispersal agents include: bromophenazine 4a ($EC_{50}$=2.6 μM), bromophenazine 28a ($EC_{50}$=2.9 μM) and bromophenazine 11 ($EC_{50}$=29.3 μM). Bromophenazines 8a and 27a demonstrated no biofilm dispersion activity ($EC_{50}$>100 μM) in head-to-head assays with active bromophenazine dispersal agents.

The bromophenazines were also evaluated against the Gram-negative bacterium Acinetobacter baumannii in order to identify biofilm modulating small molecules against this emerging pathogen. Acinetobacter baumannii is notorious for its ability to persist as bacterial biofilms on hospital surfaces, giving rise to many multidrug-resistant nosocomial infections. Clinical isolates of A. baumannii have been identified that are resistant to every class of antibiotic clinically used. The bromophenazines were evaluated against Acinetobacter baumannii ATCC 19606 in biofilm inhibition assays. Bromophenazines were allowed to incubate in 96-well plates with Acinetobacter baumannii (~7× $10^6$ $CFUmL^{-1}$ by adjusting an overnight culture to an $OD_{600}$~0.01) for 24 hours at 37° C. using Mueller-Hinton broth followed by spectrophometer readings of each plate to evaluate planktonic growth ($OD_{600}$) and biofilm formation ($OD_{540}$ after crystal violet stain of biofilms inside microtiter wells). The bromophenazine small molecules demonstrated less potent antibacterial and antibiofilm activity against Acinetobacter baumannii than against Staphylococcus

*aureus*. The most potent bromophenazine biofilm inhibitors against *Acinetobacter baumannii* that demonstrated planktonic growth inhibition activity are considered to be antibacterial agents (see Table 3); however, 11 of the 28 bromophenazines evaluated during these studies were found to be moderately active biofilm inhibitors (i.e., 30-60% biofilm inhibition at 100 μM) without inhibiting planktonic growth. Interestingly, several of the more potent *Acinetobacter baumannii* "biofilm inhibitors" (i.e., bromophenazines 9a, 23, 23, 25, 17a, 19a and 21a) gave slight increases of ~15% in planktonic growth when tested at 100 μM based on spectrophotometer readings ($OD_{600}$) and also did not inhibit planktonic growth when tested at 200 μM. This biofilm inhibition with activation of planktonic growth activity was dose-dependent with bromophenazine 17a (see FIG. 20).

Following the biofilm inhibition studies, 13 of the bromophenazines were evaluated in biofilm dispersion assays against *A. baumannii* (see Table 3). As with the biofilm inhibition studies, this collection of bromophenazines was less potent in biofilm dispersion assays against *Acinetobacter baumannii* than the dispersion activity observed against *Staphylococcus aureus*. Eight bromophenazine small molecules were identified as having biofilm dispersal activity (i.e., 30-57% dispersion at 100 μM) while the remaining 5 bromophenazines were found to be inactive. Interestingly, antibacterial bromophenazines 11, 21, 4a and 28a possessed the most potent biofilm dispersal response by dispersing 53-57% of established *Acinetobacter baumannii* biofilm at 100 μM.

TABLE 1

Exemplary minimum inhibitory concentration (MIC) values of compounds 1-27 and kanamycin against *Staphylococcus aureus*, *Staphylococcus epidermidis*, or *Pseudomonas aeruginosa*[a]

| Compound | *Staphylococcus aureus* | | *Staphylococcus epidermidis* | | *Pseudomonas aeruginosa* |
|---|---|---|---|---|---|
| | MIC (μM) | MIC (μg/mL) | MIC (μM) | MIC (μg/mL) | MIC (μM) |
| 1 | 50 | 10.6 | 50 | 10.6 | >100 |
| 2 | >100 | >19.7 | >100 | >19.7 | >100 |

TABLE 1-continued

Exemplary minimum inhibitory concentration (MIC) values of compounds 1-27 and kanamycin against *Staphylococcus aureus*, *Staphylococcus epidermidis*, or *Pseudomonas aeruginosa*[a]

| Compound | *Staphylococcus aureus* | | *Staphylococcus epidermidis* | | *Pseudomonas aeruginosa* |
|---|---|---|---|---|---|
| | MIC (μM) | MIC (μg/mL) | MIC (μM) | MIC (μg/mL) | MIC (μM) |
| 3 | >100 | >22.5 | >100 | >22.5 | >100 |
| 4 | >100 | >22.4 | >100 | >22.4 | >100 |
| 5 | 6.25 | 1.72 | 6.25 | 1.72 | >100 |
| 6 | >100 | >19.6 | >100 | >19.6 | >100 |
| 7 | >100 | >24.1 | >100 | >24.1 | >100 |
| 8 | >100 | >25.5 | >100 | >25.5 | >100 |
| 9 | 100 | 30.3 | 100 | 30.3 | >100 |
| 10 | 50 | 13.0 | 50 | 13.0 | >100 |
| 11 | 1.56 | 0.55 | 0.78-1.56 | 0.28-0.55 | >100 |
| 12 | >100 | >31.5 | >100 | >31.5 | >100 |
| 13 | >100 | >25.3 | >100 | >25.3 | >100 |
| 14 | >100 | >27.4 | — | — | >100 |
| 15 | >100 | >30.2 | — | — | >100 |
| 16 | >100 | >43.2 | — | — | >100 |
| 17 | >100 | >35.4 | — | — | >100 |
| 18 | >100 | >38.3 | — | — | >100 |
| 19 | >100 | >28.9 | — | — | >100 |
| 20 | >100 | >27.5 | — | — | >100 |
| 21 | 0.78-1.56 | 0.31-0.62 | 0.78 | 0.31 | — |
| 22 | 1.56 | 0.66 | 1.56 | 0.66 | — |
| 23 | 1.56 | 0.72 | 1.56 | 0.72 | — |
| 24 | 1.56 | 0.74 | — | — | — |
| 25 | 3.13 | 1.68 | 3.13 | 1.68 | — |
| 26 | >100 | >46.5 | — | — | — |
| 27 | >100 | >36.9 | — | — | — |
| Kanamycin | 1.56-6.25 | 0.76-3.03 | 0.78-1.56 | 0.38-0.76 | — |

[a]MIC experiments were carried out in duplicate. Certain active compounds were assayed up to 5 times.
"—" is designated for compounds that were not tested against a particular bacterium.
Strains used: *S. aureus* (ATCC 25923), *S. epidermidis* (ATCC 12228), *P. aeruginosa* (PAO1).
Sensitivity patterns of *S. aureus* and *S. epidermidis* are identical.

TABLE 2

Results from evaluating bromophenazines 11, 21-26, and 4a-29a against *Staphylococcus aureus* (ATCC 25923) and MRSA-2.

| Phenazine | MIC[a] (μM) | Biofilm Inhibition IC$_{50}$[a] (μM) | MIC/IC$_{50}$ Biofilm[a] (μM) | Phenotype[a] | Biofilm Dispersion EC$_{50}$[a] (μM) | Biofilm Dispersal Agent[a]? | Biofilm Eradication MBEC[b] |
|---|---|---|---|---|---|---|---|
| 11 | 1.56 | 0.41 | 3.8 | antibacterial | 29.3 | Yes | 100-200[c] |
| 21 | 0.78-1.56 | 0.42 | 2.8 | antibacterial | — | — | — |
| 4a | 1.56 | 0.92 | 1.7 | antibacterial | 2.6 | Yes | 125 |
| 5a | >100 | 12.1 | >8.3 | biofilm inhibitor | — | — | — |
| 22 | 1.56 | 0.99 | 1.6 | antibacterial | — | — | — |
| 26 | >100 | >100 | — | inactive | — | — | — |
| 8a | 1.56 | 0.76 | 2.1 | antibacterial | >100 | No | — |
| 9a | >100 | 14.8 | >6.8 | biofilm inhibitor | — | — | — |
| 23 | 1.56 | 1.71 | 0.9 | antibacterial | — | — | — |
| 24 | 1.56 | 2.44 | 0.6 | antibacterial | — | — | — |
| 12a | >100 | 0.81 | >123 | biofilm inhibitor | — | — | — |
| 25 | 3.13 | 0.93 | 3.4 | antibacterial | — | — | — |
| 14a | >100 | 0.64 | >156 | biofilm inhibitor | — | — | — |
| 15a | 1.56 | 0.36 | 4.3 | antibacterial | — | — | — |
| 16a | 12.5 | 1.30 | 9.6 | antibacterial | — | — | — |
| 17a | 12.5 | 1.10 | 11.4 | antibacterial | — | — | — |

TABLE 2-continued

Results from evaluating bromophenazines 11, 21-26, and 4a-29a against Staphylococcus aureus (ATCC 25923) and MRSA-2.

| Phenazine | MIC[a] (μM) | Biofilm Inhibition IC$_{50}$[a] (μM) | MIC/IC$_{50}$ Biofilm[a] (μM) | Phenotype[a] | Biofilm Dispersion EC$_{50}$[a] (μM) | Biofilm Dispersal Agent[a]? | Biofilm Eradication MBEC[b] |
|---|---|---|---|---|---|---|---|
| 18a | >100 | 0.45 | >222 | biofilm inhibitor | — | — | |
| 19a | >100 | >100 | — | inactive | — | — | |
| 20a | >100 | 0.95 | >105 | biofilm inhibitor | — | — | |
| 21a | >100 | >100 | — | inactive | — | — | |
| 22a | >100* | >100* | * | biofilm inhibitor* | — | — | |
| 23a | 0.78 | 0.76 | 1.3 | antibacterial | 1.4 | Yes | 62.5-100 |
| 24a | >100** | 0.79** | >127** | antibacterial** | — | — | |
| 25a | >100 | >100 | — | biofilm promoter | — | — | |
| 26a | >100 | >100 | — | inactive | — | — | |
| 27a | 0.78 | 0.76 | 1.0 | antibacterial | >100 | No | 125 |
| 28a | 1.56 | 0.77 | 2.0 | antibacterial | 2.9 | Yes | 250 |
| 29a | >100 | >100 | — | biofilm promoter | — | — | |
| Vancomycin | | | | | | | >2,000[d] |
| QAC 10 | | | | | | | 62.5-125 |

Biofilm inhibition/MIC data obtained in single replicate as a screen; however, all compounds that demonstrated antibacterial and biofilm inhibition/dispersion were evaluated 2 to 4 times in independent experiments.
[a]Staphylococcus aureus ATCC 25923.
[b]MRSA-2.
[c]Compound 11 showed an EC$_{50}$ value of 3.53 μM in MRSA-2 dispersion assays.
[d]MRSA-2 is "sensitive" to vancomycin (MIC 0.78 μM) as a growth inhibitor (Abouelhassan et al., Bioorg. Med. Chem. Lett., 2014, 24, 5076).
*Full dose-response was not observed although >50% biofilm inhibition was observed at all concentrations between 1.56 and 100 μM.
**Planktonic growth inhibition observed at 2.5 μM in biofilm inhibition assays despite MIC >100 μM.

TABLE 3

Results from evaluating bromophenazines 11, 21-26, and 4a-29a against Acinetobacter baumannii (ATCC 19606).

| Phenazine | % Biofilm Inhibition at 100 μM | % Growth Inhibition at 100 μM | Phenotype | % Biofilm Dispersion at 100 μM | Biofilm Dispersal Agent? |
|---|---|---|---|---|---|
| 11 | 98 ± 1% | 86 ± 3% | antibacterial | 56 ± 1% | Yes |
| 21 | 98 ± 1% | 83 ± 2% | antibacterial | 53 ± 1% | Yes |
| 4a | 99 ± 1% | 82 ± 1% | antibacterial | 57 ± 1% | Yes |
| 5a | 59 ± 11% | −1 ± 6%* | biofilm inhibitor | 30 ± 3% | Yes |
| 22 | 26 ± 12% | −13 ± 5%* | weak biofilm inhibitor | — | |
| 26 | 11 ± 1% | −25 ± 5% | inactive | — | |
| 8a | 97 ± 2% | 76 ± 10% | antibacterial | 32 ± 4% | Yes |
| 9a | 52 ± 5% | −18 ± 4%* | biofilm inhibitor | — | |
| 23 | 51 ± 6% | −13 ± 7%* | biofilm inhibitor | −1 ± 6% | No |
| 24 | 35 ± 4% | −16 ± 6%* | biofilm inhibitor | — | |
| 12a | 34 ± 4% | 3 ± 3% | biofilm inhibitor | 5 ± 12% | No |
| 25 | 49 ± 6% | −18 ± 4%* | biofilm inhibitor | — | |
| 14a | 25 ± 3% | 2 ± 3% | weak biofilm inhibitor | 7 ± 2% | No |
| 15a | 25 ± 6% | 3 ± 4% | weak biofilm inhibitor | 36 ± 2% | Yes |
| 16a | 29 ± 11% | −3 ± 2%* | weak biofilm inhibitor | — | |
| 17a | 60 ± 8% | −15 ± 3%* | biofilm inhibitor | — | |
| 18a | 1 ± 5% | −6 ± 6% | inactive | −1 ± 6% | No |
| 19a | 44 ± 10% | −14 ± 2%* | biofilm inhibitor | — | |
| 20a | 17 ± 5% | −6 ± 4% | inactive | — | |
| 21a | 35 ± 9% | −15 ± 6%* | biofilm inhibitor | — | |
| 22a | 29 ± 4% | −14 ± 5% | weak biofilm inhibitor | — | |
| 23a | 86 ± 12% | 80 ± 1% | antibacterial | 17 ± 14% | No |
| 24a | 32 ± 8% | −10 ± 7% | biofilm inhibitor | — | |
| 25a | 15 ± 1% | −3 ± 1% | biofilm promoter | — | |
| 26a | 40 ± 2% | −22 ± 8% | biofilm inhibitor | — | |
| 27a | 99 ± 1% | 68 ± 4% | antibacterial | 38 ± 6% | Yes |
| 28a | 99 ± 1% | 92 ± 1% | antibacterial | 54 ± 1% | Yes |
| 29a | 1 ± 2% | 3 ± 3% | inactive | — | |

Data obtained from 2 to 4 independent biofilm inhibition or biofilm dispersion experiments.
*No growth inhibition observed when tested at 200 μM.

Figure 24:
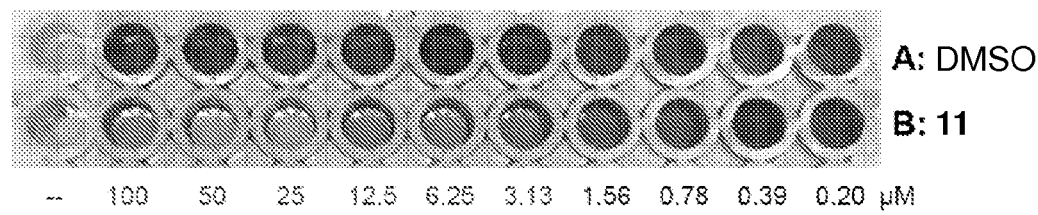
FIG. 24 depicts MRSA-2 biofilm dispersion by compound 11. Compound 11 potently dispersed established MRSA-2 biofilms ($EC_{50}$=3.53 µM).

MRSA-2 biofilm dispersion by compound 11. The protocol for MRSA-2 biofilm dispersion assays was the same as the protocol for Staphylococcus aureus (ATCC 25923) biofilm dispersion assays described herein, except that Staphylococcus aureus (ATCC 25923) was replaced with MRSA-2 and that the plates were covered and incubated for another 24 hours at 37° C., as opposed to room temperature. Compound 11 effectively dispersed MRSA-2 biofilms and exhibited an EC$_{50}$ value of 3.53 μM (FIG. 24).

Figure 25A:
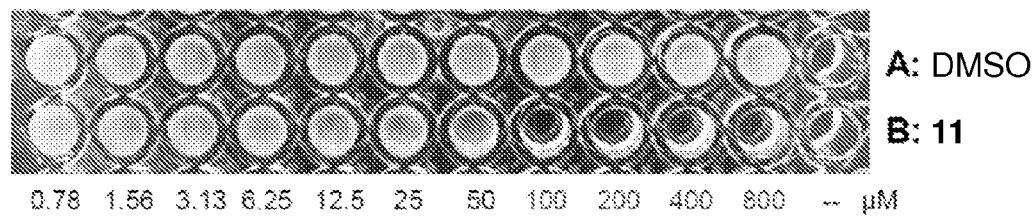
FIG. 25A depicts MRSA-2 biofilm eradication by compound 11 (minimum biofilm eradication concentration (MBEC)=100-200 µM).

Biofilm eradication assays. Since certain potent antibacterial compounds described herein demonstrated a tendency to be potent biofilm dispersal compounds, compounds 11, 4a, 23a, 27a, and 28a were evaluated in biofilm eradication assays (Fletcher et al., *Tetrahedron*, 2014, 70, 6373; Jennings et al., *ChemBioChem*, 2014, 15, 2211) against MRSA-2 to see if the active compounds were demolishing MRSA biofilms. The protocol for the biofilm eradication assays was essentially the same as the protocols reported in Eun et al., *J. Am. Chem. Soc.*, 2012, 134, 11322 and Ceri et al., *J. Clin. Microbiol.*, 1999, 37, 1771. Biofilm eradication assays were essentially biofilm dispersion assays with the addition of a final treatment with fresh media (and incubation at 37° C. for 24 hours) instead of crystal violet staining. This final incubation allowed viable cells within the biofilm to grow. At the end of this final incubation in biofilm eradication assays, microtiter wells void of turbidity represented eradicated biofilms, and the lowest concentration at which no visible growth was observed was referred to as the minimum biofilm eradication concentration (MBEC). Potent biofilm eradicating small molecules are extremely rare (Fletcher et al., *Tetrahedron*, 2014, 70, 6373; Jennings et al., *ChemBioChem*, 2014, 15, 2211). For these experiments, MRSA-2 was selected as the model since MRSA-2 is a multidrug-resistant, biofilm-forming clinical isolate of *Staphylococcus aureus* (Priyaja et al., *Cytotechnol.*, 2014, doi: 10.1007/s10616-014-9765-5). Exemplary results are shown in FIG. 25A and Table 2. Against MRSA-2, compound 11 showed an MIC value of 1.56 µM and an MBEC value of 100-200 µM (FIG. 25A and Table 2), while compounds 4a, 23a, 27a, and 28a gave MBEC values between 62.5 µM and 250 µM (Table 2). Compound 23a was found to be more potent (MBEC 62.5-100 µM) than compound 11. Compound 23a was also found to be equally potent to known biofilm eradicating agent QAC 10 (Jennings et al., *ChemBioChem*, 2014, 15, 2211) in comparative eradication assays against MRSA-2 biofilms.

Figure 25B:
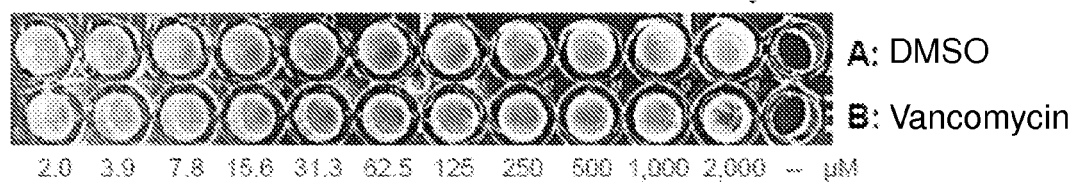
FIG. 25B depicts MRSA-2 biofilm eradication by vancomycin (MBEC >2,000 µM).

Vancomycin's activity against MRSA-2. Vancomycin was also evaluated against MRSA-2 since vancomycin has been considered to be the drug of last resort against MRSA infections. Vancomycin showed an MIC value of 0.78 µM against MRSA-2 and an MIC value of 0.39-0.78 µM against *S. aureus* ATCC 29213, therefore MRSA-2 is considered to be "sensitive" to vancomycin (Abouelhassan et al., *Bioorg. Med. Chem. Lett.*, 2014, 24, 5076). When tested against MRSA-2 in biofilm eradication assays, vancomycin exhibited an MBEC value of >2,000 µM (inactive at all concentrations; FIG. 25B and Table 2). The MRSA-2 biofilms were >2,564-fold more resistant against vancomycin when compared to their planktonic counterparts (i.e., MBEC:MIC ratio). In contrast, compound 11 showed an MBEC:MIC ratio of 64-128.

EQUIVALENTS And SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

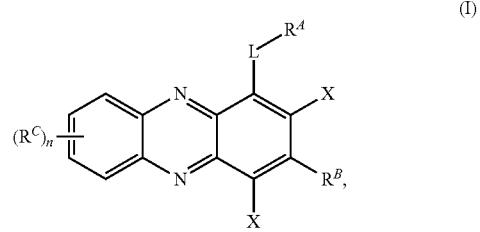

or a pharmaceutically acceptable salt, tautomer, or stereoisomer thereof, wherein:
each instance of X is independently halogen;
L is —OC(=O)O—, —OC(=O)—, —C(=O)O—, —NR$^L$C(=O)—, —C(=O)NR$^L$—, —OC(=O)NR$^L$—, —NR$^L$C(=O)O—, —NR$^L$C(=O)NR$^L$—, —OS(=O)$_2$—, —S(=O)$_2$O—, —NR$^L$S(=O)$_2$—, —S(=O)$_2$NR$^L$—, or —NR$^L$S(=O)$_2$NR$^L$—;
each instance of R$^L$ is independently hydrogen, substituted or unsubstituted alkyl, or a nitrogen protecting group;
R$^A$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, or an oxygen protecting group when attached to an oxygen atom;
R$^B$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{B1}$, —N(R$^{B1}$)$_2$, —SR$^{B1}$, —CN, —SCN, —C(=NR$^{B1}$)R$^{B1}$, —C(=NR$^{B1}$)OR$^{B1}$, —C(=NR$^{B1}$)N(R$^{B1}$)$_2$, —C(=O)R$^{B1}$, —C(=O)OR$^{B1}$, —C(=O)N(R$^{B1}$)$_2$, —NO$_2$, —NR$^{B1}$C(=O)R$^{B1}$, —NR$^{B1}$C(=O)OR$^{B1}$, —NR$^{B1}$C(=O)N(R$^{B1}$)$_2$, —OC(=O)R$^{B1}$, —OC(=O)OR$^{B1}$, or —OC(=O)N(R$^{B1}$)$_2$;
each instance of R$^{B1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{B1}$ are joined to form a substituted or unsubstituted heterocyclic ring;
each instance of R$^C$ is independently hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{C1}$, —N(R$^{C1}$)$_2$, —SR$^{C1}$, —CN, —SCN, —C(=NR$^{C1}$)R$^{C1}$, —C(=NR$^{C1}$)OR$^{C1}$, —C(=NR$^{C1}$)N(R$^{C1}$)$_2$, —C(=O)R$^{C1}$, —C(=O)OR$^{C1}$, —C(=O)N(R$^{C1}$)$_2$, —NO$_2$, —NR$^{C1}$C(=O)R$^{C1}$, —NR$^{C1}$C(=O)OR$^{C1}$, —NR$^{C1}$C(=O)N(R$^{C1}$)$_2$, —OC(=O)R$^{C1}$, —OC(=O)OR$^{C1}$, or —OC(=O)N(R$^{C1}$)$_2$, or two instances of R$^C$ are joined to form a substituted or unsubstituted carbocyclic, substituted or unsubstituted heterocyclic, substituted or unsubstituted aryl, or substituted or unsubstituted heteroaryl ring;
each instance of R$^{C1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^{C1}$ are joined to form a substituted or unsubstituted heterocyclic ring;
n is 0, 1, 2, 3, or 4;
when any one of the acyl, alkyl, alkenyl, alkynyl, carbocyclyl, heterocyclyl, heterocyclic ring, aryl, aryl ring, heteroaryl, and heteroaryl ring referred to above is substituted with one or more substituents at a carbon atom, the one or more substituents at the carbon atom are independently selected from Group (i);
when any one of the heterocyclyl, heterocyclic ring, heteroaryl, and heteroaryl ring referred to above is substituted with one or more substituents at a nitrogen atom, the one or more substituents at the nitrogen atom are independently selected from Group (ii);
Group (i) consists of halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=O)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —OP(=O)(R$^{aa}$)$_2$, —OP(=O)(OR$^{cc}$)$_2$, —NR$^{bb}$P(=O)(OR$^{cc}$)$_2$, —P(R$^{cc}$)$_2$, —OP(R$^{cc}$)$_2$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, 5-14 membered heteroaryl, =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, and =NOR$^{cc}$, wherein each of the alkyl, alkenyl, alkynyl, carbocyclyl, heterocyclyl, aryl, and heteroaryl of Group (i) is independently substituted with 0, 1, 2, 3, 4, or 5 instances of R$^{dd}$;
Group (ii) consists of hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=O)SR$^{cc}$, —P(=O)(R$^{aa}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, 5-14 membered heteroaryl, and nitrogen protecting groups, wherein each alkyl, alkenyl, alkynyl, carbocyclyl, heterocyclyl, aryl, and heteroaryl of Group (ii) is independently substituted with 0, 1, 2, 3, 4, or 5 R$^{dd}$ groups;
each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;
each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$_{cc}$, —SO$_2$OR$_{cc}$, —SOR$^{aa}$, —C(=O)SR$^{cc}$, —P(=O)(R$^{aa}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=O)SR$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl),—OC(=NH)(C$_{1-6}$ alkyl), —OC(=NH) OC$_{1-6}$ alkyl, —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=O)S(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S;

each instance of X$^-$ is a counterion independently selected from the group consisting of halide ions, NO$_3$$^-$, ClO$_4$$^-$, OH$^-$, H$_2$PO$_4$$^-$, HSO$_4$$^-$, sulfonate ions, and carboxylate ions;

each instance of the nitrogen protecting group is independently formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyflethyl carbamate (Bpoc), 1-(3,5-di-t-butylphenyl)-1-methylethyl carbamate (t-Bumeoc), 2-(2'-and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-cyclopropylmethyl carbamate, l-methyl-1-(3,5-dimethoxyphenyl)ethyl carbamate, 1-methyl-1-(p-phenylazophenyfethyl carbamate, 1-methyl-1-phenylethyl carbamate, 1-methyl-1-(4-pyridyflethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, phenacylsulfonamide, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyflethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-lphenyl(pentaacylchromium- or tungsten)acyll amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, or 3-nitropyridinesulfenamide (Npys);

each instance of the oxygen protecting group is independently methyl, methoxylmethyl (MOM), tert-butoxycarbonyl, methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dlinitrobenzhydryl,5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy) ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, or tosylate (Ts); and each instance of the sulfur protecting group is independently —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(=O)(R$^{aa}$)$_2$, or —P(=O)(OR$^{cc}$)$_2$.

2. The compound of claim 1, wherein R$^A$ is substituted or unsubstituted alkyl; or a pharmaceutically acceptable salt, tautomer, or stereoisomer thereof.

3. The compound of claim 1, wherein R$^A$ is substituted or unsubstituted alkenyl; or a pharmaceutically acceptable salt, tautomer, or stereoisomer thereof.

4. The compound of claim 1, wherein R$^A$ is substituted or unsubstituted carbocyclyl; or a pharmaceutically acceptable salt, tautomer, or stereoisomer thereof.

5. The compound of claim 1, wherein R$^A$ is substituted or unsubstituted 6- to 14-membered aryl, or substituted or unsubstituted heteroaryl; or a pharmaceutically acceptable salt, tautomer, or stereoisomer thereof.

6. The compound of claim 1, wherein R$^A$ is substituted or unsubstituted, monocyclic or bicyclic heteroaryl; or a pharmaceutically acceptable salt, tautomer, or stereoisomer thereof.

7. The compound of claim 1, wherein R$^B$ is hydrogen; or a pharmaceutically acceptable salt, tautomer, or stereoisomer thereof.

8. The compound of claim 1, wherein all instances of R$^C$ are hydrogen, or at least one instance of R$^C$ is halogen, substituted or unsubstituted alkyl, —OR$^{C1}$, or —CN; or a pharmaceutically acceptable salt, tautomer, or stereoisomer thereof.

9. The compound of claim 1, wherein L is —OC(=O)—; or a pharmacentically acceptable salt,tautomer, or stereoisomer therof.

10. The compound of claim 1, wherein L is —OC(=O)NR$^L$—, —OS(=O)$_2$—, or —OC(=O)O—; or a pharmaceutically acceptable salt, tautomer, or stereoisomer thereof.

11. The compound of claim 1, wherein X is —Cl, —Br, or —I; or a pharmaceutically acceptable salt, tautomer, or stereoisomer thereof.

12. The compound of claim 1, wherein:
each instance of X is independently —Br; and
L is —OC(=O)—, —C(=O)O—, —NR$^L$C(=O)—, —C(=O)NR$^L$—, —OC(=O)NR$^L$—, —NR$^L$C(=O) O—, —NR$^L$C(=O)NR$^L$—, —OS(=O)$_2$—, —S(=O)$_2$O—, —NR$^L$S(=O)$_2$—, —S(=O)$_2$NR$^L$—, or —NR$^L$S(=O)$_2$NR$^L$—;
or a pharmaceutically acceptable salt, tautomer, or stereoisomer thereof.

13. The compound of claim 1, wherein the compound is of the formula:

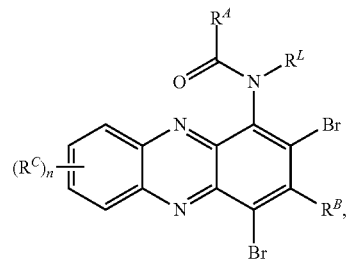

or a pharmaceutically acceptable salt, tautomer, or stereoisomer thereof.

14. The compound of claim 1, wherein the compound is of the formula:

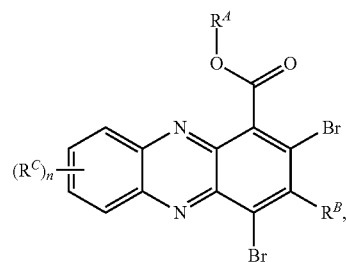

or a pharmaceutically acceptable salt, tautomer, or stereoisomer thereof.

15. The compound of claim 1, wherein the compound is of the formula:

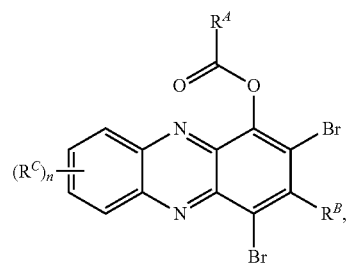

or a pharmaceutically acceptable salt, tautomer, or stereoisomer thereof.

16. The compound of claim 1, wherein the compound is of the formula:

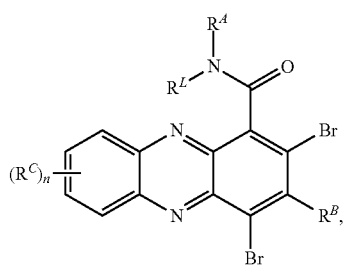

or a pharmaceutically acceptable salt, tautomer, or stereoisomer thereof.

17. The compound of claim 1, wherein the compound is of the formula:

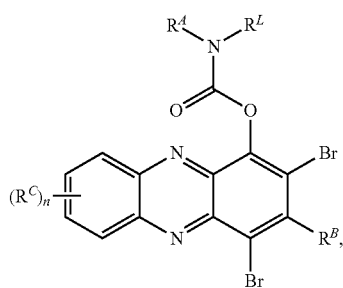

or a pharmaceutically acceptable salt, tautomer, or stereoisomer thereof.

18. The compound of claim 1, wherein the compound is of the formula:

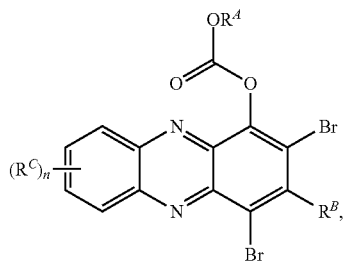

or a pharmaceutically acceptable salt, tautomer, or stereoisomer thereof.

19. The compound of claim 1, wherein the compound is of the formula:

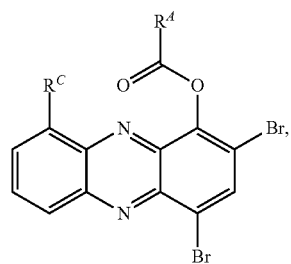

-continued

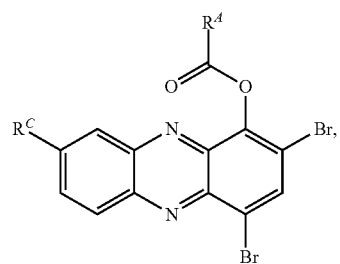

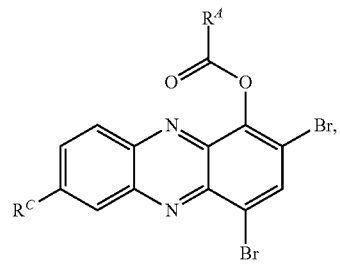

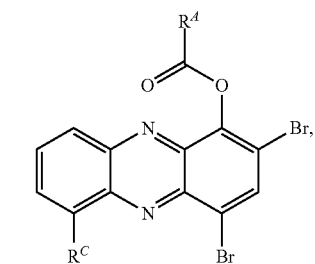

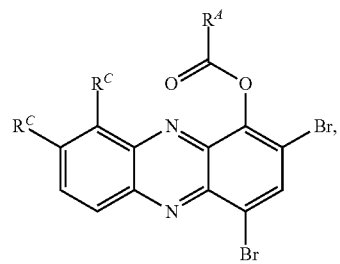

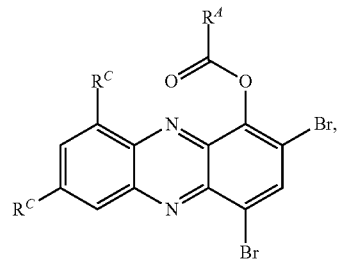

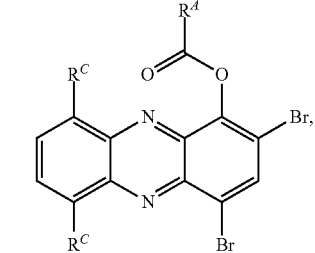

-continued

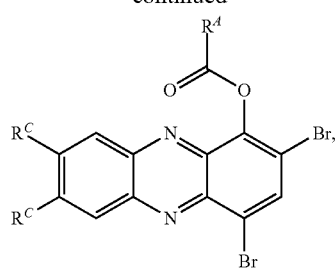

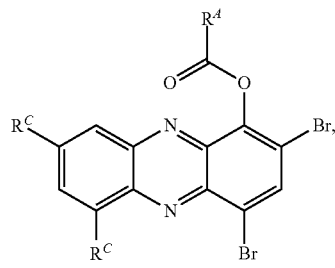

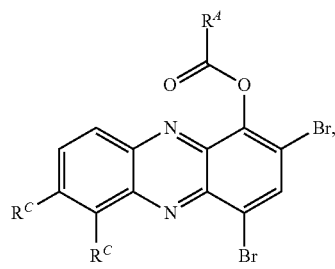

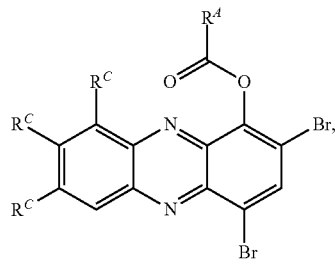

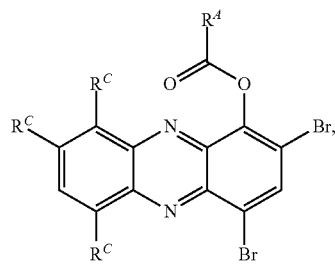

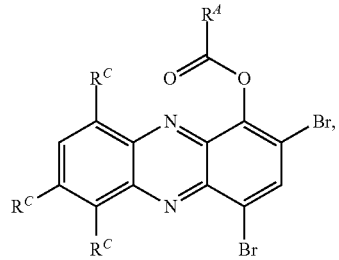

-continued

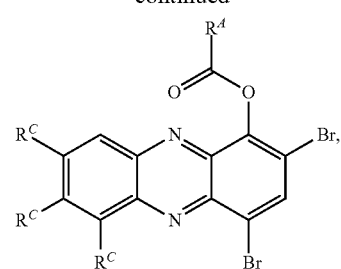

or a pharmaceutically acceptable salt, tautomer, or stereoisomer thereof.

20. The compound of claim 1, wherein the compound is of the formula:

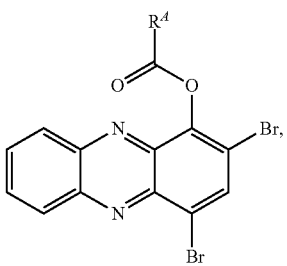

or a pharmaceutically acceptable salt, tautomer, or stereoisomer thereof.

21. The compound of claim 1, wherein the compound is of the formula:

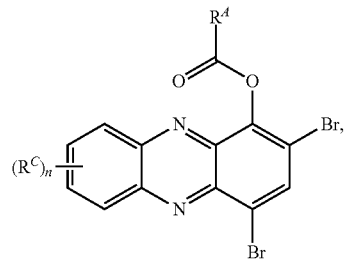

or a pharmaceutically acceptable salt, tautomer, or stereoisomer thereof.

22. The compound of claim 1, wherein the compound is of the formula:

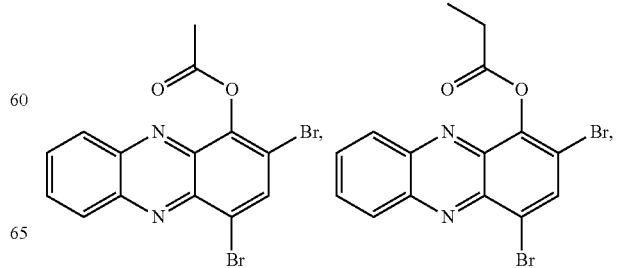

163
-continued
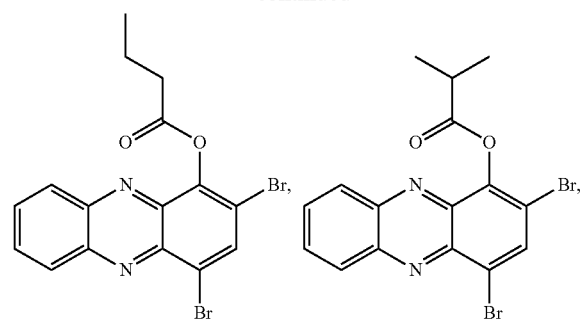
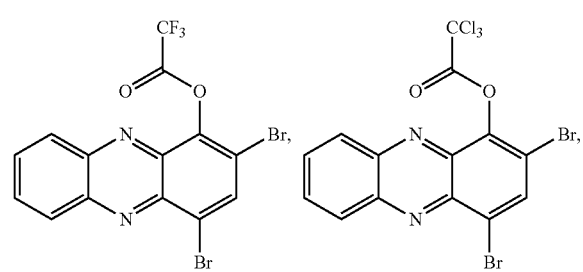
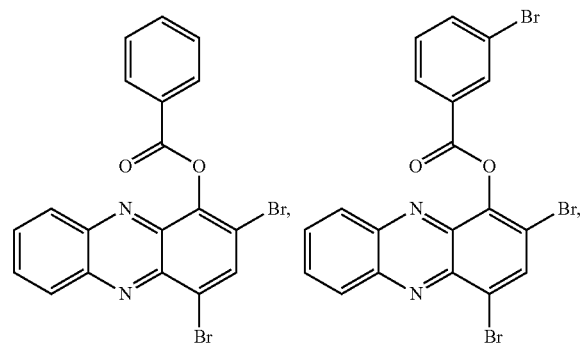
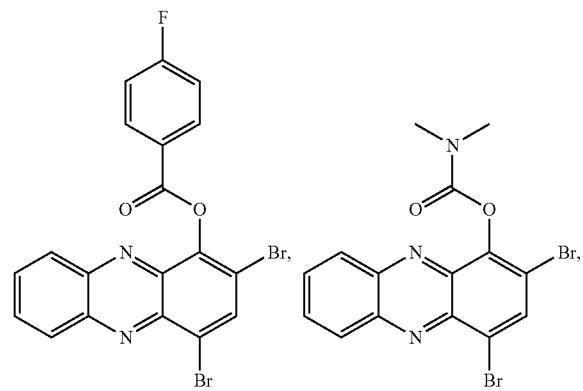
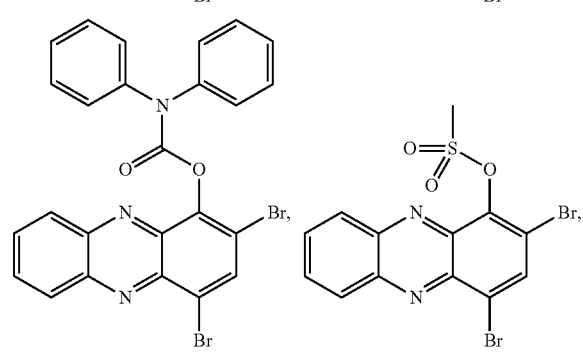
164
-continued
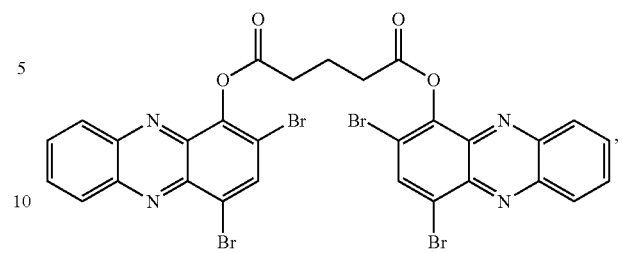
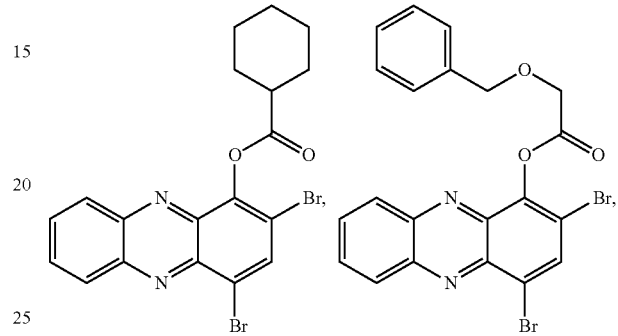
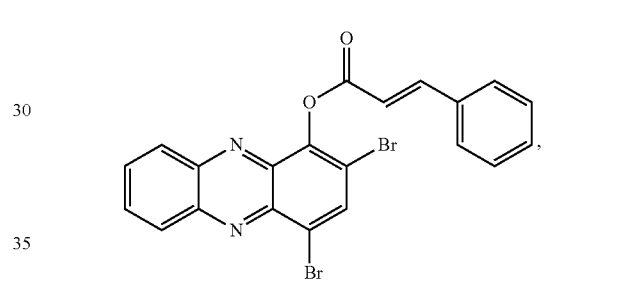
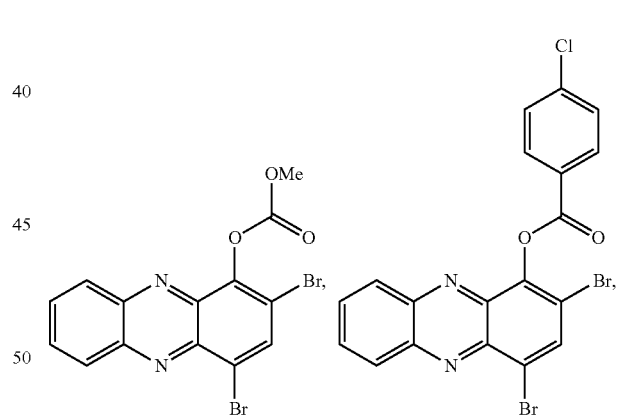
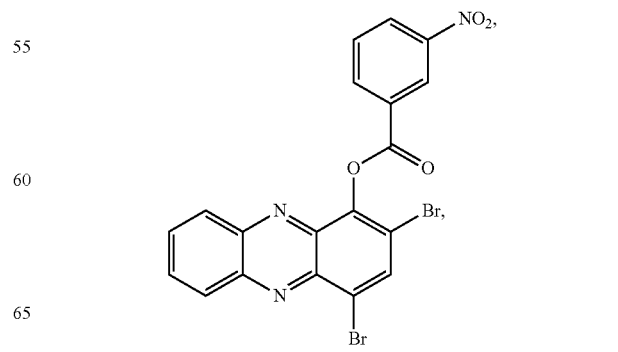

-continued
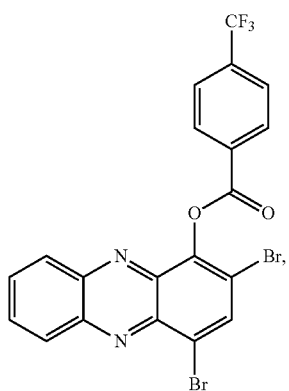
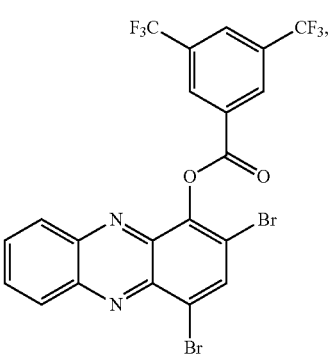
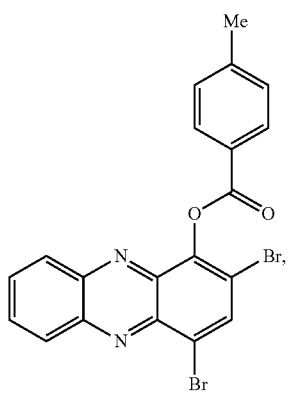
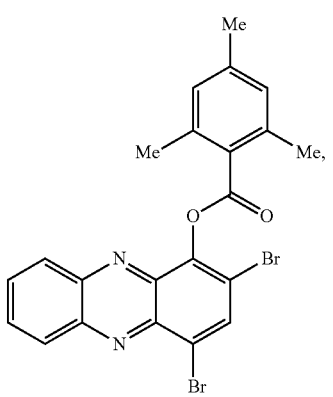
-continued
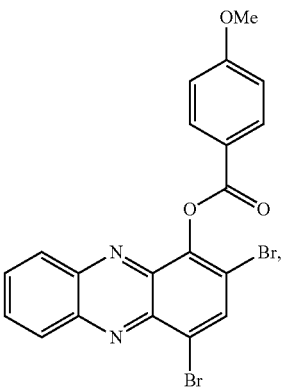
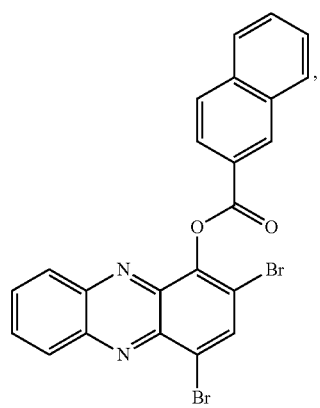
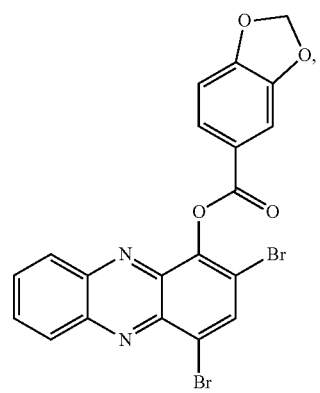
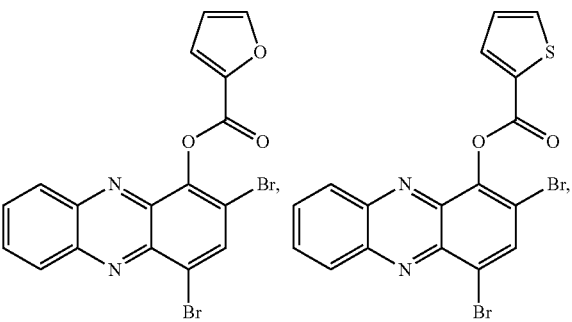

-continued

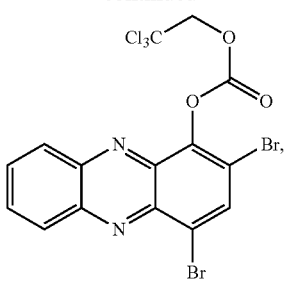

or a pharmaceutically acceptable salt, tautomer, or stereoisomer thereof.

23. The compound of claim 1, wherein the compound is of the formula:

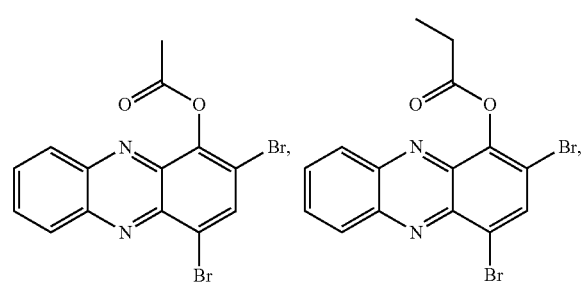

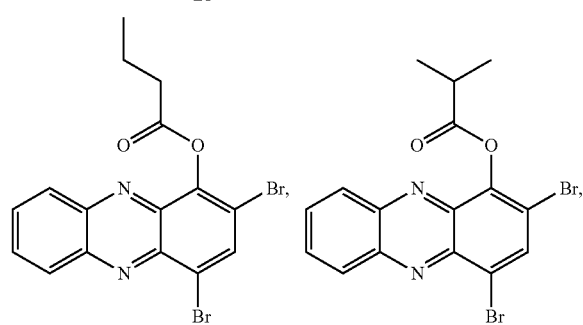

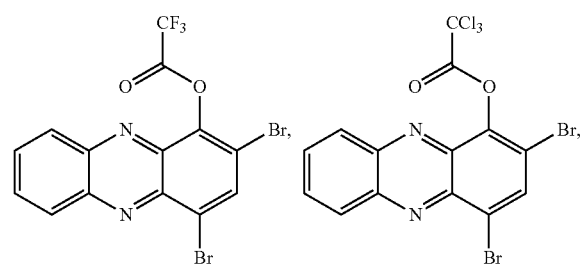

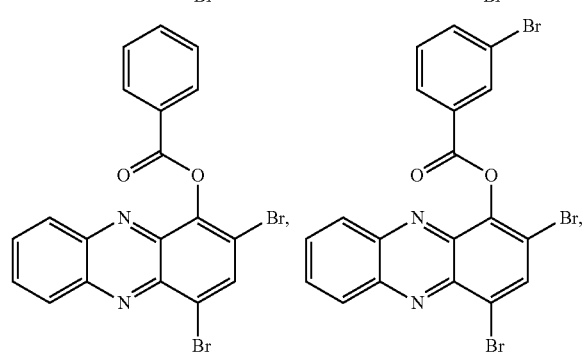

-continued

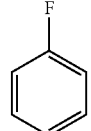

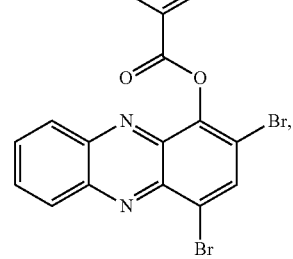
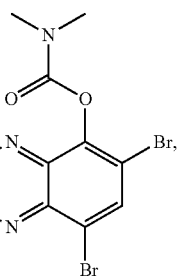

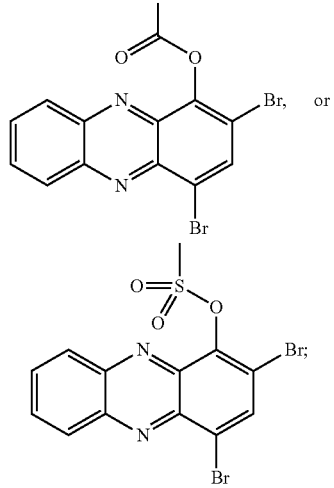

or a pharmaceutically acceptable salt, tautomer, or stereoisomer thereof.

24. The compound of claim 1, wherein the compound is of the formula:

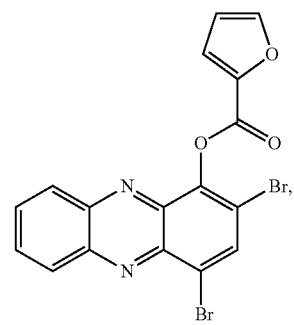 [SMILES: O=C(Oc1c(Br)cc(Br)c2nc3ccccc3nc12)c1ccco1]

or a pharmaceutically acceptable salt, tautomer, or stereoisomer thereof.

25. A pharmaceutical composition comprising a compound of claim 1, or a pharmaceutically acceptable salt, tautomer, or stereoisomer thereof, and a pharmaceutically acceptable excipient.

26. A kit comprising:
a compound of claim 1, or a pharmaceutically acceptable salt, tautomer, or stereoisomer thereof; and instructions for using the compound, or pharmaceutically acceptable salt, tautomer, or stereoisomer thereof.

27. A method of inhibiting the formation or growth of a biofilm or reducing or clearing a biofilm, the method comprising contacting the biofilm with an effective amount of a compound of claim 1, or a pharmaceutical acceptable salt, tautomer, or stereoisomer thereof.

28. A method of inhibiting the growth or reproduction of a microorganism or killing a microorganism, the method comprising contacting the microorganism with an effective amount of a compound of claim 1, or a pharmaceutical acceptable salt, tautomer, or stereoisomer thereof.

29. The method of claim 28, wherein the microorganism is a bacterium.

30. The method of claim 29, wherein the bacterium is a Gram-positive bacterium.

31. The method of claim 29, wherein the bacterium is a Gram-negative bacterium.

32. The method of claim 29, wherein the bacterium is methicillin-resistant *Staphylococcus aureus*.

33. The method of claim 29, wherein the bacterium is a *Staphylococcus, Streptococcus, Enterococcus, Listeria*, or *Clostridium* species.

34. The method of claim 29, wherein the bacterium is an *Acinetobacter* species.

* * * * *

UNITED STATES PATENT AND TRADEMARK OFFICE
CERTIFICATE OF CORRECTION

PATENT NO. : 9,856,225 B2
APPLICATION NO. : 15/107531
DATED : January 2, 2018
INVENTOR(S) : Robert William Huigens, III et al.

It is certified that error appears in the above-identified patent and that said Letters Patent is hereby corrected as shown below:

In the Claims

Claim 1, Column 152, Line 65: "4, or5 $R^{dd}$" should be replaced with: --4, or 5 $R^{dd}$--.

Claim 9, Column 157, Line 64-65: "pharmacentically acceptable salt, tautomer, or stereoisomer therof" should be replaced with: --pharmaceutically acceptable salt, tautomer, or stereoisomer thereof--.

Signed and Sealed this
Twenty-sixth Day of June, 2018

Andrei Iancu
*Director of the United States Patent and Trademark Office*